US012797471B2

(12) United States Patent
Badylak et al.

(10) Patent No.: US 12,797,471 B2
(45) Date of Patent: Nov. 17, 2026

(54) MATRIX BOUND VESICLES (MBV) FOR TREATMENT OF ACUTE RESPIRATORY DISTRESS SYNDROME

(71) Applicant: University of Pittsburgh— Of the Commonwealth System of Higher Education, Pittsburgh, PA (US)

(72) Inventors: Stephen Francis Badylak, West Lafayette, IN (US); George S. Hussey, Cranberry Township, PA (US); Raphael Crum, Pittsburgh, PA (US)

(73) Assignee: University of Pittsburgh - Of the Commonwealth System of Higher Education, Pittsburgh, PA (US)

( * ) Notice: Subject to any disclaimer, the term of this patent is extended or adjusted under 35 U.S.C. 154(b) by 1000 days.

(21) Appl. No.: 17/904,287

(22) PCT Filed: Apr. 15, 2021

(86) PCT No.: PCT/US2021/027542
§ 371 (c)(1),
(2) Date: Aug. 15, 2022

(87) PCT Pub. No.: WO2021/211885
PCT Pub. Date: Oct. 21, 2021

(65) Prior Publication Data

US 2023/0071393 A1 Mar. 9, 2023

Related U.S. Application Data

(60) Provisional application No. 63/011,177, filed on Apr. 16, 2020.

(51) Int. Cl.

| | |
|---|---|
| ***A61K 39/395*** | (2006.01) |
| ***A61K 9/00*** | (2006.01) |
| ***A61K 31/688*** | (2006.01) |
| ***A61K 35/22*** | (2015.01) |
| ***A61K 35/32*** | (2015.01) |
| ***A61K 47/24*** | (2006.01) |
| ***A61P 11/00*** | (2006.01) |

(52) U.S. Cl.
CPC ............ *A61K 47/24* (2013.01); *A61K 9/0019* (2013.01); *A61K 9/0078* (2013.01); *A61K 31/688* (2013.01); *A61K 35/22* (2013.01); *A61K 35/32* (2013.01); *A61P 11/00* (2018.01)

(58) Field of Classification Search
None
See application file for complete search history.

(56) References Cited

U.S. PATENT DOCUMENTS

| | | | | |
|---|---|---|---|---|
| 2003/0092145 | A1 | 5/2003 | Jira | |
| 2006/0292227 | A1 | 12/2006 | McPherson | |
| 2014/0031256 | A1 | 1/2014 | Lim | |
| 2018/0125874 | A1* | 5/2018 | D'Alessio | A61K 31/166 |
| 2018/0282698 | A1 | 10/2018 | Hematti et al. | |
| 2019/0117837 | A1* | 4/2019 | Badylak | A61K 35/36 |
| 2021/0106526 | A1 | 4/2021 | Badylak et al. | |
| 2024/0226170 | A9 | 7/2024 | Badylak et al. | |

FOREIGN PATENT DOCUMENTS

| | | | |
|---|---|---|---|
| AR | 110297 | A1 | 3/2019 |
| CN | 106198953 | A | 12/2016 |
| CN | 114615987 | A | 6/2022 |
| CN | 117015375 | A | 11/2023 |
| WO | WO 2009/014633 | A1 | 1/2009 |
| WO | WO 2012/108842 | A1 | 8/2012 |
| WO | WO 2015/179227 | A1 | 11/2015 |
| WO | WO 2016/112271 | A1 | 7/2016 |
| WO | WO 2018/102597 | A1 | 11/2017 |
| WO | WO 2018/204848 | A1 | 11/2018 |
| WO | WO 2019/213482 | A1 | 11/2019 |
| WO | WO 2021/243007 | A2 | 12/2021 |

OTHER PUBLICATIONS

Ali et al., "Isolation and characterization of calcifying matrix vesicles from epiphyseal cartilage," *PNAS* 67(3): 1513-1520 (Nov. 1970).

Ali, "Analysis of matrix vesicles and their role in the calcification of epiphyseal cartilage," *Federation Proceedings* 35(2): 135-42 (1976).

Ali, "Matrix vesicles and apatite nodules in arthritic cartilage," Chapter 15 in: *Perspectives in Inflammation: Future Trends in Inflammation*, Willoughby et al., (eds), University Park Press, Baltimore, MD, pp. 211-233 (1977).

Bab et al., "Ultrastructural and biochemical study of extracellular vesicles in normal alveolar bone of rats," *J. Cell Tissue Res.* 202: 1-7 (1979).

De Jong et al., "Extracellular vesicles: potential roles in regenerative medicine," *Frontiers in Immunology* 5(608): pp. 1-13 (Dec. 2014).

Deutsch et al., "Purification and further characterization of isolated matrix vesicles from rat alveolar bone," *Metabolic Bone Disease and Related Research* 3(3): 209-214 (1981).

"Fractionation of Cells," From: *Molecular Biology of the Cell 4th edition* (2002), print-out from on-line edition available at: https://www.ncbi.nlm.nih.gov/books/NBK26936/ (3 pages).

Gibson et al., "Tissue extracellular matrix nanoparticle presentation in electrospun nanofibers," *BioMed Research International* 2014(Article ID 469120): pp. 1-13 (May 29, 2014).

Gohr et al., "Calcific tendonitis: A model," *Connective Tissue Research* 48(6): 286-291 (2007).

(Continued)

*Primary Examiner* — Yunsoo Kim
(74) *Attorney, Agent, or Firm* — Klarquist Sparkman, LLP

(57) ABSTRACT

Methods are disclosed for treating an acute respiratory distress syndrome, such as an acute respiratory distress syndrome associated with a viral infection, such as SARS-CoV2 (COVID-19) in a subject in need thereof. These methods include administering to the subject a pharmaceutical preparation comprising isolated matrix bound vesicles (MBV) derived from extracellular matrix.

14 Claims, 47 Drawing Sheets

Specification includes a Sequence Listing.

(56) References Cited

OTHER PUBLICATIONS

Greening et al., "A protocol for exosome isolation and characterization: Evaluation of ultracentrifugation, density-gradient separation, and immunoaffinity capture methods," *Proteomic Profiling: Methods and Protocols* 1295: 179-210 (2015)(Abstract).
Hirschman et al., "Neutral peptidase activities in matrix vesicles from bovine fetal alveolar bone and dog osteosarcoma," *Calcified Tissue International* 35(6):791-797 (Sep. 1983).
Huleihel et al., "Matrix-bound nanovesicles recapitulate extracellular matrix effects on macrophage phenotype," *Tissue Engineering: Part A* 23(21 and 22): 1283-1294 (2017).
Huleihel et al., "Matrix-bound nanovesicles within ECM bioscaffolds," *Science Advances* 2(6): e1600502, 10 pages (Jun. 10, 2016).
Hussey et al., "Matrix bound nanovesicle-associated IL-33 activates a pro-remodeling macrophage phenotype via a non-canonical, ST2-independent pathway," *Journal of Immunology and Regenerative Medicine* 3:26-35 (Mar. 2019).
International Search Report and Written Opinion from parent PCT Application No. PCT/US2021/027542, 10 pages (mailed dated Jun. 11, 2021).
International Search Report and Written Opinion from PCT Application No. PCT/US2017/020360, 11 pages (mailed May 8, 2017).
Kapustin et al., "Vascular smooth muscle cell calcification is mediated by regulated exosome secretion," *Circulation Research* 116(8): 1312-1323 (ePub Feb. 23, 2015).
Mahida et al., "Extracellular vesicles in ARDS: New insights into pathogenesis with novel Clinical Applications," *Annual Update in Intensive Care and Emergency Medicine* 2020 3-65 (Nov. 30, 2019).
Malda et al., "Extracellular vesicles—new tool for joint repair and regeneration," *Nature Reviews* 12: 244-249 (Apr. 2016).
Martin et al., "Isolation and purification of extracellular matrix vesicles from blood vessels," *Preparative Biochemistry* 22(2): 87-103 (1992).
Mu et al., "Host matrix modulation by tumor exosomes promotes motility and invasiveness," *Neoplasia* 15(8): 875-887 (Aug. 2013).
Muhlrad et al., "Occurrence of actin-like protein in extracellular matrix vesicles," *Calcif. Tissue Int.* 34(4): 376-381 (1982).
Narita et al., "Immune responses in patients with esophageal cancer treated with SARTI peptide-pulsed dendritic cell vaccine," International Journal of Oncology vol. 46(4): 1699-1709, (published online Jan. 23, 2015).
Rutnam et al., "miRNAs regulate expression and function of extracellular matrix Molecules," *Matrix Biol.* 32(2): 74-85 (Mar. 11, 2013).
Sabin and Kikyo, "Microvesicles as mediators of tissue regeneration," *Translational Research* 1-10 (2013).
Schurgers et al., "Initiation and propagation of vascular calcification is regulated by a concert of platelet- and smooth muscle cell-derived extracellular vesicles," Frontiers in Cardiovascular Medicine 5(36): 13 pages (Apr. 2018).
Sela et al., "Ultrastructural and biochemical characterization of extracellular matrix vesicles in healing alveolar bone sockets: preliminary indications for the presence of contractile proteins," *Metab. Bone Dis. and Rel. Res.* 1(3): 185-191 (1978).
Shapiro et al., "Matrix Vesicles: Are they anchored exosomes?," *Bone* 79: 29-36 (Oct. 2015).
Thouverey et al., "Proteomic characterization of biogenesis and functions of matrix vesicles released from mineralizing human osteoblast-like cells," *Journal of Proteomics* 74: 1123-1134—(2011).
Tian et al., "A doxorubicin delivery platform using engineered natural membrane vesicle exosomes for targeted tumor therapy," Biomaterials 35(7): 2383-2390 (e-Pub Dec. 15, 2013).
Väänänen et al., "Matrix vesicles in chicken epiphyseal cartilage. Separation from lysosomes and the distribution of inorganic pyrophosphatase activity," *Calcif. Tissue Int.* 28(1): 65-72 (1979).
Van Der Merwe et al., "Matrix bound vesicles and miRNA cargoes are bioactive factors within the extracellular matrix bioscaffolds," *Neural Regeneration Research* 12(10): 1597-1599 (Oct. 2017).
Wang et al., "Comparison of in vivo adipogenic capabilities of two different extracellular matrix microparticle scaffolds," *Plastic and Reconstructive Surgery* 131(2):174e-187e (Feb. 2013).
Wolf et al., "Immunomodulatory extracellular matrix nanoparticles," *Tissue Engineering* Part A, 21(Supplement 1): S-52 (Sep. 8-1, 2015)(Abstract).
Wuthier et al., "Non-enzymatic isolation of matrix vesicles: characterization and initial studies on 45Ca and 32P-orthophosphate metabolism," *Metab. Bone Dis. and Rel. Res.*, 1(2): 125-136 (1978).
Zhou et al., "Label-free quantification proteomics reveals novel calcium binding proteins in matrix vesicles isolated from mineralizing Saos-2 cells," *BioScience Trends* 7(3):144-151 (2013).
Liu et al., "IL-33-mediated IL-13 Secretion by $ST2^+$ Tregs controls inflammation after lung injury," *JCI Insight* 4(6):e123919, E-pub Feb. 19, 2019.
Piening et al., "Matrix-Bound Nanovesicles: What Are They and What Do They Do?," *Cells Tissues Organs* 212(1):111-123, E-pub Feb. 15, 2022.
Crum et al., "Mitigation of influenza-mediated inflammation by immunomodulatory matrix-bound nanovesicles," *Sci Adv* 9(20): eadf9016, 12 pages (Epub 2023 May 19, 2023).
Juan and Feng, "Research progress of interleukin-33 in acute respiratory distress syndrome," *The Journal of Chongqing Medical University* 41(4): 425-428 (2016) (w/English language machine translation).
Jian, "The role of inflammatory mediators in the pathogenesis of acute respiratory distress syndrome and its research progress," Clinical Education of General Practice 17(5): 444-446 (May 1, 2019)(w/English language machine translation).

* cited by examiner

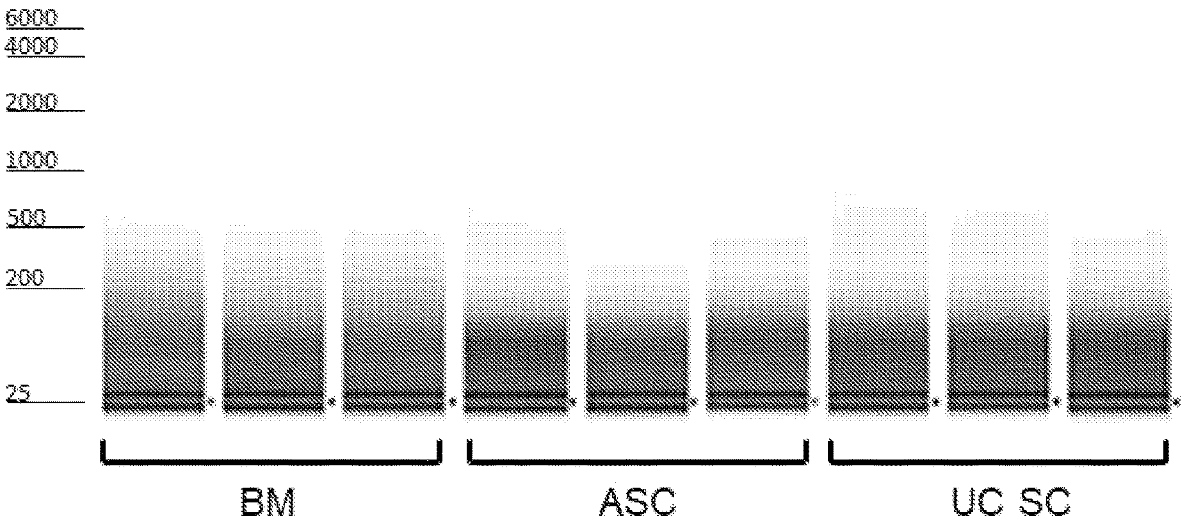
FIG. 3G
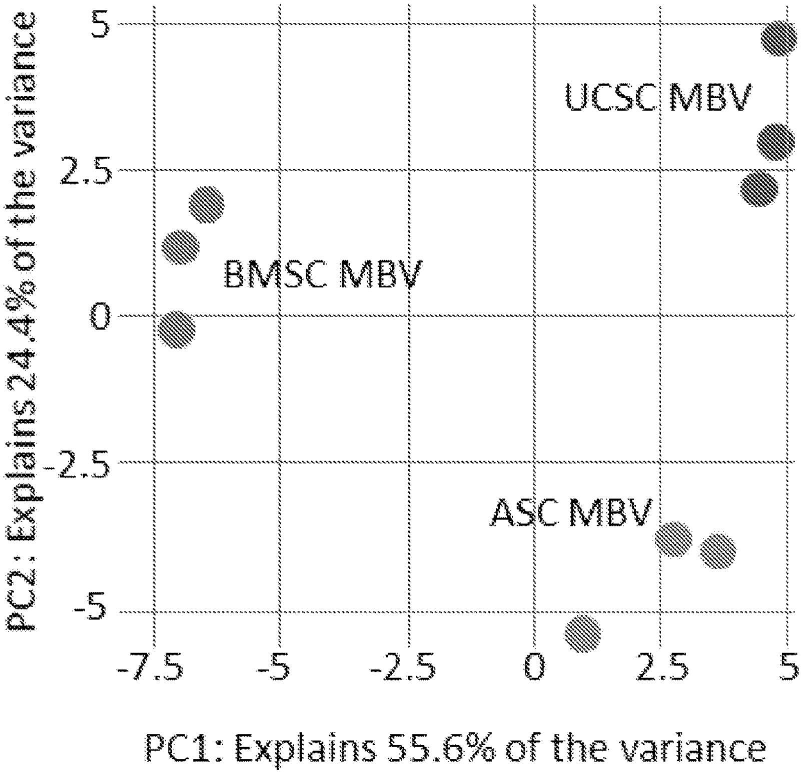

FIG. 17
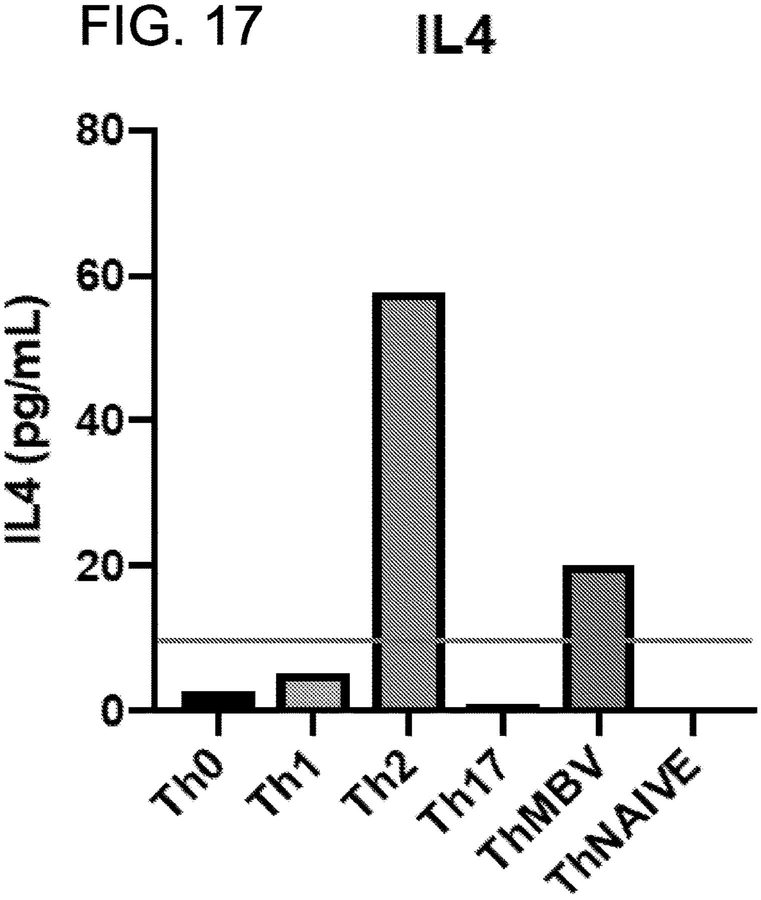
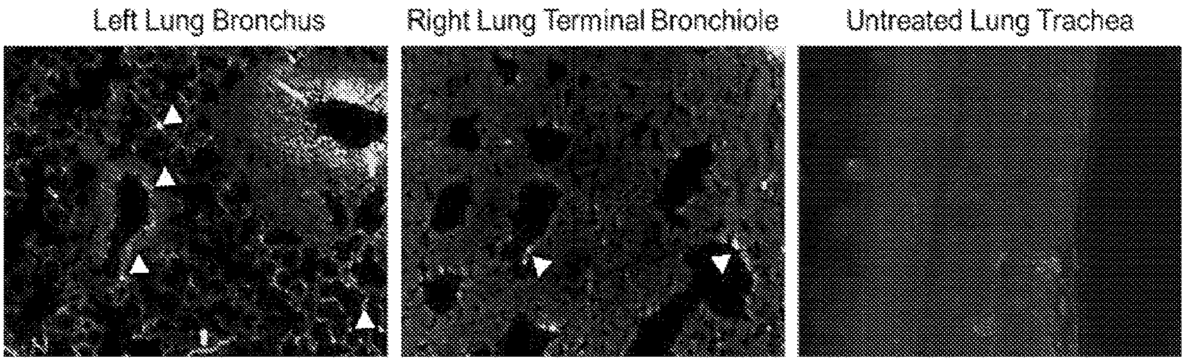
FIG. 18

FIG. 21A
Influenza + i.v. MBV
Influenza + i.v. PBS
PBS

| Lane | Sample Name | Concentration | Volume Added | Mass Added |
|---|---|---|---|---|
| 1 | 17A lysate control (Napierala lab) | 2130 ug/mL | 4.7uL | 10ug |
| 2 | 17IIA MV control (Napierala lab) | unknown | 10uL | unknown |
| 3 | 17IIA MV | 458.1ug/mL | 10uL | 4.581ug |
| 4 | Plasma exosomes | 501.0 ug/mL | 10uL | 5.010ug |
| 5 | Muscle MBV | 745.6 ug/mL | 10uL | 7.456.ug |

MATRIX BOUND VESICLES (MBV) FOR TREATMENT OF ACUTE RESPIRATORY DISTRESS SYNDROME

CROSS REFERENCE TO RELATED APPLICATIONS

This is a § 371 U.S. national stage of International Application No. PCT/US2021/027542, filed Apr. 15, 2021, which claims the benefit of U.S. Provisional Application No. 63/011,177, filed Apr. 16, 2020, which is incorporated by reference herein in its entirety.

FIELD OF THE INVENTION

The present application relates to administration of matrix bound vesicles (MBV) derived from extracellular matrix for treating acute respiratory distress syndrome (ARDS), such as ARDS caused by SARS-CoV2 (COVID-19).

BACKGROUND

The Coronavirus Disease 2019 (COVID-19) pandemic, resulting from infection with the severe acute respiratory syndrome-coronavirus-2 (SARS-CoV-2), also known in the art as 2019-novel coronavirus or 2019-nCoV, is currently the source of public health concern worldwide. Treatment has been clinically challenging in many patients. (Mehta et al. (2020) COVID-19: Consider Cytokine Storm Syndromes and Immunosuppression. *Lancet.* 395 (10229): 1033-1034). Although mobilization of massive resources to develop antiviral, anti-inflammatory, immunosuppressive drugs, and vaccines has occurred, mounting evidence suggests that hypercytokinemia, also known as cytokine release syndrome or cytokine storm syndrome, is a common feature and leading cause of mortality of COVID-19 patients with the most severe disease. (Tian, S. et al. (2020) Pulmonary Pathology of Early-Phase 2019 Novel Coronavirus (COVID-19) Pneumonia in Two Patients With Lung Cancer. *J. Thorac. Oncol.* S1556-0864(20)30132-5). Furthermore, hypercytokinemia is a strong indicator of patient mortality that typically is caused by acute respiratory distress syndrome (ARDS). Both hypercytokinemia and ARDS reflect pathologic dysregulation of the immune system triggered by the SARS-CoV-2 viral infection. Current therapeutics address aberrant inflammation by immunosuppression or inhibition of specific inflammatory mediators, allowing for increased susceptibility to secondary infections.

Accordingly, there remains a critical need for new and effective treatments for modulating the immune system in cases of immune system disorders, such as those resulting from a viral infection, such as ARDS, for example, caused by SARS-CoV-2.

SUMMARY

Provided herein are methods of treating or preventing acute respiratory distress syndrome (ARDS).

In one embodiment, the invention provides a method of treating or preventing acute respiratory distress syndrome (ARDS) in a subject at risk of developing ARDS. The method involves administering to the subject a pharmaceutical composition comprising a therapeutically effective amount of isolated matrix bound vesicles (MBV) derived from extracellular matrix, thereby treating or preventing ARDS in the subject. The disclosed methods can include selecting a subject that has, or is at risk for, ARDS.

ARDS in the patient may be caused by any number of originating conditions. For example, in one embodiment, the subject has a pulmonary infection that is viral, bacterial, or fungal in origin. For example, the subject may have a pulmonary infection with a virus selected from SARS-CoV2, SARS-CoV, MERS-CoV, an ebolavirus, an influenza virus, a cytomegalovirus, or a herpes virus. In any of the foregoing embodiments, the subject may have pneumonia. In one embodiment, the subject is infected with SARS-CoV-2 or COVID-19. In another embodiment, the subject has influenza. In another embodiment, the subject has SARS or MERS. In yet another embodiment, the subject has inhaled a toxic substance such as smoke, chemical fumes, or vapors from vaping (e.g., from an e-cigarette). In yet another embodiment, the subject has aspirated water, vomit, or food into the lung. In another embodiment, the subject has a head or chest injury damaging the lungs or the portion of the brain that controls breathing. In other embodiments, the subject has sepsis. In yet other embodiments, the subject has pancreatitis. In another embodiment, the subject has a severe burn. In another embodiment, the subject has received a blood transfusion.

According to the invention, in some embodiments, the methods of the invention are practiced in subjects experiencing hypercytokinemia. For example, administration of MBV according to the invention reverses the effects of hypercytokinemia in the subject. In some embodiments, the MBV are administered to the subject prior to the onset of ARDS to prevent onset of ARDS. Yet in other embodiments, the MBV are administered to the subject after onset of ARDS to treat the ARDS and prevent progression of ARDS.

In one embodiment of the methods of the invention, the subject is a human subject.

According to one embodiment of the invention, the pharmaceutical composition comprising the MBV is administered by systemic intravenous (IV) injection. For example, the systemic intravenous injection is via standard IV line or central line. In some embodiments, the central line is a peripherally inserted central catheter (PICC), a tunneled catheter, or an implanted port. In some embodiments, the standard IV line is in a vein in the wrist, arm, or hand. In yet other embodiments, the intravenous injection is a bolus injection, or continuous drip or pump injection.

According to another embodiment, the pharmaceutical composition is administered to the subject's lungs. For example, the pharmaceutical composition is administered as an aerosol via a nebulizer. In yet other embodiments, the pharmaceutical composition is administered by endotracheal instillation. For example, the administration is via an endotracheal tube placed in the subject. In yet other embodiments, the pharmaceutical composition is administered to the lungs by a metered dose inhaler.

According to another embodiment, the MBV (i) do not express one or more of CD63, CD81, and/or CD9, or have barely detectable levels of CD63, CD81, and/or CD9; and/or (ii) the MBV comprise (a) a phospholipid content comprising at least 55% phosphatidylcholine (PC) and phosphatidyl inositol (PI) in combination; (b) a phospholipid content comprising 10% or less sphingomyelin (SM); (c) a phospholipid content comprising 20% or less phosphatidylethanolamine (PE); and/or (d) a phospholipid content comprising 15% or greater phosphatidylinositol (PI).

In yet another embodiment, the MBV are derived from extracellular matrix of urinary bladder, small intestine, heart, dermis, liver, kidney, uterus, brain, blood vessel, lung, bone, muscle, pancreas, placenta, stomach, spleen, colon, adipose tissue, or esophagus. In one embodiment, the MBV are derived from extracellular matrix of urinary bladder, small intestine, heart, dermis, liver, kidney, uterus, brain, blood vessel, lung, muscle, pancreas, placenta, stomach, spleen, colon, adipose tissue, or esophagus. In one embodiment, the MBV are not derived from bone extracellular matrix.

In yet another embodiment, the MBV are derived from urinary bladder matrix (UBM), small intestinal submucosa (SIS), or urinary bladder submucosa (UBS). In one embodiment, the MBV are derived from urinary bladder matrix (UBM). In one embodiment, the MBV are derived from small intestinal submucosa (SIS). In one embodiment, the MBV are derived from urinary bladder submucosa (UBS).

In yet another embodiment, the MBV are derived from extracellular matrix from a mammalian vertebrate selected from a human, monkey, pig, cow, or sheep.

In another embodiment, the MBV are administered in amount of $1\times10^6$ to $1\times10^{12}$ MBV per kg of body weight per administration.

In some embodiments, the subject receives an antibiotic, an antiviral, or an anti-inflammatory medication. For example, the subject receives remdesivir, favipiravir, azithromycin, or hydroxychloroquine. For example, the subject receives remdesivir, favipiravir, azithromycin, or hydroxychloroquine and the subject has COVID-19. For example, in some embodiments, the subject receives tocilizumab, anakinra, or a Janus kinase (JAK) inhibitor. For example, the subject receives tocilizumab, anakinra, or a Janus kinase (JAK) inhibitor and the subject has COVID-19.

In another embodiment, the subject has a reduced risk of secondary infection as a result of treatment with MBV as compared to a subject treated with an immunosuppressive agent. For example, the secondary infection is a pulmonary infection. For example, the secondary infection is an infection in the blood. For example, the secondary infection is in the heart, kidney, or liver. For example, the secondary infection is a bacterial infection. For example, the secondary infection is a viral infection.

In a further embodiment, the subject experiences an increase of 10%, 15%, 20%, 25%, 30%, 35%, 40%, 45%, 50%, 55%, 60%, 70%, 75%, 80%, 85%, 90%, 95%, 100%, or more than 100% in the subject's oxygen saturation after administration of the pharmaceutical composition. In another embodiment, the subject experiences an increase of 10%, 15%, 20%, 25%, 30%, 35%, 40%, 45%, 50%, 55%, 60%, 70%, 75%, 80%, 85%, 90%, 95%, 100%, or more than 100% in the subject's oxygen saturation index after administration of the pharmaceutical composition. In another embodiment, the subject experiences an increase of 10%, 15%, 20%, 25%, 30%, 35%, 40%, 45%, 50%, 55%, 60%, 70%, 75%, 80%, 85%, 90%, 95%, 100%, or more than 100% in the subject's oxygen index after administration of the pharmaceutical compound. The increase may occur within 1 hour, 2 hours, 3 hours, 4 hours, 5 hours, 6 hours, 7 hours, 8 hours, 9 hours, 10 hours, 11 hours, 12 hours, 18 hours, or 24 hours after administration of the pharmaceutical composition.

In another embodiment, the subject experiences a decrease in the production of a pro-inflammatory cytokine after the administration of MBV. For example, the pro-inflammatory cytokine is one or more of TNF-α, IFN-γ, IL-8, IL-6, IL-1β, or IL-12. In another embodiment, the subject experiences an increase in the production of an anti-inflammatory cytokine after the administration of MBV. For example, the anti-inflammatory cytokine is TGF-β, IL-4, or IL-10. In one embodiment, the increase or decrease is measured by sampling bronchoalveolar lavage fluid from the subject's lungs before and after administration of the MBV. In yet another embodiment, the increase or decrease is measured by sampling the subject's blood before and after administration of the MBV. In another embodiment, the effectiveness of treatment is measured by a reduction in symptoms associated with ARDS and/or hypercytokinemia.

The foregoing and other objects, features, and advantages of the invention will become more apparent from the following detailed description, which proceeds with reference to the accompanying figures.

BRIEF DESCRIPTION OF THE DRAWINGS

FIG. 1A shows scanning electron microscopy images of an ECM scaffold derived from urinary bladder matrix (UBM), in which discrete spherical bodies approximately 100 nm in diameter are dispersed throughout the matrix. Scale bars=1 μm. FIG. 1B shows an illustration of the 3T3 fibroblast cell culture model used to selectively harvest vesicles from a liquid-phase (EV) or solid-phase extracellular compartment (MBV). FIG. 1C shows phase contrast microscopy, hematoxylin and eosin (H&E) staining, and 4',6-diamidino-2-phenylindole (DAPI) staining demonstrating the absence of cells and absence of intact cell nuclei following decellularization. FIG. 1D shows transmission electron microscopy images of liquid-phase EV and MBV isolated from the 3T3 fibroblast cell culture model. Scale bars=100 nm. FIG. 1E shows size distribution plots from nanoparticle tracking analysis (NTA) of liquid-phase EV and MBV isolates from the 3T3 fibroblast cell culture. FIG. 1F shows immunoblot analysis comparing CD9, CD63, CD81 and Hsp70 expression levels in liquid-phase EV and MBV. FIG. 1G shows silver stain analysis of electrophoretically separated proteins in liquid-phase EV and MBV.

FIG. 2A shows bioanalyzer analysis of total RNA isolated from 3T3 parental cells, their secreted liquid-phase EV, and their MBV. FIG. 2B shows principal-component analysis (PCA) comparing liquid-phase EV (green), MBV (blue) and cellular (red) RNA-seq datasets. FIG. 2C shows volcano plots demonstrating the differential expression of miRNAs in liquid-phase EV, MBV, and the parental cells. The inclusion criteria were a 2-fold difference of $\log_2$ (fold-change) in either direction, with a P-value <0.05. Each dot represents a specific miRNA transcript; green dots to the right of the vertical dashed line (and above the horizontal dashed line) correspond to a relative increase in expression level, and red dots to the left (and above the horizontal dashed line) correspond to a relative decrease in expression level. Blue dots (which appear below the horizontal dashed line) indicate miRNA with no significant change in expression level. FIG. 2D shows RT-qPCR validation of the results of miRNA sequencing, *p<0.05, n=4. FIG. 2E shows Ingenuity Pathway Analysis (IPA functional analysis). Significantly enriched molecular functions identified by IPA functional analysis were determined considering differentially expressed miRNA in MBV (red-bottom bar) and liquid-phase EV (blue-top bar). There is no red bar for cellular growth & proliferation, cell morphology, cell-to-cell signaling, and tissue development; there is no blue bar for digestive system development & function, hepatic system development and function and organ development and function.

FIGS. 3A-3H depict differences in miRNA cargo of MBV based on the cellular origin of the MBV. FIG. 3A shows a phase contrast microscopy image of a decellularized BMSC cell culture plate showing the absence of cells. FIG. 3B shows a transmission electron microscopy image of MBV isolated from the decellularized BMSC culture plate. Scale bars=100 nm. FIG. 3C-FIG. 3E show size distribution plots from nanoparticle tracking analysis (NTA) of MBV isolated from BMSC (FIG. 3C), ASC (FIG. 3D), and UCSC (FIG. 3E) decellularized culture plates. FIG. 3F shows bioanalyzer analysis of total RNA isolated from BMSC, ASC, and UCSC-derived MBV. FIG. 3G shows principal-component analysis (PCA) comparing BMSC MBV (green; middle left), UCSC MBV (blue; top right) and ASC MBV (red; bottom right) RNA-seq datasets. FIG. 3H shows volcano plots demonstrating the differential expression of miRNAs in BMSC, ASC and UCSC-derived MBV. The inclusion criteria was a 2-fold difference of $\log_2$ (fold-change) in either direction with a P-value <0.05. Each dot represents a specific miRNA transcript; green dots to the right of the vertical dashed line (and above the horizontal dashed line) correspond to a relative increase in expression level, and red dots to the left (and above the horizontal dashed line) correspond to a relative decrease in expression level. Blue dots (below the horizontal dashed line) indicate miRNA with no significant change in expression level.

FIG. 4A shows a typical total ion chromatogram of phospholipids obtained from MBV. FIG. 4B shows mass spectra of the major phospholipid classes in MBV. Assessment included quantification of saturated (double bond number=0), monounsaturated (double bond number=1) and polyunsaturated (double bond number=2-10) species of phospholipids. FIG. 4C shows pie plots showing the total content of major phospholipids. The data are presented as % of total phospholipids. FIG. 4D and FIG. 4E show the contents of different phospholipid molecular species. The data are presented as heat maps autoscaled to Z-scores and coded blue (low values) to red (high values). Abbreviations are: EV, exosomal vesicles; MBV, matrix-bound vesicles; PC, phosphatidylcholine; PCd, PC diacyl species; PCp, PC plasmalogens; PE, phosphatidylethanolamine, PEd, PE diacyl species; PEp, PE plasmalogens; PI, phosphatidylinositol; PS, phosphatidylserine; BMP, bis-monoacylglycerophosphate; PA, phosphatidic acid; PG, phosphatidylglycerol; and SM, sphingomyelin.

FIG. 5A shows typical mass spectra of major lyso-phospholipids obtained from MBV. FIG. 5B shows pie plots showing the total content of major lyso-phospholipids. Data are presented as % of total lyso-phospholipids. FIG. 5C and FIG. 5D show the contents of lyso-phospholipid molecular species. The data are presented as heat maps autoscaled to Z-scores and coded blue (low values) to red (high values), with n=3. Abbreviations are: EV, exosomal vesicles; MBV, matrix-bound vesicles; LPC, lyso-phosphatidylcholine; LPE, lyso-phosphatidylethanolamine; LPI, lyso-phosphatidylinositol; LPS, lyso-phosphatidylserine; LPA, lyso-phosphatidic acid; LPG, lyso-phosphatidylglycerol; and mCL, mono-lyso-cardiolipin.

FIG. 6C shows the contents of singly-, doubly- and triply-oxygenated phospholipid species in parent cells, liquid phase EV, and MBV. The data are presented as heat maps autoscaled to Z-scores and coded blue (low values) to red (high values). Abbreviations are: EV, exosomal vesicles; MBV, matrix-bound vesicles; PL, phospholipids; PC, phosphatidylcholine; PE, phosphatidylethanolamine, PI, phosphatidylinositol; PS, phosphatidylserine; BMP, bis-monoacylglycerophosphate; PA, phosphatidic acid; PG, phosphatidylglycerol; and CL, cardiolipin.

FIG. 8A shows arthritis scores across treatment groups at day 7, FIG. 8B shows arthritis scores across treatment groups at day 10, FIG. 8C shows arthritis scores across treatment groups at day 13, FIG. 8D shows arthritis scores across treatment groups at day 17, and FIG. 8E shows arthritis scores across treatment groups at day 21.

FIG. 17 shows IL4 production as determined by ELISA for T cells stimulated with a Th1 activator to promote proinflammatory response, Th2 activator to promote an anti-inflammatory response, Th17 activator to promote a proinflammatory response, or MBV.

FIG. 18 shows immunofluorescence microscopy images of formalin fixed, paraffin-embedded murine lung tissue following fluorescently-labeled MBV (Green) administration via aerosol at a dose of $10^9$ particles/mL. Representative images (left and center panels) showing that MBV are readily detectable (arrow heads) in large and small airways of treated pulmonary tissue, in particular, epithelia, but not parenchyma. Untreated control lung tissues (right panel) show non-specific, low level autofluorescence with a diffuse pattern that is dissimilar to MBV-treated tissue.

FIG. 19A: Mosaic compilations of 20× hematoxylin and eosin images of whole lung pathology demonstrated an interstitial pneumonia at day 7 post-infection associated with a diffuse mononuclear cell infiltration into the interstitial space of the lung. Systemic treatment with MBV reduced overall cellular infiltration into the lung interstitium and showed resolution of acute pulmonary inflammation 7 days post-infection. Cellular density heat maps adjacent to H+E images showed high density cell infiltration in the influenza+i.v. PBS group with a reduction in overall cell density in the influenza+i.v. MBV group. FIG. 19B: Systemic MBV significantly reduced the overall frequency of CD45+ neutrophils in the lavage (BAL), lung interstitium, and the spleen. FIG. 19C: Systemic MBV significantly reduced the concentration of pro-inflammatory cytokines and chemokines GCSF, IL-6, Il-1b, TNFα, and IFN-γ.

FIG. 20A: Systemic MBV significantly reduced the frequency of CD4+ t-cells and increased the frequency of CD8+ T-cells in the lung tissue. FIG. 20B: Systemic MBV significantly decreased the frequency of CD4 T-cells in the spleen and increased the frequency of CD8+ T-cells in the spleen. FIG. 20C: Systemic MBV induced activation of an anti-viral CD4 response by increasing the frequency of peripherally located CD69+ and Tbet+ CD4+ T-cells in the spleen and lymph nodes, respectively. FIG. 20D: Systemic MBV induced peripheral activation of an anti-viral CD8+ T-cell response as indicated by an increased frequency of CD69+ and Tbet+ CD8 T-cells.

FIG. 21A: Mosaic compilations of 20× hematoxylin and eosin images of whole lung pathology demonstrated a bronchopneumonia at day 21 post-infection associated with a focused mononuclear cell infiltration around the bronchi and large airways. Systemic treatment with MBV reduced overall cellular infiltration into the lung interstitium and showed resolution of acute pulmonary inflammation 7 days post-infection. Cellular density heat maps adjacent to H+E images showed high density cell infiltration in the influenza+i.v. PBS group with a reduction in overall cell density in the influenza+i.v. MBV group. FIG. 21B: Systemic MBV significantly reduced the overall frequency of CD45+ neutrophils in lung interstitium and spleen. FIG. 21C: Systemic MBV significantly increased the proportion of CD11b dendritic cells in the lung. FIG. 21D: Systemic MBV significantly reduced the concentration of pro-inflammatory cytokines and chemokines Il-12, Il-1b, MCP-1, and KC.

SEQUENCE LISTING

Figure 1A:
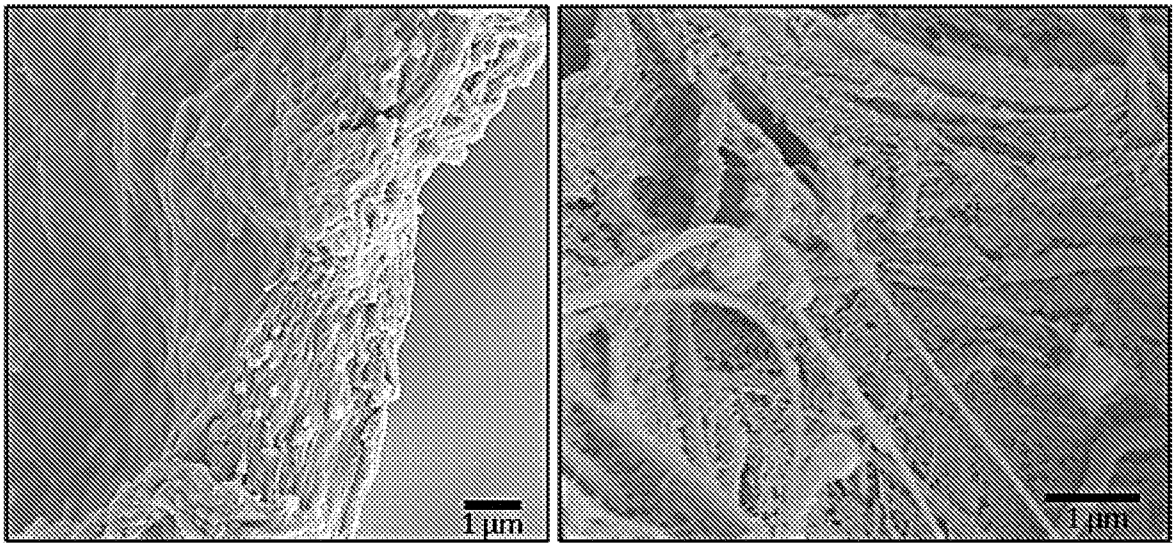
FIGS. 1A-1G show morphological characterization of liquid phase extracellular vesicles (EV) and matrix bound vesicles (MBV).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file [Sequence_Listing, Aug. 15, 2022, 1,147 bytes] which is incorporated by reference herein. In the accompanying sequence listing: SEQ ID NOS: 1-3 are miRNA sequences.

DETAILED DESCRIPTION

The present disclosure provides a method of using matrix bound nanovesicles (MBV) in the treatment of an acute respiratory distress syndrome (ARDS), such as an ARDS associated with hypercytokinemia, for example, a hypercytokinemia associated with a viral infection. Various aspects of the invention are set forth below in sections; however, aspects of the invention described in one particular section are not to be limited to any particular section.

As the data herein exemplify, MBV are potent modulators of macrophage activity, inducing anti-inflammatory properties of macrophages. When macrophages are exposed to inflammatory stimuli, they secrete cytokines such as TNF, IL-1, IL-6, I-8, and IL-12. Such cytokines increase vascular permeability and recruitment of inflammatory cells which contributes to conditions such as ARDS. However, as exemplified herein, macrophages contacted with MBV have the ability to downregulate the production of pro-inflammatory cytokines as well as upregulate negative regulators of inflammation, suggesting that MBV have the ability to dampen the "cytokine storm" of hypercytokinemia. Because of these unique properties of MBV, MBV are useful in treating ARDS which results from widespread inflammation in the lung due to hypercytokinemia which can be caused by a number of factors from viral infection to injury as described herein. In diseases, such as COVID-19, where immune response to the virus causes cytokine storm and resulting ARDS, MBV have the ability to prevent or reverse the devastating effects of cytokine storm, such as ARDS.

Overview

As disclosed herein, matrix bound nanovesicles (MBV) of the present disclosure are used in a method of treating an acute respiratory distress syndrome (ARDS), such as ARDS associated with hypercytokinemia, e.g., a hypercytokinemia associated with an infection. In certain embodiments, the hypercytokinemia is the result of an infection by a pathogen, e.g., a bacterium, a virus, a fungus, or a protozoan (e.g., an amoeba). In certain embodiments, the disease or disorder mediated by an intracellular pathogen is an acute infection. In some embodiments, the ARDS is the result of a viral infection such as MERS, SARS-CoV, or SARS-CoV2. In one embodiment, the ARDS is the result of SARS-CoV2. In one embodiment, the ARDS is the result of influenza.

Therapeutic Applications

In the absence of pre-existing immunity in the global population, COVID-19 has become a pandemic, disrupting the global economy in less than 4 months since the first cases were reported. In this short period, COVID-19 has emerged as a highly lethal infection, with a lethality of 300% to 400% of that of seasonal influenza. (WHO (2020) Coronavirus disease 2019 (COVID-19): Situation Report, 67). Currently, the treatment of COVID-19 is primarily supportive in nature, and respiratory failure from ARDS is the leading cause of mortality. (Ruan Q, et al. (2020) Clinical predictors of mortality due to COVID-19 based on an analysis of data of 150 patients from Wuhan, China. *Intensive Care Medicine:* 1-3). Viral infection and consequent tissue damage are known to initiate a cytokine storm that can culminate in ARDS. (Ware L B & Matthay M A (2000) The acute respiratory distress syndrome. *NEJM.* 342(18):1334-1349; Matthay M A, et al. (2012) The acute respiratory distress syndrome. *Journal of Clin Inves.* 122(8):2731-2740; Wheeler A P & Bernard G R (2007) Acute lung injury and the acute respiratory distress syndrome: a clinical review. *Lancet* 369(9572):1553-1564). Defining features of ARDS comprise diffuse alveolar damage, pulmonary edema, and hypoxemia due to dysregulated local and systemic inflammation that present as increased inflammatory cytokines (chemokines) in the plasma or bronchoalveolar lavage fluid (BALF), leading to accumulation of extravascular neutrophils (Matthay M A et al. (2012) The acute respiratory distress syndrome. *Journal Clin Inves.* 122(8):2731-2740). Pro-inflammatory macrophages and monocytes also play a causal role in ARDS, initiating and propagating lung tissue damage through increasing local inflammation; this inflammation then contributes to increased epithelial and endothelial tissue permeability. (Aggarwal N R et al. (2014) Diverse macrophage populations mediate acute lung inflammation and resolution. *Amer Journal of Phys Lung Cell and Mol Phys.* 306(8):L709-L725; Zemans R L & Matthay M A (2017) What drives neutrophils to the alveoli in ARDS? (BMJ Publishing Group Ltd); Thompson B T et al. (2017) Acute respiratory distress syndrome. New England *Journal of Med.* 377(6):562-572).

Despite intensive basic research and clinical studies on the subject, there remains a lack of effective treatment to prevent or resolve ARDS, and supportive procedures that reduce early inflammation are the only means to provide consistent improvement in patient outcome. (Bellani G, et al. (2016) Epidemiology, patterns of care, and mortality for patients with acute respiratory distress syndrome in intensive care units in 50 countries. *Jama* 315(8):788-800).

The early response to respiratory viral infection (e.g., SARS-CoV2), includes macrophages that release pro-inflammatory cytokines that induce severe ARDS, recruit more immune cells, and phagocytose virus-infected cells (Conti P, et al. (2020) Induction of pro-inflammatory cytokines (IL-1 and IL-6) and lung inflammation by Coronavirus-19 (COVID-19 or SARS-CoV-2): anti-inflammatory strategies. *J Biol Regul Homeost Agents.* 34(2)). Retrospective cohort studies of patients in Wuhan, China show about 93% of deaths from COVID-19 involved acute respiratory distress syndrome (ARDS) and hyperinflammation in the lungs (Zhou F, et al. (2020) Clinical course and risk factors for mortality of adult inpatients with COVID-19 in Wuhan, China: a retrospective cohort study. *Lancet.* 395(10229): 1054-1062). Recruited monocytes differentiate into macrophages that play dominant roles in host defense against the virus, but these same cells also facilitate resolution of inflammation and lung repair. Early in antiviral immune responses, M1-like macrophages release pro-inflammatory cytokines which recruit more immune cells and phagocytose virus-infected cells, and, in some cases, induce ARDS (Conti P, et al. (2020) Induction of pro-inflammatory cytokines (IL-1 and IL-6) and lung inflammation by Coronavirus-19 (COVID-19 or SARS-CoV-2): anti-inflammatory strategies. *J Biol Regul Homeost Agents.* 34(2)). Transition of the M1-like (proinflammatory) macrophage activation state to an M2-like, anti-inflammatory, pro-remodeling phenotype can mitigate respiratory distress, restore epithelial barrier function, and facilitate development of acquired immunity against a virus within 14 days (He W, et al. (2017) Alveolar macrophages are critical for broadly-reactive antibody-mediated protection against influenza A virus in mice. *Nat Commun.* 8(1):846). Without the macrophage phenotype switch, however, epithelial barrier function is destroyed and cell death and edema may lead to ARDS. Drugs such as hydroxychólorquine (HCQ) are under investigation as a treatment for COVID-19 in clinical pilot studies; importantly, however, HCQ addresses hyperinflammation, such as hyperinflammation seen in ARDS cases, by immunosuppression (Liang N, et al. (2018) Immunosuppressive effects of hydroxychloroquine and artemisinin combination therapy via the nuclear factor-kappaB signaling pathway in lupus nephritis mice. *Exp Ther Med* 15(3):2436-2442). Thus, HCQ and similar immunosuppressive drugs place the patient at greater risk for secondary infection, e.g., secondary pneumonia, and inhibit development of anti-viral immunity. (Liang N, et al. (2018) Immunosuppressive effects of hydroxychloroquine and artemisinin combination therapy via the nuclear factor-kappa B signaling pathway in lupus nephritis mice. *Exp Ther Med* 15(3):2436-2442). Satisfactory treatment of COVID-19 thus requires simultaneous resolution of the cytokine storm and the development of protective, antibody-mediated immunity. As factors within the ECM modulate the phenotypic transition of macrophages and T-helper cells from a pro-inflammatory to a pro-remodeling state, the present invention is directed to modulation/reprogramming of the host immune system—without compromising immunocompetency—promoted by molecular factors embedded within the extracellular matrix (ECM). (Hussey G S, et al. (2018) Extracellular matrix-based materials for regenerative medicine. *Nature Rev Mater*; Allman A J, et al. (2002) The Th2-restricted immune response to xenogeneic small intestinal submucosa does not influence systemic protective immunity to viral and bacterial pathogens. *Tissue Eng Part A*. 8(1):53-62). Degradation products of ECM scaffolds have potent and clinically relevant anti-inflammatory and pro-healing effects in skeletal muscle repair, a rodent model of ulcerative colitis, the optic nerve, and in the upper respiratory tract. (See, for example, International Patent Application Publication Nos. WO 2017/151862 and WO 2018/204848).

Therefore, a satisfactory and preferred treatment of COVID-19 requires resolution of the hypercytokinemia without compromising immunity. As disclosed herein, MBV of the present disclosure are used in a method of treating hyperinflammation, such as hyperinflammation associated with a hypercytokinemia (e.g., a hypercytokinemia associated with a viral infection).

The foregoing and other objects, features, and advantages of the MBV therapy of the present disclosure is capable of administration in both hospital and non-hospital environments. In some embodiments, an MBV therapy of the present disclosure is administered to treat patients with COVID-19 associated cytokine storm syndrome. Such a therapeutic platform that can be safely and easily administered to patients to redirect the default inflammatory healing response toward one that limits inflammation and promotes functional tissue remodeling does not presently exist and is therefore a long felt unmet need.

MBV are an integral component of the ECM, are distinct from exosomes, and effectively redirect hyperinflammation in preclinical models (Hussey G S, et al. (2020) Lipidomics and RNA sequencing reveal a novel subpopulation of nanovesicle within extracellular matrix biomaterials. *Sci Adv* 6(12):eaay4361; van der Merwe Y, et al. (2019) Matrix-bound nanovesicles prevent ischemia-induced retinal ganglion cell axon degeneration and death and preserve visual function. *Sci Rep* 9(1):3482)). MBV are also distinct from bone matrix vesicles involved in bone generation and mineralization. For example, bone matrix vesicles express alkaline phosphatase whereas MBV do not. In some embodiments, MBV contain immunomodulatory miRNA, proteins, and lipids and are rapidly taken up by macrophages, triggering signaling cascades and modulating gene expression essential for phenotype switching, a phenomenon well-studied in the context of ECM-based biomaterials (Hussey G S, et al. (2019) Matrix bound nanovesicle-associated IL-33 activates a pro-remodeling macrophage phenotype via a non-canonical, ST2-independent pathway. *J Immunol Regen Med* 3:26-35; Huleihel L, et al. (2017) Macrophage phenotype in response to ECM bioscaffolds. *Semin Immunol* 29:2-13). Furthermore, in some embodiments, MBV administration results in upregulation of regulatory T cells ($T_{REG}$), a phenomenon previously characterized in the context of ECM-based biomaterials. MBV rapidly and effectively induce the reparative immune response in harsh environments including rheumatoid arthritis, traumatic muscle injury, ulcerative colitis, and esophageal cancer (Huleihel L, et al. (2017) Matrix-Bound Nanovesicles Recapitulate Extracellular Matrix Effects on Macrophage Phenotype. *Tissue Eng Part A* 23(21-22):1283-1294; Dziki J L, et al. (2016) Immunomodulation and Mobilization of Progenitor Cells by Extracellular Matrix Bioscaffolds for Volumetric Muscle Loss Treatment. *Tissue Eng* Part A 22(19-20):1129-1139; Keane T J, et al. (2017) Restoring Mucosal Barrier Function and Modifying Macrophage Phenotype with an Extracellular Matrix Hydrogel: Potential Therapy for Ulcerative Colitis. *J Crohns Colitis* 11(3):360-368; Saldin L T, et al. (2019) Extracellular Matrix Degradation Products Downregulate Neoplastic Esophageal Cell Phenotype. *Tissue Eng Part A* 25(5-6):487-498.)

Cytokine cargo stored within MBV support reparative and regulatory M2 macrophages and control bacterial infections and inflammation after acute lung injury (Liu Q, et al. (2019) IL-33-mediated IL-13 secretion by ST2+ $T_{REG}$ controls inflammation after lung injury. JCI Insight 4(6)). ECM bioscaffolds are useful in a variety of clinical applications involving musculoskeletal, gastrointestinal, urogenital and CNS tissues (Badylak S F (2007) The extracellular matrix as a biologic scaffold material. *Biomaterials*. 28(25):3587-3593). ECM consists of the secreted structural and functional molecules of the resident cells of each tissue that define tissue identity. Such xenogeneic scaffolds do not elicit an adverse innate or adaptive immune response, and instead support an anti-inflammatory and reparative innate and adaptive immune response (Brown B N, et al. (2009) Macrophage phenotype and remodeling outcomes in response to biologic scaffolds with and without a cellular component. *Biomaterials*. 30(8):1482-1491). Use of these naturally occurring biomaterials is typically associated with (at least) partial restoration of functional, site-appropriate tissue; a process referred to as "constructive remodeling" (Badylak S F (2007) The extracellular matrix as a biologic scaffold material. *Biomaterials*. 28(25):3587-3593). ECM bioscaffolds, or degradation products of ECM bioscaffolds, have been shown to direct tissue repair through recruitment of an anti-inflammatory M2-like macrophage and T helper Type 2 (Th2) cell response, such a response is often associated with reduced local inflammation and constructive crosstalk with progenitor cells.

Matrix Bound Nanovesicles (MBV) activate the M2-like reparative and anti-inflammatory macrophage phenotype. Studies have shown that MBV are a distinct class of extracellular vesicle separate from exosomes found in body fluids (Hussey G S, et al. (2020) Lipidomics and RNA sequencing reveal a novel subpopulation of nanovesicle within extracellular matrix biomaterials. *Sci Advances*. 6(12):eaay4361). As MBV survive even harsh tissue decellularization processes, they can play a fundamental role in tissue and organ development and homeostasis across species, as well as a regulatory role in the tissue response to injury. MBV may be derived from multiple, varied tissue sources. MBV are plentiful, can be lyophilized, are highly stable, and can be easily administered via tracheal instillation or nebulization.

MBV can recapitulate the effects of ECM on promoting a pro-remodeling macrophage phenotype. Macrophage gene and protein expression, cell surface markers, and functional capacity as determined by phagocytic activity, nitric oxide (NO) production, and antimicrobial activity observed were most representative of a regulatory/anti-inflammatory phenotype following treatment with MBV, consistent with previous reports describing the effects of ECM-based bioscaffolds on macrophage phenotype and function. (See, for example, PCT Publication No. WO 2017/151862A1). MBV have been shown to exert an immunomodulatory effect through a combination of miRNA, protein, and phospholipid cargoes. For example, compared to exosomes present in body fluids, MBV are highly enriched in pro-resolving lipid mediators activated by different phospholipases dependent on the pro-/anti-inflammatory context of the extracellular environment (Hussey G S, et al. (2020) Lipidomics and RNA sequencing reveal a novel subpopulation of nanovesicle within extracellular matrix biomaterials. *Sci Adv* 6(12): eaay4361). Moreover, MBV are a rich and stable source of IL-33 that signals directs immune cells toward a reparative M2-like phenotype, while also stimulate repair and regulatory functions by $T_{REG}$ in the damaged lung (Liu Q, et al. (2019) IL-33-mediated IL-13 secretion by ST2+ $T_{REG}$ controls inflammation after lung injury. *JCI Insight* 4(6)). IL-33 delivery reduces bacterial super-infections after H1N1 infections by improving bacterial clearance (Robinson K M, et al. (2018) Novel protective mechanism for interleukin-33 at the mucosal barrier during influenza-associated bacterial superinfection. *Mucosal immunology.* 11(1):199-208). Additionally, MBV are enriched in miRNA 125b-5p, 143-3p, and 145-5p. Inhibition of these miRNAs within macrophages is associated with a gene and protein expression profile more consistent with a proinflammatory rather than an anti-inflammatory/regulatory phenotype (Huleihel L, et al. (2017) Matrix bound nanovesicles recapitulate extracellular matrix effects on macrophage phenotype. *Tissue Eng* Part A).

As described in Example 2, a rodent model of pristane-induced arthritis (PIA) was utilized to evaluate if MBV could mitigate arthritic score. 8-week-old, Sprague-Dawley rats received an intradermal injection of 300 μL pristane (2,6,10,14-tetramethypentadecane) on Day 0 of the study. A second dose of 300 μL pristane was administered intradermally, on Day 4. Animals receiving pristane were then randomized into the following experimental groups: Pristane-only, Intraperitoneal injection of Methotrexate (IP MTX), periarticular injection of MBV (PA MBV), and intravenous injection of MBV (IV MBV). Treatments were administered on days 7, 10, 14, 17, and 21. Beginning on Day 7, arthritis score was determined on days 7, 10, 14, 17, 21, 28, and every week thereafter through 100 days for each animal. Results from the study showed that both PA and IV administration of MBV significantly reduced arthritic score compared to pristine-only control animals. After day 21, animals did not receive any further treatment, but were tracked longitudinally to evaluate secondary flare-ups. Results from day 100 showed that MBV treated animals exhibited a sustained reduction in arthritic score compared to the control (non-treated) group even though no additional treatment was given. Furthermore, gross morphologic examination of the paws showed reduced redness and edema in the MBV treated groups. In addition, as shown in Example 4, a rodent KLH (keyhole limpet hemocyanin) immunization assay showed that in contrast to current therapeutics which address aberrant inflammation by immunosuppression, MBV therapy is directed at modulation/reprogramming of the host immune system without compromising immunocompetency. Examples 10-13 provide further evidence that systemic administration of MBV mitigates acute viral-mediated pulmonary pathology and long-term inflammation in an animal model of an influenza infection. As these data demonstrate, MBV therapy has the potential to be used in treating many disorders involving aberrant inflammatory response, such as ARDS.

Tracheal instillation of decellularized powder of urinary bladder matrix (UBM) promotes pulmonary epithelial cell chemotaxis, migration, and repair in a murine model of bleomycin-induced pulmonary fibrosis (Manni M L, et al. (2011) Extracellular matrix powder protects against bleomycin-induced pulmonary fibrosis. *Tissue Eng Part A.* 17(21-22):2795-2804). Additionally, tracheal instillation of decellularized ECM powder protects inoculated mice from severe bacterial-induced lung infection by significantly decreasing the bacterial burden and attenuating the bacterial-induced cytokine/chemokine secretion, thus suggesting that ECM scaffolds may provide protection from secondary complications that arise from acute respiratory distress syndrome, such as a bacterial-induced infection (Chen C, et al. (2019) Urinary bladder matrix protects host in a murine model of bacterial-induced lung infection. *Tissue Eng Part A.* 25(3-4):257-270). In addition, decellularized ECM delivered into rat lung by either tracheal instillation or nebulization showed ameliorative effects against acute lung damage induced by continuous hyperoxia exposure, including attenuated alveolar septal thickening, cellular apoptosis, and oxidative damage during continuous hyperoxic conditions. However, translational potential of ECM powder for treatment of IPF is limited due to the maximum concentration and volume of such an ECM suspension that can be nebulized (Wu J, et al. (2017) Lung protection by inhalation of exogenous solubilized extracellular matrix. *PloS One* 12(2): e01711650). Given their nanometer size, MBV overcome the challenges associated with ECM powder to the lungs and suggest MBV may be administered via tracheal instillation or nebulization directly to the lung.

In contrast to exosome isolation from body fluids or cell culture supernatant, the complex ultrastructure of ECM structural molecules presents unique challenges for isolating MBV from ECM-scaffold materials.

In some embodiments, MBV are nebulized and delivered via inhalation or intravenous injection, allowing for rapid targeted or systemic delivery. MBV are potent natural regulators of early immune responses after injury and restore local and systemic equilibrium. Thus, MBV can mitigate ARDS without compromising native immunity. MBV promote inflammation resolution without immunosuppression. Cytokine screens show abundant anti-inflammatory cytokines stored within the MBV, indicating MBV promote an immune phenotype that restores equilibrium and confers resilience against ARDS, with the advantage of not compromising native immunity. Thus, MBV promote resolution of inflammation without immunosuppression. Furthermore, MBV and ECM derived from decellularized porcine tissues or organs are readily available, safe, do not produce an adverse immune response, and consequently, the technology is primed for clinical translation.

Biologic scaffolds composed of extracellular matrix (ECM) have been developed as surgical mesh materials and are used in clinical applications including ventral hernia repair (Alicuban et al., Hernia. 2014; 18(5):705-712), musculoskeletal reconstruction (Mase et al., *Orthopedics.* 2010; 33(7):511), esophageal reconstruction (Badylak et al., *Tissue Eng Part A.* 2011; 17(11-12):1643-50), dura mater replacement (Bejjani et al., *J Neurosurg.* 2007; 106(6):1028-1033), tendon repair (Longo et al., *Stem Cells Int.* 2012; 2012: 517165), breast reconstruction (Salzber, Ann Plast Surg. 2006; 57(1):1-5), amongst others (Badylak et al., *Acta Biomater.* 2009; 5(1):1-13).

Matrix bound nanovesicles (MBV) are embedded within the fibrillar network of the ECM. These nanoparticles shield their cargo from degradation and denaturation during the ECM-scaffold manufacturing process.

In contrast, exosomes (or extracellular vesicles "EV") are microvesicles that previously have been identified almost exclusively in body fluids and cell culture supernatant. It has been demonstrated that MBV and exosomes are distinct. MBV differ from other vesicles, for example, as they are resistant to detergent and/or enzymatic digestion, have a unique lipid profile, and contain a cluster of different microRNAs. MBV do not have the same characteristic surface proteins found in other vesicles, such as exosomes.

As disclosed herein, MBV modulate a systemic immune response (such as through systemic administration), e.g., to preserve or to restore biological function. For example, administration of MBV may preserve or restore immune response, such as to modulate a hyperinflammatory immune response, e.g., an acute respiratory distress syndrome (ARDS), such as an ARDS associated-with a viral infection.

Treatment of ARDS Associated with Viral Infections

In certain embodiments, the ARDS is associated with a viral infection. In certain embodiments, the virus is selected from the group consisting of a retrovirus (e.g., human immunodeficiency virus (HIV), simian immunodeficiency virus (SIV), human T-cell lymphotropic virus (HTLV)-1, HTLV-2, HTLV-3, HTLV-4), Ebola virus, hepatitis A virus, hepatitis B virus, hepatitis C virus, a herpes simplex virus (HSV) (e.g., HSV-1, HSV-2, varicella zoster virus, cytomegalovirus), an adenovirus, an orthomyxovirus (e.g., influenza virus A, influenza virus B, influenza virus C, influenza virus D, thogotovirus), a flavivirus (e.g., dengue virus, Zika virus), West Nile virus, Rift Valley fever virus, an arenavirus, Crimean-Congo hemorrhagic fever virus, an echovirus, a rhinovirus, coxsackie virus, a coronavirus (e.g., Severe acute respiratory syndrome coronavirus 2 (SARS-CoV-2), MERS, or SARS-CoV), a respiratory syncytial virus, a mumps virus, a rotavirus, measles virus, rubella virus, a parvovirus (e.g., an adeno-associated virus), a vaccinia virus, a variola virus, a molluscum virus, bovine leukemia virus, a poliovirus, a rabies virus, a polyomavirus (e.g., JC virus, BK virus), an alphavirus, and a rubivirus (e.g., rubella virus). In some embodiments, the virus is a coronavirus. In some embodiments, the ARDS associated with a viral infection is associated with hypercytokinemia. In one embodiment, the ARDS is caused by SARS-CoV-2. In another embodiment, the ARDS is caused by an influenza virus. In some embodiments, the ARDS is associated with sepsis caused by a bacterial infection.

In certain embodiments, MBV described herein are used for treating ARDS associated with a viral infection, e.g., an ARDS associated with a viral infection selected from the group consisting of acquired immune deficiency syndrome (AIDS), HTLV-1 associated myelopathy/tropical spastic paraparesis, Ebola virus disease, hepatitis A, hepatitis B, hepatitis C, herpes, herpes zoster, acute varicella, mononucleosis, respiratory infections, pneumonia, influenza, dengue fever, encephalitis (e.g., Japanese encephalitis), West Nile fever, Rift Valley fever, Crimean-Congo hemorrhagic fever, Kyasanur Forest disease, Yellow fever, Zika fever, aseptic meningitis, SARS, myocarditis, common cold, lung infections, molloscum contagiosum, enzootic bovine leucosis, coronavirus disease 2019 (COVID-19), mumps, gastroenteritis, measles, rubella, slapped-cheek disease, smallpox, warts (e.g., genital warts), molluscum contagiosum, polio, rabies, and *Pityriasis rosea*. In some embodiments, the ARDS associated with a viral infection is associated with hypercytokinemia. In some embodiments, MBV described herein are used for treating ARDS associated with an ebolavirus. In some embodiments, MBV described herein are used for treating ARDS associated with influenza. In some embodiments, MBV described herein are used for treating ARDS associated with SARS. In some embodiments, MBV described herein are used for treating ARDS associated with COVID-19. In some embodiments, the MBV described herein are used for treating ARDS associated with sepsis caused by a viral infection.

In some embodiments, the virus associated with the infection is an RNA virus (having a genome that is composed of RNA), RNA viruses may be single-stranded RNA (ssRNA) or double-stranded RNA (dsRNA). RNA viruses have high mutation rates compared to DNA viruses, as RNA polymerase lacks proofreading capability (see Steinhauer D A, Holland J J (1987). "*Rapid evolution of RNA viruses*". *Annu. Rev. Microbiol.* 41: 409-33). Exemplary RNA viruses include, without limitation, bunyaviruses (e.g., hantavirus), coronaviruses (e.g., MERS-CoV, SARS-CoV, SARS-CoV-2), flaviviruses (e.g., yellow fever virus, west nile virus, dengue virus), hepatitis viruses (e.g., hepatitis A virus, hepatitis C virus, hepatitis E virus), influenza viruses (e.g., influenza virus type A, influenza virus type B, influenza virus type C), measles virus, mumps virus, noroviruses (e.g., Norwalk virus), poliovirus, respiratory syncytial virus (RSV), retroviruses (e.g., human immunodeficiency virus-1 (HIV-1)) and toroviruses. In some embodiments, the RNA virus is an influenza virus, e.g., influenza A. In some embodiments, the RNA virus is RSV. In some embodiments, the RNA virus is MERS-CoV. In some embodiments, the RNA virus is SARS-CoV. In some embodiments, the RNA virus is SARS-CoV-2. In some embodiments, the RNA virus is SARS-CoV2. In some embodiments, the RNA virus is ZIKA.

RNA viruses are classified by the type of genome (double-stranded, negative (−), or positive (+) single-stranded). Double-stranded RNA viruses contain a number of different RNA molecules, each coding for one or more viral proteins. Positive-sense ssRNA viruses utilize their genome directly as mRNA; ribosomes within the host cell translate mRNA into a single protein that is then modified to form the various proteins needed for viral replication. One such protein is RNA-dependent RNA polymerase (RNA replicase), which copies the viral RNA in order to form a double-stranded, replicative form. Negative-sense ssRNA viruses have their genome copied by an RNA replicase enzyme to produce positive-sense RNA for replication. Therefore, the virus comprises an RNA replicase enzyme. The resultant positive-sense RNA then acts as viral mRNA and is translated by the host ribosomes. In some embodiments, the virus is a dsRNA virus. In some embodiments, the virus is a negative ssRNA virus. In some embodiments, the virus is a positive ssRNA virus. In some embodiments, the positive ssRNA virus is a coronavirus.

SARS-CoV2, also sometimes referred to as the novel coronavirus of 2019 or 2019-nCoV, is a positive-sense single-stranded RNA virus. SARS-CoV2 has four structural proteins, known as the S (spike), E (envelope), M (membrane), and N (nucleocapsid) proteins. The N protein holds the RNA genome; together, the S, E, and M proteins form the viral envelope. Spike allows the virus to attach to the membrane of a host cell, such as the ACE2 receptor in human cells (Kruse R. L. (2020), Therapeutic strategies in an outbreak scenario to treat the novel coronavirus originating in Wuhan, China (version 2). *F*1000*Research,* 9:72). SARS-CoV2 is the highly contagious, causative viral agent of coronavirus disease 2019 (COVID-19), a global pandemic. In some embodiments, the acute respiratory distress syndrome is associated with SARS-CoV2 (COVID-19). In some embodiments, the ARDS being treated is associated with SARS-CoV2 (COVID-19). In some embodiments, the ARDS being treated is associated with hypercytokinemia associated with SARS-CoV2 (COVID-19).

In some embodiments, the virus associated with the infection is a DNA virus (having a genome that is composed of DNA). Exemplary DNA viruses include, without limitation, parvoviruses (e.g., adeno-associated viruses), adenoviruses, asfarviruses, herpesviruses (e.g., herpes simplex virus 1 and 2 (HSV-1 and HSV-2), epstein-barr virus (EBV), cytomegalovirus (CMV)), papillomoviruses (e.g., HPV), polyomaviruses (e.g., simian vacuolating virus 40 (SV40)), and poxviruses (e.g., vaccinia virus, cowpox virus, smallpox virus, fowlpox virus, sheeppox virus, myxoma virus). In certain embodiments, the DNA virus is an adenovirus, e.g., AdV5. In certain embodiments, the DNA virus is an enterovirus, e.g., EV71. In certain embodiments, the DNA virus is a herpesvirus, e.g., HSV-1.

In some embodiments, the infection is systemic. In some embodiments, the infection is localized, e.g., to an organ or, e.g., to a tissue. In some embodiments, infection is localized to an organ including but not limited to the eye, the ear, the inner ear, the lungs, trachea, bronchus, bronchioli, the liver, the gall bladder, the bile duct, the kidney, the bladder, the testis, the cervix, the ovary, the uterus, the skin, or the brain. In certain embodiments, the infection is localized to the lungs.

Treatment of ARDS Associated with Other Pathogenic Infections

In certain embodiments, the ARDS is associated with a bacterial infection. In certain embodiments, ARDS is associated with a bacteria selected from the group consisting of *Chlamydia* (e.g., *C. trachomatis*), *Escherichia coli* (e.g., enteropathogenic *E. coli*, enterohemmorhagic *E. coli*, uropathogenic *E. coli*, enteroinvasive *E. coli*), *Helicobacter pylori, Mycobacterium* (e.g., *M. tuberculosis, M. leprae, M. lepromatosis*), *Listeria* (e.g., *L. monocytogenes*), *Shigella* (e.g., *S. flexneri*), *Staphylococcus* (e.g., *S. aureus*), *Streptococcus* (e.g., *S. pyogenes*), *Streptomyces*, Pneumococcus, Meningococcus, Gonococcus, *Klebsiella* (e.g., *K. pneumoniae*), *Proteus, Serratia, Pseudomonas* (e.g., *P. aeruginosa*), *Legionella, Acinetobacter* (e.g., *A. baumannii*), *Corynebacterium* (e.g., *C. diphtheria*), *Coxiella* (e.g., *C. burnetii*), *Bacillus* (e.g., *B. anthricis*), *Bacteroides, Bordetella, Enterococcus* (e.g., *E. faecalis*), *Francisella* (e.g., *F. tularensis*), *Haemophilus influenza, Neisseria* (e.g., *N. meningitides, N. gonorrhoeae*), *Rickettsia, Salmonella* (e.g., *S. typhimurium*), *Vibrio cholerae, Clostridium* (e.g., *C. tetan, C. botulinum*), *Yersinia* (e.g., *Y. pestis*), Borrielia (e.g., *B. burgdorferi*), *Brucella, Burkholderia, Campylobacter*, and *Mycoplasma*. In some embodiments, the ARDS associated with a bacterial infection is associated with hypercytokinemia. In some embodiments, the ARDS is associated with sepsis caused by a bacterial infection.

In certain embodiments, MBV described herein are used for treating ARDS associated with a bacterial infection, e.g., an ARDS associated with, for example, an intracellular bacterial infection. Methods described herein can be used to treat, for example, ARDS associated with a bacterial disease or disorder selected from the group consisting of *Chlamydia*, tuberculosis, peptic ulcers, leprosy, listeriosis, sialadenitis, bacteria-caused diarrhea or food poisoning, strep throat, scarlet fever, impetigo, cellulitis, pneumonia, meningitis, bacterial endocarditis, diverticulitis, disseminated gonococcemia, septic arthritis, gonococcal ophthalmia neonatorum, urinary tract infections, soft tissue infections, spondyloarthropathies (e.g., ankylosing spondylitis), legionellosis (e.g., Legionnaires' disease, Pontiac fever), diphtheria, *Salmonellosis*, anthrax, cholera, tetanus, botulism, fasciitis, gas gangrene, plaque, Lyme disease, brucellosis, melioidosis, Q fever, tularemia, gonorrhea, typhus, *Mycoplasma* pneumonia, gastroenteritis, and walking pneumonia. In some embodiments, the ARDS associated with a bacterial infection is associated with hypercytokinemia. In some embodiments, the MBV are for use in treating ARDS associated with sepsis caused by a bacterial infection.

In certain embodiments, the ARDS is associated with a fungal infection. In certain embodiments, the ARDS is associated with a fungal infection where the fungus is selected from the group consisting of *Candida* (e.g., *C. albicans, C. krusei, C. glabrata, C. tropicalis*), *Cryptococcus* (e.g., *C. neoformans, C. gattii*), *Aspergillus* (e.g., *A. fumigatus, A. niger*), Mucorales (e.g., *M. mucor, M. absidia, M. rhizopus*), *Sporothrix* (e.g., *S. schenkii*), *Blastomyces* (e.g., *B. dermatitidis*), *Paracoccidioides* (e.g., *P. brasiliensis*), *Coccidioides* (e.g., *C. immitis*), *Histoplasma* (e.g., *H. capsulatum*), *Acremonium, Basidiobolus* (e.g., *B. ranarum*), *Cladophialophora* (e.g., *C. bantiana*), *Cunninghamella* (e.g., *C. bertholletiae*), *Epidermophyton, Exophiala, Exserohilum, Fonsecaea* (e.g., *F. pedrosoi*), *Hortaea* (e.g., *H. werneckii*), *Lacazia* (e.g., *L. loboi*), *Leptosphaeria* (e.g., *L. maculans*), *Madurella* (e.g., *M. mycetomatis*), *Malassezia, Microsporum, Mucor, Neotestudina, Onychocola, Phialophora, Piedraia, Pneumocystis* (e.g., *P. jirovecii*), *Pseudallescheria* (e.g., *P. boydii*), *Pyrenochaeta, Rhizomucor, Scedosporium, Scytalidium, Sporothrix, Trichophyton, Trichosporon*, and Zygomycete. In some embodiments, the ARDS associated with a fungal infection is associated with hypercytokinemia.

In certain embodiments, MBV described herein are used for treating an ARDS associated with an intracellular fungal infection, e.g., an ARDS associated with an intracellular fungal infection selected from the group consisting of candidiasis, cryptococcosis, aspergillosis, mucormycosis, sporotrichosis, blastomycosis, paracoccidioidomycosis, coccidioidomycosis, histoplasmosis, eumycetoma, onychomycosis, hyalohyphomycosis, subcutaneous zygomycosis, cerebral abscesses, phaeohyphomycosis, chromoblastomycosis, mycetoma, pulmonary mucormycosis, tinea corporis, tinea capitis, tinea cruris, tinea pedis, tinea unguium, tinea nigra, Lobo's disease, blackleg disease, mycetoma, *Pityriasis versicolor, Malassezia* folliculitis, steroid acne, seborrhoeic dermatitis, neonatal cephalic pustulosis, mucormycosis, maduromycosis, black *piedra, pneumocystis* pneumonia, pseudallescheriasis, scedosporiosis, sporotrichosis, and zygomycosis. In some embodiments, the ARDS associated with a fungal infection is associated with hypercytokinemia. In some embodiments, the ARDS is associated with sepsis caused by a fungal infection.

In certain embodiments, the ARDS is associated with an intracellular protozoan infection. In some embodiments, the protozoan is an amoeba. In certain embodiments, the amoeba is selected from the group consisting of Apicomplexans (*Plasmodium* (e.g., *P. vivax, P. falciparum, P. ovale, P. malariae, Toxoplasma gondii, Cryptosporidium parvum, Babesia microti, Cyclospora cayetanensis, Cystoisospora belli*), *Trypanosoma* (e.g., *Trypanosoma brucei, Trypanosoma cruzi*), and *Leishmania* (e.g., *Leishmania donovani*). In some embodiments, the ARDS associated with a protozoan infection is associated with hypercytokinemia.

In certain embodiments, MBV described herein are used for treating a disease or disorder caused by an intracellular amoebal infection, e.g., an ARDS associated with an amoebal infection selected from the group consisting of babesiosis, malaria, cryptosporidiosis, cyclosporiasis, cystoisosporiasis, toxoplasmosis, trypanosomiasis, Chagas disease, and leishmaniasis. In some embodiments, the ARDS associated with an amoebal infection is associated with hypercytokinemia.

Assays for Cytokine Release

The expression of a cytokine, such as a chemokine, can be assed in the methods disclosed herein. In some embodiments, pro-inflammatory cytokines known in the art as chemokines are studied. Examples of chemokines include, without limitation, CXCL8, CCL2, CCL3, CCL4, CCL5, CCL11, and CXCL10. In some embodiments, cytokine release is studied in vitro, e.g., in cell culture. In certain embodiments, in vitro cytokine release is quantified from the cell culture supernatant. In some embodiments, cytokine release is studied in vivo, e.g., in an animal model. In certain embodiments, in vivo cytokine release is quantified from a bodily fluid, e.g., whole blood, serum, plasma, or lymph. In certain embodiments, the animal model is a murine model. In certain embodiments, the animal model is a non-human primate. In certain embodiments, cytokine release is studied in a human patient.

In some embodiments cytokine release is assessed through quantification of cytokine expression levels. In some embodiments, cytokine expression levels are quantified using an enzymae-linked immunosorbent assay (ELISA). In some embodiments, cytokine expression levels are quantified using a multiplex immunoassay, e.g., Luminex. In some embodiments, cytokine expression levels are quantified using a cytokine array. In some embodiments, cytokine expression levels are quantified using a Western Blot. In some embodiments, cytokine expression levels are quantified using mass spectrometry.

In some embodiments, cytokine release is assayed through monitoring changes in the immune system. Methods of studying the immune system are known in the art, and include, without limitation: fluorescence activated cell sorting (FACS), transcriptomic profiling (e.g., by RNA-sequencing (RNA Seq)), blood smears, complete blood count, and hematocrit.

In certain embodiments, symptoms of a disease or disorder, such as fever, pneumonia, shortness of breath, and low blood oxygen levels, are indicative of changes in the immune system. In certain embodiments, a decrease in symptoms of a disease or disorder, such as fever, pneumonia, shortness of breath, and low blood oxygen levels, i.e., a decrease in symptoms following treatment with MBV therapy as disclosed herein, are indicative of changes in the immune system.

Treatment of Acute Respiratory Distress Syndrome

The invention also provides for methods of treating acute respiratory distress syndrome (ARDS) with MBV described herein.

Acute respiratory distress syndrome is a disorder characterized by poor blood oxygenation, fluid infiltration into the lungs, and acuity of onset (Diamond et al. (2020). Acute Respiratory Distress Syndrome (ARDS). StatPearls [Internet]. Treasure Island (FL): StatPearls Publishing). ARDS onset usually occurs within 7 days of the causal event. ARDS is clinically defined by the ratio of the patient's oxygen levels in arterial blood ($PaO_2$) to the oxygen in the inspired air ($FiO_2$). ARDS is defined as patients exhibiting a $PaO_2/FiO_2$ ratio of less than 300. ARDS has high morbidity and high mortality. Clinical ARDS is further described, for example, in Fan et al. (2018). Acute Respiratory Distress Syndrome: Advances in Diagnosis and Treatment. *JAMA*. 319 (7): 698-710.

Risk factors for ARDS include, without limitation, an infectious disease or disorder (e.g., a viral infection, e.g., a bacterial infection), graft-versus-host disease, massive blood transfusion, organ trauma, tissue trauma (e.g., a severe burn), chronic alcoholism, hemophagocytic lymphohistiocytosis, sepsis, systemic inflammatory response syndrome, drowning, (e.g., aspiration of water), drug overdose (e.g., aspiration of vomit), aspiration of food, fat embolism, inhalation of toxic fumes (e.g., smoke or chemical fumes), and pancreatitis. The smoking of e-cigarettes known as "vaping" has also been determined a risk factor for developing ARDS. In certain embodiments, the subject has a head injury that damages the portion of the brain that controls breathing. In certain embodiments, the subject has a chest injury that damages the lungs. In some embodiments, the risk factor for ARDS is an infectious disease or disorder, e.g., a virus, e.g., a coronavirus, e.g., SARS-CoV2. In some embodiments, the risk factor for ARDS is an infectious disease or disorder, e.g., a virus, e.g., an ebolavirus. In some embodiments, the risk factor for ARDS is an infectious disease or disorder, e.g., a bacteria, e.g., *Streptococcus pneumoniae*. In some embodiments, ARDS is associated with hypercytokinemia. In a particular embodiment, ARDS is associated with hypercytokinemia associated with SARS-Cov2 (COVID-19). In some embodiments, ARDS is associated with mortality associated with SARS-Cov2 (COVID-19). Any of these subjects can be selected for treatment with the methods disclosed herein.

Existing therapies for patients with ARDS comprise supportive and/or palliative care, including, without limitation, reducing shunt fraction, increasing oxygen delivery, decreasing oxygen consumption, and avoiding further injury to affected tissues and organs. In some embodiments, a patient with ARDS is placed on a mechanical ventilator. In certain embodiments, a patient on a mechanical ventilator is administered MBV as described herein. In certain embodiments, a patient on a mechanical ventilator is administered MBV as described herein intravenously. In certain embodiments, a patient receives administration of MBV before onset of ARDS if the patient is at risk of ARDS.

The invention is based on the discovery that MBV have the capacity to modulate the immune system when administered to a subject suffering from a disease or disorder characterized by pathologic dysregulation of the immune system, such as a disease or disorder triggered by a viral infection. In particular, it has been discovered that MBV delivered systemically have a therapeutic effect in treating symptoms of inflammatory disorders commensurate with the therapeutic effect achieved from local administration of MBV to an affected tissue. Furthermore, as MBV modulate the immune system rather than suppress it, the therapeutic effect of MBV administration does not present the risk of secondary infection often observed with immunosuppression. Accordingly, this positions MBV as a unique systemic therapy for inflammatory disorders, e.g., acute respiratory distress syndrome. Patients treated with MBV as opposed to traditional anti-inflammatory or immune suppressive drugs may therefore experience a decreased risk of developing secondary infection according to the infection as the methods of the invention do not suppress the innate immune system, leaving it functioning to fight off disease and prevent secondary infection. For example, a patient suffering from COVID-19 induced ARDS experiences a decreased risk for developing a secondary infection when administered MBV for the treatment of ARDS as compared to a similarly situated patient who receives traditional anti-inflammatory or immune suppressive drugs to treat the ARDS.

As described in Example 2 below, in a rat model of rheumatoid arthritis as an exemplary inflammatory disease, arthritis scores in rats administered MBV either systemically by tail vein intravenous injection or locally by periarticular injection were improved comparably to arthritis scores for rats receiving periarticular methotrexate, the gold standard of treatment for rheumatoid arthritis. Surprisingly, arthritis score improvements were comparable between rats whether receiving systemic injection or local injection. Examples 10-13 further evidence that systemic administration of MBV mitigates acute viral-mediated pulmonary pathology and long-term inflammation in an animal model of an influenza infection.

Accordingly, systemic administration of MBV can be used to treat disorders resulting from aberrant immune response, e.g. ARDS, that are not localized to one part of the body or that are not amenable to local treatment. In cases of immune hyperactivity, such as ARDS, the underlying cause (e.g., hypercytokinemia) is present in the circulation, and thus is a systemic disorder. Therefore, in some embodiments, a systemic therapy provides an efficient mechanism for modulating the immune response throughout the body.

In some embodiments, administration can be systemic. Systemic administration can be intravenous administration, oral administration, enteral administration, parenteral administration, intranasal administration, intratracheal administration, rectal administration, sublingual administration, buccal administration, sublabial administration, intraperitoneal administration, or intramuscular administration. In specific non-limiting examples, the systemic administration is intravenous administration. In certain embodiments, the administration is local, such as to the lungs. For example, the local administration is inhalational or intratracheal. For example, the administration is inhalational by nebulization, or inhalational via intranasal administration.

In some embodiments, administration of MBV results in a reduction in the number of CD45+ neutrophils in the lung of the subject. In other embodiments, administration of MBV results in an increase in the number of CD8+ T cells and a reduction in the numbers of CD4+ T cells in the lung of the subject. In other embodiments, administration of MBV results in an increase in the number of CD8+ T cells and a reduction in the numbers of CD4+ T cells in the spleen of the subject. In further embodiments, administration results in an increase in the number of CD69+CD4+ T cells in the spleen of the subject. In yet other embodiments, administration results in an increase in the number of anti-viral Tbet+ CD4+ T cells in the lymph node of the subject. In yet other embodiments, administration results in an increase in the number of anti-viral Tbet+CD8+ T cells in the spleen of the subject. In further embodiments, administration results in an increase in the number of CD69+CD8+ T cells in the spleen of the subject. In more embodiments, administration results in an increase in the numbers of immunoregulatory CD11b+ dendritic cells in the lung of the subject. In some embodiments, administration results in an increase in the number of CD62L+/CD44+ memory CD4 and CD8 T-cells in the lung of the subject. The administration can result in one or more of these effects in the subject. An increase can be 10%, 15%, 20%, 25%, 30%, 35%, 40%, 45%, 50%, 55%, 60%, 70%, 75%, 80%, 85%, 90%, 95%, 100%, or more than 100% increase as compared to the parameter in the subject prior to the administration of the MBV or as compared to a standard value. A decrease can be a 10%, 15%, 20%, 25%, 30%, 35%, 40%, 45%, 50%, 55%, 60%, 70%, 75%, 80%, 85%, 90%, 95%, 100%, or more than 100% decrease as compared to the parameter in the subject prior to the administration of the MBV, or as compared to a standard value.

In more embodiments, administration reduces viral-associated tissue damage in the subject. For example, administration can result in reduced damage to the lungs of the subject. In some embodiments, viral associated tissue damage is decreased by 10%, 15%, 20%, 25%, 30%, 35%, 40%, 45%, 50%, 55%, 60%, 70%, 75%, 80%, 85%, 90%, 95%, 100%, or more than 100% as compared to the tissue in the subject prior to the administration of the MBV.

Nanovesicles Derived from an Extracellular Matrix (ECM)

Nanovesicles derived from ECM (also called matrix bound nanovesicles, "MBV") are generally described in PCT Publication No. WO 2017/151862, WO 2018/204848, and WO 2019/213482, incorporated herein by reference. It is disclosed that MBV are embedded in the extracellular matrix. These MBV can be isolated and are biologically active. In some embodiments, the MBV do not contain alkaline phosphatase, osteopontin, osteoprogeterin, complement C5, and/or c-reactive protein. These MBV can be used for therapeutic purposes, either alone or with an ECM.

An extracellular matrix is a complex mixture of structural and functional biomolecules and/or biomacromolecules including, but not limited to, structural proteins, specialized proteins, proteoglycans, glycosaminoglycans, and growth factors that surround and support cells within mammalian tissues and, unless otherwise indicated, is acellular. Generally, the disclosed MBV are embedded in any type of extracellular matrix (ECM), and can be isolated from this location. Thus, MBV are not detachably present on the surface of the ECM, and are not exosomes (also known as extracellular vesicles or EV).

Extracellular matrices are disclosed, for example and without limitation, in U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666; each of which is incorporated by reference in its entirety). However, an ECM can be produced from any tissue, or from any in vitro source wherein the ECM is produced by cultured cells and comprises one or more polymeric components (constituents) of native ECM. ECM preparations can be considered to be "decellularized" or "acellular", meaning the cells have been removed from the source tissue or culture.

In some embodiments, the ECM is isolated from a vertebrate animal, for example, from a mammalian vertebrate animal including, but not limited to, human, monkey, pig, cow, sheep, etc. The ECM may be derived from any organ or tissue, including without limitation, urinary bladder, intestine (such as small intestine or large intestine), heart, dermis, liver, kidney, uterus, brain, blood vessel, lung, bone, muscle, pancreas, placenta, stomach, spleen, colon, adipose tissue, or esophagus. In some embodiments, the ECM may be derived from any or tissue except bone. In specific non-limiting examples, the extracellular matrix is isolated from esophageal tissue, urinary bladder (such as urinary bladder matrix or urinary bladder submucosa), small intestinal submucosa, dermis, umbilical cord, pericardium, cardiac tissue, or skeletal muscle. The ECM can comprise any portion or tissue obtained from an organ, including, for example and without limitation, submucosa, epithelial basement membrane, tunica propria, etc. In one non-limiting embodiment, the ECM is isolated from urinary bladder. In some embodiments, the ECM is from a human subject. In other embodiments, the ECM is from a porcine subject.

The ECM may or may not include the basement membrane. In another non-limiting embodiment, the ECM includes at least a portion of the basement membrane. The ECM material may or may not retain some of the cellular elements that comprised the original tissue such as capillary endothelial cells or fibrocytes. In some embodiments, the ECM contains both a basement membrane surface and a non-basement membrane surface.

In some embodiments, the ECM is harvested from porcine urinary bladders (also known as urinary bladder matrix or UBM). Briefly, the ECM is prepared by removing the urinary bladder tissue from a mammal, such as a pig, and trimming residual external connective tissues, including adipose tissue. All residual urine is removed by repeated washes with tap water. The tissue is delaminated by first soaking the tissue in a de-epithelializing solution, for example and without limitation, hypertonic saline (e.g., 1.0 *N saline*), for periods of time ranging from ten minutes to four hours. Exposure to hypertonic saline solution removes the epithelial cells from the underlying basement membrane. Optionally, a calcium chelating agent may be added to the saline solution. The tissue remaining after the initial delamination procedure includes the epithelial basement membrane and tissue layers abluminal to the epithelial basement membrane. The relatively fragile epithelial basement membrane is invariably damaged and removed by any mechanical abrasion on the luminal surface. This tissue is next subjected to further treatment to remove most of the abluminal tissues but maintain the epithelial basement membrane and the tunica propria. The outer serosal, adventitial, tunica muscularis mucosa, tunica submucosa and most of the muscularis mucosa are removed from the remaining deepithelialized tissue by mechanical abrasion or by a combination of enzymatic treatment (e.g., using trypsin or collagenase) followed by hydration, and abrasion. Mechanical removal of these tissues is accomplished by removal of mesenteric tissues with, for example and without limitation, Adson-Brown forceps and Metzenbaum scissors and wiping away the tunica muscularis and tunica submucosa using a longitudinal wiping motion with a scalpel handle or other rigid object wrapped in moistened gauze. Automated robotic procedures involving cutting blades, lasers and other methods of tissue separation are also contemplated. After these tissues are removed, the resulting ECM consists mainly of epithelial basement membrane and subjacent tunica propria.

In another embodiment, the ECM is prepared by abrading porcine bladder tissue to remove the outer layers including both the tunica serosa and the tunica muscularis using a longitudinal wiping motion with a scalpel handle and moistened gauze. Following eversion of the tissue segment, the luminal portion of the tunica mucosa is delaminated from the underlying tissue using the same wiping motion. Care is taken to prevent perforation of the submucosa. After these tissues are removed, the resulting ECM consists mainly of the tunica submucosa (see FIG. 2 of U.S. Pat. No. 9,277,999, which is incorporated herein by reference).

ECM can also be prepared as a powder. Such powder can be made according the method of Gilbert et al., Biomaterials 26 (2005) 1431-1435, herein incorporated by reference in its entirety. For example, UBM sheets can be lyophilized and then chopped into small sheets for immersion in liquid nitrogen. The snap frozen material can then be comminuted so that particles are small enough to be placed in a rotary knife mill, where the ECM is powdered. Similarly, by precipitating NaCl within the ECM tissue the material will fracture into uniformly sized particles, which can be snap frozen, lyophilized, and powdered.

In one non-limiting embodiment, the ECM is derived from small intestinal submucosa or SIS. Commercially available preparations include, but are not limited to, SURGISIS™, SURGISIS-ES™, STRATASIS™, and STRATASIS-ES™ (Cook Urological Inc.; Indianapolis, Ind.) and GRAFTPATCH™ (Organogenesis Inc.; Canton Mass.). In another non-limiting embodiment, the ECM is derived from dermis. Commercially available preparations include, but are not limited to PELVICOL™ (sold as PERMACOL™ in Europe; Bard, Covington, Ga.), REPLIFORM™ (Microvasive; Boston, Mass.) and ALLODERM™ (LifeCell; Branchburg, N.J.). In another embodiment, the ECM is derived from urinary bladder. Commercially available preparations include, but are not limited to UBM (ACell Corporation; Jessup, Md.).

MBV can be derived from (released from) an extracellular matrix using the methods disclosed below. In some embodiments, the ECM is digested with an enzyme, such as pepsin, collagenase, elastase, hyaluronidase, or proteinase K, and the MBV are isolated. In other embodiments, the MBV are released and separated from the ECM by changing the pH with solutions such as glycine HCL, citric acid, ammonium hydroxide, use of chelating agents such as, but not limited to, EDTA, EGTA, by ionic strength and or chaotropic effects with the use of salts such as, but not limited to potassium chloride (KCl), sodium chloride, magnesium chloride, sodium iodide, sodium thiocyanate, or by exposing ECM to denaturing conditions like guanidine HCl or Urea.

In particular embodiments, the MBV are prepared following digestion of an ECM with an enzyme, such as pepsin, elastase, hyaluronidase, proteinase K, salt solutions, or collagenase. The ECM can be freeze-thawed, or subject to mechanical degradation.

In some embodiments, expression of CD63, CD81, and/or CD9 cannot be detected on the MBV. Thus, in some embodiments the MBV do not express CD63 and/or CD81 and/or CD9. In one specific example, CD63, CD81, and CD9 cannot be detected on the nanovesicles. In other embodiments, the MBV have barely detectable levels of CD63, CD81, and CD9, such as that detectable by Western blot. These MBV are $CD63^{lo}CD81^{lo}CD9^{lo}$. In other embodiments, MBV do not express detectable levels of one or more of CD63, CD81, or CD9. In other embodiments, MBV express barely detectable levels of one or more of CD63, CD81, or CD9. One of skill in the art can readily identify MBV that are $CD63^{lo}$ and/or $CD81^{lo}$ and/or $CD9^{lo}$, using, for example, antibodies that specifically bind CD63, CD81, and CD9. A low level of these markers can be established using procedures such as fluorescent activated cell sorting (FACS) and fluorescently labeled antibodies to determine a threshold for low and high amounts of CD63, CD81, and CD9. In further embodiments, the MBV do not contain detectable alkaline phosphatase, osteopontin, osteoprogeterin, complement C5, and/or c-reactive protein. The disclosed MBV differ from nanovesicles, such as exosomes that may be transiently attached to the surface of the ECM due to their presence in biological fluids, as MBV in vivo are bound to the ECM and not found in biological fluids.

MBV have distinctive phospholipid content, for example, in comparison to exosomes. In some embodiments, the total phospholipid content of the MBV is at least 50%, 55%, 60%, 65%, 70%, 75%, 85%, or 90%, or about 50%-90%, 50%-65%, 50%-60%, 50%-70%, 60%-70%, 60%-90%, or 70%-90% of phosphatidylcholine (PC) and phosphatidyl inositol (PI) in combination. In specific embodiments, the total phospholipid content of the MBV is at least 55% of phosphatidylcholine (PC) and phosphatidyl inositol (PI) in combination. In specific embodiments, the total phospholipid content of the MBV is at least 60% of phosphatidylcholine (PC) and phosphatidyl inositol (PI) in combination. In some embodiments, the phospholipid content of the MBV comprises a phosphatidylcholine (PC) to phosphatidyl inositol (PI) ratio of less than 8:1 (for example, less than 7:1, less than 6:1, less than 5:1, less than 4:1, less than 3:1, or less than 2:1). In some embodiments, the phospholipid content of the MBV comprises a phosphatidylcholine (PC) to phosphatidyl inositol (PI) ratio in the range of 0.5-1:1, or in the range of 1:0.5-1, or in the range of 0.5-1:2, or in the range of 2:0.5-1, or in the range of 0.8-1:1, or in the range of 1:0.8-1. In one embodiment, the phospholipid content of the MBV comprises a phosphatidylcholine (PC) to phosphatidyl inositol (PI) ratio of about 1:1. In specific embodiments, the phospholipid content of the MBV comprises a phosphatidylcholine (PC) to phosphatidyl inositol (PI) ratio of about 0.9:1.

In some embodiments, the total phospholipid content of the MBV is 15%, 10%, 9%, 8%, 7%, 6%, 5%, 4% or less, or about 5%-10%, 5%-15%, 10%-15%, or 8%-12% of sphingomyelin (SM). In specific embodiments, the total phospholipid content of the MBV is 10% or less of sphingomyelin (SM). In some embodiments, the total phospholipid content of the is 15% or less of sphingomyelin (SM), 14% or less of sphingomyelin, 13% or less of sphingomyelin, 12% or less of sphingomyelin, 11% or less of sphingomyelin, 10% or less of sphingomyelin, 9% or less of sphingomyelin, 8% or less of sphingomyelin, 7% or less of sphingomyelin, 6% or less of sphingomyelin, 5% or less of sphingomyelin, or 4% or less of sphingomyelin.

In some embodiments, the total phospholipid content of the MBV 20%, 19%, 18%, 17%, 16%, 15%, 14%, 13%, 12%, 11%, or 10% or less, or about 10%-20%, 15%-20%, 14%-18%, or 12%-16% of phosphatidylethanolamine (PE). In specific embodiments, the total phospholipid content of the MBV is 20% or less of phosphatidylethanolamine (PE).

In some embodiments, the total phospholipid content of the MBV is 5%, 10%, 12%, 15%, 18%, 20%, 25%, or 30% or greater, or about 5%-30%, 10%-20%, 10-25%, 15%-25%, or 12%-18% of phosphatidylinositol (PI). In specific embodiments, MBV include a phospholipid content 15% or greater of phosphatidylinositol (PI).

In specific embodiments, the total phospholipid content of the MBV comprises 15% or more phosphatidylinositol, 20% or less phosphatidylethanolamine, and 10% or less sphingomyelin. In specific embodiments, the total phospholipid content of the MBV is 15% or more phosphatidylinositol and 20% or less phosphatidylethanolamine. In specific embodiments, the total phospholipid content of the MBV is 15% or more phosphatidylinositol and 10% or less sphingomyelin. In specific embodiments, the total phospholipid content of the MBV comprises 20% or less phosphatidylethanolamine and 10% or less sphingomyelin. In specific embodiments, the total phospholipid content of the MBV is more than 15% phosphatidylinositol, 20% or less phosphatidylethanolamine, 10% or less sphingomyelin, and at least 55% of phosphatidylinositol and phosphatidylcholine in combination. In one embodiment, the total phospholipid content of the MBV is at least 55% phosphatidylcholine (PC) and phosphatidyl inositol (PI) in combination and 10% or less sphingomyelin (SM). In specific embodiments, the total phospholipid content of the MBV is at least 55% of phosphatidylinositol and phosphatidylcholine in combination and more than 15% phosphatidylinositol. In specific embodiments, the total phospholipid content of the MBV is 55% of phosphatidylinositol and phosphatidylcholine in combination and 20% or less phosphatidylethanolamine.

The MBV may also comprise lysyl oxidase (Lox). Generally, nanovesicles derived from the ECM have a higher Lox content than exosomes. Lox is expressed on the surface of MBV. Nano-LC MS/MS proteomic analysis can be used to detect Lox proteins. Quantification of Lox can be performed (see, e.g., Hill R C, et al., *Mol Cell Proteomics*. 2015; 14(4):961-73, incorporated herein by reference in its entirety).

In certain embodiments, the MBV comprise one or more miRNA. In specific non-limiting examples, the MBV comprise one, two, or all three of miR-143, miR-145 and miR-181. MiR-143, miR-145 and miR-181 are known in the art.

The miR-145 nucleic acid sequence is provided in MiRbase Accession No. MI0000461, incorporated herein by reference. A miR-145 nucleic acid sequence is CACCUUGUCCUCACGGUCCAGUUUUCCCAGGAAUCCCUUAGAUGCUAAGAUGGGGA UUCCUGGAAAUACUGUUCUUGAGGUCAUGGUU (SEQ ID NO: 1). An miR-181 nucleic acid sequence is provided in miRbase Accession No. MI0000269, incorporated herein by reference. A miR-181 nucleic acid sequence is: AGAAGGGCUAUCAGGCCAGCCUUCAGAGGACUCCAAGGAACAUUCAACGCUGUCGG UGAGUUUGGGAUUUGAAAAAACCACUGACCGUUGACUGUACCUUGGGGUCCUUA (SEQ ID NO: 2). The miR-143 nucleic acid sequence is provided in NCBI Accession No. NR_029684.1, Mar. 30, 2018, incorporated herein by reference. A DNA encoding an miR-143 nucleic acid sequence is: GCGCAGCGCC CTGTCTCCCA GCCTGAGGTG CAGTGCTGCA TCTCTGGTCA GTTGGGAGTC TGAGATGAAG CACTGTAGCT CAGGAAGAGA GAAGTTGTTC TGCAGC (SEQ ID NO: 3).

Following administration, the MBV maintain expression of F4/80 (a macrophage marker) and CD-11b on macrophages in the subject. Nanovesicle treated macrophages are predominantly F4/80+Fizz1+indicating an M2 phenotype.

The MBV disclosed herein can be formulated into compositions for pharmaceutical delivery MBV are further disclosed and described in PCT Publication No. WO 2017/151862, which is incorporated herein by reference.

Isolation of MBV from the ECM

To produce MBV, ECM can be produced by any cells of interest, or can be utilized from a commercial source, as described supra. See also Quijano et al., *Tissue Eng, Part C* 2020; (10):528-540. DOI: 10.1089/ten.tec.2020.0243. PMID: 33012221, incorporated by reference in its entirety. The MBV can be produced from the same species as, or a different species than, the subject being treated. In some embodiments, these methods include digesting the ECM with an enzyme to produce digested ECM. In specific embodiments, the ECM is digested with one or more of pepsin, elastase, hyaluronidase, collagenase a metalloproteinase, and/or proteinase K. In a specific non-limiting example, the ECM is digested with only elastase and/or a metalloproteinase. In another non-limiting example, the ECM is not digested with collagenase and/or trypsin and/or proteinase K. In other embodiments, the ECM is treated with a detergent. In further embodiments, the method does not include the use of enzymes. In specific non-limiting examples, the method utilizes chaotropic agents or ionic strength to isolate MBV such as salts, such as potassium chloride. In additional embodiments, the ECM can be manipulated to increase MBV content prior to isolation of MBV. Techniques for isolating MBV from ECM are described, for example, in International Patent Application WO 2017/151862.

In some embodiments, the ECM is digested with an enzyme. The ECM can be digested with the enzyme for about 12 to about 48 hours, such as about 12 to about 36 hours. The ECM can be digested with the enzyme for about 12, about 24 about 36 or about 48 hours. In one specific non-limiting example, the ECM is digested with the enzyme at room temperature. However, the digestion can occur at about 4° C., or any temperature between about 4° C. and 25° C. Generally, the ECM is digested with the enzyme for any length of time, and at any temperature, sufficient to remove collagen fibrils. The digestion process can be varied depending on the tissue source. Optionally, the ECM is processed by freezing and thawing, either before or after digestion with the enzyme. The ECM can be treated with detergents, including ionic and/or non-ionic detergents.

The digested ECM is then processed, such as by centrifugation, to isolate a fibril-free supernatant. In some embodiments the digested ECM is centrifuged, for example, for a first step at about 300 to about 1000g. Thus, the digested ECM can be centrifuged at about 400g to about 750g, such as at about 400g, about 450g, about 500g or about 600g. This centrifugation can occur for about 10 to about 15 minutes, such as for about 10 to about 12 minutes, such as for about 10, about 11, about 12, about 14, about 14, or about 15 minutes. The supernatant including the digested ECM is collected.

In some embodiments, the MBV comprise Lox. In some embodiments, methods for isolating such MBV include digesting the extracellular matrix with elastase and/or metalloproteinase to produce digested extracellular matrix, centrifuging the digested extracellular matrix to remove collagen fibril remnants and thus to produce a fibril-free supernatant, centrifuging the fibril-free supernatant to isolate the solid materials, and suspending the solid materials in a carrier.

In some embodiments, digested ECM also can be centrifuged for a second step at about 2000g to about 3000g. Thus, the digested ECM can be centrifuged at about 2,500g to about 3,000g, such as at about 2,000g, 2,500g, 2,750g or 3,000g. This centrifugation can occur for about 20 to about 30 minutes, such as for about 20 to about 25 minutes, such as for about 20, about 21, about 22, about 23, about 24, about 25, about 26, about 27, about 28, about 29 or about 30 minutes. The supernatant including the digested ECM is collected.

In additional embodiments, the digested ECM can be centrifuged for a third step at about 10,000 to about 15,000g. Thus, the digested ECM can be centrifuged at about 10,000g to about 12,500g, such as at about 10,000g, 11,000g or 12,000g. This centrifugation can occur for about 25 to about 40 minutes, such as for about 25 to about 30 minutes, for example for about 25, about 26, about 27, about 28, about 29, about 30, about 31, about 32, about 33, about 34, about 35, about 36, about 37, about 38, about 39 or about 40 minutes. The supernatant including the digested ECM is collected. One, two or all three of these centrifugation steps can be independently utilized. In some embodiments, all three centrifugation steps are utilized. The centrifugation steps can be repeated, such as 2, 3, 4, or 5 times. In one embodiment, all three centrifugation steps are repeated three times.

In some embodiments, the digested ECM is centrifuged at about 500g for about 10 minutes, centrifuged at about 2,500 g for about 20 minutes, and/or centrifuged at about 10,000g for about 30 minutes. These step(s), such as all three steps are repeated 2, 3, 4, or 5 times, such as three times. Thus, in one non-limiting example, the digested ECM is centrifuged at about 500g for about 10 minutes, centrifuged at about 2,500 g for about 20 minutes, and centrifuged at about 10,000g for about 30 minutes. These three steps are repeated three times. Thus, a fibril-free supernatant is produced. The fibril-free supernatant is then centrifuged to isolate the MBV. In some embodiments, the fibril-free supernatant is centrifuged at about 100,000g to about 150,000g. Thus, the fibril-free supernatant is centrifuged at about 100,000g to about 125,000g, such as at about 100,000g, about 105,000g, about 110,000g, about 115,000g or about 120,000g. This centrifugation can occur for about 60 to about 90 minutes, such as about 70 to about 80 minutes, for example for about 60, about 65, about 70, about 75, about 80, about 85 or about 90 minutes. In one non-limiting example, the fiber-free supernatant is centrifuged at about 100,000g for about 70 minutes. The solid material is collected, which is the MBV. These MBV then can be re-suspended in any carrier of interest, such as, but not limited to, a buffer.

In further embodiments the ECM is not digested with an enzyme. In these methods, ECM is suspended in an isotonic saline solution, such as phosphate buffered saline. Salt is then added to the suspension so that the final concentration of the salt is greater than about 0.1 M. The concentration can be, for example, up to about 3 M, for example, about 0.1 M salt to about 3 M, or about 0.1 M to about 2M. The salt can be, for example, about 0.1M, 0.15M, 0.2M, 0.3M, 0.4 M, 0.7 M, 0.6 M, 0.7 M, 0.8M, 0.9M, 1.0 M, 1.1 M, 1.2 M, 1.3 M, 1.4 M, 1.5M, 1.6 M, 1.7 M, 1.8M, 1.9 M, or 2M. In some non-limiting examples, the salt is potassium chloride, sodium chloride or magnesium chloride. In other embodiments, the salt is sodium chloride, magnesium chloride, sodium iodide, sodium thiocyanate, a sodium salt, a lithium salt, a cesium salt or a calcium salt.

In some embodiments, the ECM is suspended in the salt solution for about 10 minutes to about 2 hours, such as about 15 minutes to about 1 hour, about 30 minutes to about 1 hour, or about 45 minutes to about 1 hour. The ECM can be suspended in the salt solution for about 15, 20, 25, 30, 35, 40, 45, 50, 55, 60, 65, 70, 75, 80, 85, 90, 95, 100, 105, 110, 115 or 120 minutes. The ECM can be suspended in the salt solution at temperatures from 4° C. to about 50° C., such as, but not limited to about 4° C. to about 25° C. or about 4° C. to about 37° C. In a specific non-limiting example, the ECM is suspended in the salt solution at about 4° C. In other specific non-limiting examples, the ECM is suspended in the salt solution at about 22° C. or about 25° C. (room temperature). In further non-limiting examples, the ECM is suspended in the salt solution at about 37° C.

In some embodiments, the method includes incubating an extracellular matrix at a salt concentration of greater than about 0.4 M; centrifuging the digested extracellular matrix to remove collagen fibril remnants, and isolating the supernatant; centrifuging the supernatant to isolate the solid materials; and suspending the solid materials in a carrier, thereby isolating MBV from the extracellular matrix.

Following incubation in the salt solution, the ECM is centrifuged to remove collagen fibrils. In some embodiments, digested ECM also can be centrifuged at about 2000g to about 5000g. Thus, the digested ECM can be centrifuged at about 2,500g to about 4,500g, such as at about 2,500g, about 3,000g, 3,500, about 4,000g, or about 4,500g. In one specific non-limiting example, the centrifugation is at about 3,500g. This centrifugation can occur for about 20 to about 40 minutes, such as for about 25 to about 35 minutes, such as for about 20, about 21, about 22, about 23, about 24, about 25, about 26, about 27, about 28, about 29, about 30 minutes, about 31, about 32, about 33 about 34 or about 35 minutes. The supernatant is then collected.

In additional embodiments, the supernatant then can be centrifuged for a third step at about 100,000 to about 150,000g. Thus, the digested ECM can be centrifuged at about 100,000g to about 125,000g, such as at about 100,000g, 110,000g or 120,000g. This centrifugation can occur for about 30 minutes to about 2.5 hour, such as for about 1 hour to about 3 hours, for example for about 30 minutes, about 45 minutes, about 60 minutes, about 90 minutes, or about 120 minutes (2 hours). The solid materials are collected and suspended in a solution, such as buffered saline, thereby isolating the MBV.

In yet other embodiments, the ECM is suspended in an isotonic buffered salt solution, such as, but not limited to, phosphate buffered saline. Centrifugation or other methods can be used to remove large particles (see below). Ultrafiltration is then utilized to isolate MBV from the ECM, particles between about 10 nm and about 10,000 nm, such as between about 10 and about 1,000 nm, such as between about 10 nm and about 300 nm.

In specific non-limiting examples, the isotonic buffered saline solution has a total salt concentration of about 0.164 mM, and a pH of about 7.2 to about 7.4. In some embodiments, the isotonic buffered saline solution includes 0.002 M KCl to about 0.164 M KCL, such as about 0.0027 M KCl (the concentration of KCL in phosphate buffered saline). This suspension is then processed by ultracentrifugation.

Following incubation in the isotonic buffered salt solution, the ECM is centrifuged to remove collagen fibrils. In some embodiments, digested ECM also can be centrifuged at about 2000g to about 5000g. Thus, the digested ECM can be centrifuged at about 2,500g to about 4,500g, such as at about 2,500g, about 3,000g, 3,500, about 4,000g, or about 4,500g. In one specific non-limiting example, the centrifugation is at about 3,500g. This centrifugation can occur for about 20 to about 40 minutes, such as for about 25 to about 35 minutes, such as for about 20, about 21, about 22, about 23, about 24, about 25, about 26, about 27, about 28, about 29, about 30 minutes, about 31, about 32, about 33 about 34 or about 35 minutes.

Microfiltration and centrifugation can be used and combined to remove large molecular weight materials from the suspension. In one embodiment, large size molecule materials, such as more than 200 nm are removed using microfiltration. In another embodiment, large size materials are removed by the use of centrifugation. In a third embodiment both microfiltration and ultracentrifugation are used to remove large molecular weight materials. Large molecular weight materials are removed from the suspended ECM, such as materials greater than about 10,000 nm, greater than about 1,000 nm, greater than about 500 nm, or greater than about 300 nm.

The effluent for microfiltration or the supernatant is then subjected to ultrafiltration. Thus, the effluent, which includes particle of less than about 10,000 nm, less than about 1,000 nm, less than about 500 nm, or less than about 300 nm is collected and utilized. This effluent is then subjected to ultrafiltration with a membrane with a molecular weight cutoff (MWCO) of 3,000 to 100,000. 100,000MWCO was used in the example.

Methods for Treating Acute Respiratory Distress Syndrome (ARDS)

Methods are disclosed herein for treating ARDS in a subject in need thereof. These methods include selecting a subject in need of treatment to decrease inflammation and administering to the subject a therapeutically effective amount of MBV (such as by administering a pharmaceutical preparation that includes a therapeutically effective amount of MBV), thereby treating the ARDS.

The subject can be a mammal. The subject can be a human. The subject can be a veterinary subject. The subject can be avian or a domestic pet, such as a cat, dog or rabbit. The subject can be a non-human, primate (such as simians), or livestock, including swine, ruminants, horses, and poultry. The methods include selecting a subject in need of treatment to decrease inflammation and administering to the subject a therapeutically effective amount of MBV (such as by administering a pharmaceutical preparation that includes a therapeutically effective amount of MBV). In some embodiments, the MBV can be administered systemically. In other embodiments, the MBV can be administered locally. The MBV can be derived from the same or a different species than the subject in need of decreased inflammation. The MBV can be autologous.

The methods disclosed herein can result in a decrease in inflammation in a subject. In some embodiments, signs or symptoms of the hyperinflammatory disorder, such as hypercytokinemia, are reduced or eliminated. For example, the methods herein can result in treatment of the ARDS in a subject. In some embodiments, the methods herein can be used to prevent progression of ARDS in a subject, or reversal of ARDS in a subject.

According to one embodiment, treatment of ARDS can be measured according to relevant clinical indicia. In some embodiments, ARDS may be severe, and may be scored, for example, using a Murray Score for Acute Lung Injury, Hypoxemia $PaO_2/FiO_2$, PEEP ($cmH_2O$), Compliance (ml/$cmH_2O$) and CXR quadrants infiltrated. In some embodiments, ARDS may be scored, for example, using a Modified Downe's Scoring System, determined by respiratory rate, cyanosis, retractions, grunting, and air entry. In some embodiments, ARDS may be scored, for example, using another scoring system known in the art. Improvements in ARDS by treatment with MBV may be indicated by a change in scoring associated with improvement in ARDS symptoms.

According to one embodiment, treatment of ARDS can be measured by according to relevant clinical indicia. For example, treatment of ARDS can be measured by, for example, improvements in Oxygen Index (01), Oxygen Saturation Index (OSI), or Oxygen Saturation (OS). Effectiveness in treating ARDS can be measured for example by increases in the 01, the OSI, or the OS. For example, in one embodiment, the oxygen saturation in the subject increases by 10%, 15%, 20%, 25%, 30%, 35%, 40%, 45%, 50%, 55%, 60%, 70%, 75%, 80%, 85%, 90%, 95%, 100%, or more than 100% after administration MBV. In another embodiment, the oxygen saturation index in the subject increases by 10%, 15%, 20%, 25%, 30%, 35%, 40%, 45%, 50%, 55%, 60%, 70%, 75%, 80%, 85%, 90%, 95%, 100%, or more than 100% after administration of the MBV. In yet another embodiment, the oxygen index in the subject increases by 10%, 15%, 20%, 25%, 30%, 35%, 40%, 45%, 50%, 55%, 60%, 70%, 75%, 80%, 85%, 90%, 95%, 100%, or more than 100% after administration of the MBV. In further embodiments, treatment of ARDS can be indicated by measuring levels of pro-inflammatory cytokines in a subject. For example, a decrease in pro-inflammatory cytokines may be indicative of effectiveness of treatment of ARDS. For, example, a decrease in TNF-α, IFN-γ, IL-8, IL-12, IL-6 and/or IL-1β after administration of MBV may be indicative of effectiveness in treating ARDS. In another embodiment, an increase in anti-inflammatory cytokines such as IL-10, IL-4, and/or TGF-β can be used as an indicator of effectiveness in treating ARDS. Cytokine levels may be determined in the foregoing embodiments by, for example, sampling from recovered from bronchoalveolar lavage fluids of the subject before and after treatment with MBV. Cytokine levels may be determined in the foregoing embodiments by, for example, sampling from blood before and after treatment with MBV. Cytokine levels in body fluids or cell samples are determined by conventional methods known by those of skill in the art. For example, cytokine concentrations in cell culture supernatants and bronchoalveolar lavage fluid can be measured as recommended by the manufacturer of ELISA kits (R&D systems, Minneapolis, MN).

The effectiveness of treatment with MBV can be measured by monitoring pulmonary function by methods known to those of skill in the art. For example, various measurable parameters of lung function can be studied before, during, or after treatment. Pulmonary function can be monitored by testing any of several physically measurable operations of a lung including, but not limited to, inspiratory flow rate, expiratory flow rate, and lung volume. A statistically significant increase, as determined by mathematical formulas well known to those skilled in the art, in one or more of these parameters indicates efficacy of the MBV treatment.

The methods of measuring pulmonary function most commonly employed in clinical practice involve timed measurement of inspiratory and expiratory maneuvers to measure specific parameters. For example, FVC measures the total volume in liters exhaled by a patient forcefully from a deep initial inspiration. This parameter, when evaluated in conjunction with the FEV1, allows bronchoconstriction to be quantitatively evaluated. A statistically significant increase, as determined by mathematical formulas well known to those skilled in the art, in FVC or FEV1 reflects a decrease in bronchoconstriction, and indicates that the MBV therapy is effective.

A problem with forced vital capacity determination is that the forced vital capacity maneuver (i.e., forced exhalation from maximum inspiration to maximum expiration) is largely technique dependent. In other words, a given subject may produce different FVC values during a sequence of consecutive FVC maneuvers. The FEF 25-75 or forced expiratory flow determined over the midportion of a forced exhalation maneuver tends to be less technique dependent than the FVC. Similarly, the FEV1 tends to be less technique-dependent than FVC. Thus, a statistically significant increase, as determined by mathematical formulas well known to those skilled in the art, in the FEF 25-75 or FEV1 reflects a decrease in bronchoconstriction, and indicates that MBV therapy is effective.

In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest airflow rate in liters per minute during a forced maximal exhalation, is well correlated with overall pulmonary function in a patient with asthma and other respiratory diseases. Thus, a statistically significant increase, as determined by mathematical formulas well known to those skilled in the art, in the peak expiratory flow following administration of MBV indicates that the therapy is effective.

A subject may be administered 1 or more administrations of MBV constituting a course of treatment. A course of treatment may be administered systemically. A course of treatment may be administration of MBV 1 time per day until the ARDS subsides. Or the course of treatment may be administration of MBV 2 times per day until the ARDS subsides. A course of treatment may be administered at one time or over a period of hours. For example, the MBV may be administered by bolus IV administration or bolus tracheal instillation, or it may be infused into the oxygen stream of a ventilator or oxygen mask for continuous administration over several minutes or hours. For example, the MBV may be administered by continuous IV drip.

In some embodiments, a subject is administered about $1\times10^{1}$ to about $1\times10^{20}$ MBV per kg of body weight per administration. A subject can be administered, for example, about $1\times10^{1}$ to about $1\times10^{3}$ MBV, such as about $1\times10^{1}$ to about $1\times10^{2}$ MBV, concentrated into a microliter volume, such as for inhalation. For example, in one embodiment, the volume is 50 μL-500 μL. For example, in one embodiment the volume is 100 μL-300 μL. For example, in one embodiment the volume is 200 μL-400 μL. For example, in one embodiment the volume is 300 μL-400 μL. In a further embodiment, the volume is 250 μL. In a further embodiment, the volume is 300 μL. In more embodiments, the volume can be about 1 μL to about 5 μL, such as about 1 μL to about 4 μL, about 1 μL to about 3 μL, or about 1 μL to about 2 μL. In one embodiment, about $1\times10^{1}$ to about $1\times10^{3}$ MBV is provided for inhalation administration in a volume of about 50-500 μL.

According to additional embodiments, a subject is administered about $1\times10^{6}$ to about $1\times10^{20}$ MBV/kg of body weight, such as about $1\times10^{6}$ to about $1\times10^{12}$ MBV per kg of body weight per administration. In embodiments, a subject is administered about $1\times10^{6}$ to about $1\times10^{19}$ MBV, about $1\times10^{6}$ to about $1\times10^{18}$ MBV, about $1\times10^{6}$ to about $1\times10^{17}$ MBV, about $1\times10^{6}$ to about $1\times10^{16}$ MBV, about $1\times10^{6}$ to about $1\times10^{15}$ MBV, about $1\times10^{6}$ to about $1\times10^{14}$ MBV, about $1\times10^{6}$ to about $1\times10^{13}$ MBV, or about $1\times10^{6}$ to about $1\times10^{12}$ MBV. In another embodiment, a subject is administered about $1\times10^{7}$ to about $1\times10^{11}$ MBV per kg of body weight per administration. In another embodiment, a subject is administered $1\times10^{7}$ to $1\times10^{8}$ MBV per kg of body weight per administration. In another embodiment, a subject is administered $1\times10^{8}$ to $1\times10^{10}$ MBV per kg of body weight per administration. In another embodiment, a subject is administered $1\times10^{9}$ to $1\times10^{10}$ MBV per kg of body weight per administration. In another embodiment, a subject is administered $1\times10^{6}$ to $1\times10^{8}$ MBV per kg of body weight per administration. In another embodiment, a subject is administered $1\times10^{7}$ to $1\times10^{9}$ MBV per kg of body weight per administration. In another embodiment, a subject is administered $1\times10^{8}$ to $1\times10^{11}$ MBV per kg of body weight per administration. In another embodiment, a subject is administered $1\times10^{9}$ to $1\times10^{11}$ MBV per kg of body weight per administration. In another embodiment, a subject is administered $1\times10^{10}$ to $1\times10^{11}$ MBV per kg of body weight per administration. In another embodiment, a subject is administered $1\times10^{11}$ to $1\times10^{12}$ MBV per kg of body weight per administration. In another embodiment, a subject is administered $1\times10^{6}$ to $1\times10^{14}$ MBV per kg of body weight per administration. In another embodiment, a subject is administered $1\times10^{12}$ to $1\times10^{14}$ MBV per kg of body weight per administration. In one embodiment, administration of MBV according to any of the aforementioned amounts is by systemic administration. For example, in one embodiment, the administration is intravenous. In another embodiment, the administration is by inhalation. In one embodiment, the inhalation is by nebulizer or inhaler pump.

In another embodiment, the MBV are administered in an amount per dose in a set volume of liquid by intranasal administration. For example, in one embodiment, the volume is 50 μL-500 μL. For example, in one embodiment the volume is 100 μL-300 μL. For example, in one embodiment the volume is 200 μL-400 μL. For example, in one embodiment the volume is 300 μL-400 μL. In a further embodiment, the volume is 250 μL. In a further embodiment, the volume is 300 μL. In more embodiments, the volume can be about 1 μL to about 5 μL, such as about 1 μL to about 4 μL, about 1 μL to about 3 μL, or about 1 μL to about 2 μL. In one embodiment, about $1\times10^{1}$ to about $1\times10^{3}$ MBV is provided for intranasal administration in a volume of about 50-500 μL. In one embodiment, a subject is administered about $1\times10^{1}$ to about $1\times10^{3}$ MBV concentrated into 50-200 μL carrier, such as saline, for intranasal administration, such as by a nasal spray pump. In one embodiment, a subject can be administered multiple doses of an MBV concentrated solution such that the total of all doses administered provides MBV in an amount of about $1\times10^{8}$ to about $1\times10^{20}$ MBV per kg of body weight.

In one embodiment, the number of MBV in the dose is $1\times10^{8}$ to $1\times10^{10}$ MBV. For example, in one embodiment, the number of MBV in the dose is $1\times10^{9}$ MBV. In one embodiment, the MBV are nebulized in a physiologically acceptable carrier, for example, physiologic saline. For example, the number of MBV in a dose to be nebulized is $1\times10^{6}$ to $1\times10^{20}$ MBV per kg of body weight per administration. For example, the number of MBV in a dose to be nebulized is $1\times10^{6}$ to $1\times10^{12}$ MBV per kg of body weight per administration. For example, the dose is $1\times10^{7}$ to $1\times10^{11}$ MBV per kg of body weight per administration or $1\times10^{7}$ to $1\times10^{8}$ MBV per kg of body weight per administration or $1\times10^{8}$ to $1\times10^{10}$ MBV per kg of body weight per administration or $1\times10^{9}$ to $1\times10^{10}$ MBV per kg of body weight per administration or $1\times10^{6}$ to $1\times10^{8}$ MBV per kg of body weight per administration or $1\times10^{7}$ to $1\times10^{9}$ MBV per kg of body weight per administration or $1\times10^{8}$ to $1\times10^{11}$ MBV per kg of body weight per administration or $1\times10^{9}$ to $1\times10^{11}$ MBV per kg of body weight per administration or $1\times10^{10}$ to $1\times10^{11}$ MBV per kg of body weight per administration or $1\times10^{11}$ to $1\times10^{12}$ MBV per kg of body weight per administration.

In another embodiment, the MBV are administered in an amount of $1\times10^{7}$ to $1\times10^{11}$ MBV per dose in a set volume of liquid by intratracheal administration. For example, in one embodiment, the volume is 0.5 mL to 5.0 mL. In other embodiments, the volume is a microliter amount. In another embodiment, the volume is 1 mL to 3 mL. For example, in one embodiment, the volume is 2 mL to 4 mL. In yet another embodiment, the volume is 3 mL. For example, in one embodiment, the number of MBV in the dose is $1\times10^{8}$ to $1\times10^{10}$ MBV. For example, in one embodiment, the number of MBV in the dose is $1\times10^{9}$ MBV. For example, in one embodiment, the number of MBV in the dose is $1\times10^{10}$ to $1\times10^{11}$ MBV per kg of body weight per administration. For example, in one embodiment, the number of MBV in the dose is $1\times10^{11}$ to $1\times10^{12}$ MBV per kg of body weight per administration.

In another embodiment, the MBV are administered in an amount $1\times10^{7}$ to $1\times10^{11}$ MBV per dose in a set volume of liquid by intravenous administration. For example, in one embodiment, the volume is 0.5 mL to 10.0 mL. In another embodiment, the volume is 1 mL to 5 mL. In another embodiment, the volume is 3 mL to 8 mL. In yet another embodiment, the volume is 3 mL. For example, in one embodiment, the number of MBV in the dose is $1\times10^{8}$ to $1\times10^{10}$ MBV. For example, in one embodiment, the number of MBV in the dose is $1\times10^{9}$ MBV. For example, the number of MBV in a dose to be intravenously administered is $1\times10^{6}$ to $1\times10^{20}$ MBV per kg of body weight per administration. For example, the number of MBV in a dose to be intravenously administered is $1\times10^{6}$ to $1\times10^{12}$ MBV per kg of body weight per administration. For example, the dose is $1\times10^{7}$ to $1\times10^{11}$ MBV per kg of body weight per administration or $1\times10^{7}$ to $1\times10^{8}$ MBV per kg of body weight per administration or $1\times10^{8}$ to $1\times10^{10}$ MBV per kg of body weight per administration or $1\times10^{9}$ to $1\times10^{10}$ MBV per kg of body weight per administration or $1\times10^{6}$ to $1\times10^{8}$ MBV per kg of body weight per administration or $1\times10^{7}$ to $1\times10^{9}$ MBV per kg of body weight per administration or $1\times10^{8}$ to $1\times10^{11}$ MBV per kg of body weight per administration or $1\times10^{9}$ to $1\times10^{11}$ MBV per kg of body weight per administration or $1\times10^{10}$ to $1\times10^{11}$ MBV per kg of body weight per administration or $1\times10^{11}$ to $1\times10^{12}$ MBV per kg of body weight per administration or $1\times10^{12}$ to $1\times10^{14}$ MBV per kg of body weight per administration or $1\times10^{14}$ to $1\times10^{20}$ MBV per kg of body weight per administration.

In another embodiment, the MBV are administered in an amount $1\times10^{7}$ to $1\times10^{11}$ MBV per dose in a set volume of liquid by intraperitoneal administration. For example, in one embodiment, the volume is 10 mL to 200 mL. In another embodiment, the volume is 50 mL to 100 mL. In another embodiment, the volume is 50 mL-125 mL. In yet another embodiment, the volume is 50 mL. For example, in one embodiment, the number of MBV in the dose is $1\times10^{8}$ to $1\times10^{10}$ MBV. For example, in one embodiment, the number of MBV in the dose is $1\times10^{9}$ MBV. For example, the number of MBV in a dose to be intraperitoneally administered is $1\times10^{6}$ to $1\times10^{20}$ MBV per kg of body weight per administration. For example, the dose is $1\times10^{6}$ to $1\times10^{12}$ MBV per kg of body weight per administration or $1\times10^{7}$ to $1\times10^{11}$ MBV per kg of body weight per administration or $1\times10^{7}$ to $1\times10^{8}$ MBV per kg of body weight per administration or $1\times10^{8}$ to $1\times10^{10}$ MBV per kg of body weight per administration or $1\times10^{9}$ to $1\times10^{10}$ MBV per kg of body weight per administration or $1\times10^{6}$ to $1\times10^{8}$ MBV per kg of body weight per administration or $1\times10^{7}$ to $1\times10^{9}$ MBV per kg of body weight per administration or $1\times10^{8}$ to $1\times10^{11}$ MBV per kg of body weight per administration or $1\times10^{9}$ to $1\times10^{11}$ MBV per kg of body weight per administration or $1\times10^{10}$ to $1\times10^{11}$ MBV per kg of body weight per administration or $1\times10^{11}$ to $1\times10^{12}$ MBV per kg of body weight per administration or $1\times10^{12}$ to $1\times10^{14}$ MBV per kg of body weight per administration or $1\times10^{14}$ to $1\times10^{20}$ MBV per kg of body weight per administration.

In some embodiments, administration is systemic. Exemplary routes of systemic administration include, but are not limited to, intravenous administration, oral administration, enteral administration, parenteral administration, intranasal administration, inhalational administration, intratracheal administration, rectal administration, sublingual administration, buccal administration, vaginal administration, intraperitoneal administration, transdermal, transmucosal, or intramuscular administration.

In some embodiments, the systemic administration comprises intravenous administration. In some embodiments, intravenous administration comprises systemic intravenous (IV) injection. In certain embodiments, the IV comprises bolus injection, a continuous drip, or a pump injection. In some embodiments, systemic intravenous injection comprises use of a standard IV line or a central line. In certain embodiments, the standard IV line is placed in a vein in the wrist, arm, or hand. In certain embodiments, the central line is selected from the group consisting of a peripherally inserted central catheter (PICC), a subclavian line, an internal jugular line, a femoral line, a tunneled catheter, or an implanted port. In particular embodiments, a patient with expected long-term therapy, i.e., long-term hospitalization, e.g., a patient with COVID-19, is placed on a central line for systemic intravenous injection.

In some embodiments, administration is local, for example, to the lung. For example, the administration is inhalational via the nose and/or mouth. For example, the administration is intratracheal. In a patient with COVID-19, for example, intratracheal administration or inhalational administration by the nose and/or mouth may be used.

Inhalational administration may be mediated through an oral and/or nasal cavity. In certain embodiments, inhalation is facilitated through an aerosol administration of a pharmaceutical composition comprising MBV. In some embodiments, inhalation comprises the aid of a nebulizer or an inhaler (e.g., a metered dose inhaler or a dry powder inhaler). In some embodiments, administration comprises inhalation of a liquid mist. In some embodiments, administration is through inhalation of a solid form. In certain embodiments, the solid is nanosized and formulated in combination with nanoparticles, nanodiamonds, or nanocarbons, or packaged in liposomes or liposome-based packages. In some embodiments, the systemic administration comprises endotracheal administration, also known as intratracheal instillation. In certain embodiments, systemic administration of MBV comprises administration via an endotracheal tube for rapid administration to the lungs of a subject in need thereof, e.g., a subject with severe ARDS, e.g., a subject with severe ARDS associated with COVID-19.

For administration by inhalation, the MBV can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch. Inhalational preparations can include aerosols, particulates, and the like. In general, the goal for particle size for inhalation is about 1 μm or less in order that the pharmaceutical reach the alveolar region of the lung for absorption. However, the particle size can be modified to adjust the region of disposition in the lung. Thus, larger particles can be utilized (such as about 1 to about 5 μm in diameter) to achieve deposition in the respiratory bronchioles and air spaces.

Pharmaceutical compositions comprising MBV as described herein as an active ingredient will normally be formulated with an appropriate solid or liquid carrier, depending upon the particular mode of administration chosen. For example, pharmaceutically and physiologically acceptable fluid vehicles such as water, physiological saline, other balanced salt solutions, aqueous dextrose, glycerol or the like can be used for injectable formulations, or for nebulized or aerosolized formulations. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

The pharmaceutical compositions that comprise MBV, in some embodiments, will be formulated in unit dosage form, suitable for individual administration of precise dosages. The amount of active compound(s) administered will be dependent on the subject being treated, the severity of the disease, and the manner of administration, and is best left to the judgment of the prescribing clinician. Within these bounds, the formulation to be administered will contain a quantity of the active component(s) in amounts effective to achieve the desired effect in the subject being treated.

By way of example, one method of administration to the lungs of an individual is by inhalation through the use of a nebulizer or inhaler. For example, the MBV is formulated in an aerosol or particulate and drawn into the lungs using a standard nebulizer well known to those skilled in the art.

Dosage treatment may be a single dose schedule or a multiple dose schedule to ultimately deliver $1\times10^6$ to $1\times10^{12}$ MBV (i.e., an absolute number of vesicles) per kg body weight per administration. Administration may be provided as a single administration, a periodic bolus or as continuous infusion, such as by continuous release for a specific period from a sustained-release drug or drug delivery device. The subject may be administered as many doses as appropriate. If multiple doses are administered, administration can be intermittent. In example embodiments, administration (such as systemic administration, for example, intravenous administration, or any other route of administration) of a therapeutically effective amount of MBV can be performed once, or can be performed repeatedly, such as 1, 2, 3, 4, 5, 6, 7, 8, 9, or 10 times. In example embodiments, administration can be performed once daily, twice daily, every other day until symptoms of ARDS subside. In other embodiments, only a single administration is required to achieve therapeutic benefit.

Individual doses are typically not less than an amount required to produce a measurable effect on the subject, and may be determined based on the pharmacokinetics and pharmacology for absorption, distribution, metabolism, and excretion ("ADME") of the subject composition or its by-products and, thus, based on the disposition of the composition within the subject. This includes consideration of the route of administration as well as dosage amount, which can be adjusted for local and systemic (for example, intravenous) applications. Effective amounts of dose and/or dose regimen can readily be determined empirically from preclinical assays, from safety and escalation and dose range trials, individual clinician-patient relationships, as well as in vitro and in vivo assays. Generally, these assays will evaluate the inflammatory disorder (such as encephalitis or atopic dermatitis).

A therapeutically effective amount of MBV can be suspended in a pharmaceutically acceptable carrier (such as in a pharmaceutical preparation), for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. Other agents can be added to the compositions, such as preservatives and anti-bacterial agents. These compositions can be administered locally or systemically, such as intravenously.

Pharmaceutical preparations that include a therapeutically effective amount of MBV can be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated. In some embodiments, treatment with the MBV results in a decrease or a reduction in a sign or symptom of an acute respiratory distress syndrome (ARDS) present at the time of administration.

In some examples, treatment with the MBV can result in a decrease or a reduction in inflammation in a subject over the level of inflammation prior to administration of the MBV. In some examples, treatment with MBV can result in a reduction or elimination of signs or symptoms of an ARDS, e.g., ARDS associated with a viral infection, e.g., COVID-19.

Combination Therapies

Methods of MBV treatment of the present invention can be used as a monotherapy or in combination with one or more other therapies (e.g., anti-infective agents, such as anti-viral agents) that can be used to treat a disease or disorder, for example, acute respiratory distress syndrome (ARDS) or an infection associated with ARDS. The term "combination," as used herein, is understood to mean that two or more different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In certain embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

The subject can be administered additional therapeutic agents, in the same or different composition or pharmaceutical preparation. In some embodiments, the subject has ARDS and the subject is administered additional therapeutic agents, such as anti-inflammatories, such as nonsteroidal anti-inflammatory drugs (NSAIDs, for example, aspirin, ibuprofen, and naproxen), antileukotrienes, immune selective anti-inflammatory derivatives (ImSAIDs), bioactive compounds, steroids (such as corticosteroids), and opioids.

Accordingly, in certain embodiments, the subject has received, is receiving, or is scheduled to receive one or more other therapies suitable for use in treating the disease or disorder. In certain embodiments, the method of treatment of the present invention further comprises administering to the subject one or more other therapies suitable for use in treating a disease or disorder, for example, an infection. In certain embodiments, the one or more other therapies comprise an agent that ameliorates one or more symptoms of infection with an intracellular pathogen. In certain embodiments, the one or more other therapies comprise surgical removal of an infected tissue.

It is understood that a method of use disclosed herein can be used in combination with an agent, for example, an anti-infective agent that ameliorates one or more symptoms of a disease or disorder associated with an intracellular pathogen. For example, a method of use disclosed herein can be used in combination with an antiviral agent.

Therapies suitable for treating infections by intracellular pathogens are generally known in the art and are reviewed, for example, by Kamaruzzaman et al. (2017) Br. J. Pharmacol. 174(14): 2225-36 and De Clercq et al. (2016) Clin. Microbiol. Rev. 29(3): 695-747. In certain embodiments, the anti-infective agent inhibits or reduces the viability, proliferation, infectivity, and/or virulence of the intracellular pathogen. Intracellular pathogens may evade immune surveillance and challenge by residing in a latent state. Accordingly, in certain embodiments, the anti-infective agent reverses the latency of the intracellular pathogen such that the infection can be recognized by the host's immune system.

In certain embodiments, the intracellular pathogen is a virus, and the anti-infective agent is an antiviral agent. Exemplary antiviral agents that can be used in the combination include but are not limited to abacavir, acyclovir, adefovir, amprenavir, atazanavir, cidofovir, darunavir, delavirdine, didanosine, docosanol, efavirenz, elvitegravir, emtricitabine, enfuvirtide, entecavir, etravirine, famciclovir, favipiravir, foscarnet, fomivirsen, ganciclovir, indinavir, idoxuridine, lamivudine, lopinavir, maraviroc, MK-2048, nelfinavir, nevirapine, penciclovir, raltegravir, rilpivirine, ritonavir, saquinavir, stavudine, tenofovir trifluridine, valaciclovir, valganciclovir, vidarabine, ibacitabine, amantadine, oseltamivir, rimantidine, tipranavir, zalcitabine, zanamivir, peramivir, danoprevir, remdesivir, and zidovudine. In particular, where the intracellular pathogen is an HIV, exemplary anti-HIV agents that can be used in the combination include, but are not limited to, nucleoside/nucleotide reverse transcriptase inhibitors (e.g., lamivudine, abacavir, zidovudine, stavudine, didanosine, emtricitabine, and tenofovir), non-nucleoside reverse transcriptase inhibitors (e.g., delavirdine, efavirenz, etravirine, and nevirapine), protease inhibitors (e.g., amprenavir, fosamprenavir, atazanavir, darunavir, indinavir, lopinavir, ritonavir, nelfinavir, saquinavir, and tipranavir), fusion or entry inhibitors (e.g., enfuvirtide and maraviroc), integrase inhibitors (e.g., raltegravir and cabotegravir), and latency-reversing agents (e.g., HDAC inhibitors (e.g., vorinostat) and TLR7 agonists (e.g., GS-9620, e.g., as described in U.S. Patent Publication No. US20160008374A1)). In certain embodiments, the virus is SARS-CoV2, and the combination therapy comprises hydroxychloroquine. In certain embodiments, the virus is SARS-CoV2, and the combination therapy comprises an antiviral agent. In certain embodiments, the virus is SARS-CoV2, and the combination therapy comprises an anti-bacterial agent as a prophylactic treatment against secondary infection.

In certain embodiments, the intracellular pathogen is a bacterium, and the anti-infective agent is an anti-bacterial agent. Exemplary anti-bacterial agents that can be used in the combination include but are not limited to azithromycin, vancomycin, metronidazole, gentamicin, colistin, fidaxomicin, telavancin, oritavancin, dalbavancin, daptomycin, cephalexin, cefuroxime, cefadroxil, cefazolin, cephalothin, cefaclor, cefamandole, cefoxitin, cefprozil, ceftobiprole, cipro, Levaquin, floxin, tequin, avelox, norflox, tetracycline, minocycline, oxytetracycline, doxycycline, amoxicillin, ampicillin, penicillin V, dicloxacillin, carbenicillin, methicillin, ertapenem, doripenem, imipenem/cilastatin, meropenem, amikacin, kanamycin, neomycin, netilmicin, tobramycin, paromomycin, cefixime, cefdinir, cefditoren, cefoperazone, cefotaxime, ceftazidime, ceftibuten, ceftizoxime, ceftriaxone, cefoxotin, and streptomycin.

In certain embodiments, the intracellular pathogen is a fungus, and the anti-infective agent is an anti-fungal agent. Exemplary anti-fungal agents that can be used in the combination include but are not limited to natamycin, rimocidin, filipin, nystatin, amphotericin B, candicin, and hamycin, miconazole, ketoconazole, clotrimazole, econazole, omoconazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole, terconazole, and albaconazole, abafungin, terbinafine, naftifine, butenafine, anidulafungin, caspofungin, micafungin, polygodial, benzoic acid, ciclopirox, tolnaftate, undecylenic acid, flucytosine or 5-fluorocytosine, griseofulvin, and haloprogin.

In certain embodiments, the intracellular pathogen is a protozoan, and the anti-infective agent is an anti-protozoal agent. Exemplary anti-protozoal agents that can be used in the combination include but are not limited to quinine (optionally in combination with clindamycin), chloroquine, amodiaquine, artemisinin and its derivatives (e.g., artemether, artesunate, dihydroartemisinin, arteether), doxycycline, pyrimethamine, mefloquine, halofantrine, hydroxychloroquine, eflornithine, nitazoxanide, ornidazole, paromomycin, pentamidine, primaquine, pyrimethamine, proguanil (optionally in combination with atovaquone), sulfonamides (e.g., sulfadoxine, sulfamethoxypyridazine), tafenoquine, and tinidazole. In specific embodiments, the intracellular pathogen is a *Plasmodium* (e.g., *P. vivax, P. falciparum, P. ovale, P. malariae*), and the anti-infective agent is an anti-malarial agent. Exemplary anti-malarial agents that can be used in the combination include but are not limited to quinine (optionally in combination with clindamycin), chloroquine, amodiaquine, artemisinin and its derivatives (e.g., artemether, artesunate, dihydroartemisinin, arteether), doxycycline, halofantrine, mefloquine, primaquine, proguanil (optionally in combination with atovaquone), sulfonamides (e.g., sulfadoxine, sulfamethoxypyridazine), tafenoquine. These anti-malarial agents may be used in combination with MBV for treating ARDS.

An additional class of agents that may be used as part of a combination therapy in treating ARDS or a hypercytokinemia associated with ARDS are anti-inflammatory and/or immunosuppressive agents, e.g., cytokine inhibitors, calcineurin inhibitors, mTOR inhibitors, or steroids: In some embodiments, the anti-inflammatory agents comprise calcineurin inhibitors, e.g., tacrolimus and cyclosporine. In some embodiments, the anti-inflammatory agents comprise mTOR inhibitors, e.g., sirolimus. In some embodiments, the anti-inflammatory agents comprise steroids, e.g., prednisone. In some embodiments, anti-inflammatory agents comprise cytokine inhibitors, e.g., an IL-6 antagonist, an IL-1 antagonist, a soluble tumor necrosis factor receptor, an IL-1 receptor agonist, and a TGF-β1 latency-associated peptide. In certain embodiments, the cytokine inhibitor comprises tocilizumab, sarilumab, anakinra, or siltuximab. In certain embodiments, the anti-inflammatory agents comprise a Janus kinase (JAK) inhibitor, e.g., tofacitinib, ruxolitinib, or baricitinib.

Appropriate therapies can be selected according to diagnosis of the specific infection. Wherein the subject is infected with a plurality of pathogens (e.g., a plurality of intracellular pathogens, e.g., a plurality of viral infections, e.g., SARS-CoV2 and a secondary infection), two or more appropriate therapies for treating these infections may be used in combination with an MBV therapy disclosed herein.

In one embodiment, the compositions of the invention are used as part of a combination therapy with antibody therapies against SARS-CoV2, for example, bamlanivimab, etesevimab, casirivimab, or imdevimab, or combinations thereof.

In some embodiments, the method comprises the step of detecting that a therapeutic benefit has been achieved. Measures of therapeutic efficacy will be applicable to the particular disease being modified, and a person of skill in the art will recognize the appropriate detection methods to use to measure therapeutic efficacy. The subject can be evaluated for response using any methods known in the art. In example embodiments, the subject has an inflammatory disorder (such as encephalitis or atopic dermatitis), and the therapeutic response in a subject can be measured by white blood cell count, number of polymorphonuclear neutrophils (PMN), degree of PMN activation (such as luminol enhanced-chemiluminescence), amount of cytokines, C-reactive protein, and other measures known in the art.

Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Dates of GENBANK® Accession Nos. referred to herein are the sequences available at least as early as Sep. 16, 2015. All references, patent applications and publications, and GENBANK® Accession numbers cited herein are incorporated by reference. Unless otherwise indicated, "about" indicates within five percent. In order to facilitate review of the various embodiments of the disclosure, the following explanations of specific terms are provided:

Acute Respiratory Distress Syndrome: Acute Respiratory Distress Syndrome, or "ARDS", refers to a type of respiratory failure characterized by rapid onset of widespread inflammation in the lungs, with severe hypoxemia being a hallmark symptom. The signs and symptoms usually being within a few hours of an inciting event, but can occur within a few days or up to a week. In ARDS, fluid leaks from the smallest blood vessels in the lungs into the alveoli of the lungs. In normal physiology, the alveolar-capillary membrane protects the lungs from such fluid. However, in cases of severe pulmonary and/or systemic damage to the alveolar-capillary membrane, the membrane may become compromised, leading to ARDS. In certain embodiments, ARDS is associated with a pulmonary infection.

Symptoms of ARDS may include, without limitation, shortness of breath, rapid breathing, decreased blood oxygenation, headache, low blood pressure, fever, coughing, confusion, extreme fatigue, and discolored skin and/or nails due to hypoxemia. ARDS impairs the ability of the lungs to exchange oxygen and carbon dioxide. Chest radiography of patients with ARDS reveals bilateral infiltrates in the lung, for example, with widespread "ground-glass" appearing opacities in both lungs. From a diagnostic standpoint, according to Berlin criteria ARDS is diagnosed when the $PaO_2/FiO_2$ (ratio of partial pressure of arterial oxygen and fraction of inspired oxygen) is less than 300 mm Hg despite a positive end-expiratory pressure (PEEP) of more than 5 cm $H_2O$. In mild cases, the $PaO_2/FiO_2$ is greater than 200 mg Hg and less than 300 mg. In moderate cases, the $PaO_2/FiO_2$ is greater than 100 mg Hg and less than 200 mg. In severe cases, the $PaO_2/FiO_2$ is less than 100 mm Hg. Primary treatment involves administration of oxygen and/or mechanical ventilation.

Administration: The introduction of a composition (such as MBV or a pharmaceutical preparation that includes MBV) into a subject by a chosen route. The route can be local or systemic. For example, if the chosen route is intravenous, the composition is administered by introducing the composition into a vein of the subject. If the chosen route is local, the composition can be administered by introducing the composition directly into a tissue of the subject.

Animal: Living multi-cellular vertebrate organisms, a category that includes, for example, mammals and birds. The term "mammal" includes both human and non-human mammals. Similarly, the term "subject" includes both human and veterinary subjects.

Arthritis: Arthritis is an inflammatory disease that affects the synovial membranes of one or more joints in the body. It is the most common type of joint disease and is characterized by inflammation of the joint. The disease is usually oligoarticular (affects few joints), but may be generalized. The joints commonly involved include the hips, knees, lower lumbar and cervical vertebrae, proximal and distal interphalangeal joints of the fingers, first carpometacarpal joints, and first tarsometatarsal joints of the feet. Symptoms include joint pain and stiffness, redness, warmth, swelling, and decreased range of motion of the affected joints. In some embodiments, the compositions and methods disclosed herein can be used to treat arthritis. Types of arthritis include, without limitation, rheumatoid arthritis and psoriatic arthritis.

Biocompatible: Any material, that, when implanted in a mammalian subject, does not provoke an adverse response in the subject. A biocompatible material, when introduced into an individual, is able to perform its' intended function, and is not toxic or injurious to that individual, nor does it induce immunological rejection of the material in the subject.

Enriched: A process whereby a component of interest, such as a nanovesicle, that is in a mixture has an increased ratio of the amount of that component to the amount of other undesired components in that mixture after the enriching process as compared to before the enriching process.

Extracellular matrix (ECM): A complex mixture of structural and functional biomolecules and/or biomacromolecules including, but not limited to, structural proteins, specialized proteins, proteoglycans, glycosaminoglycans, and growth factors that surround and support cells within tissues and, unless otherwise indicated, is acellular. ECM preparations can be considered to be "decellularized" or "acellular", meaning the cells have been removed from the source tissue through processes described herein and known in the art. By "ECM-derived material," such as an "ECM-derived nanovesicle," "Matrix bound nanovesicle," "MBV" or "nanovesicle derived from an ECM" it is a nanovesicle that is prepared from a natural ECM or from an in vitro source wherein the ECM is produced by cultured cells. ECM-derived nanovesicles are defined below.

Hypercytokinemia or "cytokine release syndrome:" An acute overreaction of the immune system also known in the art as a "cytokine storm" or "cytokine storm syndrome"; such an immune response is a systemic inflammatory response syndrome that can result from an infectious disease or disorder. Hypercytokinemia occurs when large numbers of white blood cells are activated and release inflammatory cytokines, which in turn activate yet more white blood cells in a positive feedback loop of pathogenic inflammation. In addition, pro-inflammatory cytokines binding their cognate receptor on immune cells results in activation and stimulation of further cytokine production. Hypercytokinemia pathology is associated with inflammation that begins at a local site and spreads throughout the body, for example, via systemic circulation, and can lead to multi-organ failure. Hypercytokinemia pathology resulting from viral infection is associated with acute lung injury and acute respiratory distress syndrome. Hypercytokinemia pathology is described, for example, in Tisonick et al., (2012) "Into the Eye of the Cytokine Storm," Microbiol. Mol. Biol. Rev., 76(1):16-32. Cytokines released in excess may include, but are not limited to, for example, IL-6, IFN-γ, IL-8 (CXCL8), IL-10, GM-CSF, MIP-1α/β, MCP-1 (CCL2), CXCL9, and CXCL10.

Infection: refers to the invasion and proliferation of pathogens, e.g., viruses, bacteria, fungi, or protozoa that are not normally present within the host, e.g., a patient, or that are not normally present at a particular location in the host invade another location in the host, (e.g., when a pathogen normally present in the digestive tract enters the urinary tract, or a pathogen normally present on the skin enters the blood stream). An infection may cause no symptoms and be subclinical, or it may cause symptoms and be clinically apparent. An infection may remain localized, or it may spread, for example, through the blood or lymphatic vessels, to become systemic.

Inflammation: Inflammation is a localized protective response elicited by injury to tissue that serves to sequester the inflammatory agent. Inflammation is orchestrated by a complex biological response of vascular tissues to harmful stimuli, such as pathogens, damaged cells, or irritants. It is a protective attempt by the organism to remove the injurious stimuli as well as initiate the healing process for the tissue. An inflammatory response is characterized by an accumulation of white blood cells, either systemically or locally at the site of inflammation. The inflammatory response may be measured by many methods, including, but not limited to measuring the number of white blood cells, the number of polymorphonuclear neutrophils (PMN), a measure of the degree of PMN activation, such as luminol enhanced-chemiluminescence, or a measure of the amount of cytokines present. C-reactive protein is a marker of a systemic inflammatory response.

An inflammatory disorder is a genus of disorders in which inflammation disrupts normal or regular physiological function. Inflammatory disorders can include a variety of conditions, such as autoimmune disorders (an inappropriate inflammatory response to an endogenous antigen), and disorders caused by inflammation due to traumatic injury or exogenous antigens. A primary inflammatory disorder is a disease or disorder that is caused by inflammation itself. A secondary inflammatory disorder is inflammation that is the result of another disorder. Inflammation can lead to inflammatory disorders, e.g., acute respiratory distress syndrome (ARDS).

In some embodiments, anti-inflammatories are administered to treat an inflammatory disease or disorder, e.g., ARDS. Anti-inflammatories include, without limitation, nonsteroidal anti-inflammatory drugs (NSAIDs, for example, aspirin, ibuprofen, and naproxen), antileukotrienes, immune selective anti-inflammatory derivatives (ImSAIDs), bioactive compounds, steroids (such as corticosteroids), and opioids.

Influenza: Influenza (also known as "flu") is an infectious disease caused by an influenza virus. Influenza viruses of three types may infect humans: Type A, Type B, and Type C; type D has not been shown to infect humans. The influenza virus is highly contagious; in a non-limiting example, the influenza virus is spread through the air in droplets from coughs or sneezes of an infected individual. Influenza spreads globally in yearly outbreaks, resulting in in about three to five million cases of severe illness and about 290,000 to 650,000 deaths ("Influenza (Seasonal)". World Health Organization (WHO). 6 Nov. 2018). Yearly vaccinations against influenza are recommended by the World Health Organization (WHO) for those at high risk. Larger, global outbreaks of virulent influenza strains may occur, e.g. Spanish influenza in 1918 (resulting in 17-100 million deaths), Asian influenza in 1957 (resulting in two million deaths), and Hong Kong influenza in 1968 (resulting in one million deaths). In June 2009, the WHO declared an outbreak of a new type of influenza A, H1N1, (also known as "swine flu") to be a pandemic (Chan M. (2009). "World now at the start of 2009 influenza pandemic". World Health Organization (WHO). Archived from the original on 12 Jun. 2009). Symptoms of influenza infection comprise, without limitation, fever, runny nose, sore throat, muscle and joint pain, headache, coughing, and fatigue. In certain embodiments, influenza is associated with viral pneumonia. In certain embodiments, influenza is associated with secondary bacterial pneumonia.

Isolated: An "isolated" biological component (such as a nucleic acid, protein cell, or nanovesicle) has been substantially separated or purified away from other biological components in the cell of the organism or the ECM, in which the component naturally occurs. Nucleic acids and proteins that have been "isolated" include nucleic acids and proteins purified by standard purification methods. MBV that have been isolated are removed from the fibrous materials of the ECM. The term also embraces nucleic acids and proteins prepared by recombinant expression in a host cell as well as chemically synthesized nucleic acids.

Lysyl oxidase (Lox): A copper-dependent enzyme that catalyzes formation of aldehydes from lysine residues in collagen and elastin precursors. These aldehydes are highly reactive, and undergo spontaneous chemical reactions with other lysyl oxidase-derived aldehyde residues, or with unmodified lysine residues. In vivo, this results in cross-linking of collagen and elastin, which plays a role in stabilization of collagen fibrils and for the integrity and elasticity of mature elastin. Complex cross-links are formed in collagen (pyridinolines derived from three lysine residues) and in elastin (desmosines derived from four lysine residues) that differ in structure. The genes encoding Lox enzymes have been cloned from a variety of organisms (Hamalainen et al., Genomics 11:508, 1991; Trackman et al., Biochemistry 29:4863, 1990; incorporated herein by reference). Residues 153-417 and residues 201-417 of the sequence of human lysyl oxidase have been shown to be important for catalytic function. There are four Lox-like isoforms, called LoxL1, LoxL2, LoxL3 and LoxL4.

Macrophage: A type of white blood cell that phagocytoses and degrades cellular debris, foreign substances, microbes, and cancer cells. In addition to their role in phagocytosis, these cells play an important role in development, tissue maintenance and repair, and in both innate and adaptive immunity in that they recruit and influence other cells including immune cells such as lymphocytes. Macrophages can exist in many phenotypes, including phenotypes that have been referred to as M1 and M2. Macrophages that perform primarily pro-inflammatory functions are called M1 macrophages (CD86+/CD68+), whereas macrophages that decrease inflammation and encourage and regulate tissue repair are called M2 macrophages (CD206+/CD68+). The markers that identify the various phenotypes of macrophages vary among species. It should be noted that macrophage phenotype is represented by a spectrum that ranges between the extremes of M1 and M2. F4/80 (encoded by the adhesion G protein coupled receptor E1 (ADGRE1) gene) is a macrophage marker, see GENBANK® Accession No. NP_001243181.1, Apr. 6, 2018 and NP_001965, Mar. 5, 2018, both incorporated herein by reference. Without wishing to be bound by theory, it is believed that MBV have the ability to modulate the phenotype of macrophages, leading to an increase in M2-like, regulatory, or pro-remodeling macrophages. The effect of MBV on macrophages is further characterized in WO 2017/151862A1, incorporated herein by reference in its entirety. In some embodiments, MBV of the present invention can be used to induce an M2 phenotype in macrophages and inhibit M1 macrophages in a subject.

MicroRNA: A small non-coding RNA that is about 17 to about 25 nucleotide bases in length, that post-transcriptionally regulates gene expression by typically repressing target mRNA translation. A miRNA can function as negative regulators, such that greater amounts of a specific miRNA will correlates with lower levels of target gene expression. There are three forms of miRNAs, primary miRNAs (pri-miRNAs), premature miRNAs (pre-miRNAs), and mature miRNAs. Primary miRNAs (pri-miRNAs) are expressed as stem-loop structured transcripts of about a few hundred bases to over 1 kb. The pri-miRNA transcripts are cleaved in the nucleus by an RNase II endonuclease called Drosha that cleaves both strands of the stem near the base of the stem loop. Drosha cleaves the RNA duplex with staggered cuts, leaving a 5' phosphate and 2 nucleotide overhang at the 3' end. The cleavage product, the premature miRNA (pre-miRNA) is about 60 to about 110 nucleotides long with a hairpin structure formed in a fold-back manner. Pre-miRNA is transported from the nucleus to the cytoplasm by Ran-GTP and Exportin-5. Pre-miRNAs are processed further in the cytoplasm by another RNase II endonuclease called Dicer. Dicer recognizes the 5' phosphate and 3' overhang, and cleaves the loop off at the stem-loop junction to form miRNA duplexes. The miRNA duplex binds to the RNA-induced silencing complex (RISC), where the antisense strand is preferentially degraded and the sense strand mature miRNA directs RISC to its target site. It is the mature miRNA that is the biologically active form of the miRNA and is about 17 to about 25 nucleotides in length.

Nanovesicle: An extracellular vesicle that is a nanoparticle of about 10 to about 1,000 nm in diameter. Nanovesicles are lipid membrane bound particles that carry biologically active signaling molecules (e.g. microRNAs, proteins) among other molecules. Generally, the nanovesicle is limited by a lipid bilayer, and the biological molecules are enclosed and/or can be embedded in the bilayer. Thus, a nanovesicle includes a lumen surrounded by plasma membrane. The different types of vesicles can be distinguished based on diameter, subcellular origin, density, shape, sedimentation rate, lipid composition, protein markers, nucleic acid content and origin, such as from the extracellular matrix or secreted. A nanovesicle can be identified by its origin, such as a matrix bound nanovesicle from an ECM (see above), protein content and/or the miR content.

An "exosome" or "liquid phase extracellular vesicle (EV)" is a membranous vesicle which is secreted by a cell, and ranges in diameter from 10 to 150 nm. Generally, late endosomes or multivesicular bodies contain intralumenal vesicles which are formed by the inward budding and scission of vesicles from the limited endosomal membrane into these enclosed vesicles. These intralumenal vesicles are then released from the multivesicular body lumen into the extracellular environment, typically into a body fluid such as blood, cerebrospinal fluid or saliva, during exocytosis upon fusion with the plasma membrane. An exosome is created intracellularly when a segment of membrane invaginates and is endocytosed. The internalized segments which are broken into smaller vesicles and ultimately expelled from the cell contain proteins and RNA molecules such as mRNA and miRNA. Plasma-derived exosomes largely lack ribosomal RNA. Extra-cellular matrix derived exosomes include specific miRNA and protein components, and have been shown to be present in virtually every body fluid such as blood, urine, saliva, semen, and cerebrospinal fluid. Exosomes can express CD11c, CD63, CD81, and/or CD9, and thus can be $CD11c^+$ and/or $CD63^+$ and/or $C81^+$ and/or $CD9^+$. Exosomes do not have high levels of lysyl oxidase on their surface.

A "nanovesicle derived from an ECM," "matrix bound nanovesicle," "MBV" or an "ECM-derived nanovesicle" all refer to the same membrane bound particles, ranging in size from 10 nm-1000 nm, present in the extracellular matrix, which contain biologically active signaling molecules such as protein, lipids, nucleic acid, growth factors and cytokines that influence cell behavior. The terms are interchangeable, and refer to the same vesicles. These nanovesicles are embedded within, and bound to, the ECM and are not simply attached to the surface or circulating freely in body fluids. These nanovesicles are resistant to harsh isolation conditions, such as freeze-thawing and digestion with proteases such as pepsin, elastase, hyaluronidase, proteinase K, and collagenase, and digestion with detergents. MBV are distinct from other extracellular vesicles including exosomes and have a phospholipid composition distinct from exosomes. In certain circumstances, MBV can also be distinguished from exosomes based on the absence of certain markers commonly attributed to exosomes. They are also distinct from bone matrix vesicles involved in generation and mineralization of bone which express alkaline phosphatase. MBV do not express alkaline phosphatase.

Figure 24:
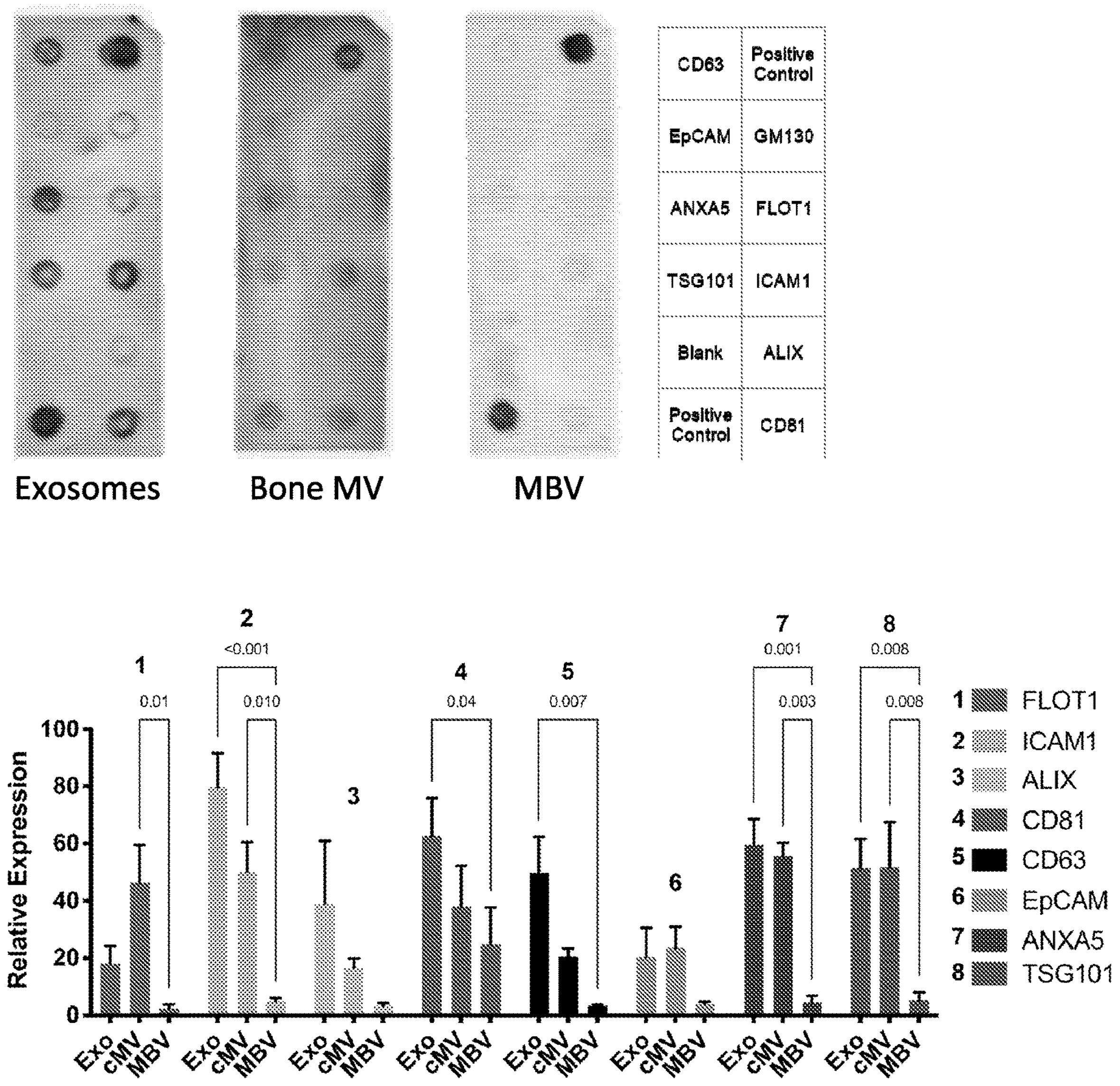
FIG. 24 shows the results of EXO-CHECK™ Exosome Antibody Arrays (System Biosciences) comparing levels of the various markers noted in murine exosomes, murine bone matrix vesicles (bone MV), and murine matrix bound nanovesicles (MBV). The upper panel provides digital images of the arrays and the lower panel is a graph showing the relative expression of each of the noted markers in the exosomes verses bone MV verses MBV.

In some embodiments, MBV are characterized by one or more of the following features of protein expression or lipid content:

(i) MBV may not express one or more of CD63 and/or CD81 and/or CD9 or have low or barely detectable levels of CD63 and/or CD81 and/or CD9 ($CD63^{lo}$ and/or $CD81^{lo}$ and/or $CD9^{lo}$)(see, e.g., Example 1) compared with other vesicles, such as exosomes. (See also Example 17 and FIG. 24). A variety of methods can be used to distinguish low, barely detectable, or absent expression of CD63 and/or CD81 and/or CD9 in MBV, for example, antibody-based methods, such as western blotting or flow cytometry (see, e.g., Bashashati and Brinkman, *Adv Bioinformatics,* 2009: 584603). In some embodiments, MBV expression of CD63 and/or CD81 and/or CD9 is considered low or barely detectable compared with other vesicles where the expression of CD63 and/or CD81 and/or CD9 in MBV is at least one standard deviation or at least two standard deviations below the mean expression of other vesicles, such as exosomes;

(ii) MBV have a phospholipid content wherein at least 55% of total phospholipids comprise phosphatidylcholine (PC) and phosphatidyl inositol (PI) in combination;

(iii) MBV have a phospholipid content wherein 10% or less of total phospholipids comprise sphingomyelin (SM);

(iv) MBV have a phospholipid content wherein 20% or less of total phospholipids comprise phosphatidylethanolamine (PE);

(v) MBV have a phospholipid content wherein 15% or greater of the total phospholipid content comprises phosphatidylinositol (PI) with the percent representing the percent of lipid concentration.

In some embodiments, MBV are characterized by all of the following features:

(i) do not express one or more of CD63 and/or CD81 and/or CD9 or have low or barely detectable levels of CD63 and/or CD81 and/or CD9 ($CD63^{lo}$ and/or $CD81^{lo}$ and/or $CD9^{lo}$)(as further described above);

(ii) a phospholipid content wherein at least 55% of total phospholipids comprise phosphatidylcholine (PC) and phosphatidyl inositol (PI) in combination;

(iii) a phospholipid content wherein 10% or less of total phospholipids comprise sphingomyelin (SM);

(iv) a phospholipid content wherein 20% or less of total phospholipids comprise phosphatidylethanolamine (PE); and (v) a phospholipid content wherein 15% or greater of the total phospholipid content is phosphatidylinositol (PI).

In some embodiments, MBV are characterized by all of the following features:

(i) a phospholipid content wherein at least 55% of total phospholipids comprise phosphatidylcholine (PC) and phosphatidyl inositol (PI) in combination;

(ii) a phospholipid content wherein 10% or less of total phospholipids comprise sphingomyelin (SM);

(iii) a phospholipid content wherein 20% or less of total phospholipids comprise phosphatidylethanolamine (PE); and (iv) a phospholipid content wherein 15% or greater of the total phospholipid content is phosphatidylinositol (PI).

In some embodiments, MBV are characterized by one or more of the following features:

(i) a phospholipid content wherein at least 55% of total phospholipids comprise phosphatidylcholine (PC) and phosphatidyl inositol (PI) in combination;

(ii) a phospholipid content wherein 10% or less of total phospholipids comprise sphingomyelin (SM);

(iii) a phospholipid content wherein 20% or less of total phospholipids comprise phosphatidylethanolamine (PE); and (iv) a phospholipid content wherein 15% or greater of the total phospholipid content is phosphatidylinositol (PI).

The ECM from which MBV are isolated can be an ECM from a tissue, can be produced from cells in culture, or can be purchased from a commercial source.

In some embodiments, MBV are characterized by one or more of the following features:

(i) do not contain detectable levels of alkaline phosphatase;

(ii) do not contain detectable levels of osteopontin;

(iii) do not contain detectable levels of osteoprogeterin;

(iv) do not contain detectable levels of complement C5; and/or (v) do not contain detectable levels of c-reactive protein.

In some embodiments, MBV are characterized by one or more of the following features:

(i) contain low or do not contain detectable levels of EpCAM, (ii) contain low or do not contain detectable levels of ANXA5, (iii) contain low or do not contain detectable levels of TSG101;

(iv) contain low or do not contain detectable levels of FLOT1;

(v) contain low or do not contain detectable levels of ICAM1;

(vi) contain low or do not contain detectable levels of GM130; and/or (vii) contain low or do not contain detectable levels of ALIX.

In one embodiment, MBV are characterized by low or undetectable levels of ANXA5, TSG101, and ICAM1.

In one embodiment, MBV are characterized by low or undetectable levels of CD81, CD63, ANXA5, TSG101, and ICAM1.

Oxygen Saturation Index (OSI): Oxygen saturation index is a non-invasive surrogate for Oxygen Index (01) which is calculated using specific oxygen levels ($SpO_2$). OSI=($FiO_2$× mean airway pressure×100)/$SpO_2$. $SpO_2$ (oxygen saturation) can be measured non-invasively, for example, by pulse oximetry and is a measure of the fraction of oxygen-saturated hemoglobin to total hemoglobin (unsaturated and saturated) in the blood.

Oxygen Index (OI): Oxygen Index=($FiO_2$×mean airway pressure×100)/$PaO_2$, and unlike OSI, requires an arterial blood gas measurement, which is invasive.

Pharmaceutically acceptable carriers: The pharmaceutically acceptable carriers useful in the claimed pharmaceutical preparations are conventional. *Remington's Pharmaceutical Sciences*, by E. W. Martin, Mack Publishing Co., Easton, PA, 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically-neutral carriers, pharmaceutical preparations to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject or a cell.

Phospholipid: A class of lipids having a structure consisting of two hydrophobic fatty acid tails and a hydrophilic head consisting of a phosphate group. Major classes of phospholipids include phosphatidylcholine (PC), phosphatidylethanolamine (PE), phosphatidylinositol (PI), phosphatidylserine (PS), phosphatidylglycerol (PG), sphingomyelin (SM), cardiolipin (CL), phosphatidic acid (PA), and bismonoacylglycerophosphate (BMP). Phospholipids can be measured in a variety of ways. For example, LC-MS based global lipidomics and redox lipidomics can be used. In some embodiments, specific phospholipid content is indicated as the percent concentration of the total phospholipids (such as total phospholipids in MBV), where the percent concentration is weight/weight.

Pneumonia: An infection that inflames the alveoli (air sacs) in one or both lungs. In some embodiments, the lungs fill with fluid or pus. In some embodiments, pneumonia is associated with a viral infection, e.g., a coronavirus (e.g., SARS-CoV2, SARS-CoV, MERS-CoV), e.g., an influenza virus (e.g., influenza A), e.g., an ebolavirus. In some embodiments, pneumonia is associated with a bacterial infection, e.g., *Streptococcus pneuroniae*. In some embodiments, pneumonia is associated with a fungal infection, e.g., *Pneunocystis jirovecii*. In some embodiments, pneumonia is a secondary infection, i.e., a patient with an existing infection (e.g., COVID-19), develops pneumonia. In some embodiments, pneumonia is hospital-acquired. In some embodiments, pneumonia is community-acquired. Symptoms of pneumonia comprise, without limitation, cough, fever, rapid breathing, shortness of breath, chest pain, and fatigue. In certain embodiments, pneumonia is associated with ARDS.

Polynucleotide: A nucleic acid sequence (such as a linear sequence) of any length. Therefore, a polynucleotide includes oligonucleotides, and also gene sequences found in chromosomes. An "oligonucleotide" is a plurality of joined nucleotides joined by native phosphodiester bonds. An oligonucleotide is a polynucleotide of between 6 and 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Prophylactic: as used herein refers to a medication or a treatment designed and used to prevent a disease or disorder from occurring. As used herein, the terms "prophylactic" and "prevention" are used interchangeably.

Purified: The term "purified" does not require absolute purity; rather, it is intended as a relative term. Thus, for example, a purified nucleic acid molecule preparation is one in which the nucleic referred to is more pure than the nucleic in its natural environment within a cell. For example, a preparation of a nucleic acid is purified such that the nucleic acid represents at least 50% of the total protein content of the preparation. Similarly, a purified MBV preparation is one in which the exosome is more pure than in an environment including cells, wherein there are microvesicles and exosomes. A purified population of nucleic acids or MBV is greater than about 90%, 91%, 92%, 93%, 94%, 95%, 96%, 97%, 98%, 99% or 100% pure, or free other nucleic acids or cellular components, respectively.

Preventing or treating a disease: "Preventing" a disease refers to inhibiting the development of a disease, for example in a person who is known to have a predisposition to a disease. An example of a person with a known predisposition is someone with a history of a disease in the family, or who has been exposed to factors that predispose the subject to a condition. "Treatment" refers to a therapeutic intervention that ameliorates a sign or symptom of a disease or pathological condition after it has begun to develop.

SARS-CoV-2 or the severe acute respiratory syndrome-coronavirus-2 (SARS-CoV-2), also known in the art as 2019-novel coronavirus or 2019-nCoV is a novel coronavirus that originated in Wuhan, China in late 2019 and is the cause of a global pandemic in 2020. The disease caused by SARS-CoV-2 is called Coronavirus Disease 2019 or COVID-19. COVID-19 causes a variety of symptoms including coughing, fever, fatigue, body aches, and shortness of breath. COVID-19 patients with severe disease may experience acute respiratory distress syndrome and require mechanical ventilation.

Sepsis: Sepsis is a disorder that may occurs when cytokines and chemokines released in the bloodstream (e.g., to fight an infection, e.g., an intracellular pathogen or virus) produce systemic inflammation throughout the body. Sepsis can lead to widespread organ damage, organ failure, and death. Symptoms of sepsis comprise, without limitation, elevated heart rate, confusion or disorientation, extreme pain or discomfort, fever, and shortness of breath. In some embodiments, sepsis is associated with ARDS. In some embodiments, sepsis is associated with hypercytokinemia.

Subject: Human and non-human animals, including all vertebrates, such as mammals and non-mammals, such as non-human primates, mice, rabbits, sheep, dogs, cats, horses, cows, chickens, amphibians, and reptiles. In many embodiments of the described methods, the subject is a human. "Subject" is used interchangeably with the term "patient." A subject may be an individual diagnosed with a high risk of developing a disease or disorder, for example, an infectious disease or disorder (e.g., an immunocompromised individual, a healthcare professional), someone who has been diagnosed with a disease or disorder, for example, an infectious disease or disorder, someone who previously suffered from a disease or disorder, for example, an infectious disease or disorder, or an individual evaluated for symptoms or indications of a disease or disorder, for example, an infectious disease or disorder.

Therapeutically effective amount: A quantity of a specific substance, such as an MBV, sufficient to achieve a desired effect in a subject being treated. When administered to a subject, a dosage will generally be used that will achieve target tissue concentrations (for example, in the lung) that has been shown to achieve a desired in vitro effect.

Total phospholipid content: "Total phospholipids" or "total phospholipid content", as used herein, with respect to MBV, refers to the sum of all phospholipids present in a given quantity of isolated MBV, i.e., MBV isolated from the ECM. MBV can be isolated, for example, by enzymatic digestion of decellularized ECM and differential centrifugation. The total phospholipid content can be determined by methods such as LC-MS based global lipidomics and redox lipidomics. The total phospholipid content is measured by weight. A percentage of the total phospholipid content refers to a percent concentration on a weight/weight basis Transplanting: The placement of a biocompatible substrate, such as an MBV, into a subject in need thereof.

Treating, Treatment, and Therapy: Any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, or improving a subject's physical or mental well-being. The treatment may be assessed by objective or subjective parameters; including the results of a physical examination, neurological examination, or psychiatric evaluations.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The description above describes multiple aspects and embodiments of the invention. The patent application specifically contemplates all combinations and permutations of the aspects and embodiments.

Additional Aspects of the Disclosure

Aspect 1. A method of treating or preventing acute respiratory distress syndrome (ARDS) in a subject at risk of developing ARDS comprising administering to the subject a pharmaceutical composition comprising a therapeutically effective amount of isolated matrix bound vesicles (MBV) derived from extracellular matrix, thereby treating or preventing ARDS in the subject.

Aspect 2. The method of Aspect 1, wherein the subject has a pulmonary infection that is viral, bacterial, or fungal in origin.

Aspect 3. The method of Aspect 1 or 2, wherein the subject has a pulmonary infection with a virus selected from the group consisting of SARS-CoV2, SARS-CoV, MERS-CoV, an ebolavirus, an influenza virus, a cytomegalovirus, or a herpes virus.

Aspect 4. The method of any one of Aspects 1-3, wherein the subject has pneumonia.

Aspect 5. The method of any one of Aspects 1-4, wherein the subject is infected with SARS-CoV-2 or COVID-19.

Aspect 6. The method of any one of Aspects 1-5, wherein the subject has influenza.

Aspect 7. The method of any one of Aspects 1-6, wherein the subject has SARS or MERS.

Aspect 8. The method of any one of Aspects 1-7, wherein the subject has inhaled a toxic substance.

Aspect 9. The method of Aspect 8, wherein the toxic substance is smoke, chemical fumes, or vapors from vaping.

Aspect 10. The method of any one of Aspects 1-9, wherein the subject has aspirated water, vomit, or food into the lung.

Aspect 11. The method of any one of Aspects 1-10, wherein the subject has a head or chest injury damaging the lungs or the portion of the brain that controls breathing.

Aspect 12. The method of any one of Aspects 1-11, wherein the subject has sepsis.

Aspect 13. The method of any one of Aspects 1-12, wherein the subject has pancreatitis.

Aspect 14. The method of any one of Aspects 1-13, wherein the subject has a severe burn.

Aspect 15. The method of any one of Aspects 1-14, wherein the subject has received a massive blood transfusion.

Aspect 16. The method of any one of Aspects 1-15, wherein the subject experiences hypercytokinemia.

Aspect 17. The method of Aspect 16, wherein administration of the MBV reverses hypercytokinemia in the subject.

Aspect 18. The method of any one of Aspects 1-17, wherein the MBV are administered to the subject prior to the onset of ARDS to prevent onset of ARDS.

Aspect 19. The method of any one of Aspects 1-17, wherein the MBV are administered to the subject after onset of ARDS to treat the ARDS and prevent progression of ARDS.

Aspect 20. The method of any one of Aspects 1-19, wherein the subject is a human subject.

Aspect 21. The method of any one of Aspects 1-20, wherein the pharmaceutical composition is administered by systemic intravenous (IV) injection.

Aspect 22. The method of Aspect 21, wherein the systemic intravenous injection is via standard IV line or central line.

Aspect 23. The method of Aspect 22, wherein the central line is a peripherally inserted central catheter (PICC), a tunneled catheter, or an implanted port.

Aspect 24. The method of Aspect 23, wherein the standard IV line is in a vein in the wrist, arm, or hand.

Aspect 25. The method of any one of Aspects 20-24, wherein the intravenous injection is a bolus injection, or continuous drip or pump injection.

Aspect 26. The method of any one of Aspects 1-20, wherein the pharmaceutical composition is administered to the subject's lungs as an aerosol via a nebulizer.

Aspect 27. The method of any one of Aspects 1-20, wherein the pharmaceutical composition is administered by endotracheal instillation via an endotracheal tube placed in the subject.

Aspect 28. The method of any one of Aspects 1-20, wherein the pharmaceutical composition is administered to the lungs by a metered dose inhaler via intranasal administration.

Aspect 29. The method of any one of Aspects 1-28, wherein:

(i) the MBV do not express one or more of CD63, CD81, and/or CD9, or have barely detectable levels of CD63, CD81, and/or CD9; and/or (ii) the MBV comprise:

(a) a phospholipid content comprising at least 55% phosphatidylcholine (PC) and phosphatidyl inositol (PI) in combination;

(b) a phospholipid content comprising 10% or less sphingomyelin (SM);

(c) a phospholipid content comprising 20% or less phosphatidylethanolamine (PE); and/or (d) a phospholipid content comprising 15% or greater phosphatidylinositol (PI).

Aspect 30. The method of any of Aspects 1-29, wherein the MBV are derived from extracellular matrix of urinary bladder, small intestine, heart, dermis, liver, kidney, uterus, brain, blood vessel, lung, bone, muscle, pancreas, placenta, stomach, spleen, colon, adipose tissue, or esophagus.

Aspect 31. The method of any of Aspects 1-30, wherein the MBV are derived from urinary bladder matrix (UBM), small intestinal submucosa (SIS), or urinary bladder submucosa (UBS).

Aspect 32. The method of any one of Aspects 1-31, wherein the MBV are derived from extracellular matrix from a mammalian vertebrate selected from a human, monkey, pig, cow, or sheep.

Aspect 33. The method of any one of Aspects 1-32, wherein the MBV are administered in an amount of $1\times10^6$ to $1\times10^{20}$ MBV per kg of body weight per administration.

Aspect 34. The method of any one of Aspects 1-33, wherein the MBV are administered in an amount of $1\times10^6$ to $1\times10^{12}$ MBV per kg of body weight per administration.

Aspect 35. The method of any one of Aspects 1-33, wherein the MBV are administered in an amount of $1\times10^9$ to $1\times10^{14}$ MBV per kg of body weight per administration.

Aspect 36. The method of any one of Aspects 1-35, wherein the subject receives an antibiotic, an antiviral, or an anti-inflammatory medication.

Aspect 37. The method of any one of Aspects 1-36, wherein the subject receives remdesivir, favipiravir, azithromycin, or hydroxychloroquine.

Aspect 38. The method of any one of Aspects 1-37, wherein the subject receives tocilizumab, anakinra, or a Janus kinase (JAK) inhibitor.

Aspect 39. The method of any one of Aspects 1-38, wherein the subject has a reduced risk of secondary infection as a result of treatment with MBV as compared to a subject treated with an immunosuppressive agent.

Aspect 40. The method of Aspect 39, wherein the secondary infection is a pulmonary infection.

Aspect 41. The method of Aspect 39, wherein the secondary infection is an infection in the blood.

Aspect 42. The method of Aspect 39, wherein the secondary infection is in the heart, kidney, or liver.

Aspect 43. The method of any one of Aspects 39-42, wherein the secondary infection is a bacterial infection.

Aspect 44. The method of any one of Aspects 39-42, wherein the secondary infection is a viral infection.

Aspect 45. The method of any one of Aspects 1-44, wherein the oxygen saturation in the subject increases by 10%, 15%, 20%, 25%, 30%, 35%, 40%, 45%, 50%, 55%, 60%, 70%, 75%, 80%, 85%, 90%, 95%, 100%, or more than 100% after administration of the pharmaceutical composition.

Aspect 46. The method of any one of Aspects 1-44, wherein the oxygen saturation index in the subject increases by 10%, 15%, 20%, 25%, 30%, 35%, 40%, 45%, 50%, 55%, 60%, 70%, 75%, 80%, 85%, 90%, 95%, 100%, or more than 100% after administration of the pharmaceutical composition.

Aspect 47. The method of any one of Aspects 1-44, wherein the oxygen index in the subject increases by 10%, 15%, 20%, 25%, 30%, 35%, 40%, 45%, 50%, 55%, 60%, 70%, 75%, 80%, 85%, 90%, 95%, 100%, or more than 100% after administration of the pharmaceutical compound.

Aspect 48. The method of any one of Aspects 45-47, wherein the increase occurs within 1 hour, 2 hours, 3 hours, 4 hours, 5 hours, 6 hours, 7 hours, 8 hours, 9 hours, 10 hours, 11 hours, 12 hours, 18 hours, or 24 hours after administration of the pharmaceutical composition.

Aspect 49. The method of any one of Aspects 1-48, wherein the subject experiences a decrease in the production of a pro-inflammatory cytokine after the administration of MBV.

Aspect 50. The method of Aspect 49, wherein the pro-inflammatory cytokine is one or more of TNF-α, IFN-γ, IL-8, IL-6, IL-1, or IL-12.

Aspect 51. The method of any one of Aspects 1-50, wherein the subject experiences an increase in the production of anti-inflammatory cytokine after the administration of MBV.

Aspect 52. The method of Aspect 51, wherein the anti-inflammatory cytokine is TGF-β, IL-4, or IL-10.

Aspect 53. The method of Aspects 50-52, wherein the increase or decrease is measured by sampling bronchoalveolar lavage fluid from the subject's lungs before and after administration of the MBV.

Aspect 54. The method of Aspects 50-53, wherein the increase or decrease is measured by sampling the subject's blood before and after administration of the MBV.

Aspect 55. The method of any one of Aspects 1-54, wherein administering the pharmaceutical composition to the subject results in one of more of:

a) a reduction in the number of CD45+ neutrophils in a lung of the subject;
b) an increase in the number of CD8+ cells and a reduction in the numbers of CD4+ T cells in the lung or spleen of the subject;
c) an increase in the number of CD69+CD4+ T cells in a spleen of the subject;
d) an increase in the number of anti-viral tbet+CD4+ T cells in the lymph node of the subject;
d) an increase in the number of anti-viral tbet+CD8+ T cells in the spleen of the subject;
e) an increase in the number of CD69+CD8+ T-cells in the spleen of the subject;
f) an increase in the numbers of immunoregulatory CD11b+ dendritic cells in the lung; and
g) an increase in the number of CD62L+/CD44+ memory CD4 and CD8 T-cells in the lung.

Aspect 56. The method of any one of Aspects 1-55, wherein administering the pharmaceutical composition to the subject reduces viral-associated tissue damage in the subject.

Aspect 57. The method of any one of Aspects 1-56, wherein the MBV express low or undetectable levels of one or more of the following markers: EpCAM, ANXA5, TSG101, FLOT1, ICAM1, GM130, or ALIX.

Aspect 58. The method of any one of Aspects 1-56, wherein the MBV express low or undetectable levels of one or more of the following markers: ANXA5, TSG101, or ICAM1.

Aspect 59. The method of any one of Aspects 1-56, wherein the MBV express low or undetectable levels of CD81, CD63, ANXA5, TSG101, and ICAM1.

Aspect 60. Use of isolated matrix bound vesicles (MBV) derived from extracellular matrix to treat acute respiratory distress syndrome (ARDS).

EXAMPLES

The disclosure now being generally described, will be more readily understood by reference to the following examples, which are included merely for purposes of illustration of certain aspects and embodiments of the present disclosure, and are not intended to limit the scope of the disclosure in any way.

Example 1: Differentiating Matrix Bound Vesicles (MBV) and Extracellular Vesicles (EV) Through Lipidomics and RNA Sequencing Matrix-bound nanovesicles (MBV) have been reported as an integral component of ECM bioscaffolds. Although liquid-phase extracellular vesicles (EV) have been the subject of intense investigation, their similarity to MBV is limited to size and shape. This example utilized LC-MS-based lipidomics and redox lipidomics to conduct a detailed comparison of liquid-phase EV and MBV phospholipids. Combined with comprehensive RNA sequencing and bioinformatic analysis of the intravesicular cargo, this example shows that MBV are a distinct and unique subpopulation of EV, and a distinguishing feature of ECM-based biomaterials.

This example identifies similarities and differences between liquid phase (i.e., exosomes) and matrix bound forms (i.e., MBV) of EV. However, given that EV present in biological fluids and MBV present in native tissue ECM and ECM-based biomaterials represent heterologous populations secreted from multiple cell sources, a direct comparative in-vivo analysis between these putative EV populations is problematic. As an alternative to using body fluid or tissue-derived vesicles, ECM and conditioned media produced in-vitro by cultured cells can be isolated (Fitzpatrick et al., *Biomater Sci.,* 3, 12-24 (2015). This approach offers several advantages such as the use of a single cell type source thereby obviating any doubts regarding vesicle origin; the ability to selectively harvest vesicles from either liquid or solid phase compartments; and the ability to control the cell culture environment and thus also control vesicle composition and cargo.

Materials and Methods

Preparation of in vitro cell-derived ECM: Human bone marrow stem cells (BMSC), human adipose stem cells (ASC) and human umbilical cord stem cells (UCSC) ECM plates were provided by StemBioSys (San Antonio, Texas) and prepared according to a published protocol (Lai et al., *Stem cells and development* 19, 1095-1107 (2010)). Briefly, human BMSC, human ASC, or human UCSC were seeded onto a 75 $cm^2$-cell culture flask coated with human fibronectin (1 h at 37° C.) at a cell density of 3,500 cells/$cm^2$ and cultured in α-MEM medium supplemented with 20% fetal bovine serum (FBS) and 1% penicillin-streptomycin for 14 days. The medium was refreshed the day after initial seeding and then every 3 days. At day 7, ascorbic acid 2-phosphate (Sigma Aldrich) was added to the medium at a final concentration of 50 μM. At day 14, plates were decellularized using 0.5% Triton in 20 mM ammonium hydroxide for 5 min, rinsed two times with Hank's Balanced Salt Solution containing both calcium and magnesium (HBSS+/+), and once with ultra-pure $H_2O$. Murine NIH 3T3 fibroblast cells were seeded onto a 75 $cm^2$-cell culture flask at a cell density of 3,500 cells/$cm^2$ and cultured in DMEM medium supplemented with exosome-depleted FBS (G. V. Shelke, et al, *Journal of extracellular vesicles* 3, 24783 (2014)), 1% penicillin-streptomycin and ascorbic acid 2-phosphate (Sigma Aldrich) at a final concentration of 50 μM for 7 days. At day 7, the supernatant from cultured 3T3 fibroblast cells was collected, and the plated culture was washed 3 times with PBS, decellularized using 0.5% Triton in 20 mM ammonium hydroxide for 5 min, and then rinsed three times with ultra-pure $H_2O$.

Isolation of MBV and liquid-phase EV: MBV were isolated (L. Huleihel et al., Science advances 2, e1600502 (2016)). Briefly, the decellularized ECM was enzymatically digested with 100 ng/ml Liberase DL (Roche) in buffer (50 mM Tris pH 7.5, 5 mM $CaCl_2$, 150 mM NaCl) for 1 hr at 37° C. The cell culture supernatant containing the liquid-phase EV and the digested ECM containing the MBV were subjected to differential centrifugation at 500 g (10 min), 2500 g (20 min), and 10,000 g (30 min), and the supernatant passed through a 0.22 μm filter (Millipore). The clarified supernatant containing the liberated MBV or liquid-phase EV was then centrifuged at 100,000×g (Beckman Coulter Optima L-90K Ultracentrifuge) at 4° C. for 70 min to pellet the vesicles. The vesicle pellets were then washed and resuspended in 1×PBS, and stored at −20° C. until further use.

Preparation of urinary bladder matrix (UBM): UBM was prepared from market-weight pigs (Tissue Source; LLC, Lafayette, IN) (L. Huleihel et al., Science advances 2, e1600502 (2016)). Briefly, the tunica serosa, muscularis externa, submucosa, and muscularis mucosa were removed by mechanical delamination, and the urothelial cells of the tunica mucosa were dissociated from the basement membrane by washing with deionized water. The remaining basement membrane and the lamina propria (collectively referred to as UBM) were decellularized by agitation in 0.1% peracetic acid with 4% ethanol for 2 h at 300 rpm followed by phosphate-buffered saline (PBS) and type 1 water washes. UBM was then lyophilized and milled using a Wiley Mill with a #60 mesh screen.

Scanning Electron Microscopy (SEM): UBM was fixed in cold 2.5% glutaraldehyde for 24 hours followed by three 30 minute washes in 1×PBS. Samples were then dehydrated in a graded alcohol series (30%, 50%, 70%, 90%, 100% ethanol) for 30 minutes per wash, and then placed in 100% ethanol overnight at 4° C. Samples were washed 3 additional times in 100% ethanol for 30 minutes each and critical point dried using a Leica EM CPD030 Critical Point Dryer (Leica Microsystems, Buffalo Grove, IL, USA) with carbon dioxide as the transitional medium. Samples were then sputter-coated with a 4.5 nm thick gold/palladium alloy coating using a Sputter Coater 108 Auto (Cressington Scientific Instruments, UK) and imaged with a JEOL JSM6330f scanning electron microscope (JEOL, Peabody, MA, USA)

Transmission Electron Microscopy (TEM): TEM imaging was conducted on MBV or liquid-phase EV loaded on carbon-coated grids and fixed in 4% paraformaldehyde (L. Huleihel et al., *Science advances* 2, e1600502 (2016)). Grids were imaged at 80 kV with a JEOL 1210 TEM with a high-resolution Advanced Microscopy Techniques digital camera. Size of the MBV was determined from representative images using JEOL TEM software.

Nanoparticle Tracking Analysis (NTA): Particle size and concentration of the liquid-phase EV and the MBV were calculated using a Nanosight (NS300) instrument equipped with fast video capture and particle-tracking software. Samples were diluted 1:500 to a final volume of 1000 μl using particle-free water. A syringe pump was used to dispense the sample into the system. Measurements were performed from three captures of 45 seconds each sample. For the video processing and particle calculation, the detection threshold was adjusted to 4. Data is presented as concentration vs. particle size for each of the evaluated samples.

RNA isolation: Total RNA was isolated from 3T3 cells, liquid-phase EV and MBV using the RNeasy mini kit (Qiagen) according to the manufacturer's instructions. Before RNA isolation, liquid-phase EV and MBV samples were treated with RNase A (10 μg/ml) at 37° C. for 30 min to degrade any contaminating RNA. RNA quantity was determined using NanoDrop spectrophotometer, and its quality was determined by Agilent Bioanalyzer 2100 (Agilent Technologies).

RNA sequencing and bioinformatic analysis: The miRNA library preparation was initiated with 100 ng of each sample, and the QIASEQ™ miRNA Library Kit (Qiagen) following manufacturer's instructions. Briefly, mature miRNAs were ligated to adapters on their 3' and 5' ends. The ligated miRNAs were then reverse transcribed to cDNA using a reverse transcription (RT) primer with a unique molecular indices (UMI). The cDNA was then cleaned up to remove adapter primers, followed by amplification of the library with a universal forward primer and one of 48 reverse primers that assigns a sample index. A pre-sequencing quality control was performed using the Agilent RNA ScreenTape System. Next Generation Sequencing was performed on a NextSeq 500 instrument with a loading concentration of 2.5 μM. Bioinformatic analysis was conducted by Genevia Technologies (Tampere, Finland). The quality of the sequencing reads was inspected using FastQC software. TrimGalore! [Version 0.4.5;] was used to remove the adapter sequences, with default settings, on all the samples. All reads were shortened to 21 bases, the typical size of micro-RNAs, using the fastx_trimmer software (FASTX Toolkit by Hannon Lab; Version 0.0.14).

The reads of each sample were then aligned against the corresponding reference genome (hg38, GRCm38). Tables of miRNA counts across samples were created using the software bowtie [Version 1.2.2] and miRDeep2 [Version 0.0.8]. In this process, precursor-miRNA and mature-miRNA sequences for each species involved in the study were taken from miRbase. Counts of mature miRNAs were obtained by taking the median of all precursor miRNAs associated with them. The counts of mature miRNAs of all samples were normalized using DESeq2. To ensure data quality before further analyses, principal component analysis (PCA) was performed and the results were visualized using ggplot2, separately for murine and human samples.

Normalization of mature miRNA data and statistical testing between sample groups was performed with DESeq2. P values were corrected for multiple testing using Benjamini-Hochberg method. miRNAs with adjusted p value <0.05 and absolute log 2 fold change >1 were considered as significantly differentially expressed. Tables of differentially expressed miRNAs were annotated with their targets and their confidences using the mirTARbase database of experimentally tested miRNA—target interactions. Differentially expressed miRNAs were also annotated with predicted targets using the R package miRNAtap. miRNAtap aggregates the miRNA target predictions from five different databases (PicTar, DIANA, TargetScan, miRanda, miRDB) and calculates an overall miRNA target score. The minimum amount of database sources required for a potential miRNAtarget interaction to be included into the annotations was 3.

Ingenuity pathway analysis (IPA): Ingenuity Pathway Analysis software (Version 01-14) was used for functional analysis of differentially expressed (DE) miRNAs. miRNA targets were identified using the IPA Core Analysis. The filter was set to Experimentally Observed findings to obtain information about significantly enriched molecular and cellular functions and physiological system development functions that were affected by the miRNAs.

qPCR validation: Reverse transcription (RT) and quantitative polymerase chain reaction (qPCR) were performed using the TAQMAN® Advanced miRNA Assays Protocol (Applied Biosystems). Briefly, 10 ng total RNA were used with The TAQMAN® Advanced miRNA cDNA Synthesis Kit (Applied Biosystems, Cat No. A28007) to synthetize and adapt a 3'-poly(A) tail to the miRNAs. Universal RT primers recognizing the poly(A) tail were used to synthetize the cDNA in the RT reaction, followed by a miR-AMP step, using miR-AMP forward and reverse universal primers, to increase the number of cDNA molecules. The qPCR was made on a QUANTSTUDIO™ system machine using the TAQMAN® Fast Advanced Master Mix (Applied Biosystems, Cat No. 4444556) and specific TAQMAN® Advanced miRNA Assays (Applied Biosystems, Cat No. A25576) recognizing mmu-miR-163-5p, mmu-miR-27a-5p, mmu-miR-92a-1-5p, mmu-miR-451a, mmu-miR-93-5p, and mmu-miR-99b-5p. Fold change expression on the MBV sample was calculated for each of the specific targets using Liquid-phase EV as a reference.

Immunoblot and silver stain assays: Liquid-phase EV and MBV, derived from three separate cultures of 3T3 fibroblasts, were respectively pooled and quantified by nanotracking particle analysis. For both immunoblot and silver stain analysis, an equal number of vesicles for both the liquid-phase EV and MBV samples were loaded onto the gel. $21\times10^{11}$ MBV or liquid-phase EV were mixed with 2× Laemmli buffer (R&D Systems) containing 5% R mercaptoethanol (Sigma-Aldrich), resolved on a 4 to 20% gradient SDS-PAGE (Bio-Rad), and then transferred onto a PVDF membrane. Membranes were incubated overnight with the following primary antibodies: rabbit anti-CD63, rabbit anti-CD81, rabbit anti-CD9, and rabbit anti-Hsp70, at 1:1000 dilution (System Biosciences). Membranes were washed three times for 15 min each before and after they were incubated with goat anti-rabbit secondary antibody, at 1:5,000 dilution (System Biosciences). The washed membranes were exposed to chemiluminescent substrate (Bio-Rad) and then visualized using a ChemiDoc Touch instrument (Bio-Rad). Silver staining of gels was performed using the Silver Stain Plus Kit (Bio-Rad) according to the manufacturer's instruction and visualized using a ChemiDoc Touch instrument (Bio-Rad).

LC/MS analysis of phospholipids: Lipids were extracted from 3T3 cells, exosomes and MBV by Folch procedure (J. Folch, et al, *J biol Chem* 226, 497-509 (1957)). MS analysis of phospholipids and their oxygenated products was performed on an Orbitrap™ Fusion™ Lumos™ mass spectrometer (ThermoFisher) (Y. Y. Tyurina et al., *ACS nano* 5, 7342-7353 (2011)). Briefly, phospholipids were separated on a normal phase column (Luna 3 μm Silica (2) 100 Å, 150×2.0 mm, (Phenomenex)) at a flow rate of 0.2 ml/min on a DIONEX ULTIMATE 3000 HPLC system. The column was maintained at 35° C. The analysis was performed using gradient solvents (A and B) containing 10 mM ammonium acetate. Solvent A contained propanol:hexane:water (285:215:5, v/v/v) and solvent B contained propanol:hexane:water (285:215:40, v/v/v). All solvents were LC/MS grade. The column was eluted for 0-23 min with a linear gradient from 10% to 32% B; 23-32 min using a linear gradient of 32-65% B; 32-35 min with a linear gradient of 65-100% B; 35-62 min held at 100% B; 62-64 min with a linear gradient from 100% to 10% B followed by and equilibration from 64 to 80 min at 10% B. Spectra were acquired in negative ion mode. Deuterated phospholipids were used as internal standards (Avanti Polar Lipids). Three technical replicates for each sample were run to evaluate reproducibility. Analysis of LC/MS data was performed using software package Compound DISCOVERER™ (ThermoFisher) with an in-house generated analysis workflow and non-oxidized/oxidized phospholipid database. Lipids were further filtered by retention time and confirmed by fragmentation mass spectrum.

LC/MS Analysis of free fatty acids and their oxidation products: Free fatty acids were analyzed by LC/MS using a DIONEX ULTIMATE™ 3000 HPLC system coupled online to Q-Exactive hybrid quadrupole-orbitrap mass spectrometer (ThermoFisher Scientific, San Jose, CA) (Y. Y. Tyurina et al., *Nature chemistry* 6, 542 (2014)). Briefly, fatty acids and their oxidative derivatives were separated by a C18 column (Accliam PepMap RSLC, 300 μm 15 cm, Thermo Scientific) using a gradient of solvents (A: Methanol (20%)/Water (80%) (v/v) and B: Methanol (90%)/Water (10%) (v/v) both containing 5 mM ammonium acetate. The column was eluted at a flow rate of 12 μL/min using a linear gradient from 30% solvent B to 95% solvent B over 70 min, held at 95% B from 70 to 80 min followed by a return to initial conditions by 83 min and re-equilibration for an additional 7 min. Spectra were acquired in negative ion mode. Analytical data were acquired and analyzed using Xcalibur software. A minimum of three technical replicates for each sample was run to increase the reproducibility.

Results

Figure 1B:
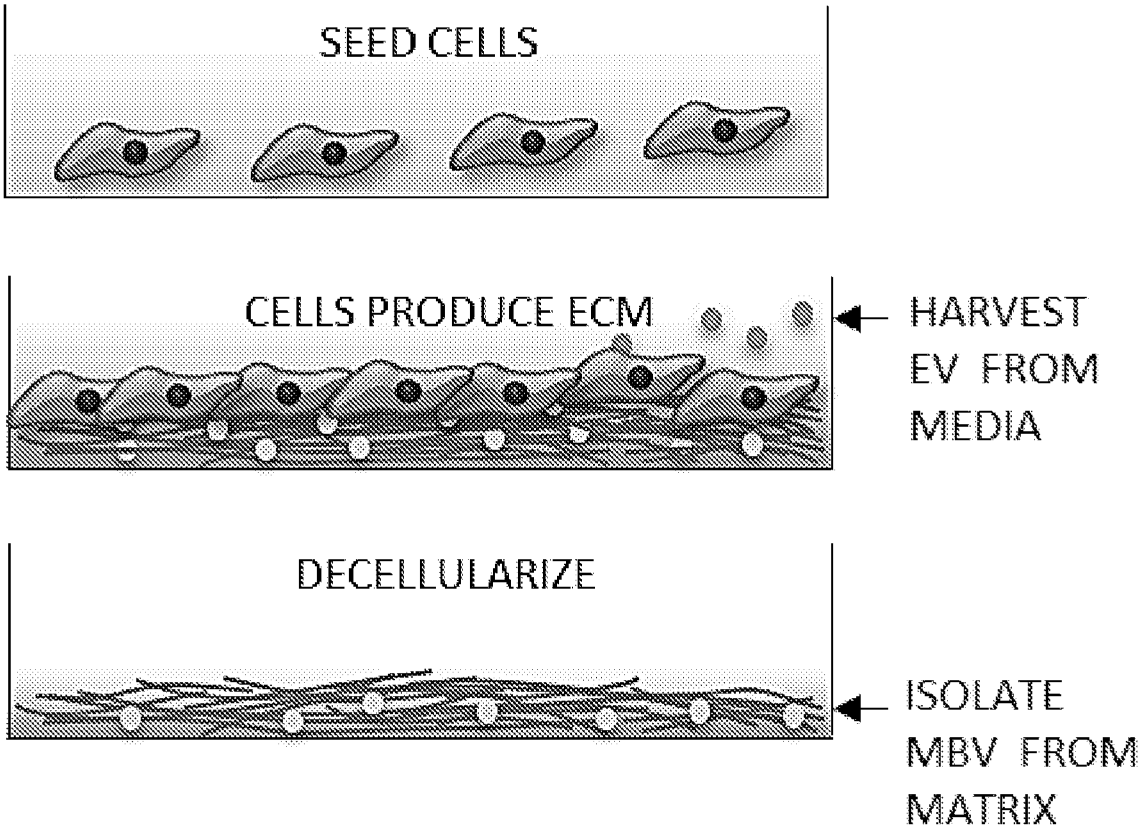
Figure 1C:
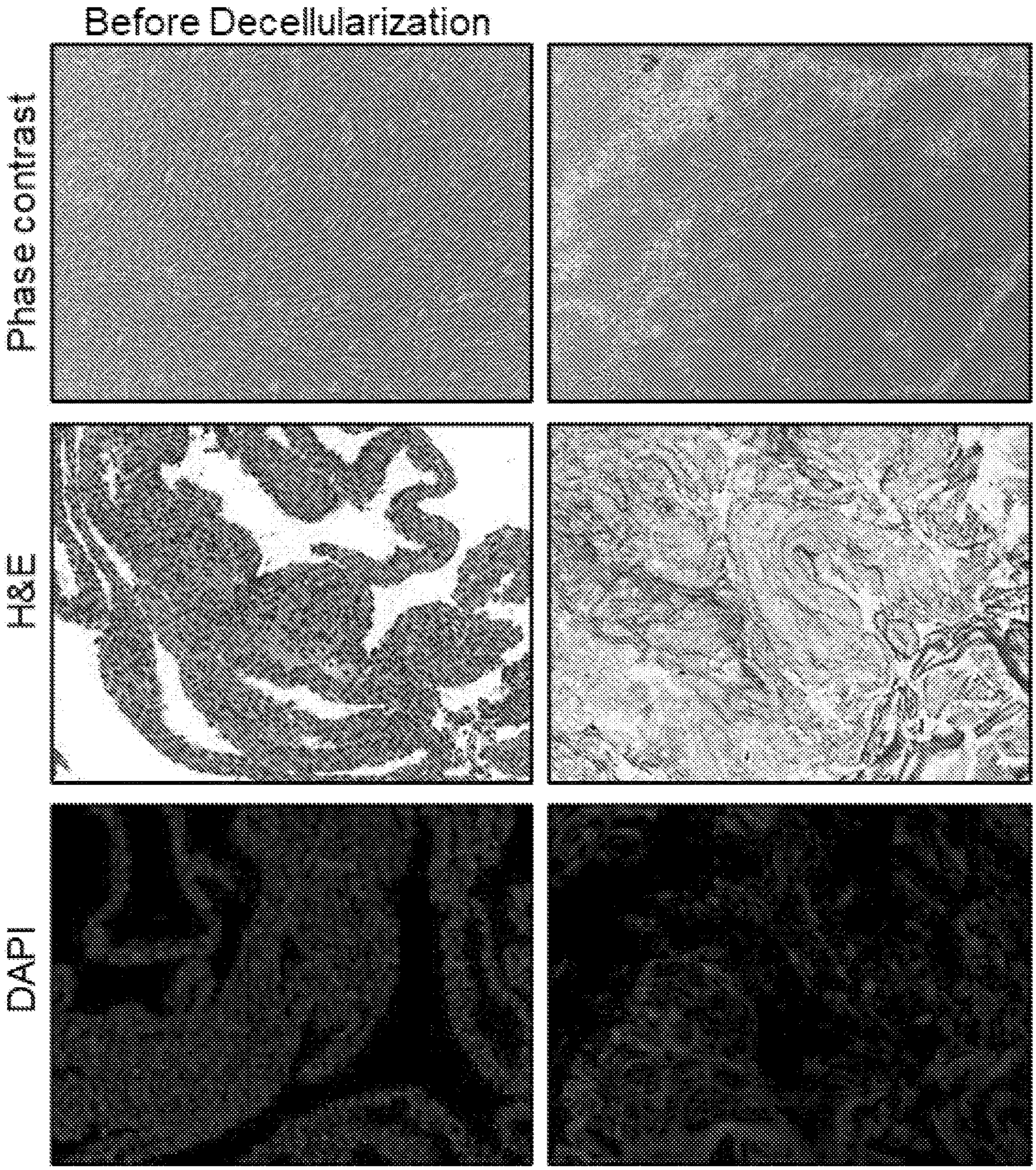
Figure 1D:
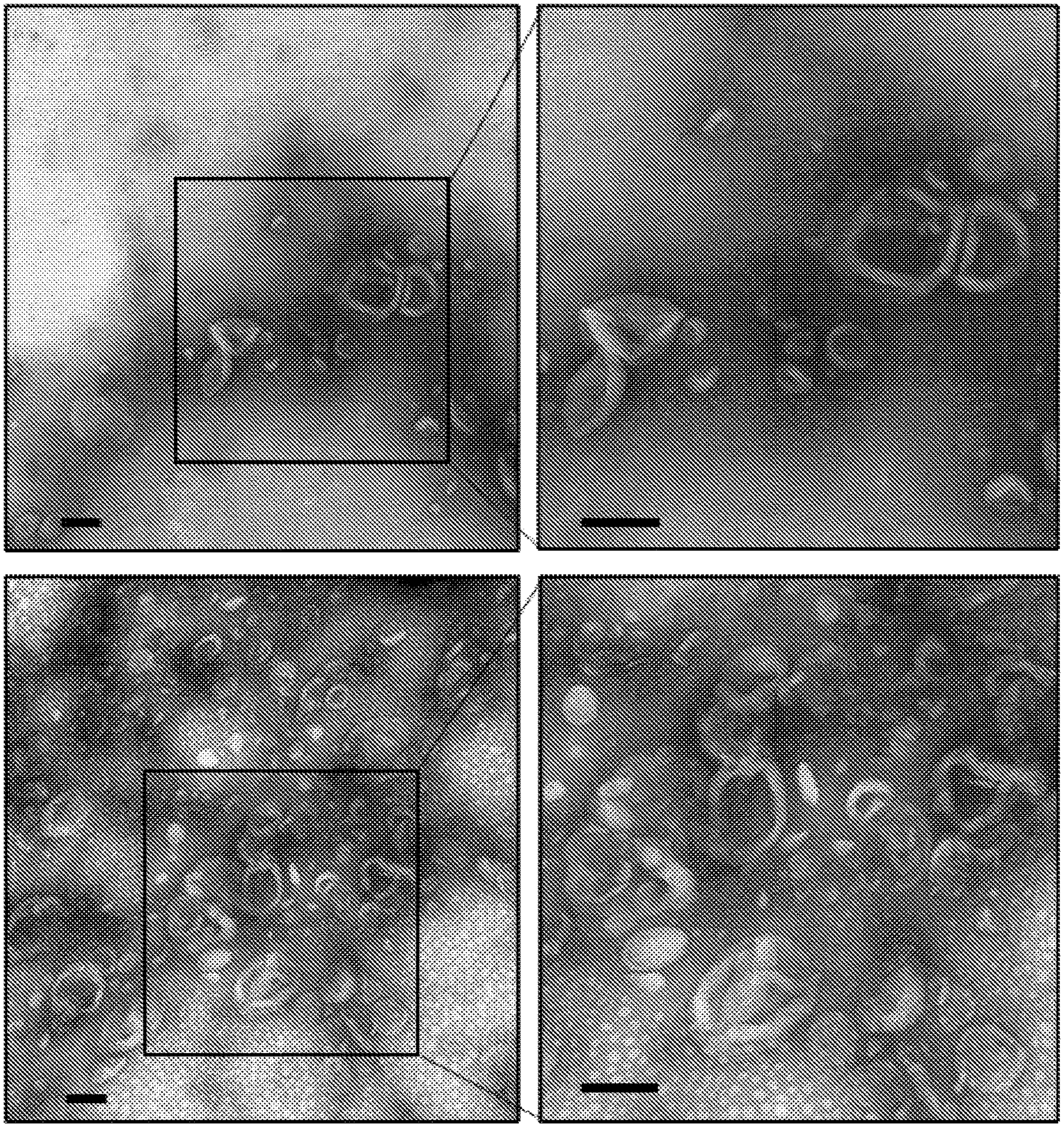
Figure 1E:
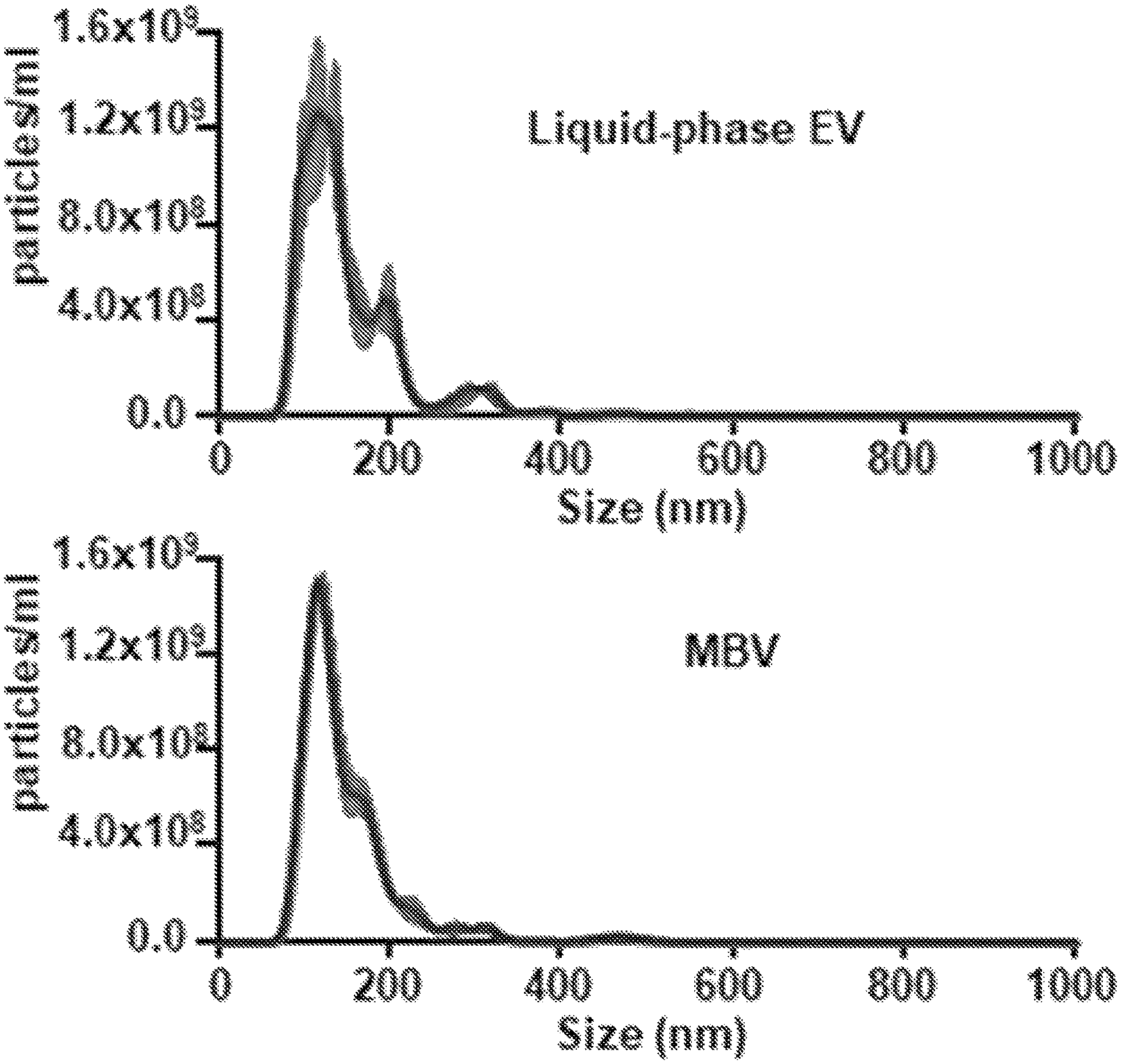

Isolation of liquid-phase EV and matrix bound nanovesicles: Scanning electron microscopy (SEM) was performed to provide high-resolution, high-magnification imaging of MBV embedded within an ECM bioscaffold derived from porcine urinary bladder matrix (UBM). SEM images revealed discrete spheres approximately 100 nm in diameter dispersed throughout the collagen fibers (FIG. 1A). To examine if MBV deposited into a solid ECM substrate are a unique class of extracellular vesicle separate from EV secreted into a liquid-phase, an in-vitro 3T3 fibroblast cell culture model that allows for selective harvesting of vesicles from a liquid-phase or solid-phase extracellular compartment was used (FIG. 1B). Representative images from phase contrast microscopy, and H&E and DAPI stained sections showed that no residual cells or intact nuclei were visible after decellularization of the cell culture plate (FIG. 1C). TEM imaging of liquid-phase EV harvested from the cell culture supernatant and MBV isolated from decellularized ECM (FIG. 1D) showed that these two populations of vesicles shared a similar morphology. Moreover, nanoparticle tracking analysis (NTA) distribution plots showed similar vesicle size of both liquid-phase EV and MBV, with the majority of vesicles having a diameter <200 nm (FIG. 1E).

Figure 1F:
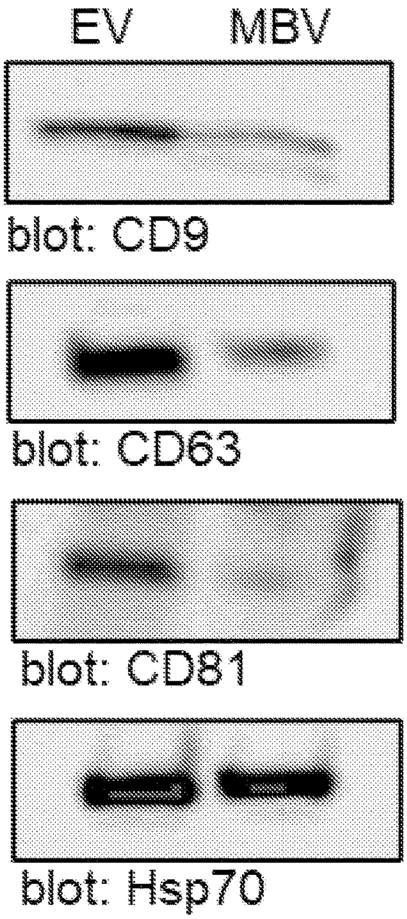
Figure 1G:
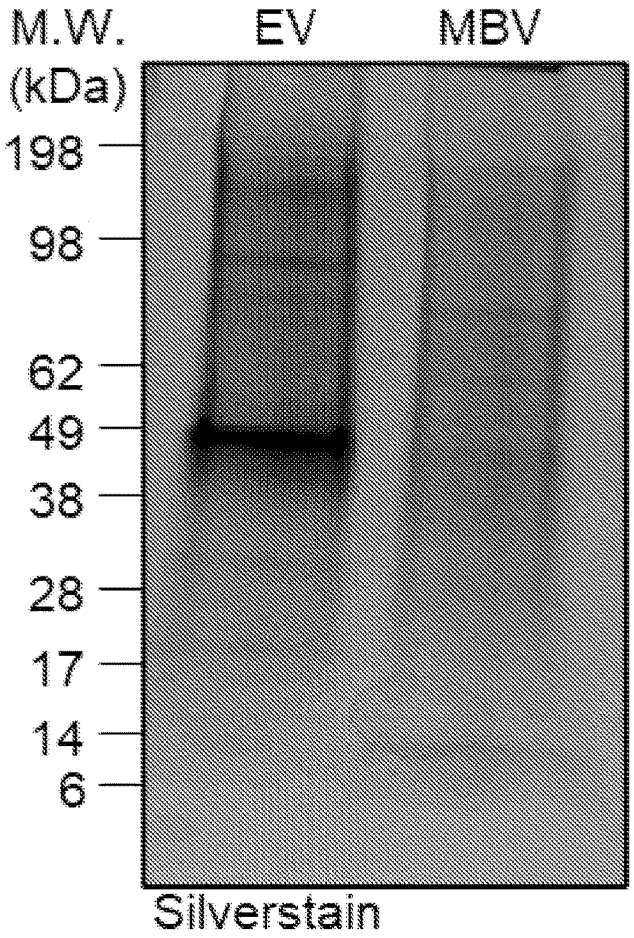
Figure 2A:
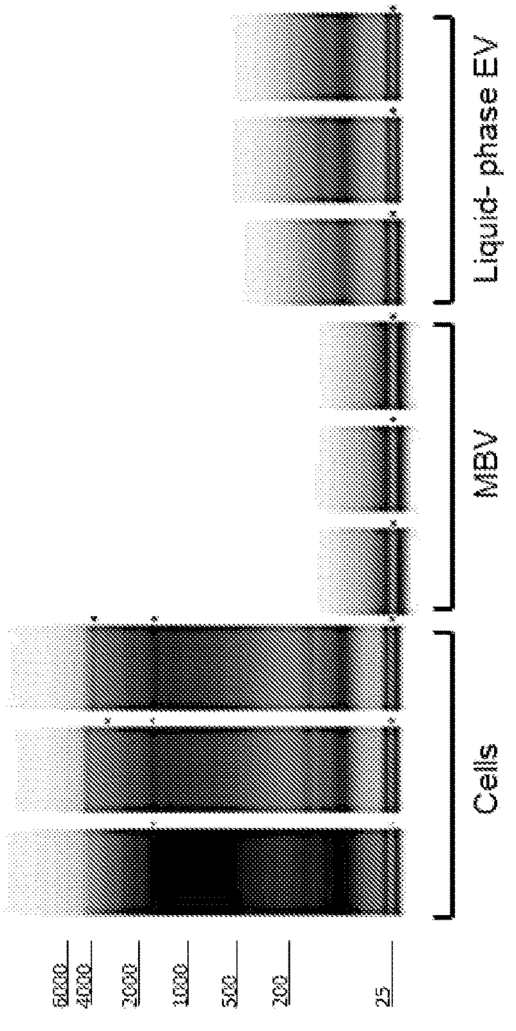
FIGS. 2A-2E depict differences in miRNA cargo between EV and MBV.
Figure 2B:
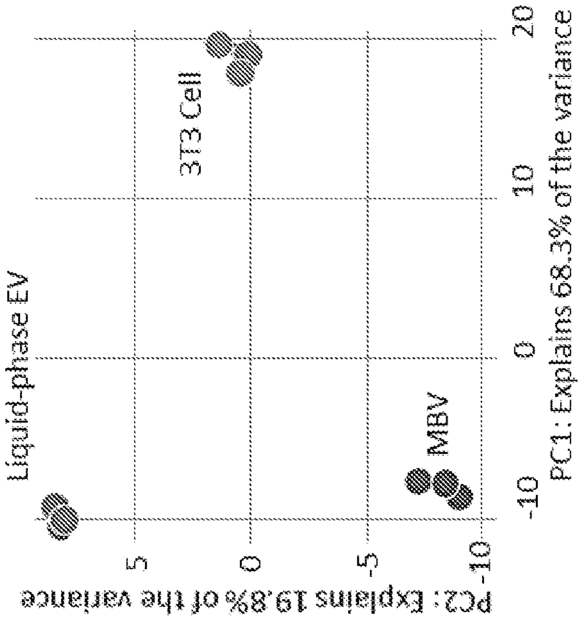

To determine whether MBV contained markers commonly attributed to exosomes, immunoblot analysis was performed for CD63, CD81, CD9, and Hsp70(J. Lötvall et al. (Taylor & Francis, 2014)). Results showed that in contrast to liquid-phase EV, the MBV showed a marked decrease in CD63, CD81, CD9. MBV expressed levels of CD9 and CD81 that were barely detectable in the immunoblot assay and markedly decreased relative to the levels expressed in EV. MBV also displayed significantly lower expression of CD63 than was observed in EV.(FIG. 1F). In other words, liquid phase EV (i.e., exosomes) are enriched in expressed levels of CD63, CD81, CD9 as compared to MBV. Furthermore, silver staining of electrophoretically-separated proteins showed that MBV contained a protein cargo that was distinctly different than the liquid-phase EV (FIG. 1G), suggesting that MBV may be a unique subpopulation of nanovesicles.

miRNA is selectively packaged into liquid-phase EV and MBV derived from 3T3 fibroblasts: Comprehensive next generation RNA-sequencing (RNA-seq) was employed to catalog differentially expressed miRNA in MBV and liquid-phase EV relative to the 3T3 fibroblast parent cell from which these vesicles were derived. Bioanalyzer analysis revealed the absence of 18S and 28S ribosomal RNA, and an enrichment of small RNA molecules (<200 nt) in total RNA isolated from liquid-phase EV and MBV. However, the small RNA size distribution from liquid phase EV was much broader than MBV with a marked enrichment of small RNA molecules between 100-200 nt in liquid-phase EV (FIG. 2A). Analysis was focused on differential miRNA signatures by conducting next generation sequencing of miRNA libraries generated from the parental cellular RNA, the liquid-phase EV, and the MBV isolates (n=3 per group). Principal component analysis (PCA) showed that within respective groups, the replicate miRNA profiles clustered close to one another (FIG. 2B).

Figure 2C:
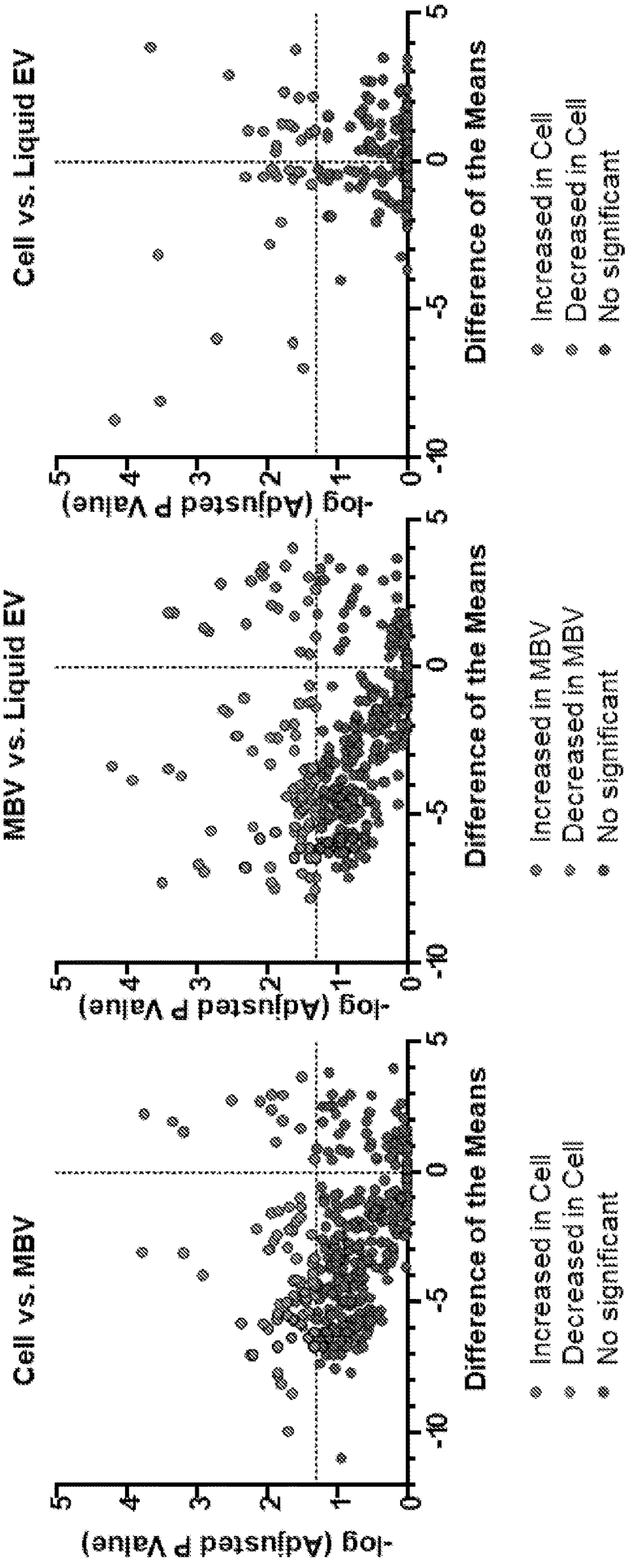
Figure 2D:
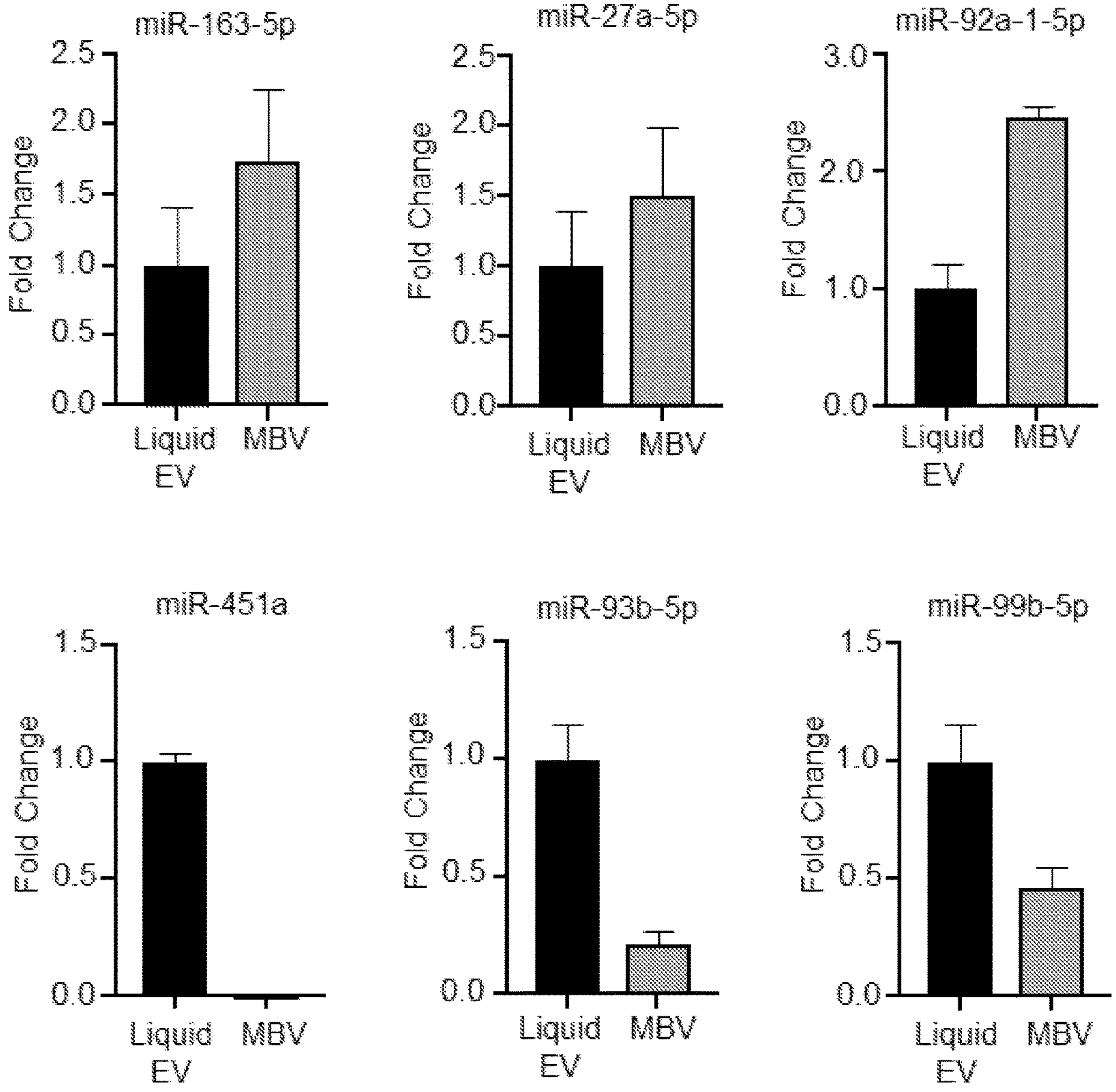
Figure 2E:
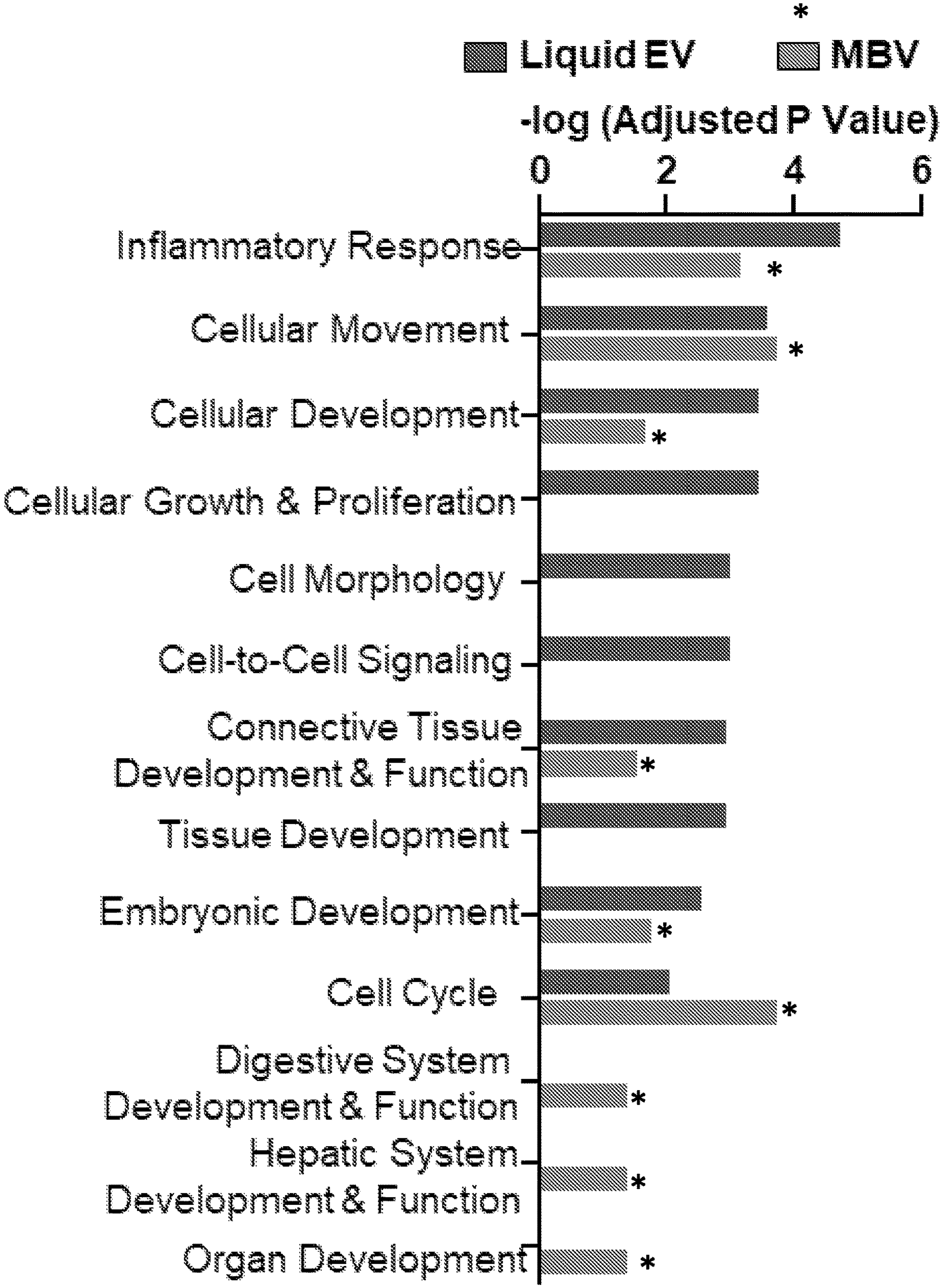

Extensive differences in miRNA content were observed between the parental cell and the liquid-phase EV and MBV isolates. Overall, 28 (50.91%) miRNAs were found to be differentially expressed in MBV compared to liquid-phase EV by at least two-fold (FIG. 2C). Additionally, respective liquid-phase EV or MBV and the parental cellular miRNA profiles were clearly distinct (FIG. 2B, FIG. 2C). To validate the results of miRNA sequencing, RT-qPCR was conducted to detect 3 upregulated miRNAs (miR-163-5p, miR-27a-5p, miR-92a-1-5p) and 3 downregulated miRNAs (miR-451a, miR-93b-5p, miR-99b-5p) in MBV compared to liquid phase EV isolated from 3T3 fibroblasts (FIG. 2D). The results showed that the levels of miR-163-5p, miR-27a-5p and miR-92a-1-5p were upregulated, and miR-451a, miR-93b-5p and miR-99b-5p were downregulated in MBV compared to liquid-phase EV, thereby corroborating the results from the miRNA sequencing data. Ingenuity Pathway Analysis (IPA) of differentially enriched miRNAs in MBV compared to liquid-phase EV showed a strong association with organ and system development and function. In contrast, miRNA differentially enriched in liquid-phase EV compared to MBV were associated with pathways involved in cellular growth, development, proliferation and morphology (FIG. 2E).

Figure 3A:
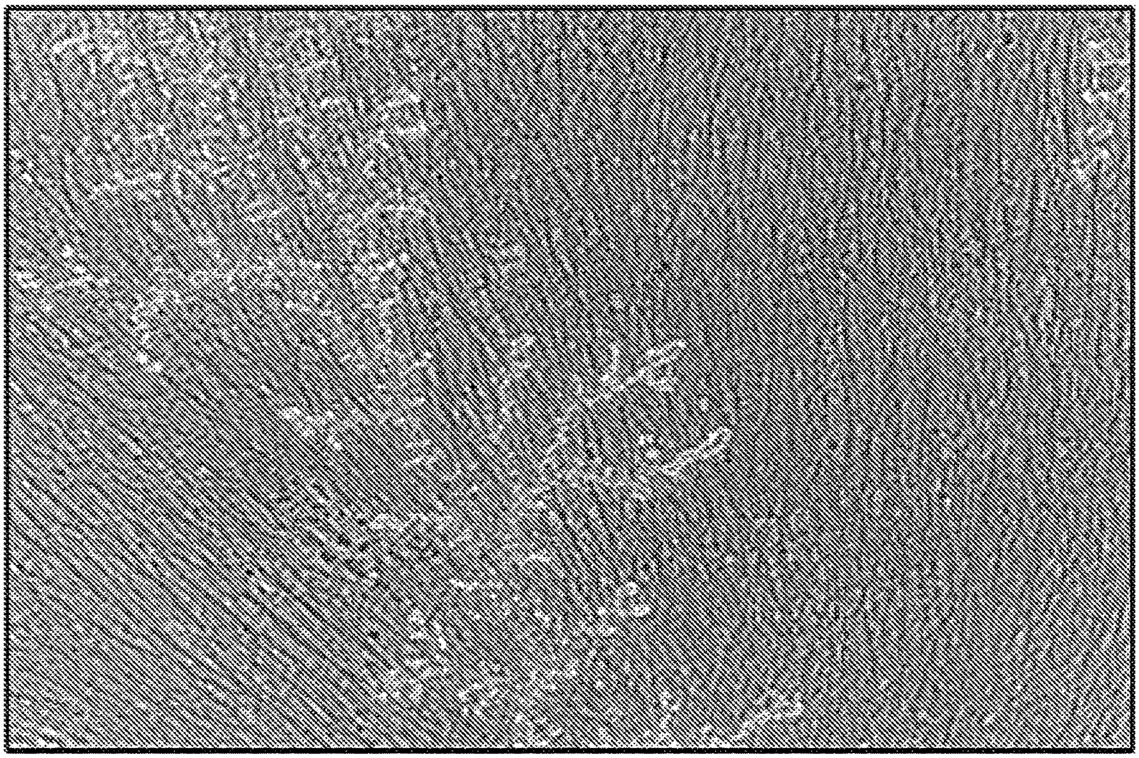
Figure 3B:
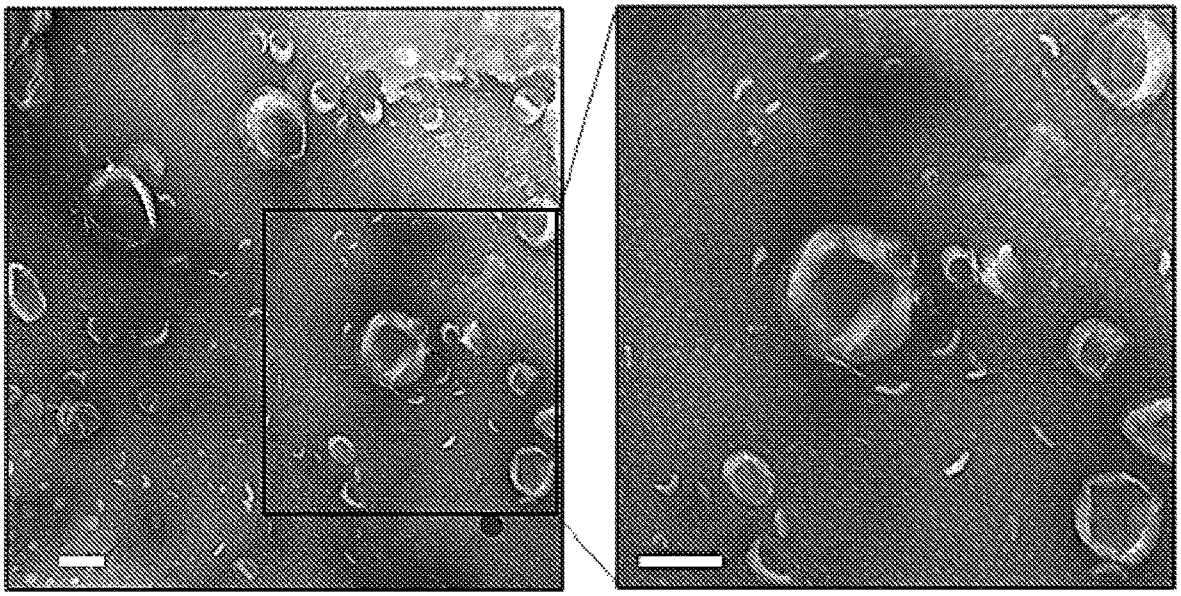
Figure 3C:
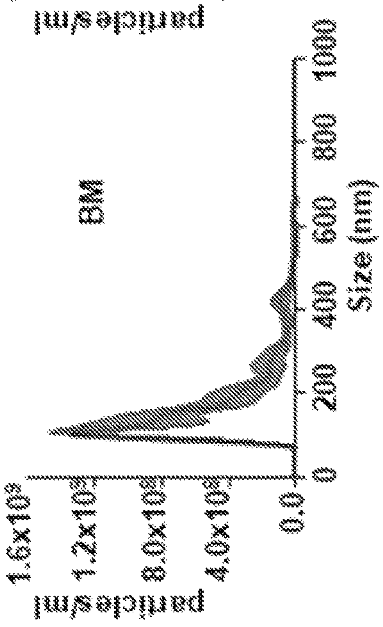
Figure 3D:
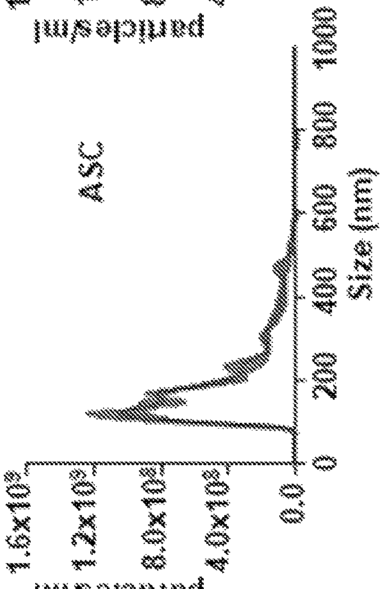
Figure 3E:
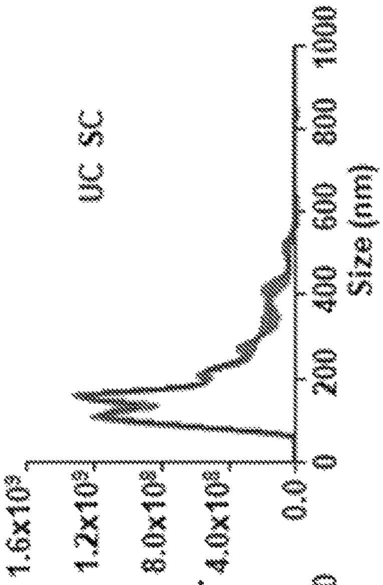
Figure 3H:
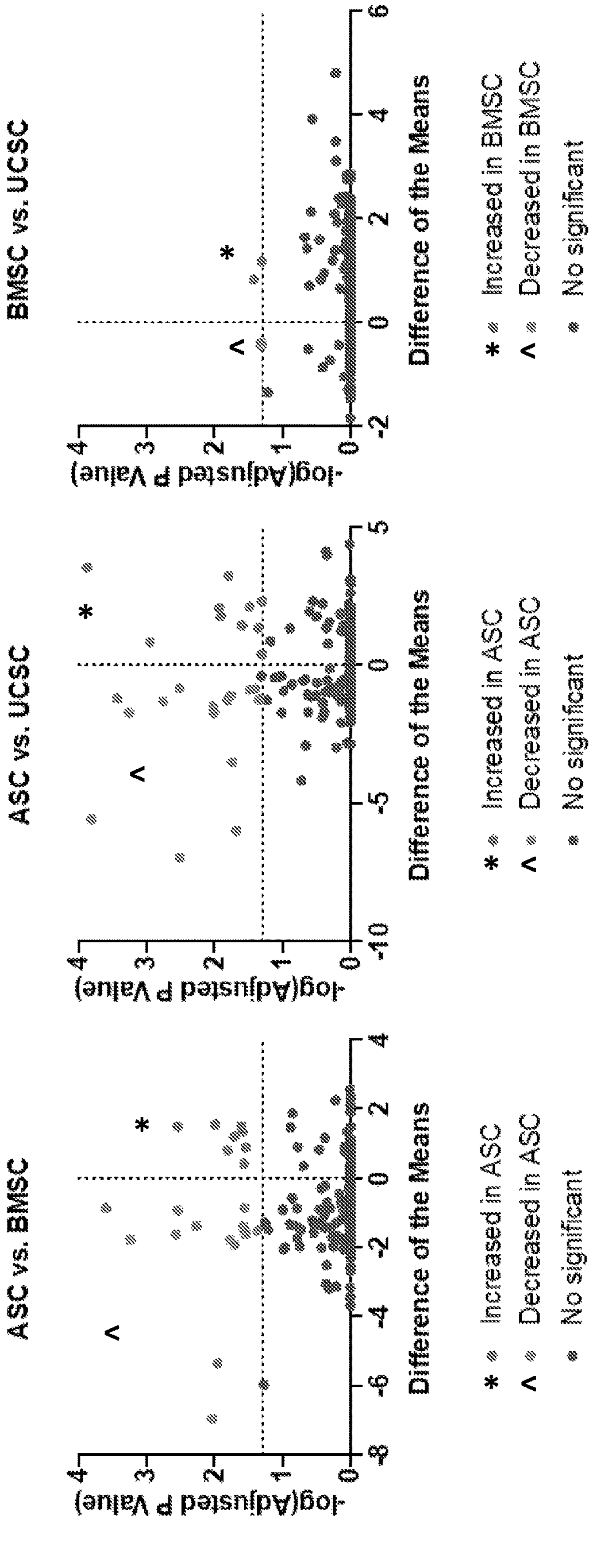

MBV miRNA content is unique to the cellular origin: Results with the 3T3 fibroblast cell model showed selective packaging of miRNA within MBV deposited in the ECM compared to liquid-phase EV secreted into the cell culture supernatant. To determine if MBV miRNA cargo is unique to the cellular origin, the miRNA composition of MBV isolated from ECM produced in-vitro by bone marrow-derived stem cells (BMSC), adipose stem cells (ASC) and umbilical cord stem cells (UCSC) isolated from different human donors, were characterized and compared through next generation sequencing methods. A representative phase contrast microscopy image of a decellularized BMSC cell culture plate showed the absence of cells and the presence of branched fibrillar structures (FIG. 3A). TEM imaging of isolated MBV from a decellularized BMSC cell culture plate showed the characteristic morphology attributed to extracellular vesicles (FIG. 3B). Furthermore, nanoparticle tracking analysis showed similar distribution plots between BMSC, ASC, and UCSC-derived MBV, with the majority of vesicles having a diameter <200 nm (FIGS. 3C-3E). After isolation of total RNA from these samples, bioanalyzer analysis showed the absence of ribosomal RNA and an enrichment of small RNA molecules (<200 nt) (FIG. 3F). miRNA libraries were generated from the samples (BMSC, n=3 human donors; ASC, n=3 human donors; UCSC, n=3 human donors) and subjected to miRNA sequencing. A principal component analysis showed that samples clustered primarily by the cell type from which they were derived (FIG. 3G). Despite the use of three separate human donors for each cell type used to generate the MBV samples, the principal component analysis showed a high degree of homogeneity in the miRNA profile within the respective groups (FIG. 3G). In addition, volcano plots showed that fewer miRNAs were found differentially expressed between BMSC and UCSC-derived MBV than between BMSC-ASC and UCSC-ASC.

Figure 4A:
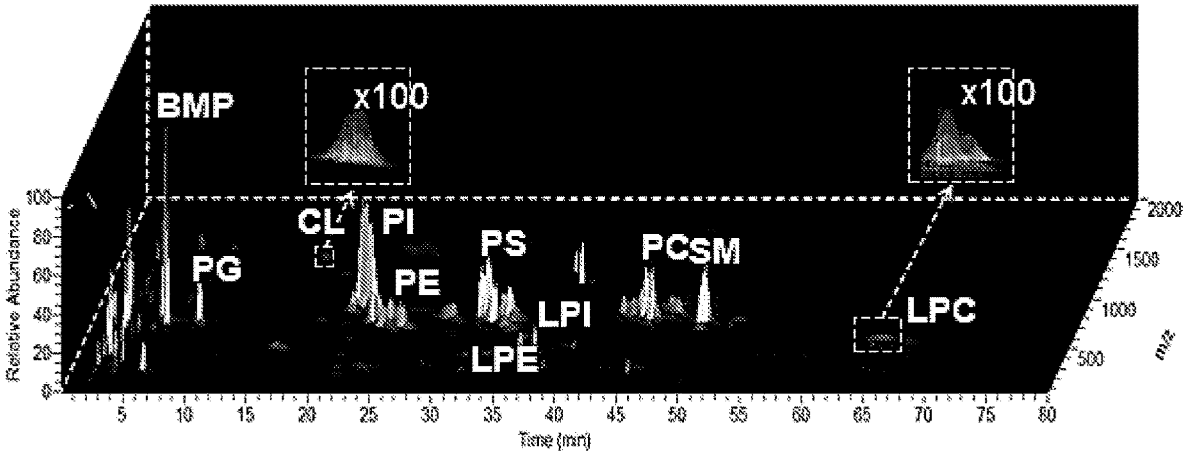
FIGS. 4A-4E show LC/MS characterization of phospholipids between MBV, liquid-phase EV, and the parent cells.
Figure 4B:
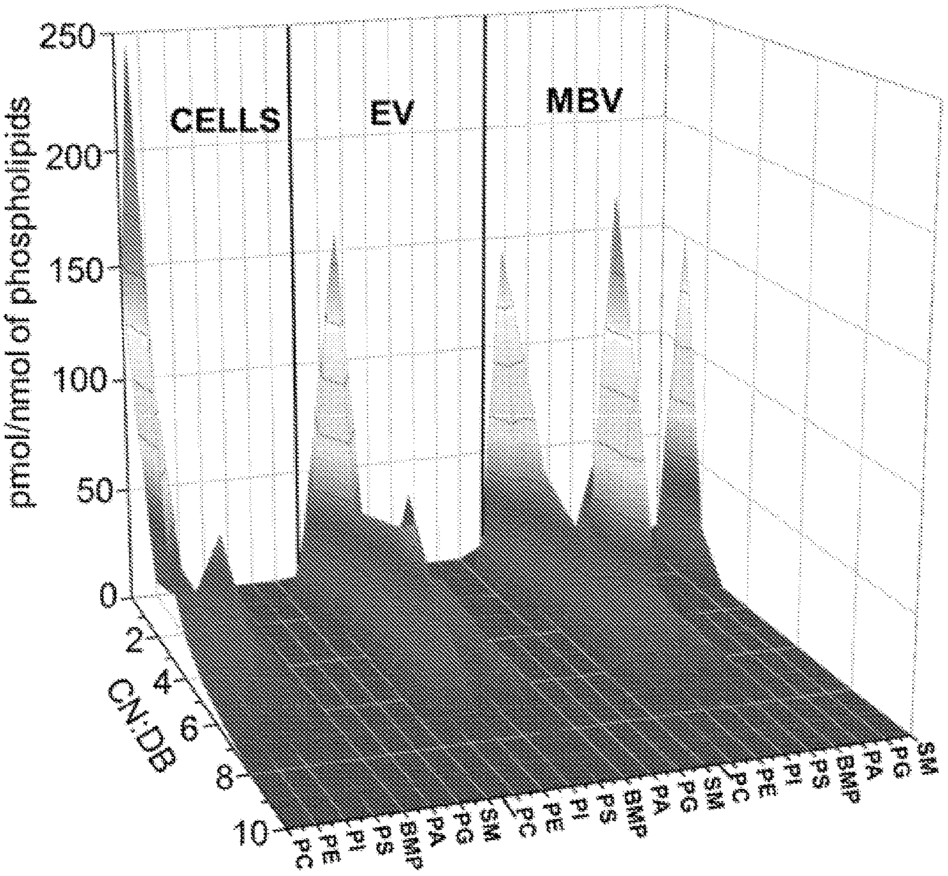
Figure 4C:
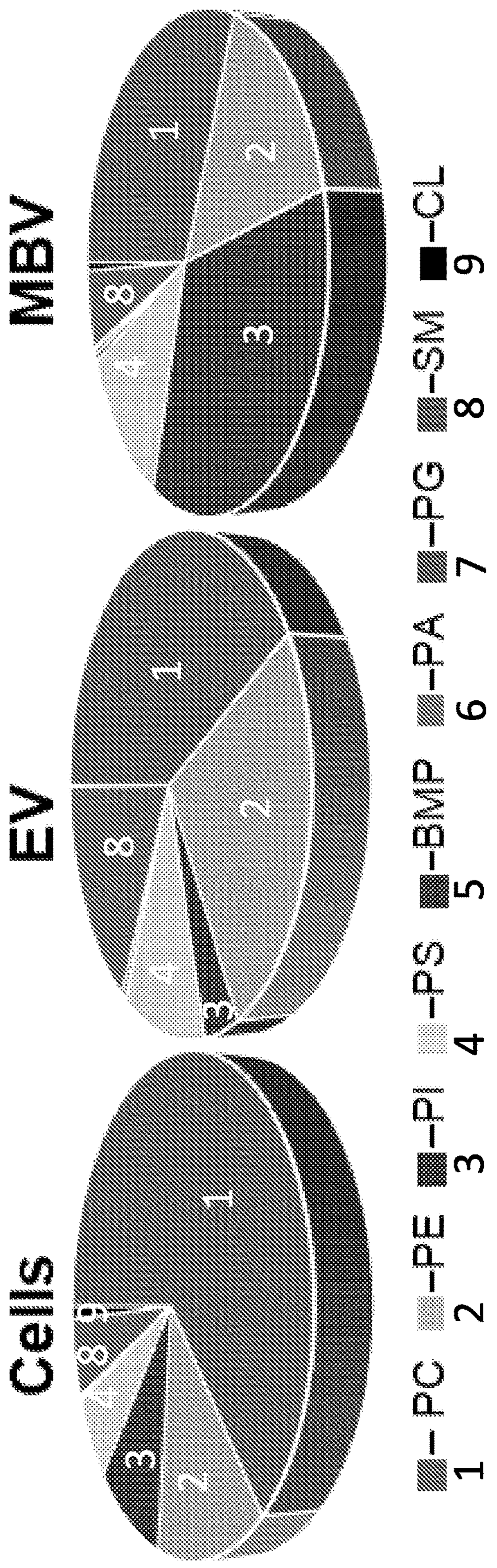
Figure 4D:
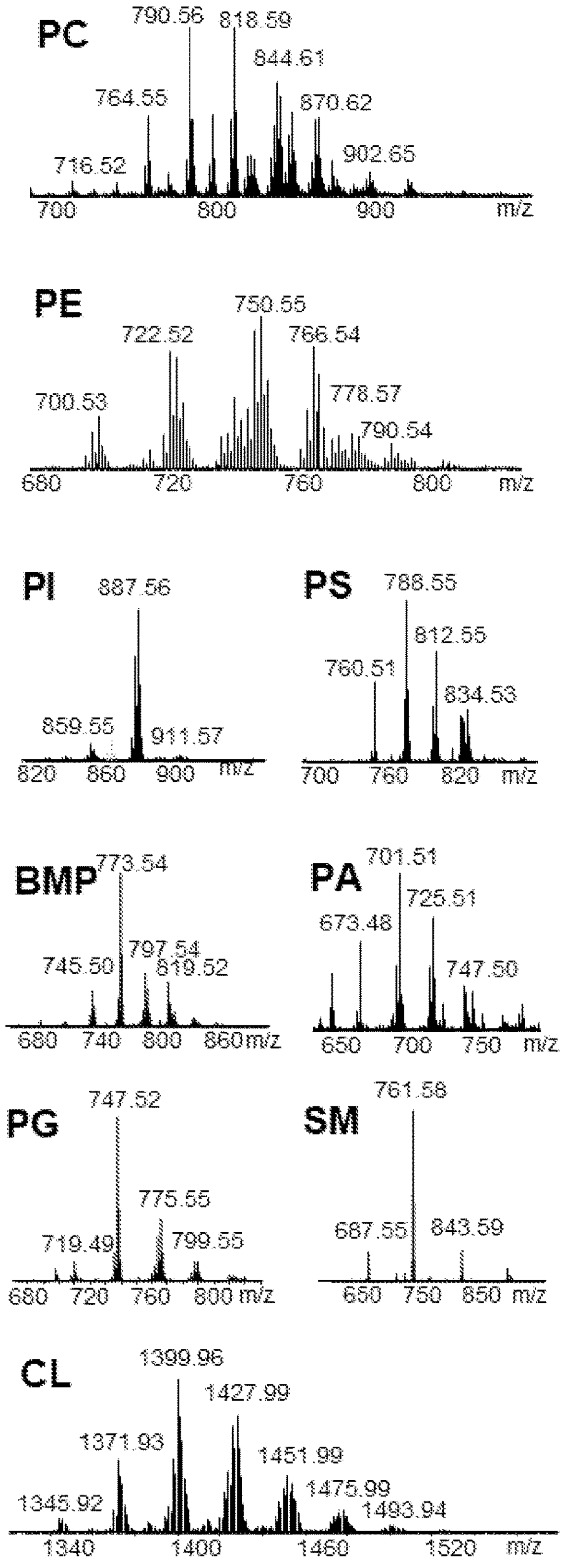
Figure 4E:
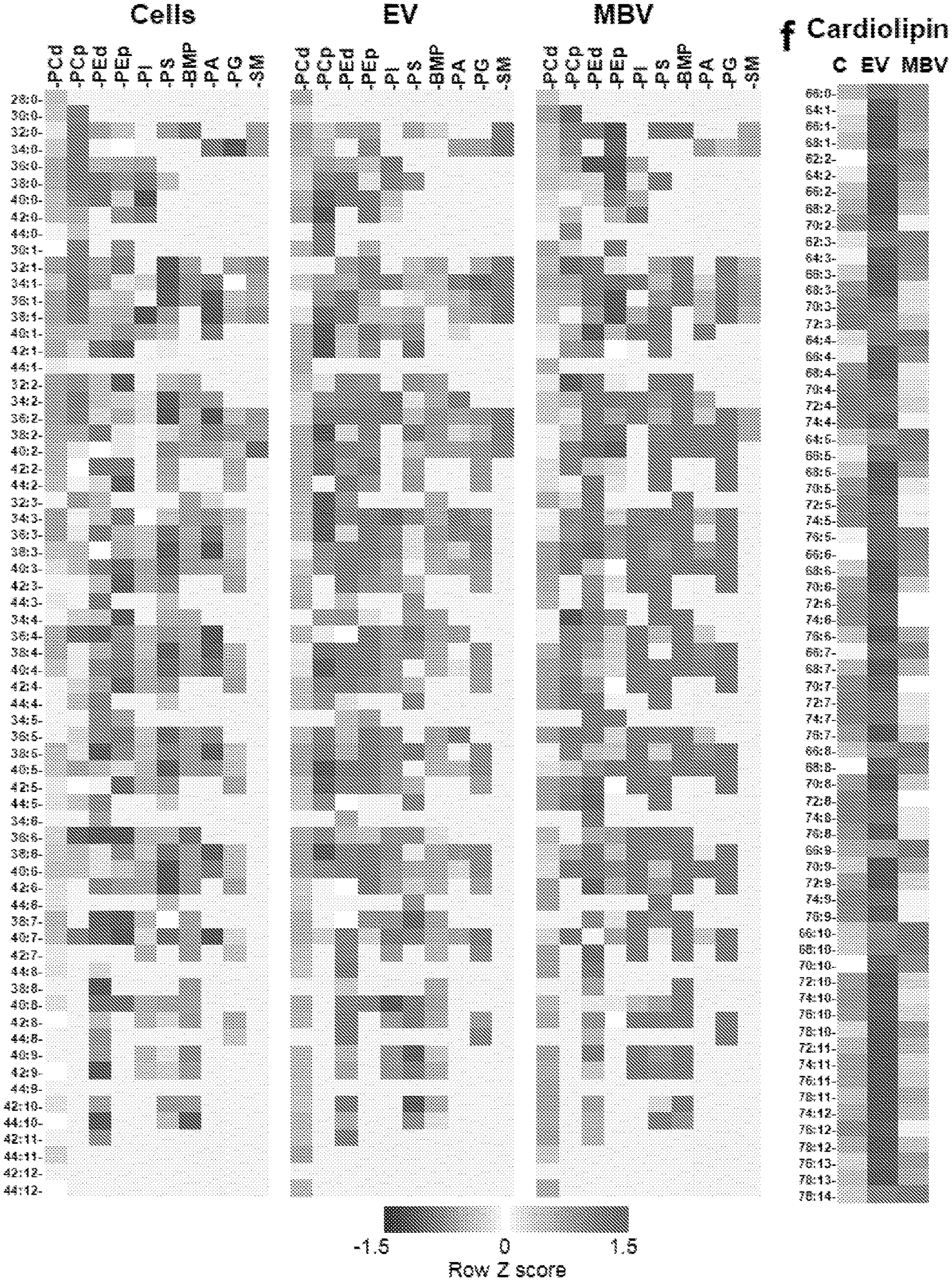

Phospholipid profiles of liquid-phase EV, MBV, and parent cells: Several studies have characterized the lipid composition of EV(T. Skotland, et al, *Journal of lipid research* 60, 9-18 (2019)). However, there is no data on phospholipid composition of MBV. LC-MS based global lipidomics and redox lipidomics analyses were therefore conducted to comparatively evaluate the phospholipid composition of MBV and liquid-phase EV compared to their 3T3 fibroblast parent cells (FIG. 4A, FIG. 4D). Nine major phospholipid classes were detected across the three types of samples, with the total number of detected molecular species of 536 distributed between the following major classes: bis-monoacylglycerophosphate (BMP)—59 species, phosphatidylglycerol (PG)—37 species, cardiolipin (CL)—117 species, phosphatidylinositol (PI)—33 species, phosphatidylethanolamine (PE)—102 species, phosphatidylserine (PS)—45 species, phosphatidic acid (PA)—26 species, phosphatidylcholine (PC)—107 species, and sphingomyelin (SM)—10 species (FIG. 4D). In terms of their content of polyunsaturated fatty acid (PUFA) residues, PE, PI, PC and PS represented the major reservoir of these polyunsaturated PL species containing four-seven double bonds (FIG. 4B). These PUFA phospholipids represent the likely precursors of the signaling lipid mediators. The formation of the mediators occurs via the catalytic oxygenation of PUFA phospholipids by 5-lipoxygenase or 15-lipoxygenase to yield oxygenated phospholipids that are subsequently hydrolyzed by one of specialized phospholipases A2 to release oxygenated fatty acids (lipid mediators) (Z. Zhao et al., *Endocrinology* 151, 3038-3048 (2010); Y. Y. Tyurina et al., *Journal of leukocyte biology*, (2019)). In addition, oxidized PUFA phospholipids act as signaling molecules coordinating many intracellular processes and cell responses, including apoptosis, ferroptosis and inflammation (Y. Y. Tyurina et al., *Antioxidants & redox signaling* 29, 1333-1358 (2018)). Significant differences in molecular speciation of these phospholipids and their relative contents were observed between liquid-phase EV and MBV (FIG. 4E). With a notable exception of SM, arachidonic acid (AA)- and docosahexaenoic acid (DHA)-residues were detected in all phospholipids (FIG. 4E). For many of the phospholipids, the amounts were significantly higher in MBV vs liquid-phase EV and parent cells (FIG. 4E), which identify MBV as a rich reservoir of PUFA-phospholipids. PUFA phospholipids can be hydrolyzed by $PLA_2$ resulting in the release of free PUFA and LPL(V. D. Mouchlis, et al, *Biochimica et Biophysica Acta* (*BBA*)-*Molecular and Cell Biology of Lipids* 1864, 766-771 (2019)). The former can be further utilized by two major oxygenases, COX and LOX to produce lipid mediators with pro- or anti-inflammatory capacities (Y. Y. Tyurina et al., Redox (phospho) lipidomics of signaling in inflammation and programmed cell death. *Journal of leukocyte biology*, (2019); C. A. Rouzer, et al., *Chemical reviews* 103, 2239-2304 (2003); H. Kuhn, et al., *Biochimica et Biophysica Acta* (*BBA*)-*Molecular and Cell Biology of Lipids* 1851, 308-330 (2015)). This finding qualifies MBV as potential precursors for synthesis of these lipid mediators dependently on the cell/tissue context (Y. Y. Tyurina et al., *Journal of leukocyte biology*, (2019)). Quantitatively, MBV were enriched in PI, PS, PG and BMP (FIG. 4C and Table 2). The phospholipid content shown in FIG. 4C is also provided in Table 1.

TABLE 1

Phospholipid Content as Percent of Total Phospholipids

| | Cells | EV | MBV |
|---|---|---|---|
| PC, phosphatidylcholine | 62.95 | 41.54 | 31.38 |
| PE, phosphatidylethanolamine | 13.84 | 24.47 | 14.75 |
| PI, phosphatidylinositol | 9.6 | 4.21 | 33.58 |
| PS, phosphatidylserine | 6.49 | 11.18 | 12.68 |
| BMP, bis- monoacylglycerophosphate | 0.13 | 0.13 | 0.55 |
| PA, phosphatidic acid | 0.11 | 0.64 | 0.42 |
| PG, phosphatidylglycerol | 0.04 | 0.02 | 0.11 |
| SM, sphingomyelin | 5.87 | 17.64 | 5.87 |
| CL, cardiolipin | 0.97 | 0.17 | 0.66 |

In contrast, the content of PE, PA and SM was higher in liquid-phase EV. PC was a predominant phospholipid in cells and liquid-phase EV. The content of a unique mitochondrial phospholipid, cardiolipin (CL), was significantly lower in liquid-phase EV compared to MBV and parent cells (FIG. 4F). Because CL is a unique mitochondria-specific phospholipid localized predominantly in the inner mitochondrial membrane (M. Schlame, et al., *Biochimica et Biophysica Acta* (*BBA*)-*Molecular and Cell Biology of Lipids* 1862, 3-7 (2017)), this finding represents a possible link of the MBV biogenesis with the mitochondrial compartment of cells. Plasmalogen phospholipids (or ether phospholipids) are structurally different from diacyl-phospholipids (or ester-phospholipids) (M. Schlame, et al., *Biochimica et Biophysica Acta* (*BBA*)-*Molecular and Cell Biology of Lipids* 1862, 3-7 (2017)). In plasmalogens, vinyl ether bond is linking the sn-1 saturated or monounsaturated chain to the glycerol backbone of phospholipids (N. E. Braverman, et al., *Biochimica et Biophysica Acta* (*BBA*)-*Molecular Basis of Disease* 1822, 1442-1452 (2012)). It has been shown that ether lipids, PE and PC plasmalogens, can facilitate membrane fusion (P. E. Glaser, et al., *Biochemistry* 33, 5805-5812 (1994)) and increase membrane thickness of extracellular vesicles (X. Han, et al., *Biochemistry* 29, 4992-4996 (1990); T. Rog, et al., *Biochimica et Biophysica Acta* (*BBA*)-*Biomembranes* 1858, 97-103 (2016)), and therefore may play a role in nanovesicle uptake by cells. Detailed MS/MS analysis showed a high level of ether PE and PC species (plasmalogens) in both liquid-phase EV and MBV. These species were identified as PE-16:0p/20:4, PE-16:1p/20:4, PE-18:1p/20:4, PE-18:1p/22:6 and PC-16:0p/20:4, PC-18:0p/20:4, PC-20:0p/20:4, PC-18:0p/22:6, respectively (FIG. 4E).

TABLE 2

Contents of cardiolipin, phosphatidic acid, phosphatidylglycerol and bis-monoglycerophosphate in MBV, exosomes and parent 3T3 cells.

| | 3T3 cells | Liquid-phase EV | MBV |
|---|---|---|---|
| Cardiolipin, CL | 0.97 ± 0.06 | 0.17 ± 0.01* | 0.66 ± 0.20* |
| Phosphatidic acid, PA | 0.11 ± 0.01 | 0.64 ± 0.29* | 0.42 ± 0.21 |
| Phosphatidylglycerol, PG | 0.04 ± 0.01 | 0.02 ± 0.02* | 0.11 ± 0.02** |
| bis-monoglycerophosphate, BMP | 0.13 ± 0.01 | 0.13 ± 0.04 | 0.55 ± 0.12#* |

Data are presented as pmol/nmol of phospholipids, means ± s.d.,
*$p < 0.05$ vs cells,
#$p < 0.05$ vs liquid-phase EV.

Figure 5A:
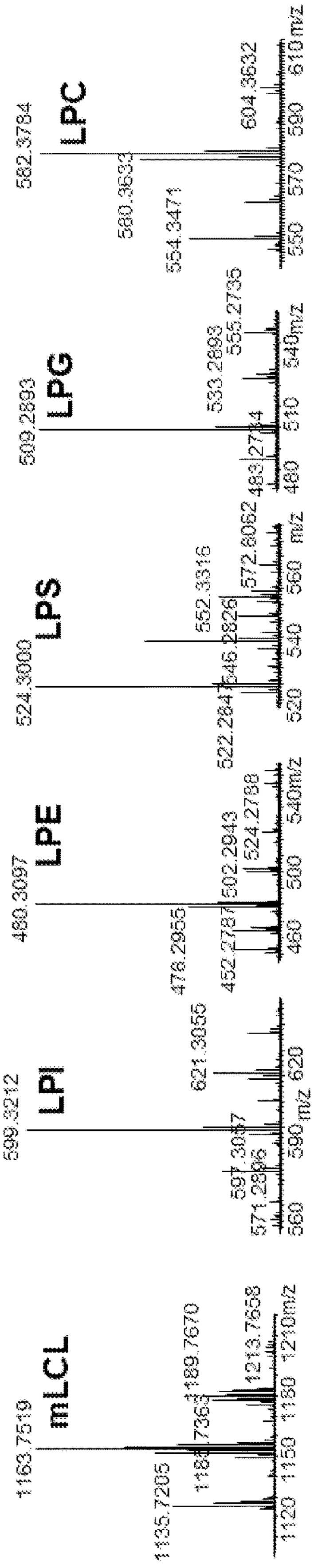
FIGS. 5A-5D show LC/MS characterization and follow-up analyses examining differences in LPE, LPA and LPG between MBV, liquid-phase EV, and the parent cells.
Figure 5B:
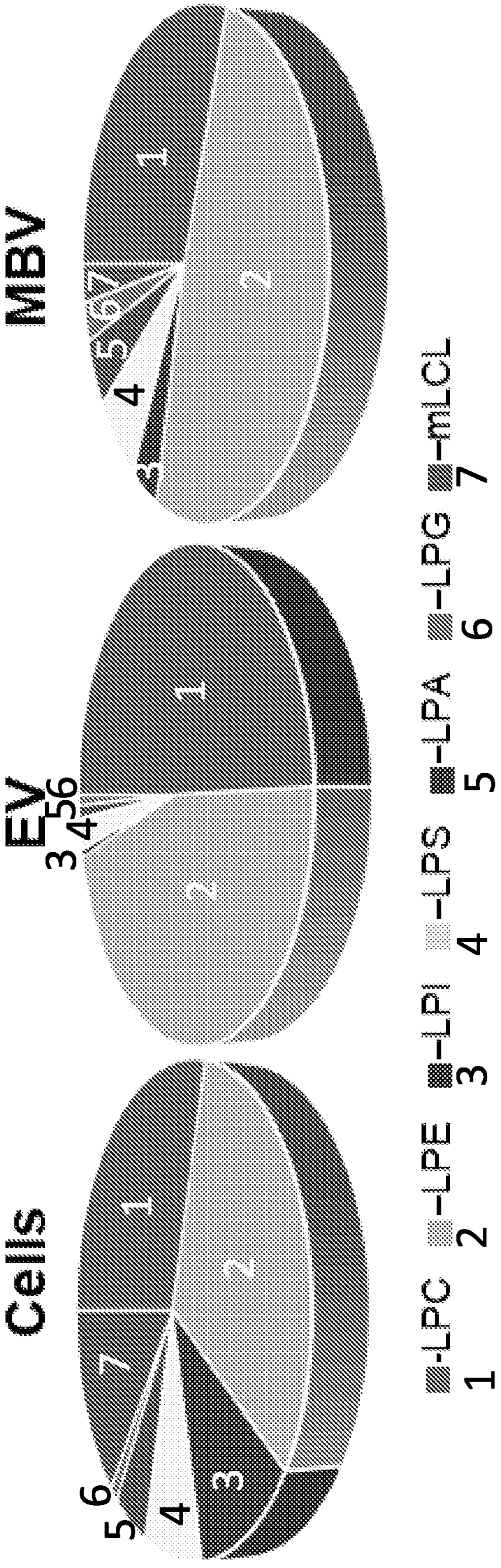
Figure 5D:
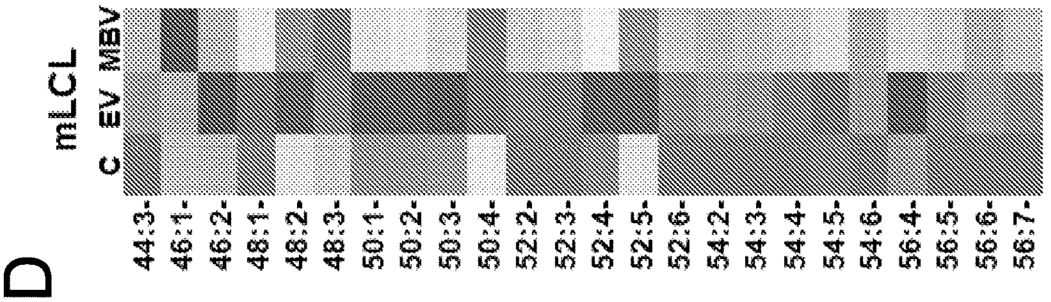
Figure 5C:
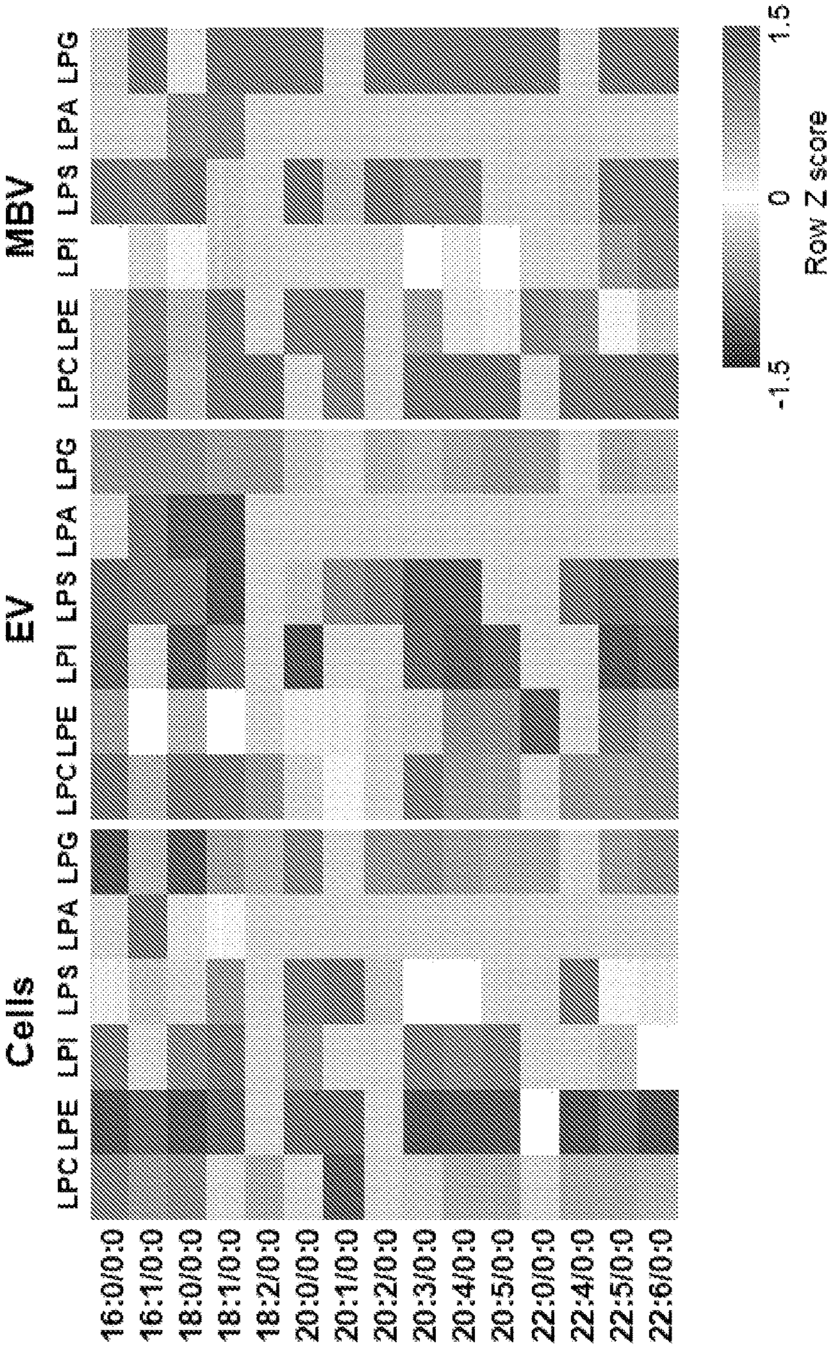

Lysophospholipid profiles of liquid-phase EV, MBV, and parent cells. Lysophospholipids (LPL), hydrolytic metabolites of phospholipids created by phospholipases A, are bioactive signaling molecules that modulate a variety of physiological responses, including macrophage activation (R. Ray, et al., *Blood* 129, 1177-1183 (2017)) inflammation and fibrosis (A. M. Tager et al., *Nature medicine* 14, 45 (2008)), tissue repair and remodeling (K. Masuda, et al., *The FEBS journal* 280, 6600-6612 (2013)), and wound healing (K. M. Hines et al., *Analytical chemistry* 85, 3651-3659 (2013)), among others. LC-MS analysis showed that LPL were present in all three types of samples albeit with their total content in MBV and liquid-phase EV being 1.7-1.8 times greater compared to the parent cells. More specifically, seven classes of LPL have been identified: lysophosphatidylethanolamine (LPE), lysophosphatidylcholine (LPC), lysophosphatidylserine (LPS) lysophosphoinositol (LPI), lysophosphatidic acid (LPA), lysophosphatidylglycerol (LPG) and monolysocardiolipin (mCL) (FIG. 5A). MBV were enriched in LPE, LPA and LPG compared to parent cells (FIG. 5B). The content of LPI and mCL was significantly lower in MBV and liquid-phase EV vs cells. The content of LPA and LPG was significantly higher in MBV compared to EV. The levels of mLCL and LPI in MBV were 3- and 6.3 times higher than in EV but 3.3- and 1.9 times lower compared to cells (FIG. 5C, FIG. 5D). No significant changes in the contents of LPE, LPC and LPS between MBV and EV were found. The non-oxidizable molecular species containing 16:0, 16:1, 18:0 and 18:1 were the major types found in all LPL species detected (FIG. 5C). These findings suggest that high levels of lysophospholipids, bioactive molecules that are important for macrophage differentiation, tissue repair, remodeling and wound healing, is a characteristic feature of MBV.

Figure 6A:
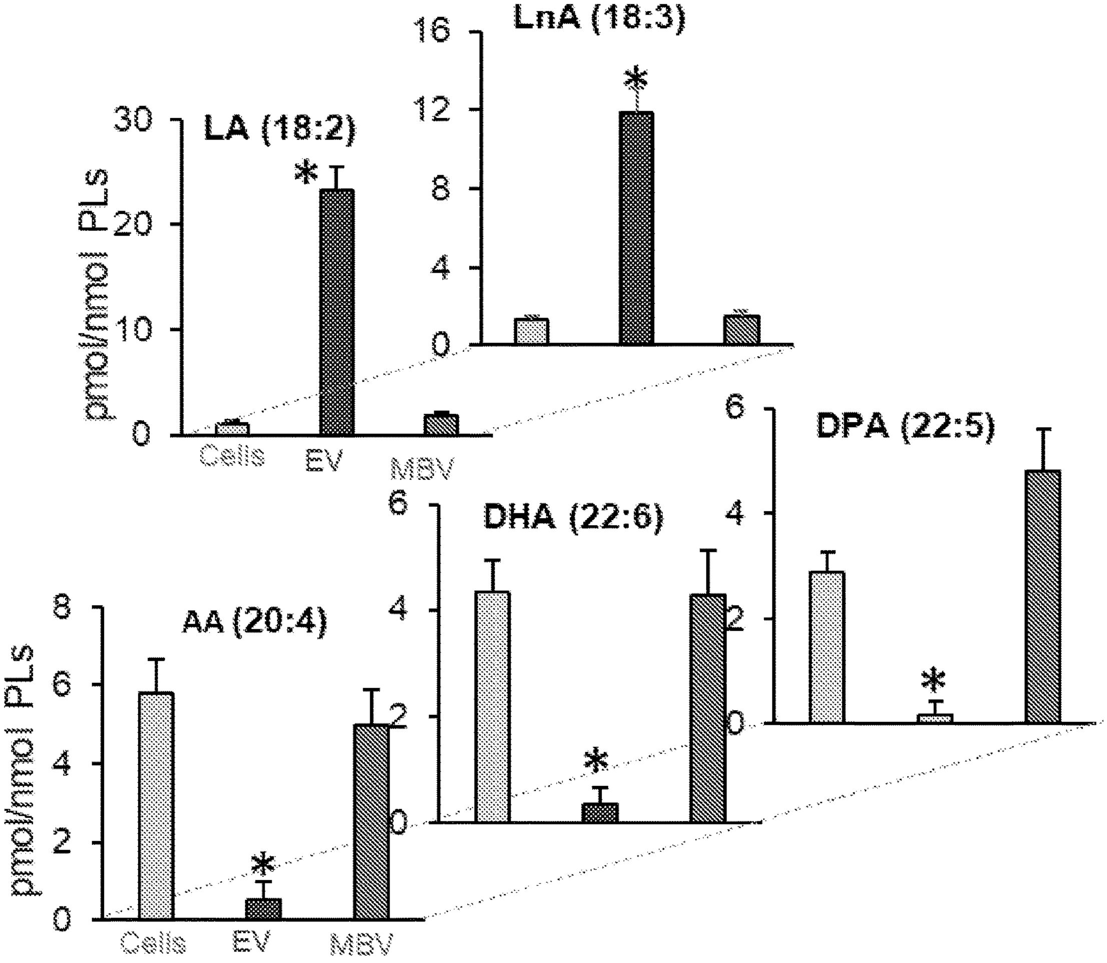
FIGS. 6A-6C demonstrate that levels of PUFA-containing phospholipids and their oxidatively modified molecular species are higher in MBV compared to those in liquid-phase EV. Content of free PUFA (FIG. 6A) and their oxygenated metabolites (FIG. 6B) in parent cell, liquid phase EV and MBV was assessed. Data are presented as mean±s.d., *p<0.05 and compared to cells or MBV, with n=3.

Analysis of free and oxygenated fatty acids of MBV and liquid-phase EV: As exposure of murine bone-marrow derived macrophages to MBV results in expression of M2-like markers, Fizzl and Arg1, which are associated with a constructive macrophage phenotype (L. Huleihel et al., *Science advances* 2, e1600502 (2016)), LC/MS analysis of PUFA and their oxygenated products in MBV vs liquid phase EV and parent cells was performed. MBV were strongly enriched in arachidonic (20:4, AA), docosahexaenoic (22:6, DHA) and docosapentaenoic (22:5, DPA) fatty acids (FIG. 6A). In other words, MBV represent a reservoir of substrates for the biosynthesis of signaling lipid mediators by the respective enzymatic mechanisms—COXs and LOXs. In liquid phase EV, the major PUFA were linoleic (18:2) and linolenic (18:3) acids (FIG. 6A).

Figure 6B:
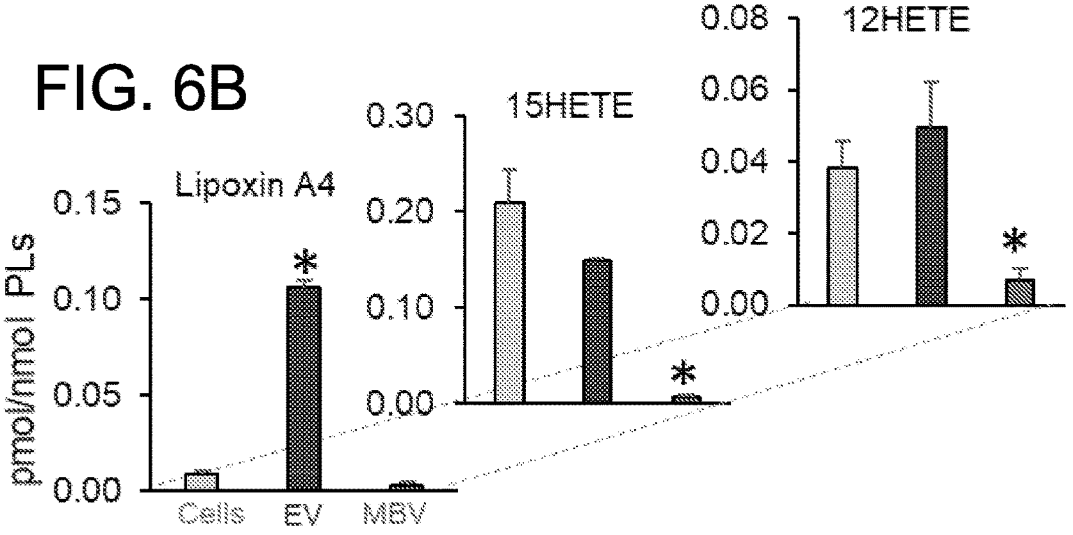
Figure 6C:
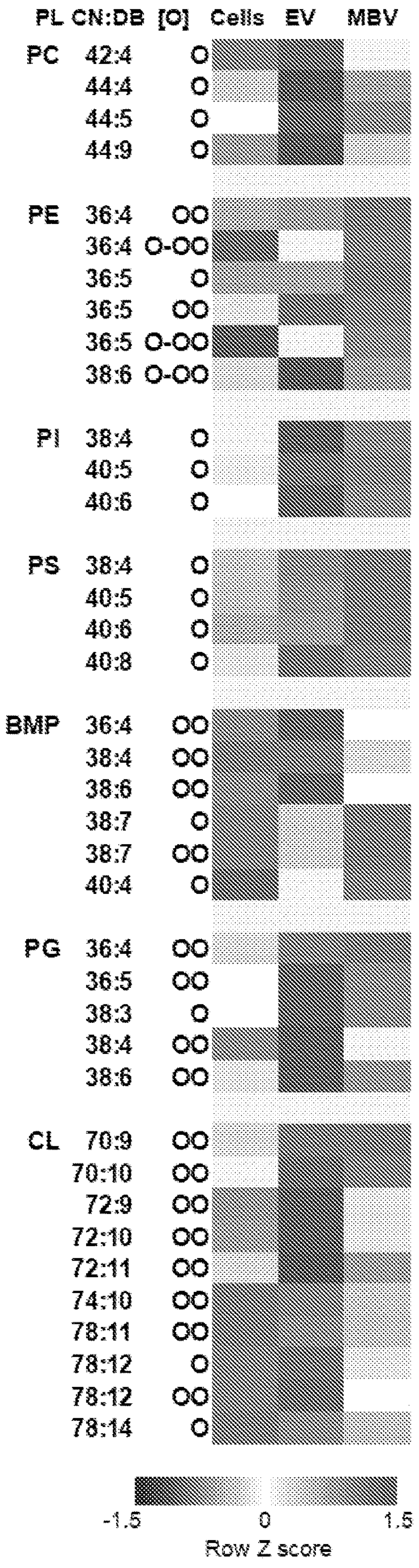

As extracellular vesicles contain enzymatic machinery for biosynthesis of AA-derived lipid mediators (E. Boilard, *Journal of lipid research* 59, 2037-2046 (2018)), redox lipidomics analysis of oxygenated fatty acids was performed. Higher levels of AA metabolites such as 12-HETE, 15-HETE, lipoxin $A_4$ were found in liquid-phase EV vs MBV (FIG. 6B). In the context of tissue repair, lipoxin $A_4$ ($LXA_4$) and D-series resolvin D1 (RvD1)—produced by 12/15-LOX from arachidonic (20:4, AA) and docosahexaenoic (22:6, DHA) acids—stimulate macrophage activation to the M2-like phenotype (C. N. Serhan, *The American journal of pathology* 177, 1576-1591 (2010)). Finally, oxidized phospholipids containing oxygenated AA and DHA in MBV and liquid-phase EV were characterized. The levels of oxygenated species were higher in MBV than liquid-phase EV, where PS, PI and PC were represented by mono-oxygenated species. BMP, PG and CL contained singly- and doubly-oxygenated AA- and DHA-residues; triply-oxygenated PUFA were found only in PE (FIG. 6C). Overall, lipidomics and oxidative lipidomics results show that the levels of free AA, DHA and DPA and PUFA-containing phospholipids as well as their oxidatively modified molecular species are higher in MBV compared to those in liquid-phase EV. MBV, but not liquid-phase EV, were enriched in PUFA non-oxygenated and oxygenated phospholipids and therefore represent a potential reservoir of oxidized and oxidizable esterified PL species, representing a potential source of lipid mediators activated by different phospholipases dependent on the pro-/anti-inflammatory contexts of the extracellular environment.

The above-mentioned LC-MS-based lipidomics and redox lipidomics studies were undertaken to conduct a detailed comparison of liquid-phase EV and MBV phospholipids. Combined with comprehensive RNA sequencing and bioinformatic analysis of the intravesicular cargo, these data reflect that MBV are a distinct and unique subpopulation of EV, distinct from liquid phase EV (i.e., exosomes), and a distinguishing feature of ECM-based biomaterials, with similarities limited to size and shape of the vesicles.

Herein, vesicle populations were fractionated based on their compartmentalization into either the liquid-phase cell culture medium or the solid-phase ECM substrate. In terms of composition, MBV isolated from the ECM of 3T3 fibroblasts contained a differential miRNA and lipid signature compared with liquid-phase EV and with the parent cell. These data are suggestive of a scenario in which molecular sorting occurs during vesicle biogenesis to specifically distribute miRNA and lipids to vesicles destined for different extracellular locations. Moreover, the cell's capacity to differentiate between a liquid interface and a solid substrate, and to selectively deposit tailored subpopulations of vesicles with distinct lipid signatures into these disparate compartments, provides evidence for a different and independent membrane biogenesis of MBV from the biogenesis of EV secreted into a liquid-phase. Considering that MBV were shown to be integrated within the dense fibrillar network of the extracellular matrix, MBV should be secreted by cells in concert with ECM components during matrix deposition during tissue development and homeostasis, and during dynamic matrix remodeling following injury. Furthermore, given that the ECM is a complex mixture of proteins, proteoglycans and glycosaminoglycans arranged in a tissue-specific 3D architecture (Hussey et al., *Nature Review Materials,* 3(7):159-173, 2018), MBV cargo and lipid content should also be unique to the tissue and cellular origin. MBV isolated from ECM bioscaffolds derived from anatomically distinct source tissue have differential miRNA signatures (Huleihel et al., Science Advances, 2, e1600502, 2016). Results from the present study further show that MBV isolated from ECM produced in vitro by bone marrow-derived stem cells, adipose stem cells and umbilical cord stem cells derived from different human donors contained a distinctive miRNA signature specific to the cell source. In addition, fewer miRNAs were found differentially expressed between BMSC and UCSC-derived MBV than between BMSC-ASC and UCSC-ASC, a finding that may be attributed to tissue-specific differentiation potentials of adipose stem cells (L. Xu et al., *Stem cell research & therapy* 8, 275 (2017)). These findings further underline the cell-specific features of MBV miRNA profiles, which was not significantly affected by the intrinsic variability of donors. However, given that the three human donors were all male, further studies to determine sex-related variations in the miRNA cargo of MBV from the stem cells samples are warranted. Importantly, principal component analysis showed a high degree of batch-to-batch consistency of the miRNA cargo from MBV deposited by specific cell types isolated from different human donors, supporting MBV and ECM biomaterial manufacturing as research tools or clinical therapeutics. The present study establishes that MBV integrated into the matrix are a unique subpopulation of EV. In addition, MBV showed a marked decrease in proteins commonly attributed to exosomes (e.g., CD63, CD81, CD9).

In contrast to EV that are secreted into body fluids and readily available for cell-cell communication, MBV embedded within tissue ECM are stably associated with the matrix and can only been isolated following degradation of the ECM material (Huleihel et al., Science advances 2, e1600502 (2016)). The requirement for matrix degradation to release MBV may partially define their mechanism of action, including those related to their capacity to generate pro-resolving lipid mediators. Because MBV remain intact and attached to ECM even after decellularization, the molecular speciation of their constituent phospholipids likely facilities such MBV-ECM interactions. Using LC-MS-based lipidomics and redox lipidomics approaches, detailed characterization of the molecular speciation of MBV phospholipids, lysophospholipids and the oxygenated and non-oxygenated PUFA were performed. High levels of lysophospholipids, bioactive molecules that are important for macrophage differentiation, tissue repair, remodeling and wound healing, is a characteristic feature of MBV. In addition, as fusogenic lipids, lysophospholipids can facilitate the transfer of the vesicular contents to intracellular targets. MBV, but not liquid-phase EV, were enriched in PUFA non-oxygenated and oxygenated phospholipids and therefore represent a potential reservoir of oxidized and oxidizable esterified PL species. Notably, PUFA-enriched MBV are an important source of lipid mediators activated by different phospholipases dependent on the pro-/anti-inflammatory context of the extracellular environment.

Example 2: Use of MBV for Treatment of Pristane-Induced Arthritis

Urinary bladder matrix was prepared using the methodologies as described in Example 1.

MBV were isolated from laboratory produced porcine UBM by enzymatic digestion with Liberase TL (highly purified Collagenase I and Collagenase II) in buffer (50 mM Tris pH7.5, 5 mM $CaCl_2$, 150 mM NaCl) for 24 hours at room temperature on an orbital rocker. Digested ECM was then subjected to centrifugation at 10,000×g for 30 minutes to remove ECM debris. The clarified supernatant containing the liberated MBV was then centrifuged at 100,000×g (Beckman Coulter Optima L-90K Ultracentrifuge) at 4° C. for 2 hours to pellet the MBV.

Figure 7:
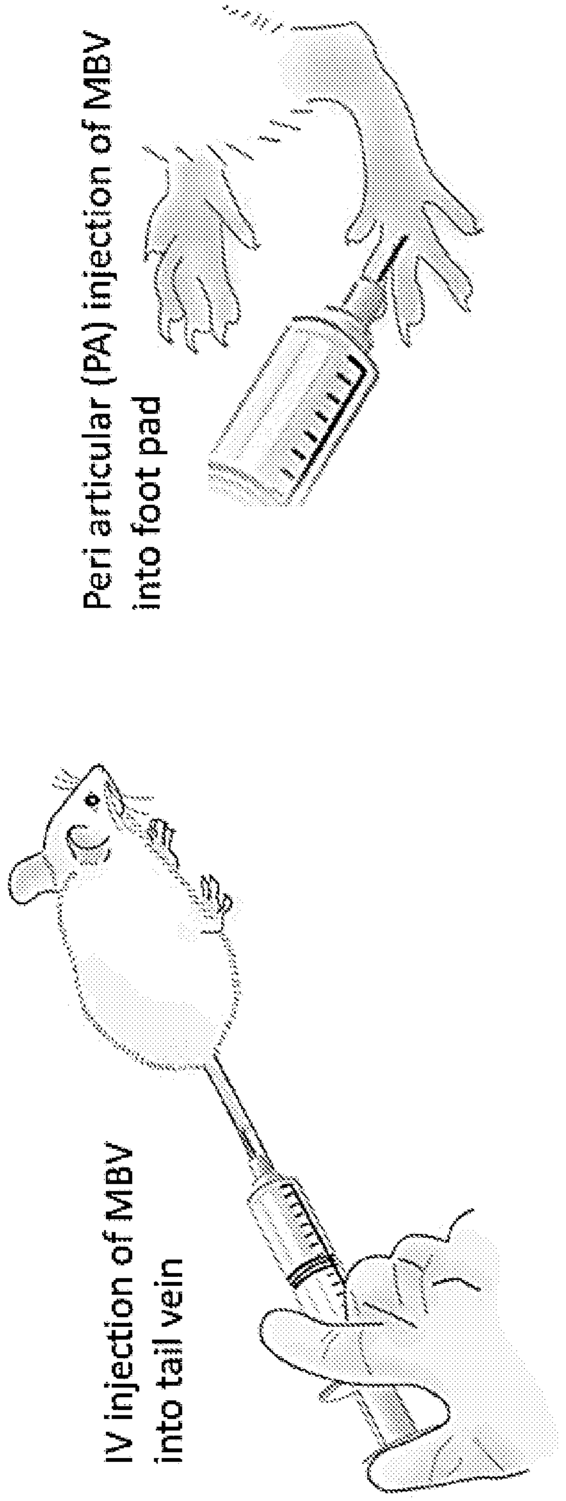
FIG. 7 depicts routes of administration of MBV for treatment of rheumatoid arthritis in rat animal models.

In this example, anti-inflammatory effects were assessed following systemic or local administration of MBV in a murine model treated with an inflammatory agent, pristane. The pristane-induced arthritis model in rats has been established as a clinically-relevant animal model for studying rheumatoid arthritis (Tuncel et al. *PLoS One.* 2016; 11(5): e0155936). Pristane induced arthritis was induced in 8-week-old, female, Sprague-Dawley rats by an intradermal injection of 300 μL pristane (2,6,10,14-tetramethypentadecane) at the dorsal side of the tail, 1 cm distal to the base on Day 0 of the study. Control animals did not receive an intradermal injection of pristane on Day 0. A second dose of 300 μL pristane was administered intradermally, approximately 1 cm distally to the dorsal tail base on Day 4. Animals receiving pristane were housed together in cages. Animals receiving pristane were randomized into the following experimental groups: pristane-only, methotrexate, periarticular MBV, and intravenous MBV. A depiction of periarticular and intravenous MBV routes of administration is shown in FIG. 7.

Arthritis score was determined on days 7, 10, 14, 17, 21, 28, and every week thereafter through an endpoint of 100 days for each animal. Photographs of each forepaw and hind paw were taken as viewed from the volar and plantar perspectives, respectively. Arthritis was evaluated using a 60-point arthritis scoring criteria: 1 point was given for each inflamed knuckle or toe and up to 5 points was assigned for an affected ankle (15 points per paw, 60 points per each rat). Animals designated as Pristane-only did not receive any treatment on days 7, 10, 14, 17, and 21. The methotrexate animals received 0.1 mg/kg methotrexate in 1× sterile PBS delivered intra-peritoneally on days 7, 10, 14, 17, and 21. The periarticular MBV animals received 25 μL of 500 μg/mL porcine-derived, UBM MBV delivered in the plantar and volar surfaces of hind paws and forepaws, respectively. The intravenous MBV group received 100 μL of 500 μg/mL UBM MBV delivered intravenously into the lateral tail vein of the animal. Four animals in each group were assigned to a short-term study of 28 days and four animals were assigned to a 100 day study. Sample size was determined using previously published effect size of methotrexate with a predetermined alpha 0.05 and beta 0.80. Arthritis score was represented as mean+/−standard error of mean. Days 7-21 represent an n of 8 for each group and then days 28 and onward represent an n of 4 for each group. Differences in groups were analyzed using two-way analysis of variance with Tukey's post-hoc correction. Significance was determined prior to the study with an alpha of 0.05.

Figures 8A, 8B, 8C, 8D, 8E:
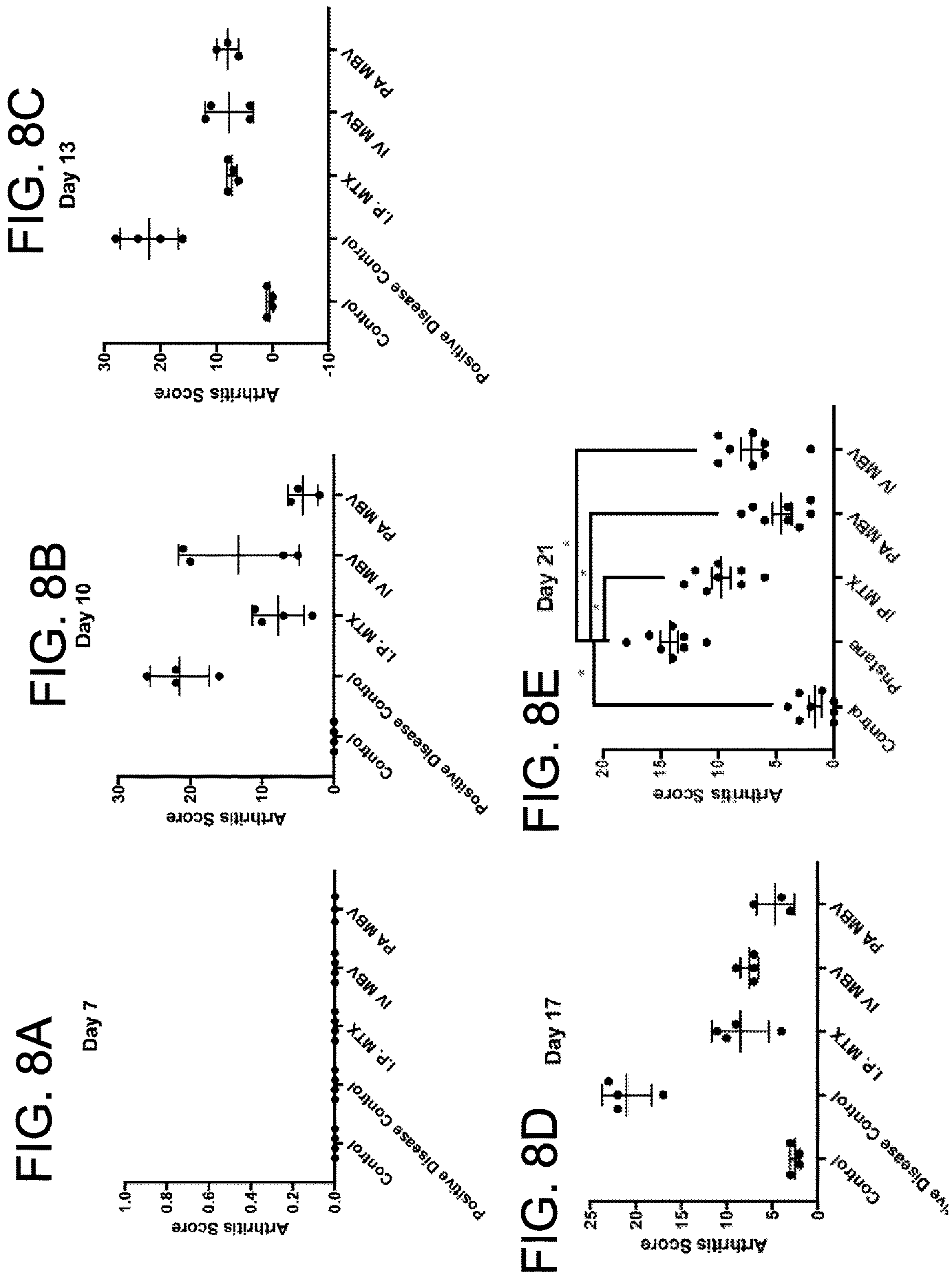
FIGS. 8A-8E show the individual arthritis scores of control and arthritis rat models treated with pristane-only, intraperitoneal (IP) methotrexate (MTX), periarticular (PA) MBV, or intravenous (IV) MBV.
Figure 9A:
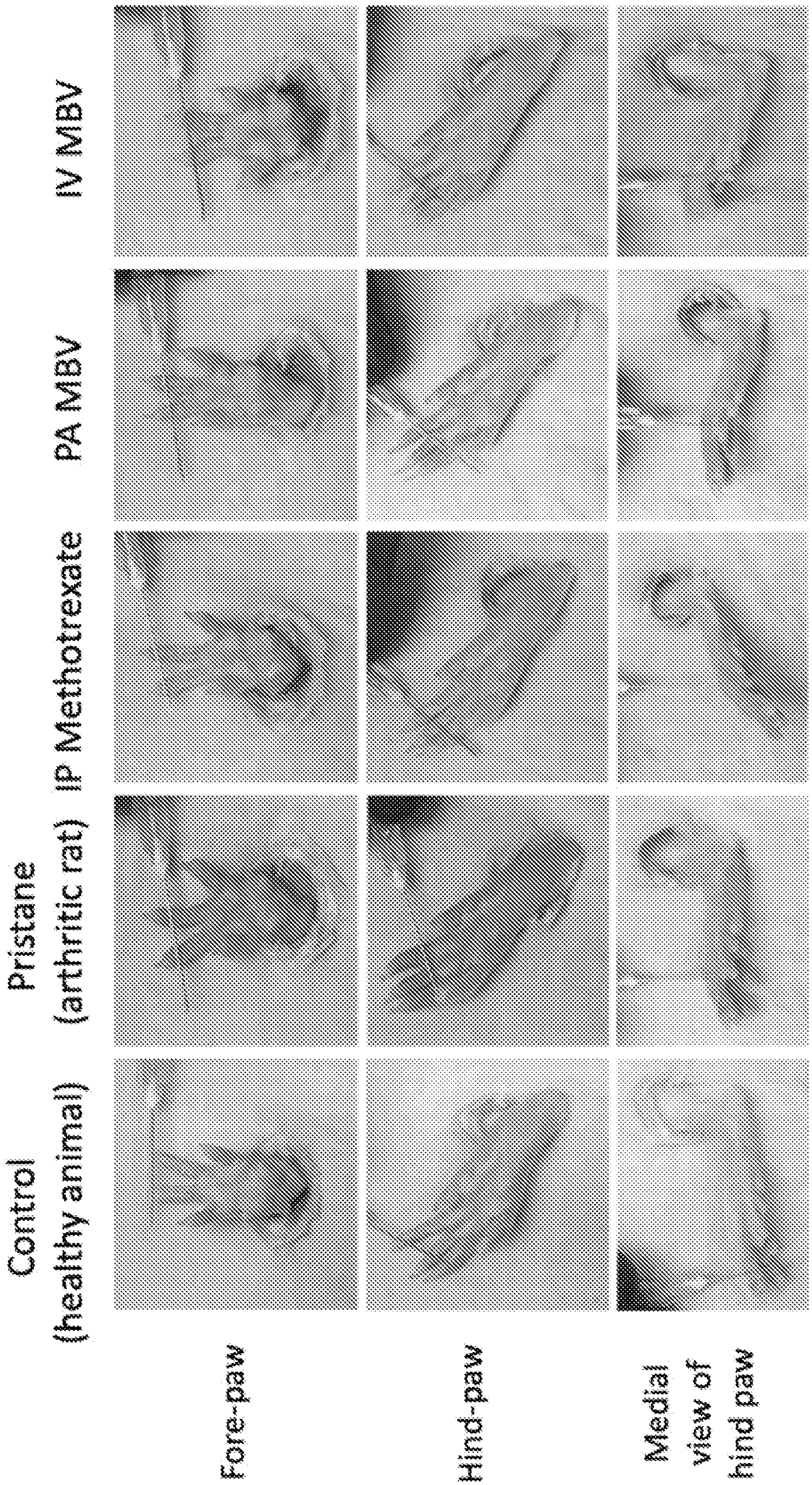
FIG. 9A shows photographs taken from multiple views of Sprague-Dawley rats induced to phenocopy clinical arthritis through pristane and treated with pristane-only, IP methotrexate, PA MBV, or IV MBV.
Figure 9B:
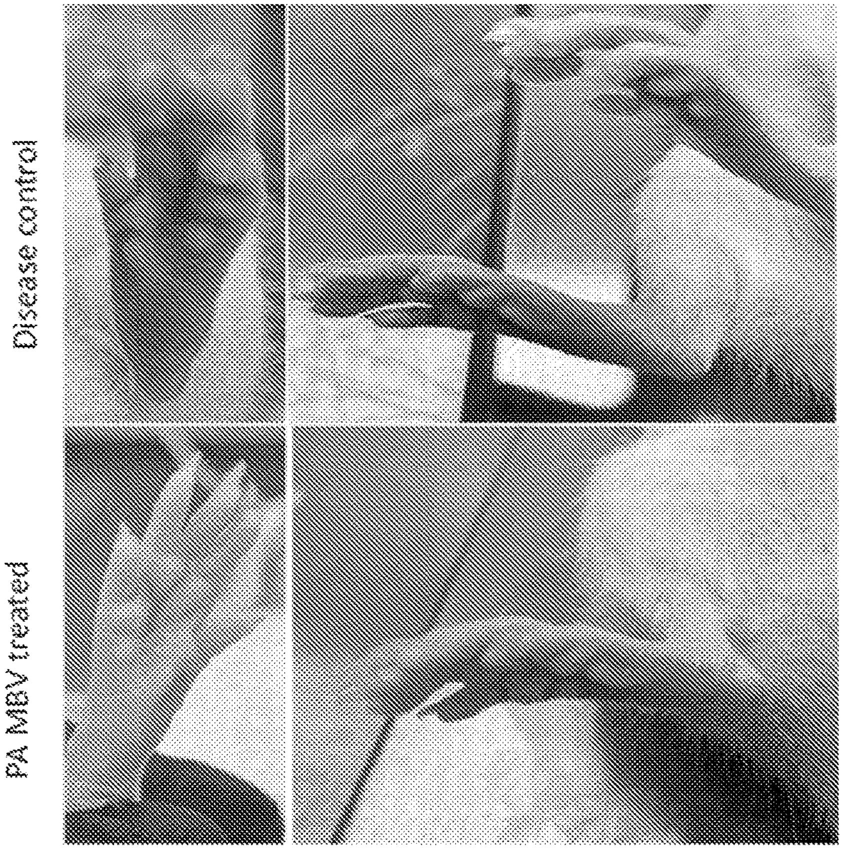
FIG. 9B shows a closer view of disease control and periarticular MBV treated rat paws.
Figure 10:
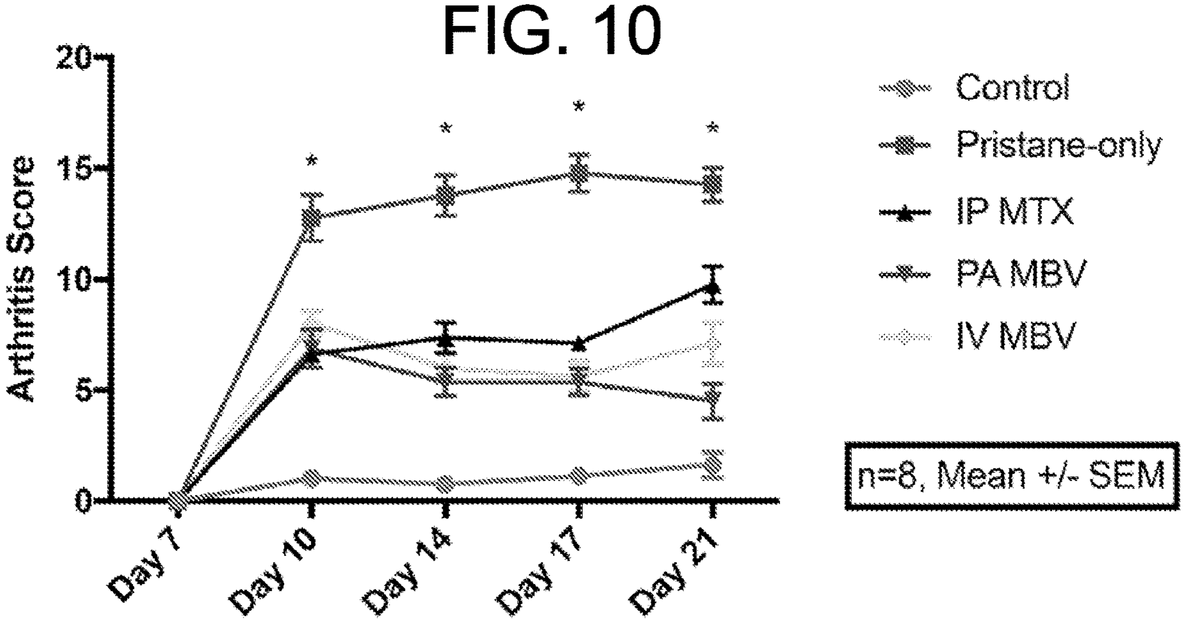
FIG. 10 shows the average arthritis scores over the first 21 days of treatment in the control and arthritis rat models treated with pristane-only, IP methotrexate, PA MBV, or IV MBV.

Administration of MBV, both through targeted PA (periarticular) and systemic IV administration, significantly reduced the severity of arthritis in the rats, displaying similar efficacy to the gold standard of care, methotrexate. While all rats displayed arthritis scores of 0 at Day 7 (FIG. 8A), as early as Day 10, high arthritis score was observed in pristane-only rats, and all rats receiving treatment displayed lower arthritis scores (FIG. 8B). Surprisingly, beginning at Day 13, MBV treatment was as efficient as the gold-standard of arthritis treatment, methotrexate (FIG. 8C and FIG. 8D). By Day 21, MBV treated rats (both IV and PA treated) displayed lower arthritis scores than methotrexate treated rats (FIG. 8E). Photographs taken of the rat paws demonstrate differences in erythema and edema in pristane-only and methotrexate and MBV treated rats (FIG. 9A-FIG. 9B). Average arthritis scores across treatment groups for the first 21 days of the experiment is shown in FIG. 10. While PA administration of MBV administration displayed a comparable reduction in arthritis score compared to pristane-only rats, and a reduced arthritis score comparable to methotrexate treatment, it was unexpectedly discovered that intravenous administration had the same efficacy in reducing arthritis score as PA and methotrexate. While it was predicted that IV administration would result in a dilution of the potency of MBV and thus would have a limited, if any, effect on inflamed joints, this was not observed. Surprisingly, both PA and IV routes of MBV administration displayed comparable reductions in arthritis score compared to pristane-only rats, and both reduced arthritis score comparably to methotrexate treatment. As peri-articular injection at a site of inflammation is painful and many joints in an individual may be inflamed, the unexpected finding that intravenous administration of MBV is just as effective as PA administration suggests that the systemic delivery route can be used for a less invasive yet equally effective therapeutic effect, requiring only a single injection per administration (rather than multiple injections per joint) and therefore being more comfortable for a patient.

Figure 11A:
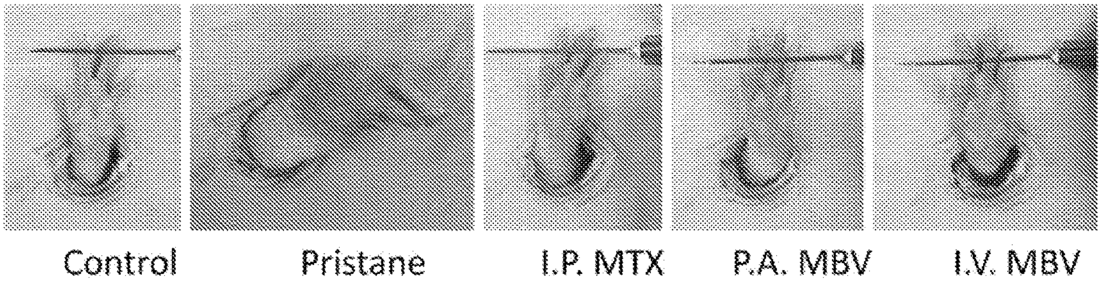
FIG. 11A shows photographs taken of paws of control and arthritis rat models treated with IP methotrexate, PA MBV, and IV MBV.
Figure 11B:
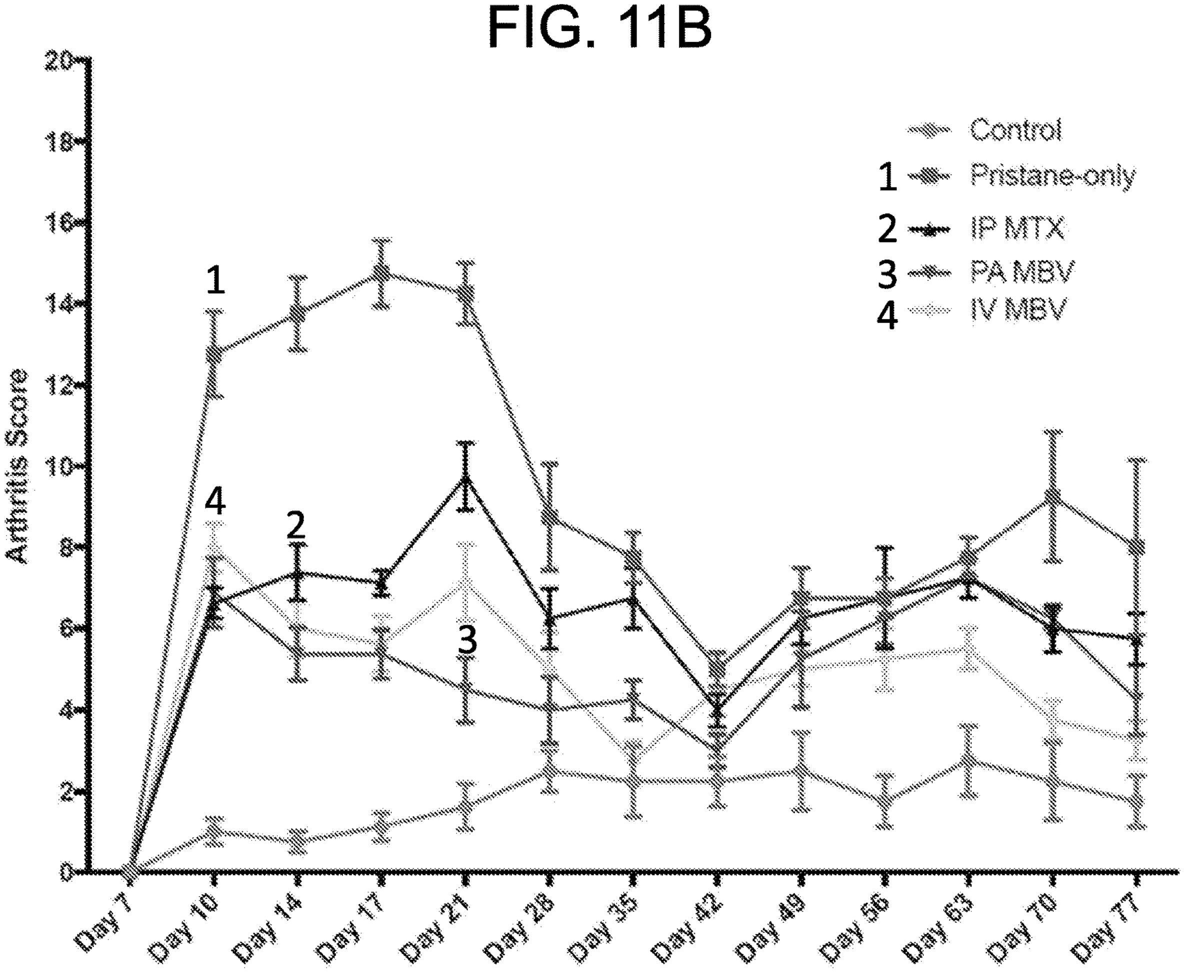
FIG. 11B shows the average arthritis scores over the first 77 days of treatment in the arthritic-rat model treated with IP methotrexate, PA MBV, and IV MBV.

Unexpectedly, inflammatory recurrence was also decreased in rats receiving MBV both by IV and PA administration. Data collected through Day 77 of the experiment support MBV treatment as an efficient therapy for arthritis in chronic and relapsing phases of inflammation. As shown in the photographs in FIG. 11A, phenotypically, rat paws treated with PA or IV MBV display equivalent erythema and edema to those treated with methotrexate. PA and IV MBV reduce pristane-induced arthritis clinical scoring in the chronic and relapsing phases of inflammation at equal efficacy to methotrexate, the gold standard of care for Rheumatoid Arthritis (FIG. 11B). Analysis of tissue from the rat model of rheumatoid arthritis resulted in tissue inflammation and decreased space between the tissue. In the MBV-treated samples, there was restoration of space and decreased inflammation comparable to that observed with methotrexate treatment, revealing the efficacy of MBV at both the organismal and tissue-levels.

Figure 12A:
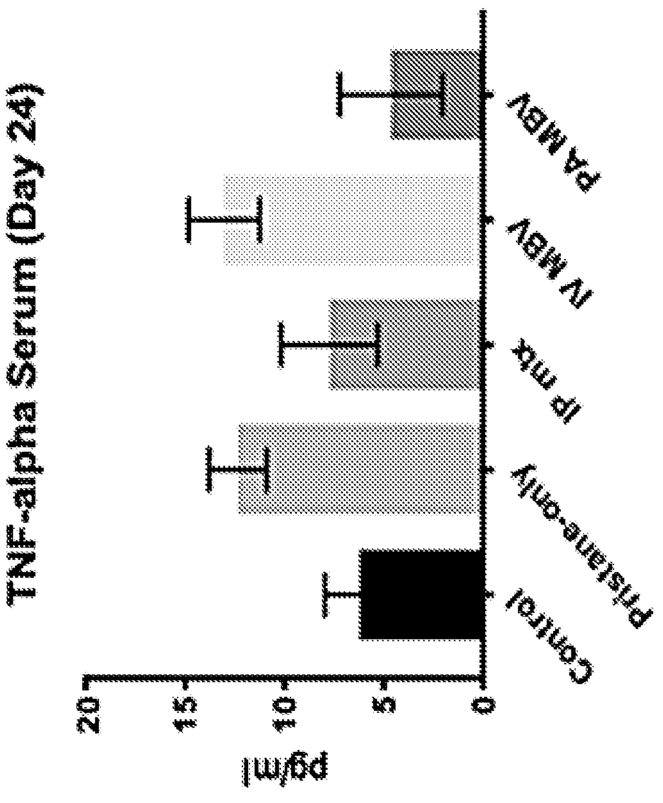
FIGS. 12A-12B show serum levels of TNFα (FIG. 12A) and IL1β (FIG. 12B) in arthritis rat models treated with IP methotrexate, PA MBV, and IV MBV.
Figure 12B:
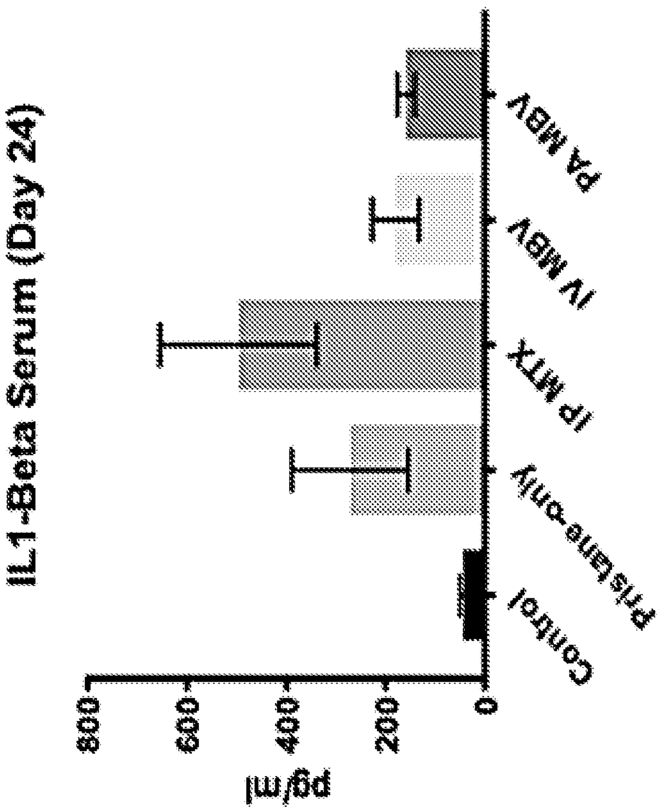

Using blood serum samples collected from the mice on Day 24, analysis of pro-inflammatory cytokines was assessed by enzyme-linked immunosorbent assay (ELISA). As shown in FIG. 12, compared to pristane-only animals, MBV administered either periarticularly or intravenously significantly decreased IL-1-beta sera levels (FIG. 12B). Additionally, locally administered MBV (i.e. PA MBV) resulted in a decrease in TNFalpha sera levels (FIG. 12A). These data strongly suggest MBV are modulators of the immune system.

Taken together, the data from these experiments suggest that an initial treatment course of MBV, either systemically or locally, can have a therapeutic effect in relieving arthritis symptoms for weeks to months after the initial treatment course of MBV ends, thereby reducing the severity or frequency of subsequent flares of rheumatoid arthritis symptoms or even eliminating them, resulting in remission.

The data also suggest the usefulness, generally, of MBV to modulate inflammatory immune responses and shows that MBV can downregulate production of proinflammatory cytokines. This suggests the effectiveness of MBV in mitigating hyperinflammatory events such as cytokine storm, thereby making MBV useful for treating conditions such as ARDS which result from hyperinflammation in the lungs.

Example 3: Use of MBV for Treatment of Imiquimod-Induced Psoriasis

UBM and MBV derived from UBM are prepared using the methodologies as described in Example 2 supra.

Imiquimod (IMQ), a compound known to induce a psoriatic-like condition in mice when applied topically, was administered to 8-week-old, female, C57/bl6 mice by daily, topical application of 62.5 mg of 5% imiquimod cream to the shaved back and right pinna of the mice for 15 days. Control animals did not receive topical imiquimod throughout the study, and instead received topical administration of petroleum jelly to a shaved back and right pinna. Treatment groups and therapeutic paradigms were divided down into prevention of psoriasis flares and management of existing flares. Those animals receiving preventative therapy received treatment between days 0-16 of the study and those animals receiving management therapy received treatment between days 7-16 of the study. Treatment groups consisted of intraperitoneal MBV and vehicle-only control. Animals receiving intraperitoneal MBV received $10^9$ porcine-derived, UBM MBV on each day of the study as designated by treatment timeline.

Figure 13:
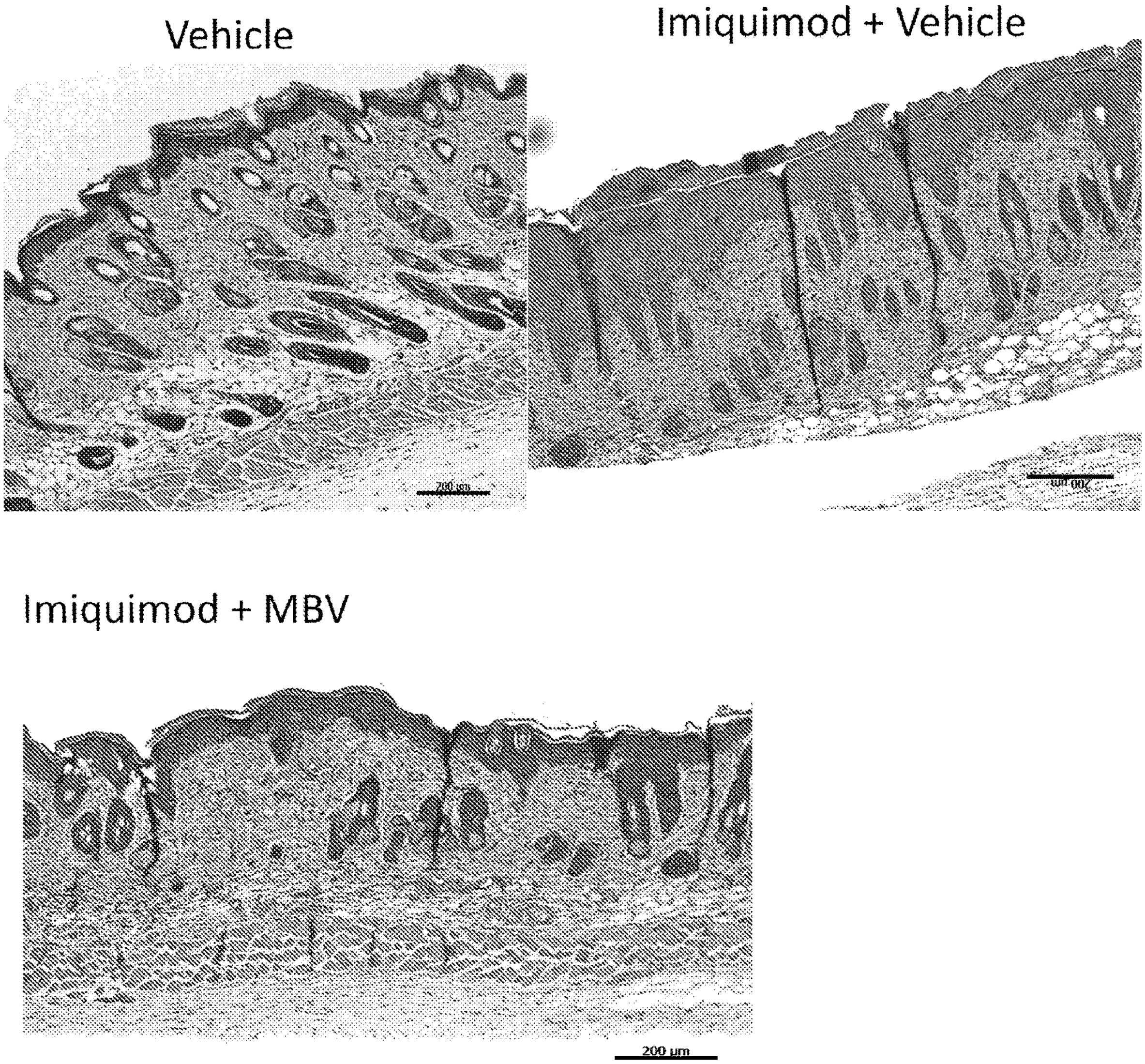
FIG. 13 shows histological images of mouse imiquimod models of psoriasis treated with vehicle control or MBV.

At day 7, tissue samples were collected and assessed by histology. When MBV are administered by intra-peritoneal injection ($10^9$ MBV daily dose over a treatment period of 7 days), the psoriatic lesions are resolved, as shown in FIG. 13.

Figure 14:
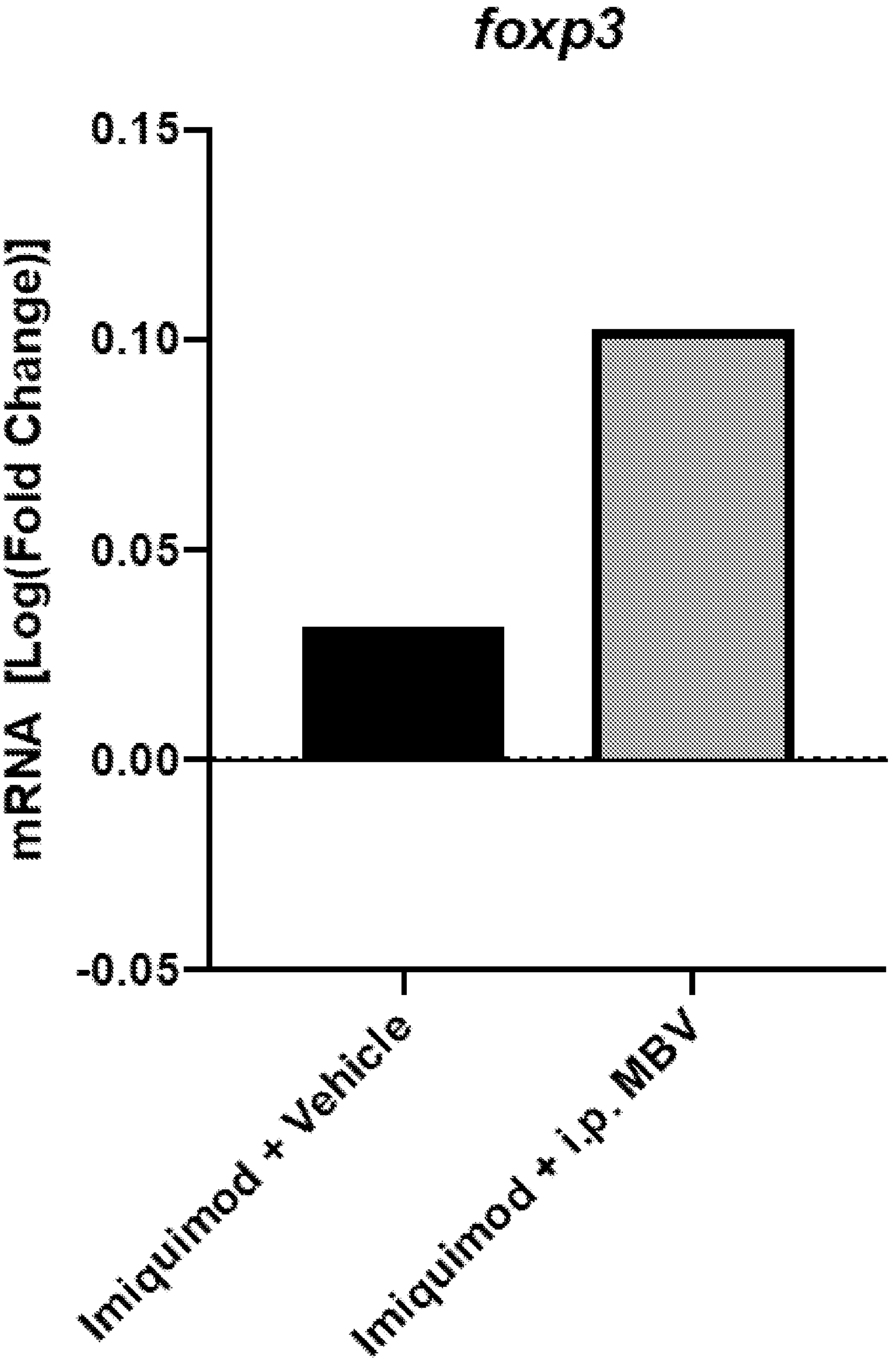
FIG. 14 shows FOXP3 RNA levels as a marker of $T_{REG}$ cells in mouse imiquimod models of psoriasis treated with vehicle control or MBV.

As Foxp3 expressing cells are directly regulated by $T_{REG}$ cells, to determine if treatment affected $T_{REG}$ activities, Foxp3 RNA was quantified. RNA was isolated from tissue biopsies of the test site using Trizol according to the manufacturer's instructions. RNA quantity and A260/280 was determined using NanoDrop spectrophotometer (NanoDrop). cDNA was synthesized by first-strand reverse transcription using SuperScript III reverse transcriptase enzyme. qPCR for foxp3 was performed using Power SYBER Green PCR Master Mix (Applied Biosystems). All qPCR performed using SYBR Green was conducted at 50 C for 2 min, 95 C for 10 min, and for 40 cycles of 95 C for 15s and 60 C for 1 min. qPCR was analyzed by the DeltaDeltaCT method and Log (fold change) is relative to foxp3 expression in negative control (No imiquimod+PBS vehicle). Foxp3 primers (forward: 5'-TCTCCAGGTTGCTCAAAGTC-3' and reverse: 5'-GCAGAAGTTGCTGCTTTAGG-3') and Gapdh primers (forward: 5'-CTGGAGAAACCTGCCAAGTA-3' and reverse: 5'-TGTTGCTGTAGCCGTATTCA-3'). As shown in FIG. 14, treatment with MBV significantly increased Foxp3 RNA levels, indicating MBV stimulate $T_{REG}$ cells. Taken together, these data indicate MBV treatment results in increased numbers of anti-inflammatory cell phenotypes in the same tissues, even when administered systemically. Thus, both local and systemic administration can be used for the treatment of ARDS.

Example 4: Use of MBV in a Keyhole Limpet Hemocyanin (KLH) Mouse Model

UBM and MBV derived from UBM are prepared using the methodologies as described in Example 2 supra.

Figure 15:
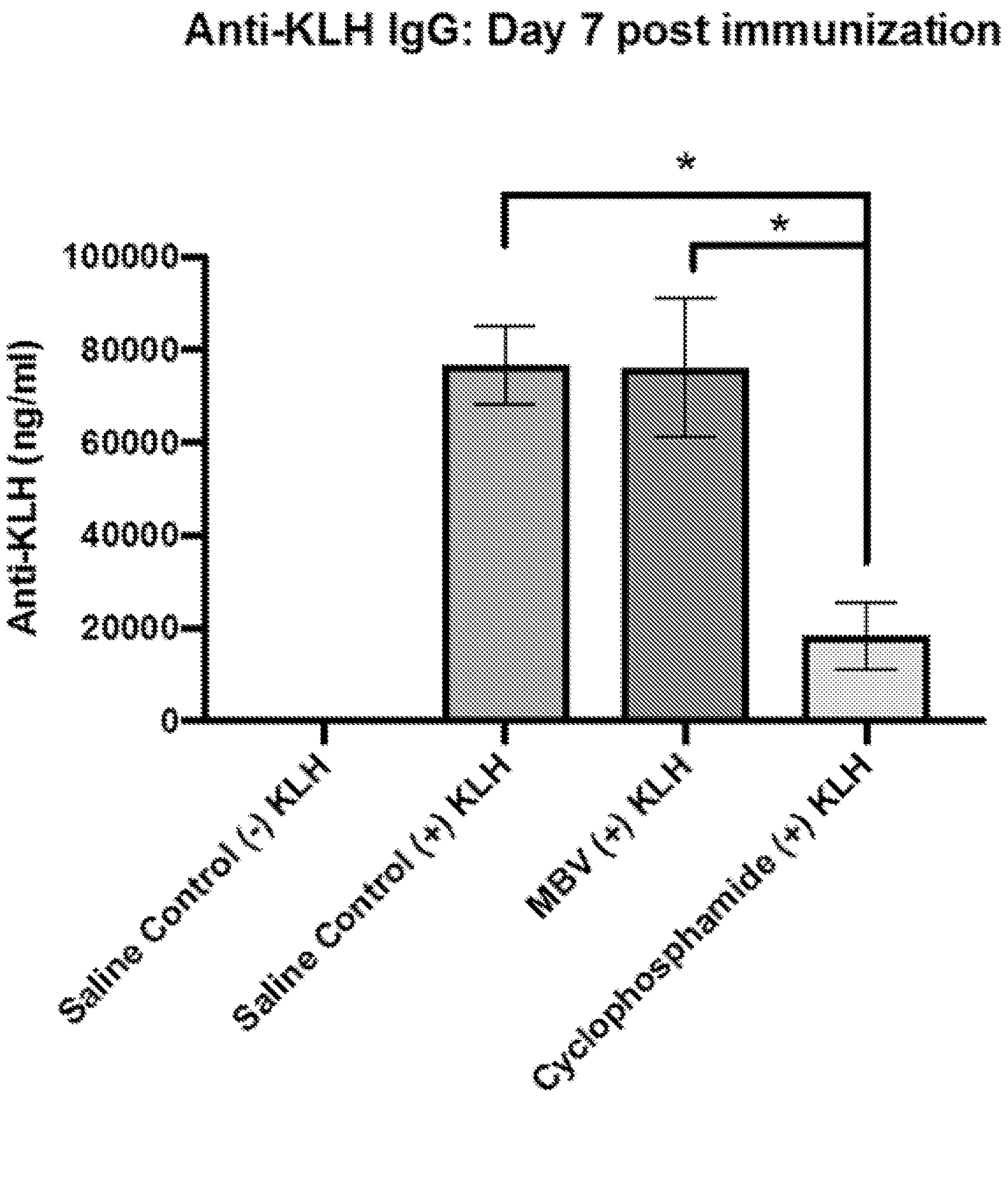
FIG. 15 shows anti-KLH IgG as determined by ELISA in Keyhole limpet hemocyanin (KLH) rat models treated with saline (negative control), MBV, or cyclophosphamide (positive control).

In this experiment, a Keyhole limpet hemocyanin (KLH) rat model of immunosuppression and immunotoxicity was used to assess immunotoxicity of MBV delivered systemically. 8-week-old Sprague-Dawley rats were separated into four separate groups: A KLH control used to demonstrate normal anti-KLH response after immunization with KLH, a vehicle control was used to control for any potential effects not related to treatment or KLH immunization, a cyclophosphamide positive control was used as a potent immunosuppressive, and an MBV treatment group was used to assess the effect of MBV administration on systemic immunity. On Day −7, the cyclophosphamide treated animals received 200 mg/kg intraperitoneally. The MBV treated animals received $1\times10^9$ particles MBV intravenously on Days −7, −4, and −1. On Day 0, all groups besides the vehicle control were immunized with 0.4 mL of 1000 μg/ml reconstituted KLH in Freund's incomplete adjuvant. On Days 7, 14, and 21 post-immunization, whole blood was collected from the lateral tail vein, and serum was isolated for analysis of anti-KLH IgG. Anti-KLH IgG was assessed in the serum of all animals using enzyme-linked immunosorbent assay (ELISA), as shown in FIG. 15. Taken together, these data suggest that animals treated with MBV are still immunocompetent and capable of mounting an immunoglobulin-based response.

This finding has broad implications for the usefulness of MBV as an anti-inflammatory treatment. Many standard treatments for reducing inflammation including hyperinflammation resulting from, e.g., hypercytokinemia, are immunosuppressive and leave a subject at risk of secondary infection and with a decreased ability to mount a sufficient immune response against the agent causing the immune response, interfering with recovery and development of immunity. However, because MBV are demonstrated to not interfere with the subject's ability to mount an immune response, MBV are useful as an anti-inflammatory treatment, for example, in ARDS, for example, caused by viral infection such as SARS-CoV-2 because MBV should not interfere with a subject's ability to mount an immune response to the virus while still reducing the production of inflammatory cytokines and modulating the immune response towards repair and healing.

Example 5: Administration of MBV Increases $T_{REG}$ In Vivo

UBM and MBV derived from UBM are prepared using the methodologies as described in Example 2 supra.

Cardiotoxin muscle injury surgeries were performed on knockout or wild-type C57/bl6 mice; mice were wild-type IL-33 expressing Arg-$1^{GFP}$ ("WT B6") or knockout IL-33 deficient Arg-$1^{GFP}$ B6 ("KO B6"). Arginase expression in cells of these mice could be detected by GFP expression, allowing for identification of the M-2 like phenotype. MBV, which naturally contain IL-33 (see International Patent Application Publication No. WO 2019/213482) were administered to the muscle injury sites in a quantity of $1\times10^9$ MBV. On post-operative day (POD) POD3 and POD7, injured transverse abdominal (TA) muscles were surgically harvested from the mice, tissue specimens were minced, treated with dispase and rinsed in saline, and the process was repeated to remove non-cellular debris. Infiltrating leukocytes were assessed by flow cytometric analysis (FACS).

Figure 16A:
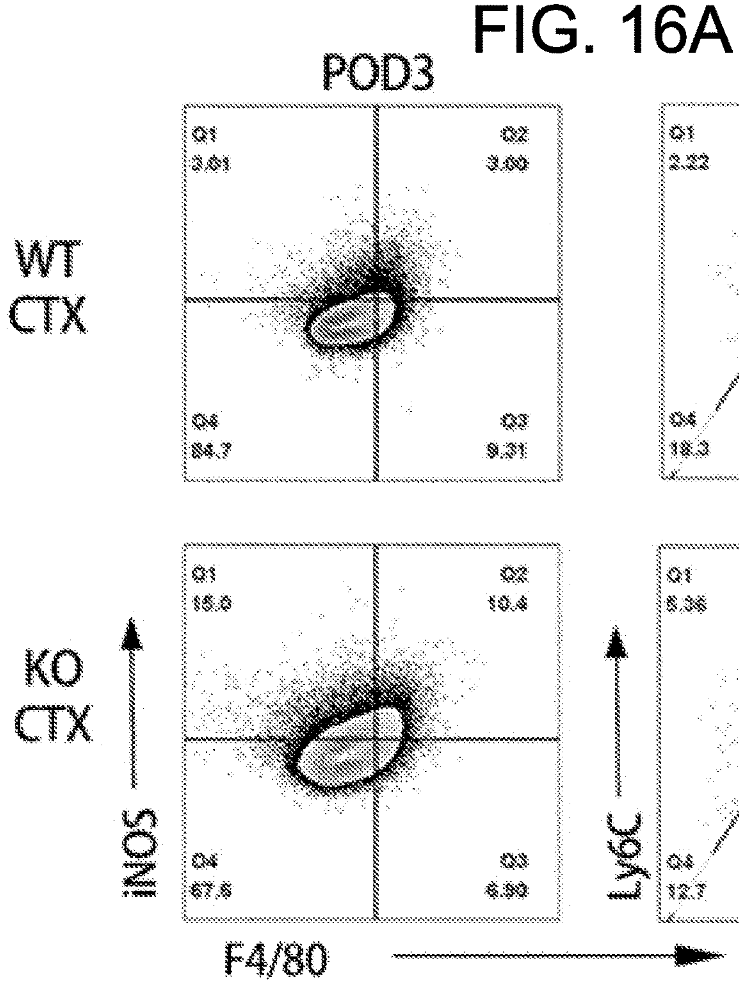
FIG. 16A shows dot plots for inflammatory macrophages infiltrating a site of cardiotoxin injury following treatment with MBV containing IL-33, as determined by fluorescence activated cell sorting (FACS) $CD45^+CD3^-B220^-CD11b^+$ $Ly6G^-$ cells.
Figure 16B:
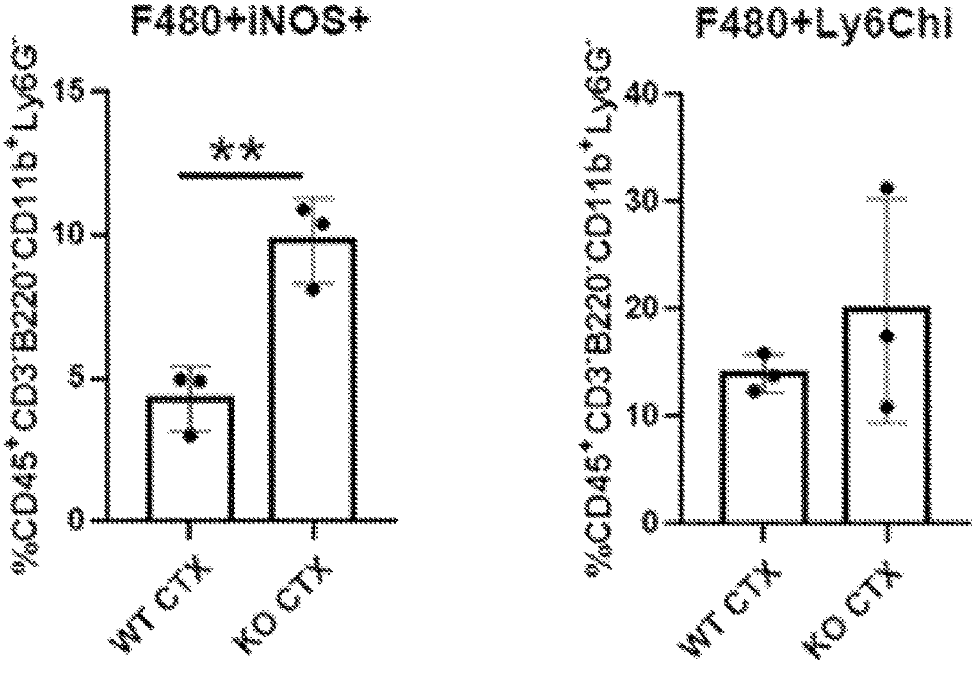
FIG. 16B shows inflammatory macrophage frequency.

FIG. 16A and FIG. 16B show representative dot plots and frequency for inflammatory macrophages in the $CD45^+CD3^-B220^-CD11b^+Ly6G^-$ gate. Without IL-33 there are increased numbers of macrophages and they are of the M1 proinflammatory phenotype. MBV containing IL-33 decrease the inflammatory response significantly.

Figure 16C:
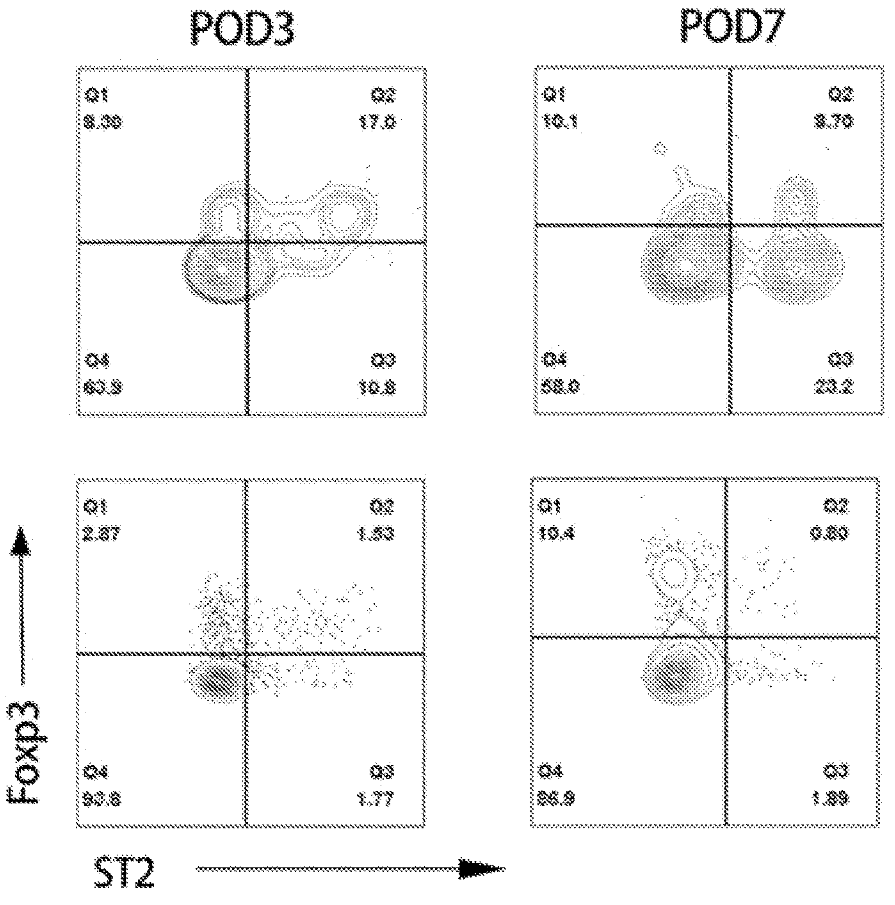
FIG. 16C shows dot plots for ST2+ $T_{REG}$ infiltrating a site of cardiotoxin injury following treatment with MBV containing IL-33, as determined by fluorescence activated cell sorting (FACS) for $CD45^+CD3^+B220^-CD4^+$ cells.
Figure 16D:
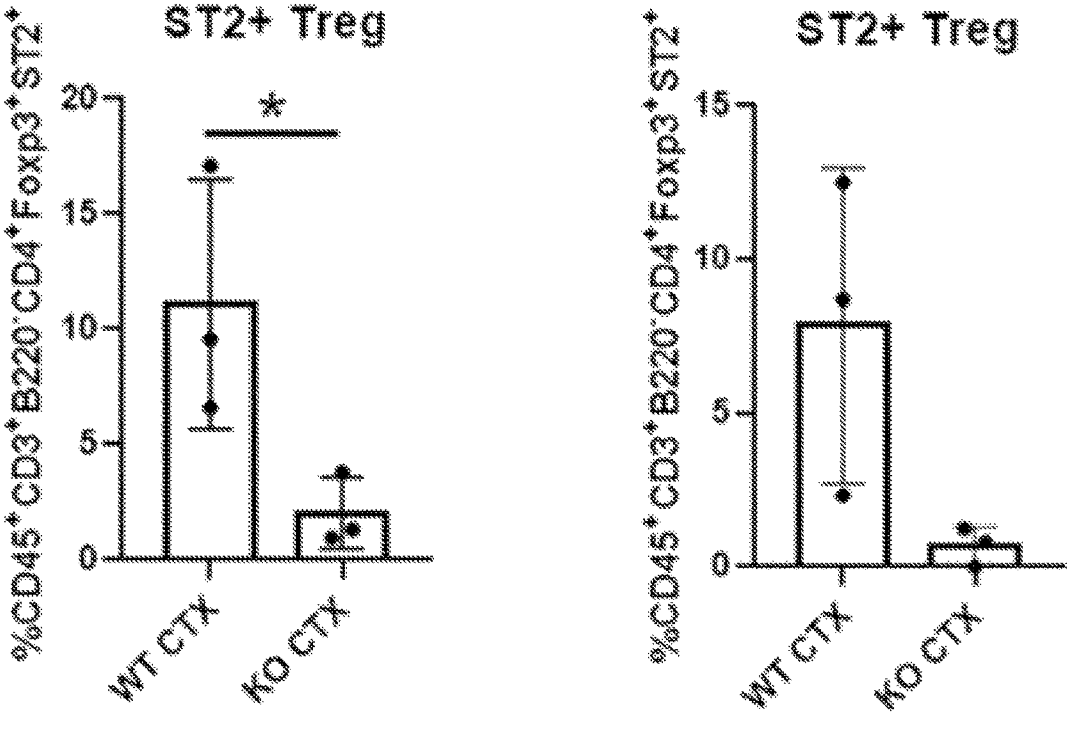
FIG. 16D shows frequency of ST2+ $T_{REG}$.

FIG. 16C and FIG. 16D show representative dot plots and frequency for ST2+ $T_{REG}$ in the $CD45^+CD3^+B220^-CD4^+$ gate. These results show that the IL-33 is needed to increase the number of $T_{REG}$ cells which are Foxp3 positive. All p-values were calculated using one-way ANOVA. (*P<0.05, **P<0.01).

Example 6: Administration of MBV Induces IL-4 Production

UBM and MBV derived from UBM are prepared using the methodologies as described in Example 2 supra.

In this experiment, naïve T-lymphocytes were isolated from the spleens of normal mice. T-lymphocytes were stimulated to induce T-cell response. Primary murine CD4+ T-cells were isolated from the spleens of 8-week-old C57/B16J mice by depletion of non-CD4+ T-cells using a cocktail of biotin-conjugated antibodies against CD8a, CD11b, CD11c, CD19, CD45R, CD49b, CD105, Anti-MHC-class II, Ter-119, and TCR as the primary labeling reagents. The cells were magnetically labeled with anti-biotin microbeads and non-labeled CD4+ T-cells were separated using magnet assisted cell sorting. Isolated CD4+ cells were cultured on 12-well plates precoated with anti-mouse CD3epsilon (3 μg/mL) at a final concentration of $1.0\times10^{6}$ cells/mL for each well in 10% fetal bovine serum, complete RPMI 1640 media.

Each respective Th (T-helper) subset was induced by 5 days of culture in the following culture conditions. Th1: anti-mouse CD28 (3 μg/ml), anti-mouse IL-4, clone (10 μg/mL), recombinant mouse Il-2 (5 ng/mL), and recombinant mouse Il-12 (10 ng/mL). Th2: anti-mouse CD28 (3 μg/ml), anti-mouse IFN-gamma (10 μg/mL), recombinant mouse 11-2 (5 ng/mL), and recombinant mouse Il-4 (10 ng/ml). Th17: anti-mouse CD28 (3 μg/ml), recombinant mouse TGFb (2.5 ng/ml), IL6 (20 ng/ml), anti-IFNg (10 μg/ml), anti-IL4 (10 μg/ml), and anti-IL2 (10 μg/ml). ThMBV: anti-mouse CD28 (3 μg/ml), recombinant mouse Il-2 (5 ng/mL), and $1\times10^{9}$ particles MBV. T-cells were cultured in these conditions for 5 days. On day 5, cells were washed and replaced with serum-free complete RPMI 1640 and stimulated for 24 hours with 50 ng/mL Phorbol 12-myristate 13-acetate. After 24 hours, cell culture supernatants were collected and ELISA for Il-4 was performed.

As shown in FIG. 17, when stimulated with known activators of a Th1 (proinflammatory response), minimal IL-4 (a potent anti-inflammatory signaling molecule) was produced by these cells. When activators of a Th2 (anti-inflammatory response) were given, abundant IL-4 was produced by the cells as expected. When the cells were activated toward a proinflammatory Th17 phenotype, no IL-4 was produced. When cells were exposed to MBV ($10^{9}$ MBV/well), a marked increase in IL-4 production occurred. Taken together, these data indicate that treatment with MBV induces a strong anti-inflammatory phenotype of T-helper cells.

Example 7: MBV Downregulate Mediators of the Cytokine Storm and Increase Expression of Negative Regulators of Cytokine Storm in Macrophages UBM and MBV derived from UBM are prepared using the methodologies as described in Example 2 supra.

Murine bone marrow was harvested from 6- to 8-week-old B6 mice. Harvested cells from the bone marrow were washed and plated at $2\times10^{6}$ cells/mL and were allowed to differentiate into macrophages for 7 days in the presence of macrophage colony-stimulating factor (MCSF) with complete medium changes every 48 h. Macrophages were then treated with or without $1\times10^{9}$ MBV/ml (n=3 per group). After a 24 hour incubation period at 37° C., cells were washed with sterile PBS and total RNA was harvested and analyzed using RNA sequencing. Bioinformatic analysis was conducted by Genevia Technologies (Tampere, Finland). Differential expression (DE) analysis was conducted using R package DESeq2, version 1.24.0 (Love et al., 2014. Genome Biology 15: 550). Wald test was used for statistical testing with p of 0.05 set as the significance cutoff used for optimizing the independent filtering, and with null hypothesis being that the log 2 fold changes between contrast groups are equal to zero. P-values were adjusted for multiple testing using the Benjamini-Hochberg procedure (Benjamini et al. 1995. *Journal of the Royal Statistical Society B* 57: 289-300). The obtained results were then post-hoc filtered using 0.05 as the threshold for adjusted p-value and 1 as the threshold for absolute log 2 fold change. Genes were also annotated with MGI symbols, gene descriptions and gene biotypes using biomaRt, version 2.40.5 (Durinck et al. 2009. Nature Protocols, 4: 1184-1191). Sequencing results showed that MBV treatment significantly decreased the expression of genes known to be critical mediators of the cytokine storm including: CD163, Igf1, Nlrp inflammasome, C5ar2, Hrh1, Hdac9, Igfbp4, and Pparg, as shown in Table 3. Furthermore, MBV were shown to increase the expression of negative regulators of the cytokine storm including IL-10, and Socs1-3, as shown in Table 4.

TABLE 3

MBV decreased the expression of genes involved in cytokine storm.

| MGI symbol | Gene description | Log2 foldchange | P-value |
|---|---|---|---|
| Cd163 | CD163 antigen [Source: MGI Symbol; Acc: MGI: 2135946] | −1.35125 | 1.15E−08 |
| Igf1 | insulin-like growth factor 1 [Source: MGI Symbol; Acc: MGI: 96432] | −1.61572 | 3.05E−49 |
| Nlrp1b | NLR family, pyrin domain containing 1B [Source: MGI Symbol; Acc: MGI: 3582959] | −1.10099 | 3.5E−16 |
| C5ar2 | complement component 5a receptor 2 [Source: MGI Symbol; Acc: MGI: 2442013] | −1.04594 | 8.99E−12 |
| Hrh1 | histamine receptor H1 [Source: MGI Symbol; Acc: MGI: 107619] | −1.09193 | 0.001739 |
| Hdac9 | histone deacetylase 9 [Source: MGI Symbol; Acc: MGI: 1931221] | −1.69487 | 7.36E−31 |
| Igfbp4 | insulin-like growth factor binding protein 4 [Source: MGI Symbol; Acc: MGI: 96439] | −1.00582 | 1.08E−08 |
| Pparg | peroxisome proliferator activated receptor gamma [Source: MGI Symbol; Acc: MGI: 97747] | −1.6901 | 3.89E−31 |

TABLE 4

MBV increased the expression of genes that act as negative regulators of the cytokine storm.

| MGI symbol | Gene description | Log2 foldchange | P-value |
|---|---|---|---|
| Il10 | interleukin 10 [Source: MGI Symbol; Acc: MGI: 96537] | 2.648439 | 5.71E−17 |
| Socs3 | suppressor of cytokine signaling 3 [Source: MGI Symbol; Acc: MGI: 1201791] | 2.613971 | 3.51E−15 |
| Socs1 | suppressor of cytokine signaling 1 [Source: MGI Symbol; Acc: MGI: 1354910] | 2.435243 | 2.48E−22 |

As this data demonstrate, MBV are shown to be potent modulators of proinflammatory cytokine production, and particularly of pro-inflammatory cytokines that contribute to hypercytokinemia ("cytokine storm"). This feature of MBV suggests its usefulness as candidate for treatment or mitigation of cytokine storm and ARDS, which results from hyperinflammation in the lungs.

Example 8: Use of MBV for Treatment of Viral-Induced Immune Response in a Murine Influenza Model UBM and MBV derived from UBM are prepared using the methodologies as described in Example 2 supra.

To determine the capacity of MBV to localize to the lung, PKH67 fluorescently-labeled MBV were 250 μl administered in aerosol form intranasally to C57BL/6 mice at a dose of $10^9$ particles/mL. Strikingly, immunofluorescence microscopy of mouse tissue showed significant enrichment of MBV in the lung airways and alveoli. As shown in FIG. 18, MBV were clearly detectable (indicated with arrow heads) in large and small airways of treated pulmonary tissue, particularly in the epithelia, but were not observed in the parenchyma. Untreated control lung tissues (right panel) show non-specific, low level autofluorescence with a diffuse, pattern that is dissimilar to MBV-treated tissue, demonstrating the fluorescence in the left and center panels is indeed indicative of MBV localization.

To assess therapeutic efficacy of MBV against viral-induced acute respiratory distress syndrome (ARDS), such as ARDS associated with COVID-19, a murine model of H1N1 is used. Influenza H1N1 induces similar lung pathology to that observed in COVID-19 patients, and follows a similar pathogenic time course, including symptom-free days, rapid ARDS-like lung injury, and persistent alveolitis that lasts for weeks or months. The 2009 H1N1 pandemic virus further resembles SARS-CoV2 in terms of its high transmissibility and global spread.

Male and Female C57BL/6 mice are infected with influenza A/CA/07/2009 (H1N1 pandemic influenza) by oropharyngeal aspiration at either a lethal dose of $10^6$ pfu for survival studies or a sublethal dose of $10^4$ pfu for immunologic studies. On Day 3 or Day 5 post-infection, mice are treated with MBV by intranasal or intravenous delivery.

Mice are randomly assigned to the following six experimental groups (8 mice per group, run in two cohorts of 4 mice/group, both male and female mice): 1) influenza A/CA/07/2009 only; 2) influenza A/CA/07/2009+control (vehicle only); 3) influenza A/CA/07/2009+intranasal MBV treatment dose of 250 μL of $1\times10^6$ MBV/ml; 4) influenza A/CA/07/2009+intranasal MBV treatment dose 250 μL of $1\times10^9$ MBV/ml; 5) influenza A/CA/07/2009+intravenous MBV treatment dose 250 μL of $1\times10^6$ MBV/ml; 6) influenza A/CA/07/2009+intravenous MBV treatment dose 250 μL of $1\times10^9$ MBV/ml. A healthy group of mice is used for baseline controls. Mice are followed by daily weight tracking as a surrogate for morbidity and mice are sacrificed when 25% weight loss is observed. These survival studies demonstrate the effectiveness of MBV against viral induced mortality and further demonstrate efficacy of MBV based on dosage and delivery route.

Immunological studies are conducted using the most efficacious dosing strategy as determined supra on 3 experimental groups: 1) influenza A/CA/07/2009; 2) influenza A/CA/07/2009+control; 3) influenza A/CA/07/2009+MBV. Mouse tissue samples (including but not limited to lung and lymph nodes (LN), bronchoalveolar lavage fluid (BALF), and serum) are collected on Days 7 and 21 post-infection. Lung function is measured at each time point by FLEXIVENT® (SCIREQ, Quebec, CA) to determine quasi-static lung compliance as a measure of inflammation and edema. Lung function measurements are taken according to the manufacturer's instructions.

Lung injury and inflammation are assessed using lung protein homogenate to determine local cytokine levels by Bio-Plex™ Cytokine Assays (Bio-Rad) according to the manufacturer's instructions. Histological analysis, such as hematoxylin and eosin staining, of a lung lobe for pathological assessment is performed. Blood assessment, including white blood cell counts, quantification of antibody isotypes and levels by enzyme-linked immunosorbent assay (ELISA), anti-hemagglutinin antibody levels, and Bio-Plex™ Cytokine Assay assessment of serum cytokines, is conducted. Additionally, bronchoalveolar lavage is conducted for collection of samples for determining airspace cytokine levels by Bio-Plex™ Cytokine Assay and differential inflammatory cell counting.

Single cells from lung digests, LN suspensions, and the BALF are stained with fluorescently labeled antibodies and multiparameter spectral flow cytometry is completed using a Cytek® Aurora, according to the manufacturer's instruction. The flow cytometry assessment is used to quantify changes in both the myeloid compartment (i.e. pro-inflammatory cytokine secreting M1 macrophages and/or reparative and regulatory M2 macrophages) and the lymphoid compartment (i.e. regulatory T cells, as well as viral specific T effectors cells). Single cell RNA sequencing analysis of LN and lung tissue is also performed to identify how viral infections and MBV therapy together and independently shape the tissue and immune cell populations at a molecular level.

The results show that animals treated with MBV demonstrate significantly decreased viral morbidity compared to untreated control animals. More surprisingly, the infected animals treated with MBV display decreased lung injury and inflammation as seen in the white blood cell counts and cytokine levels. These data show that administration of MBV is an effective therapeutic for immunomodulation of disease and disorder that lead to acute respiratory distress and that MBV can reduce severity or incidence of ARDS induced by viral infection. This provides an efficacious therapy for, amongst other indications, viral disease for which no therapeutic exists, such as pandemic H1N1 or SARS-CoV2 and other influenza and coronavirus-induced respiratory diseases.

Example 9: Use of MBV for Treatment of COVID-19 Associated Acute Respiratory Distress Syndrome in the Clinic UBM and MBV derived from UBM are prepared using the methodologies as described in Example 2 supra.

Patients diagnosed with SARS-CoV2-induced acute respiratory distress syndrome (ARDS), COVID-19 positive patients are treated with MBV. Patients who are able to breath on their own receive a dose of approximately $1\times10^9$ MBV in 3 mL of physiologic saline that is nebulized and inhaled through the nose and/or mouth into the lungs via the nebulizer apparatus. Intubated patients receive a dose of $1\times10^9$ MBV in 3 mL of physiologic saline that is delivered intratracheally. Some patients for whom it is determined that intraperitoneal injection is a preferred mode of administration receive $1\times10^9$ MBV in about 50 mL of physiologic saline by intraperitoneal administration.

Blood oxygenation levels are measured in each patient prior to and after receiving a dose of MBV therapy to determine therapeutic efficacy of treatment. Additionally, fluid samples from the lung by lavage are obtained, and cytokine expression levels, such as the cytokines provided in Tables 3 and 4 supra, are determined by ELISA. Patients continue to receive the dose every 6-24 hours until patients show signs of improvement which include ability to maintain oxygen levels without continuous ventilation or oxygen support and improvement in chest x-ray indicating clearance of fluid from lungs and/or decrease in pro-inflammatory cytokine levels as determined from lavage fluid testing.

Example 10: Materials and Methods for Examples 11-15

To assess therapeutic efficacy of MBV against viral-induced acute respiratory distress syndrome (ARDS), such as ARDS associated with COVID-19, a murine model of H1N1 was used. Influenza H1N1 induces similar lung pathology to that observed in COVID-19 patients, and follows a similar pathogenic time course, including symptom-free days, rapid ARDS-like lung injury, and persistent alveolitis that lasts for weeks or months. The 2009 H1N1 pandemic virus further resembles SARS-CoV2 in terms of its high transmissibility and global spread.

Male and Female C57BL/6 mice were infected with influenza A/CA/07/2009 (H1N1 pandemic influenza) by oropharyngeal aspiration at either a lethal dose of $10^6$ pfu for survival studies or a sublethal dose of $10^4$ pfu for immunologic studies. On Day 3 or Day 5 post-infection, mice were treated with MBV by intravenous delivery.

Mice were randomly assigned to the following six experimental groups (8 mice per group, run in two cohorts of 4 mice/group, both male and female mice): 1) influenza A/CA/07/2009 only; 2) influenza A/CA/07/2009+control (vehicle only); 3) influenza A/CA/07/2009+intravenous MBV treatment dose 250 μL of $1\times10^6$ MBV/ml; 4) influenza A/CA/07/2009+intravenous MBV treatment dose 250 μL of $1\times10^9$ MBV/ml. A healthy group of mice was used for baseline controls. Mice were followed by daily weight tracking as a surrogate for morbidity and mice are sacrificed when 25% weight loss is observed. These survival studies demonstrate the effectiveness of MBV against viral induced mortality and further demonstrate efficacy of MBV based on dosage and delivery route.

Immunological studies were conducted using the most efficacious dosing strategy as determined supra on 3 experimental groups: 1) influenza A/CA/07/2009; 2) influenza A/CA/07/2009+control; 3) influenza A/CA/07/2009+MBV. Mouse tissue samples (including but not limited to lung and lymph nodes (LN), bronchoalveolar lavage fluid (BALF), and serum) were collected on Days 7 and 21 post-infection.

Lung injury and inflammation were assessed using lung protein homogenate to determine local cytokine levels by BIO-PLEX™ Cytokine Assays (Bio-Rad) according to the manufacturer's instructions. Histological analysis, such as hematoxylin and eosin staining and trichrome staining, of a lung lobe for pathological assessment was performed. Blood assessment, including white blood cell counts, quantification of antibody isotypes and levels by enzyme-linked immunosorbent assay (ELISA), anti-hemagglutinin antibody levels, and BIO-PLEX™ Cytokine Assay assessment of serum cytokines, was conducted. Additionally, bronchoalveolar lavage was conducted for collection of samples for determining airspace cytokine levels by BIO-PLEX™ Cytokine Assay and differential inflammatory cell counting.

Single cells from lung digests, LN suspensions, and the BALF were stained with fluorescently labeled antibodies and multiparameter spectral flow cytometry is completed using a CYTEK® Aurora, according to the manufacturer's instruction. The flow cytometry assessment was used to quantify changes in both the myeloid compartment (i.e. pro-inflammatory cytokine secreting M1 macrophages and/or reparative and regulatory M2 macrophages) and the lymphoid compartment (i.e. regulatory T cells, as well as viral specific T effectors cells). Single cell RNA sequencing analysis of LN and lung tissue is also performed to identify how viral infections and MBV therapy together and independently shape the tissue and immune cell populations at a molecular level.

Figure 19A:
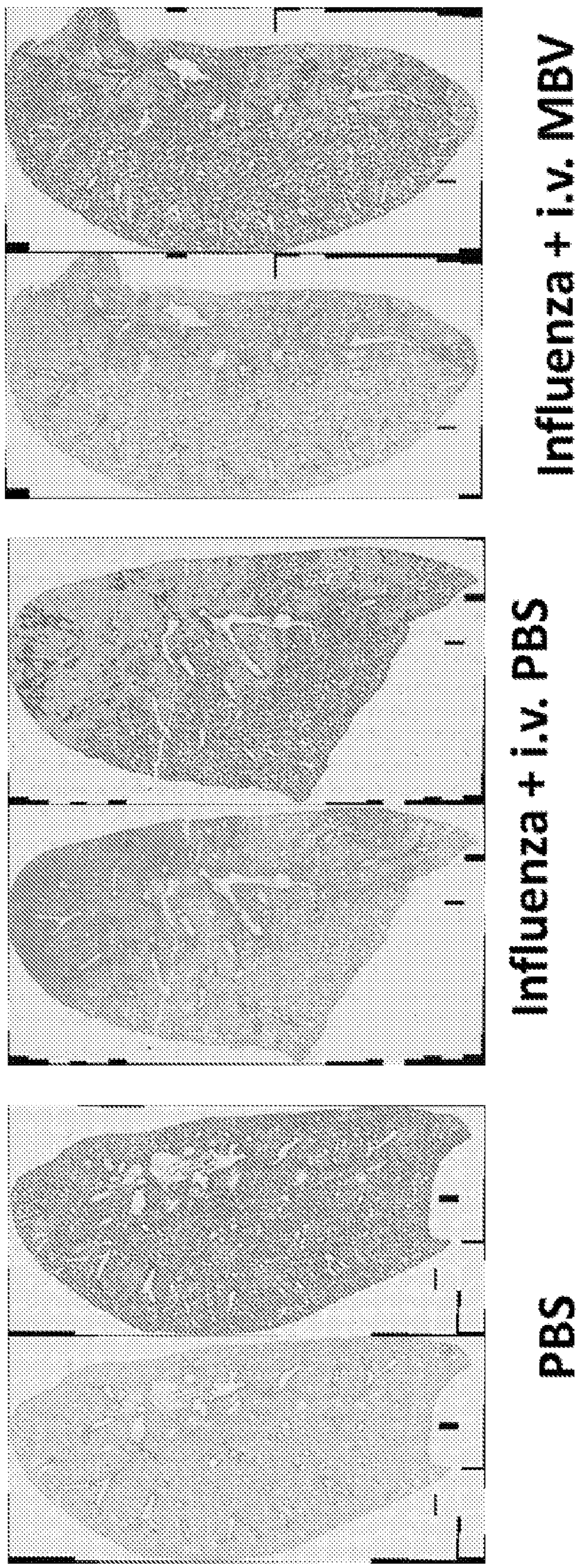
FIGS. 19A-19C show that systemic administration of matrix-bound nanovesicles mitigates viral-mediated pulmonary pathology and mononuclear neutrophil cellular infiltration at day 7 post-infection.
Figure 19B:
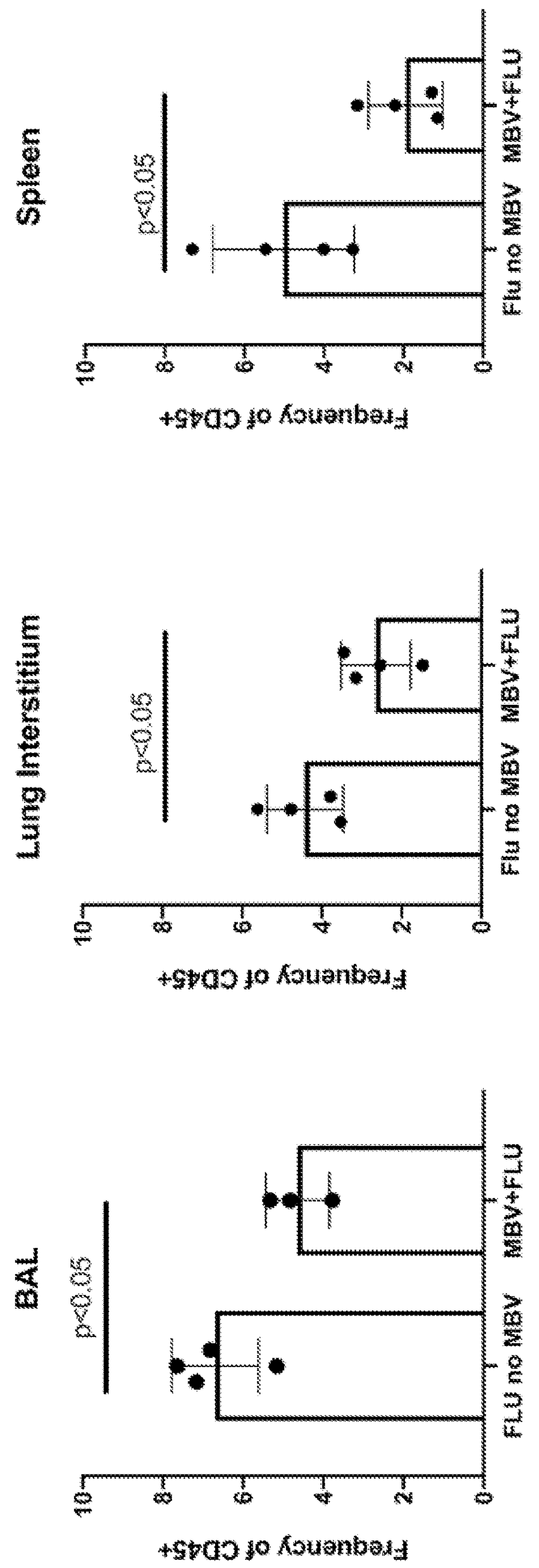
Figure 19C:
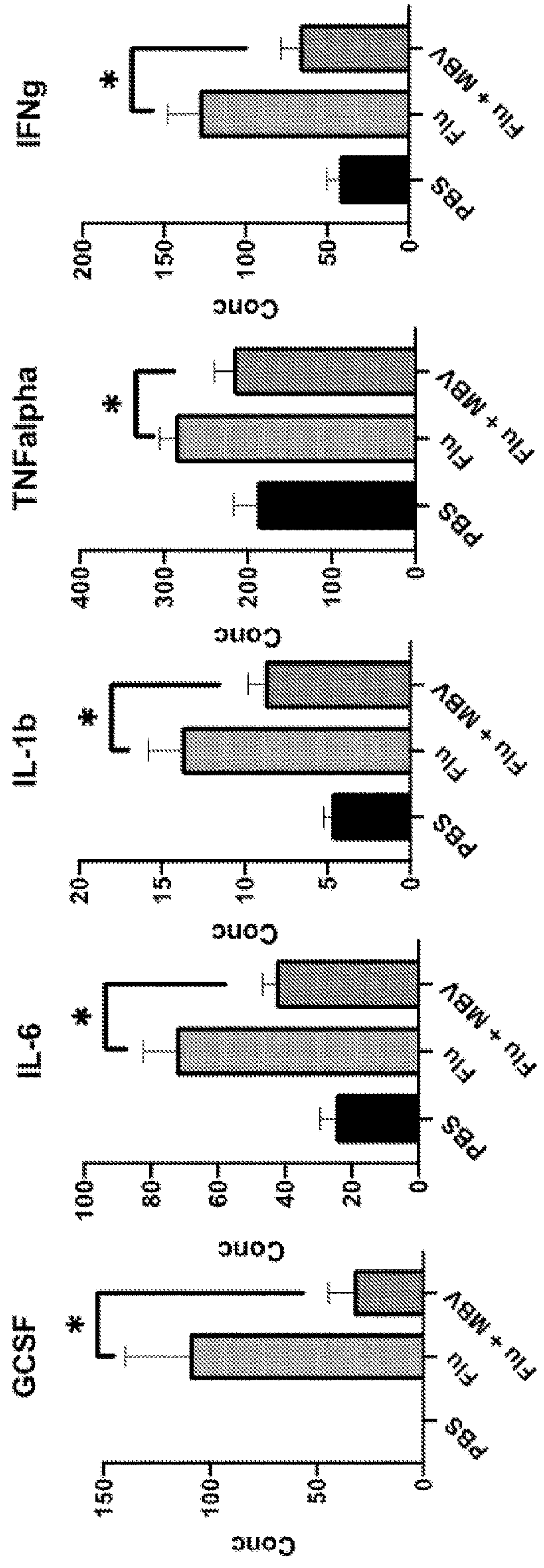

Example 11: Systemic Administration of MBV Mitigates Acute Viral-Mediated Pulmonary Pathology After 7 days following intra-tracheal inoculation with H1N1, systemic administration of matrix-bound nanovesicles substantially mitigated acute viral-associated pulmonary pathology as evident on H+E staining of lung tissues. At day 7, the Influenza+i.v. PBS vehicle control group demonstrated an increase in cellular density and consolidation in the lung interstitial space while the Influenza+i.v. MBV group shows a reduction in cellular density as well as a reduction in interstitial inflammatory infiltrate (FIG. 19A). Using quPath artificial intelligence to visualize cellular density in the form of a heat map, the Influenza+i.v. MBV group showed a reduction in cellular density compared to the Influenza+i.v. PBS group (FIG. 19A). Further investigation of the composition of cellular infiltrate of lungs following influenza infection showed an increase in CD45+ neutrophils in the bronchiolar lavage fluid (BALF), lung interstitial space, and spleen (FIG. 19B, $p<0.05$). Intravenous MBV significantly reduced the frequency of CD45+ neutrophils in the BALF, lung interstitial space, and spleen (FIG. 19B, $p<0.05$). The reduction in cellular infiltration and neutrophil presence with systemic MBV administration was associated with a reduction in pro-inflammatory cyto- and chemokines (FIG. 19C). Specifically, systemic MBV reduced lung produced G-CSF which is involved in neutrophil and myeloid cell recruitment to the tissue in infection (FIG. 19C, $p<0.05$). Systemic administration of MBV decreased the lung concentration of pro-inflammatory cytokines including Il-6, Il-1b, TNF-alpha, and IFN-gamma compared to the Influenza+i.v. PBS group (FIG. 19C, $p<0.05$).

Figure 20A:
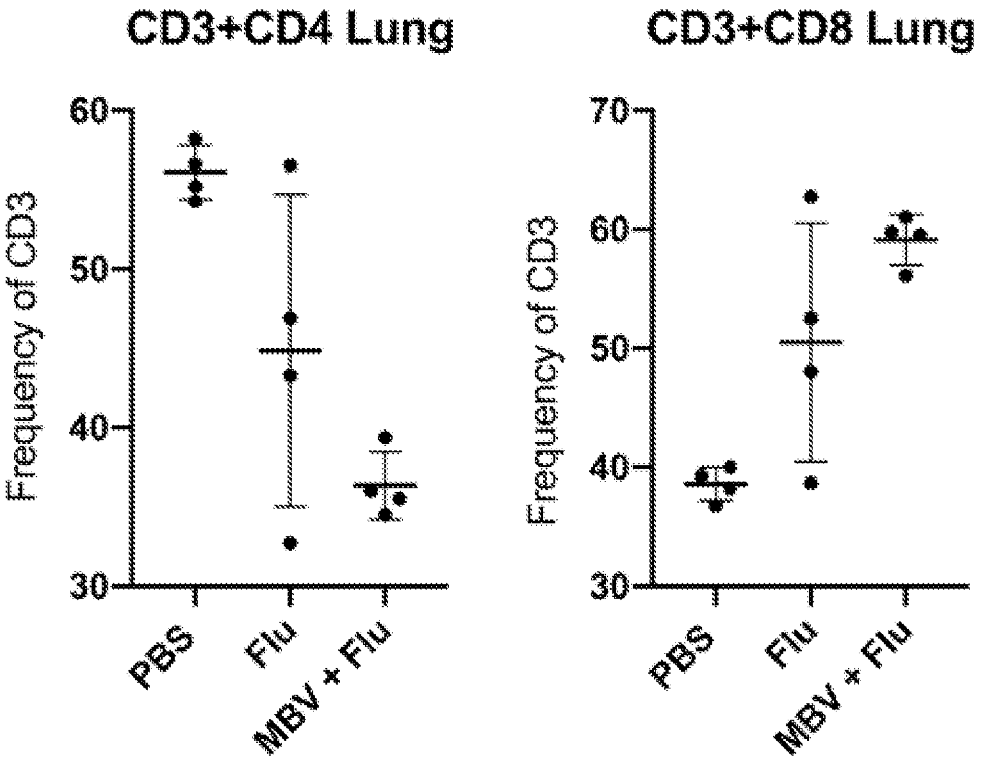
FIGS. 20A-20D show that systemic administration of MBV decreases lung and spleen population of CD4+ t-cells and increases the presence of activated, anti-viral CD8+ T-cells.
Figure 20B:
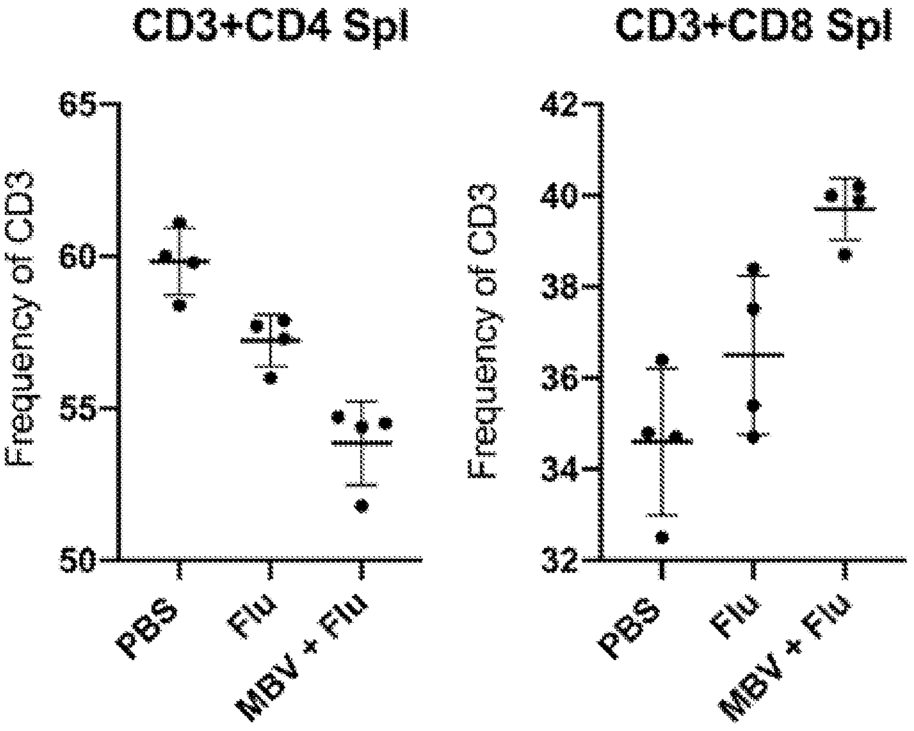
Figure 20C:
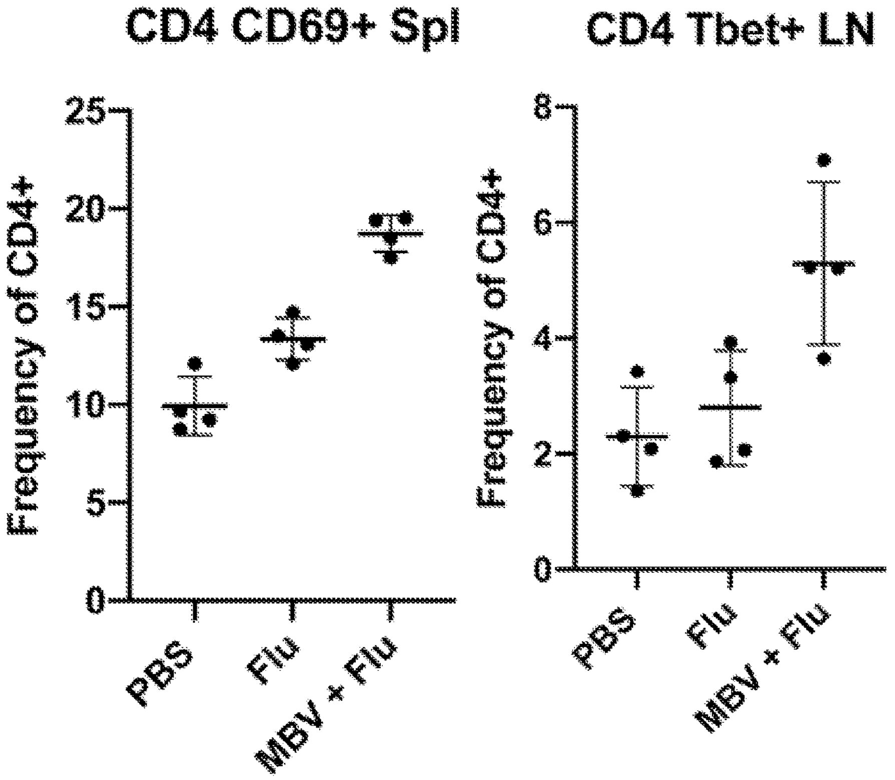
Figure 20D:
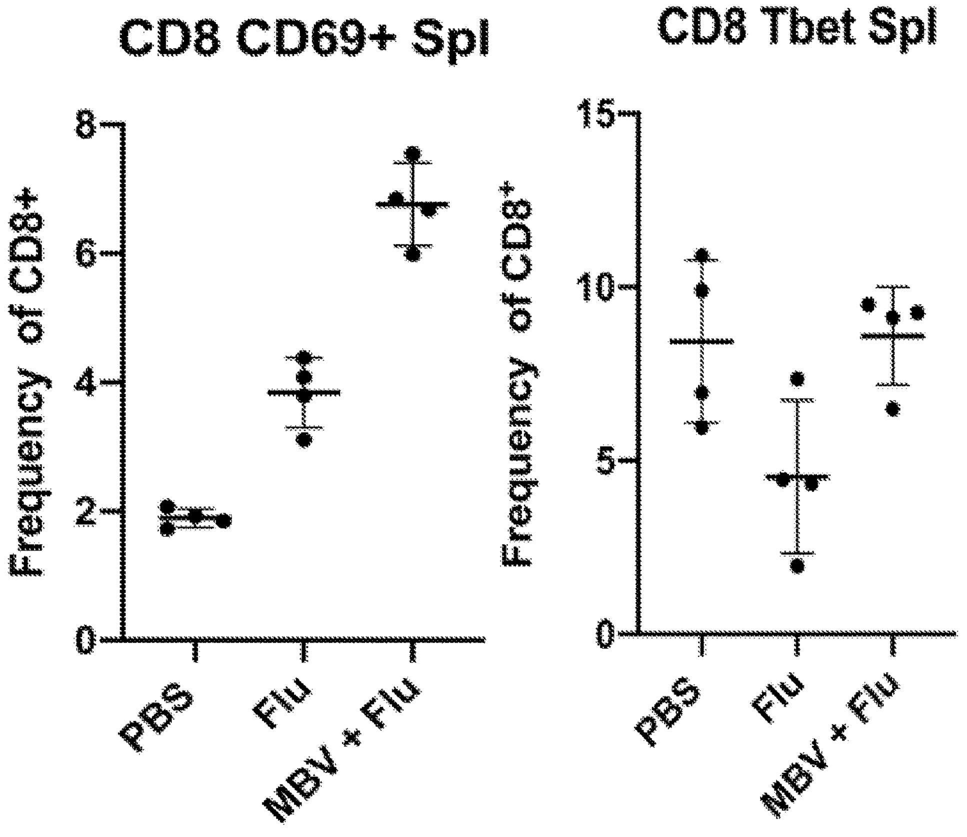

Example 12: MBV Promote an Anti-Viral CD4 and CD8 Phenotype Following H1N1 Inoculation At day 7 following intra-tracheal H1N1 inoculation, systemic administration of MBV significantly altered the ratio of CD4:CD8 T-cells in the lung compared to the baseline ratio in the PBS-only control (FIG. 20A, $p<0.05$). This promotion of an increased CD8:CD4 T-cell ratio with MBV administration was seen both locally at the site of infection in the lung and also systemically in the spleen (FIGS. 20A and 20B, $p<0.05$). Upon further investigation of the CD4 and CD8 T-cells, MBV not only promoted a shift favoring an increased ratio of CD8:CD4 T-cells but also promoted an increase in both activated (CD69+) and antiviral (Tbet+) CD4 and CD8 T-cells compared to the PBS-only control (FIGS. 20C and 20D, $p<0.05$). Specifically, at the level of the spleen, MBV increased the frequency of CD69+CD4 T-cells compared to the PBS-only and Influenza+i.v. PBS groups (FIG. 20C. $p<0.05$). Systemic MBV also increased the frequency of anti-viral Tbet+ CD4 T-cells in the lymph nodes compared to the PBS only and influenza+i.v. PBS group (FIG. 20C, $p<0.05$). The MBV also increased the frequency of CD69+ activated CD8 T-cells in the spleen compared to both the PBS only and influenza+i.v. PBS groups (FIG. 20D, $p<0.05$). While not significant, there was a trend in the systemic MBV group of an increasing frequency of Tbet+ anti-viral CD8 t-cells in the spleen compared to the influenza+i.v. PBS group (FIG. 2. D. $p>0.05$).

Example 13: MBV Mitigate Long-Term Viral-Mediated Pulmonary Inflammation

Figure 21A:
FIGS. 21A-21D illustrate that systemic administration of MBV reduces chronic post-viral lung inflammation through decreased cellular infiltration and decreases pro-inflammatory cytokine production.
Figure 21B:
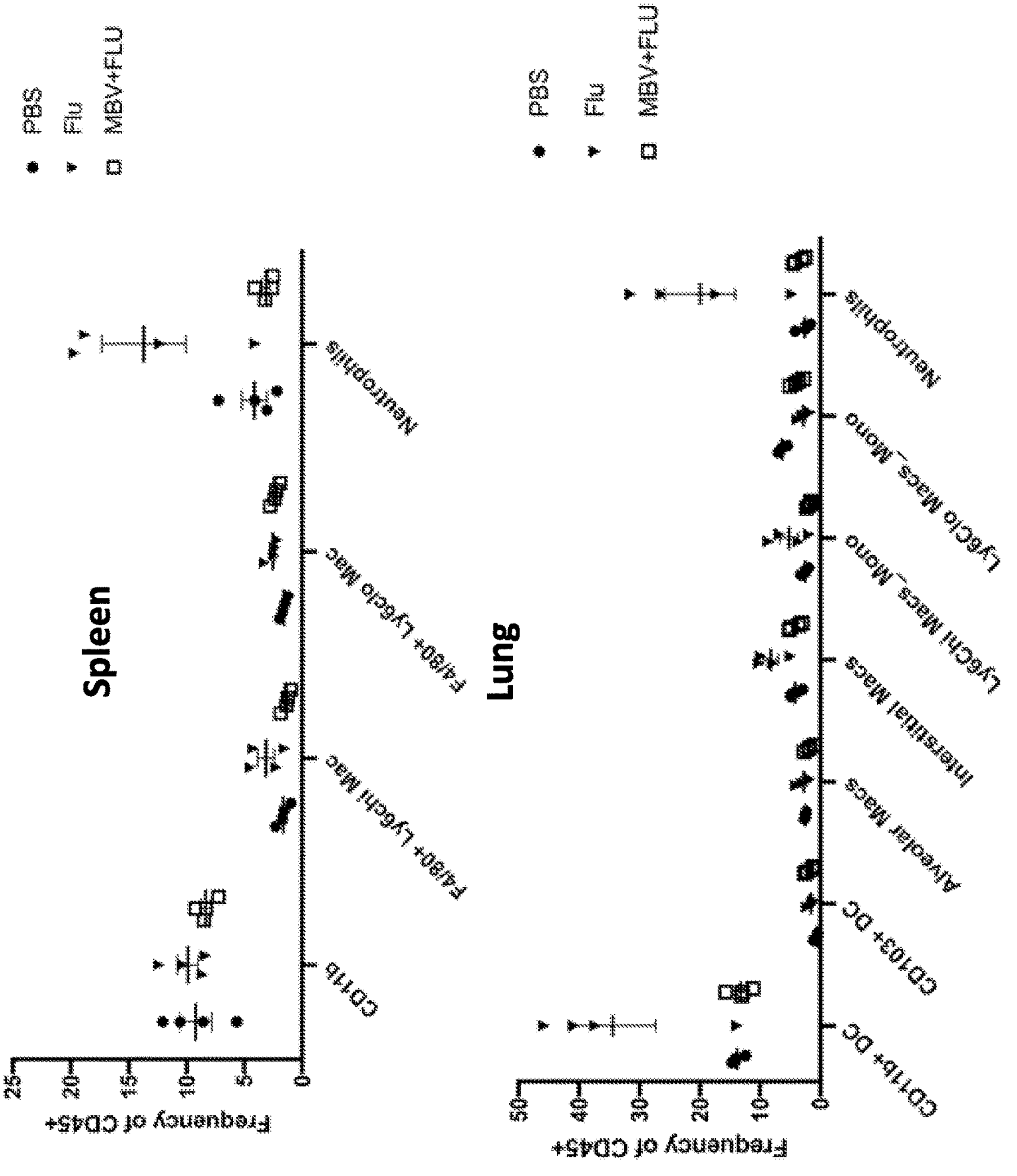
Figure 21C:
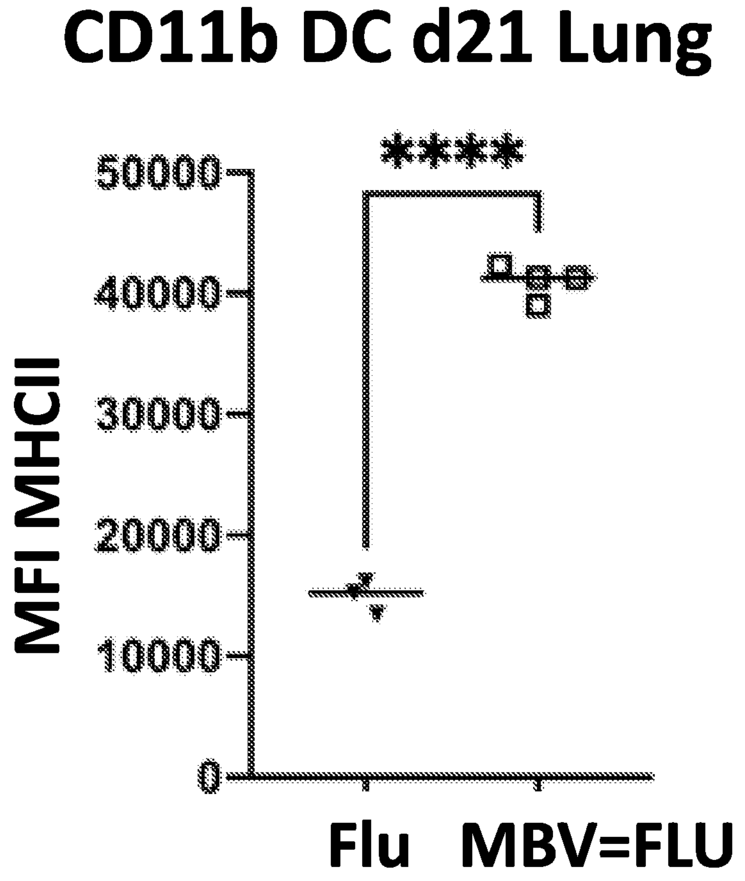
Figure 21D:
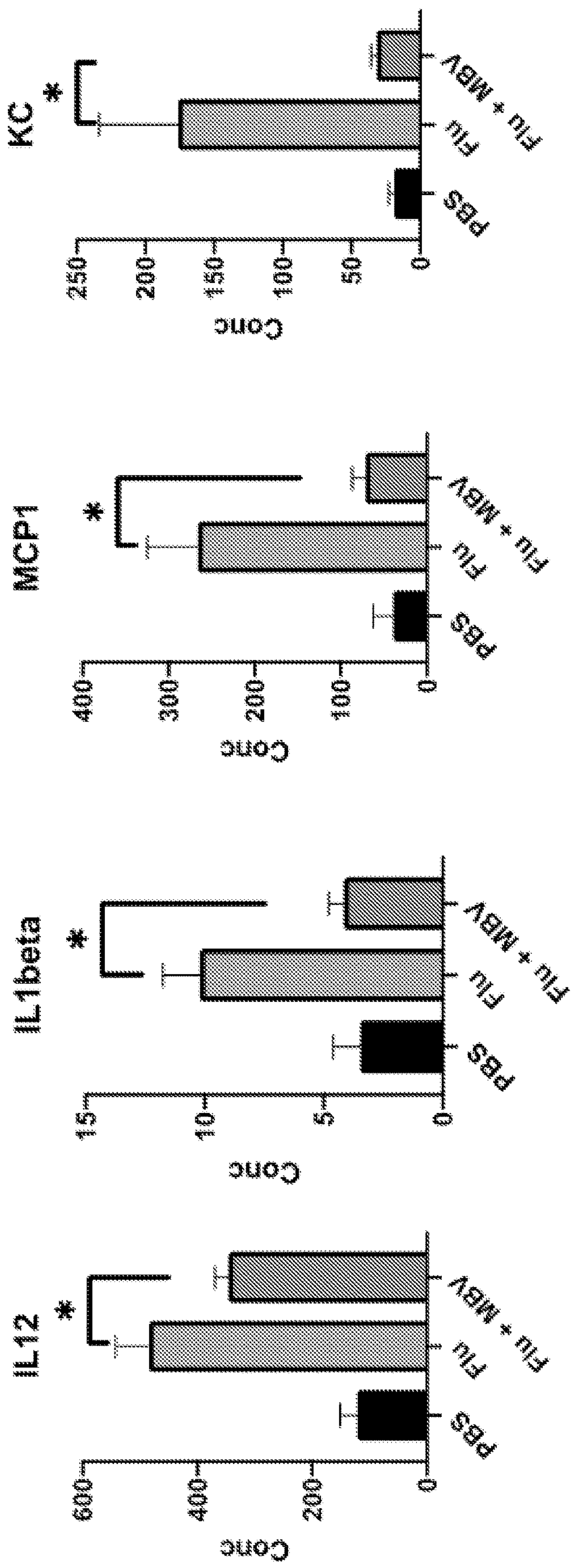

After 21 days following intra-tracheal inoculation with H1N1, systemic administration of MBV substantially reduced overall cellular density in the lung tissue compared to the influenza+i.v. PBS group (FIG. 21A). Similar to day 7 following infection, systemic administration of MBV significantly reduced the overall frequency of CD45+ neutrophils at both the local level in the lung as well as systemically in the spleen (FIG. 21B). In combination with the reduction of pro-inflammatory neutrophils, there is a concurrent increase in the frequency of immunoregulatory CD11+ dendritic cells in the lung (FIG. 21G). Furthermore, systemic administration of MBV reduces pro-inflammatory chemokines and cytokines compared to those elevated in long-term viral inflammation (FIG. 3. D, $p<0.05$). Specifically, MBV reduces the lung concentration of IL12, Ill-beta, MCP1, and KC (FIG. 3. D, $p<0.05$).

Figure 22:
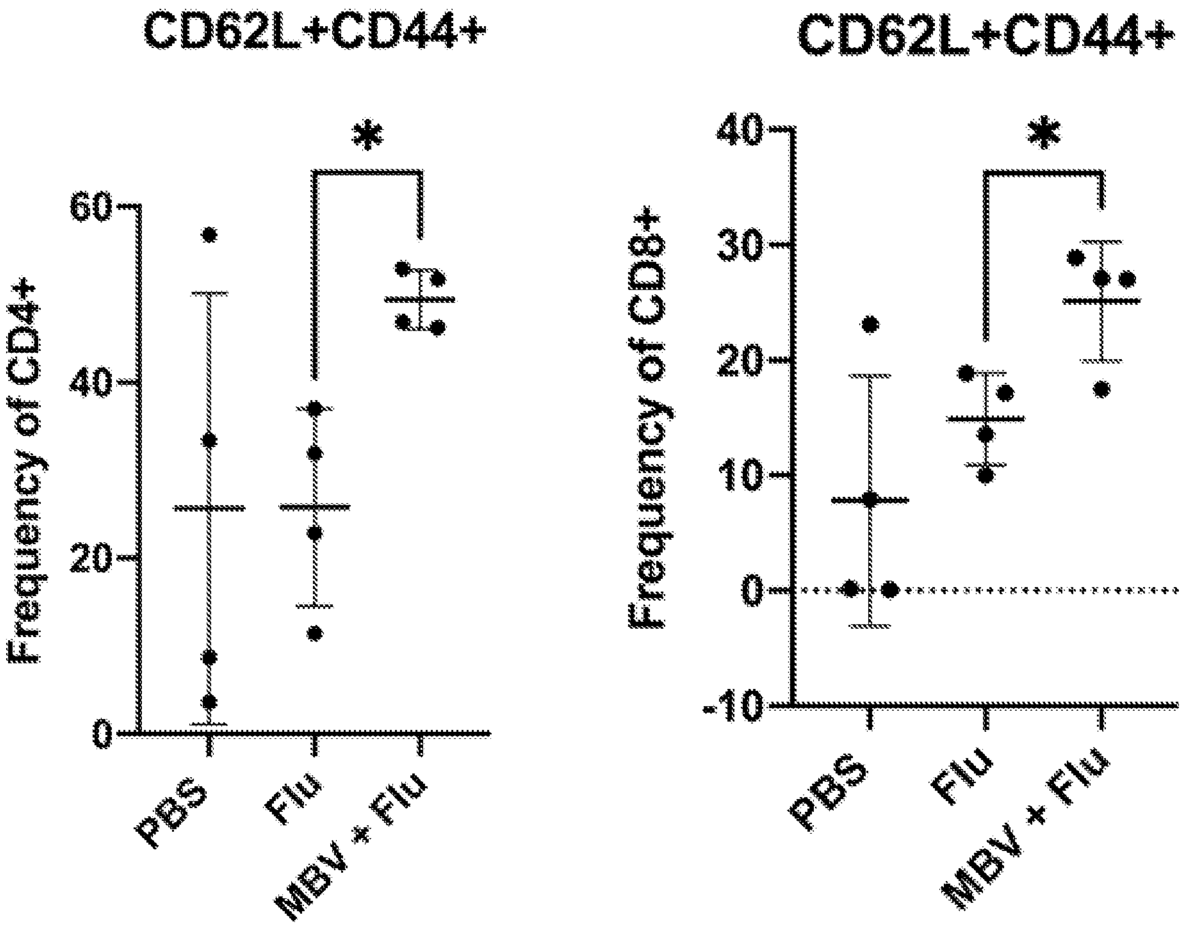
FIG. 22 is a set of bar graphs showing that systemic administration of MBV significantly increased the proportion of CD62L+CD44+ memory CD4 and CD8 T-cells supporting long-term anti-viral resistance.

Example 14: Systemic Administration of MBV Induces a Pro-Memory Immune Response in Both CD4 and CD8 T-Cells Compared to influenza+i.v. PBS, the administration of MBV i.v. not only promoted resolution of inflammation and cellular infiltration in viral-mediated lung pathology but also promoted a memory immune response. Specifically, systemic administration of MBV increased the frequency of CD621+/CD44+ memory CD4 and CD8 T-cells compared to the influenza+i.v. PBS group (FIGS. 22A and 22B, $p<0.05$).

Figure 23:
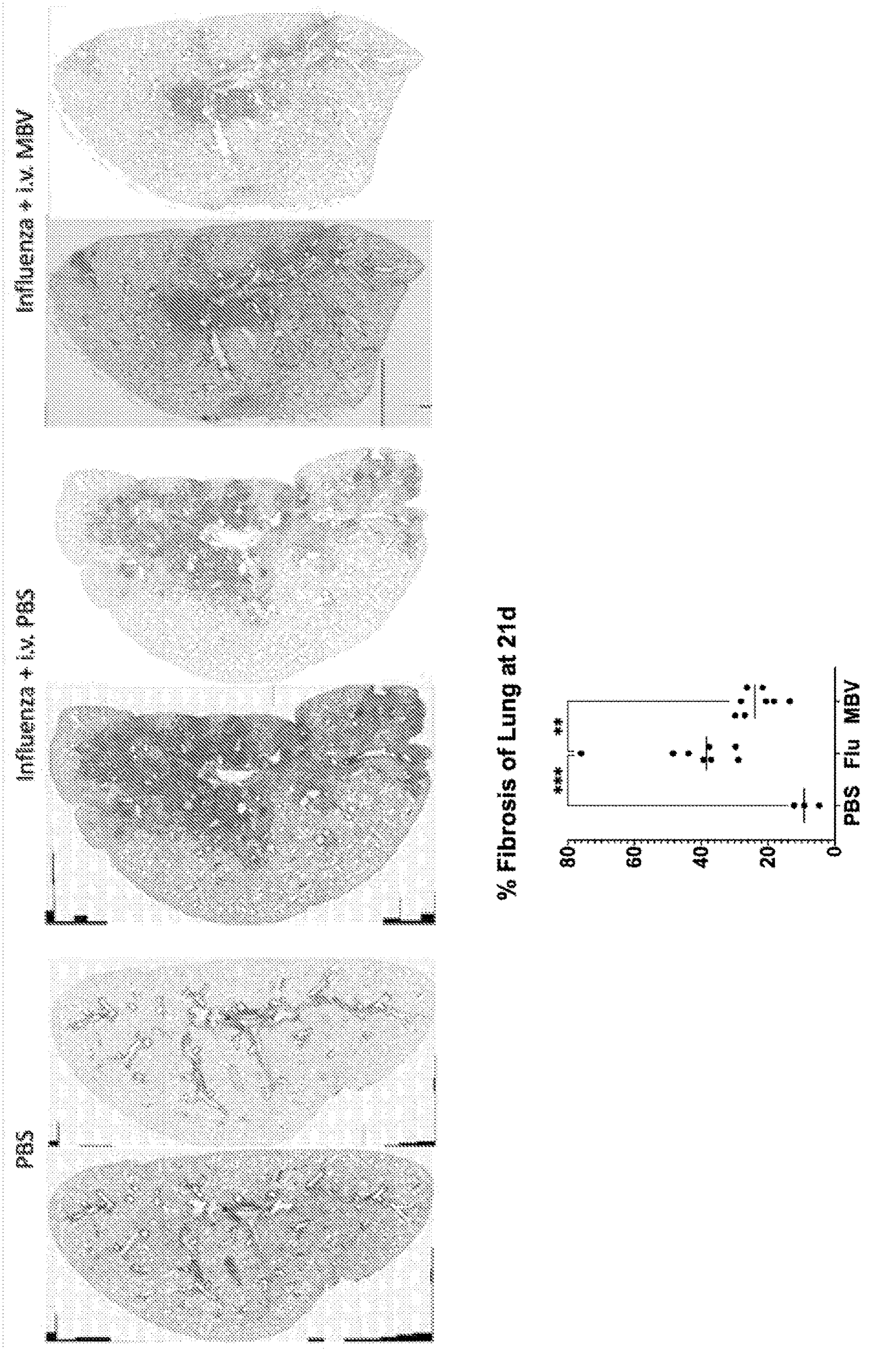
FIG. 23 is a set of digital images and a graph showing that systemic administration of MBV significantly reduces HIN1-associated consolidation and interstitial fibrosis at day 21 following infection. Top images represent trichrome staining and quPath rendered images. Histopathological analysis was performed using QuPath software. Briefly, Mason's trichrome stained cells were counted using optical density data and classified based on phenotype by a Random Trees machine-learning architecture. The ML classifier was trained on six representative images, with multiple (n>10) training regions denoting the four possible classes: connective tissue, blood vessel, lung stromal tissue, diseased tissue. In the bottom section, the percent of total tissue fibrosis/consolidation per surface area of the lung was calculated and showed a significant decrease in the total diseased tissue in the MBV treated animals compared to those untreated animals with H1N1.

Example 15: Viral-Associated Tissue Damage and Extracellular Matrix Deposition is Decreased with Systemic Administration of MBV After 21 days following H1N1 inoculation, systemic MBV compared to influenza+i.v. PBS significantly reduced viral-associated tissue damage and new extracellular matrix deposition as visualized on trichrome images quantified with quPath artificial intelligence (FIGS. 23A and 23B, $p<0.05$).

The results show that animals treated with MBV demonstrate significantly decreased viral morbidity compared to untreated control animals. More surprisingly, the infected animals treated with MBV display decreased lung injury and inflammation as seen in the white blood cell counts and cytokine levels. These data showed that administration of MBV was an effective therapeutic for immunomodulation of disease and disorder that lead to acute respiratory distress and that MBV can reduce severity or incidence of ARDS induced by viral infection. This provides an efficacious therapy for, amongst other indications, ARDS, viral disease for which no therapeutic exists, such as disease caused by H1N1, or SARS-CoV2. The data also provide methods for treating other influenza and coronavirus-induced respiratory diseases.

Example 16: Materials and Methods for Examples 17-19

Quadriceps muscle was first decellularized with 0.02% trypsin and 0.05% EDTA and disinfected with 0.01% peracetic acid prior to enzymatic digestion with Liberase TH in buffer (50 mM Tris pH 7.5, 5 mM $CaCl_2$), 150 mM NaCl) at room temperature overnight to release MBV from the ECM.

Exosomes were isolated from C57B16 mouse plasma obtained from Innovative Research.

cMV were isolated from 17IIA pre-odontoblast cells as previously described in Chaudhary et al. *Matrix Biol.* 52-54: 284-300, 2016. Briefly, osteogenic differentiation of 17IIA cells was induced with 10 mM Na-Pi buffer (pH 7.4) and 50 μg/ml ascorbic acid for 24 hr prior to enzymatic digestion with 1 mg/ml collagenase IA in buffer for 2 hr at 37° C.

Isolation of vesicles: After appropriate preparation as described above, samples were then subjected to centrifugation at 500×g for 10 min, 2,500×g for 20 min, and 10,000×g for 30 min to remove cells and ECM debris, and the supernatant passed through a 0.22 μm filter. The clarified supernatant containing the vesicles were then centrifuged at 100,000×g (Beckman Coulter Optima L-90K Ultracentrifuge) at 4° C. for 70 min to pellet the vesicles. The vesicle pellet was resuspended in 1×PBS, aliquoted, and stored at −20° C. until further use.

Characterization of vesicle protein markers: Vesicle subtypes were analyzed to determine the expression levels of protein markers commonly associated with exosomes. Protein markers were analyzed using the Exo-Check™ Exosome Antibody Array (System Biosciences) with 50 μg vesicle protein. ImageJ was used to quantify the relative expression of each protein analyzed.

Isolation and treatment of murine bone marrow-derived macrophages: Bone marrow-derived macrophages were isolated from the tibia and femur of C57B16 mice as previously described by Sicari et al., *Biomaterials* 35:8605-8612, 2014. Harvested mononuclear cells were seeded at a ratio of $2\times10^6$ cells/mL and monocytes were differentiated into macrophages by culture at 37° C. and 5% $CO_2$ for 7 days with macrophage-colony-stimulating-factor (MCSF)-containing media. The resulting cells were designated as naïve macrophages. Naïve macrophages were exposed to one of the following treatments for 24 hr: 1) LPS/IFNγ to derive M1 macrophages, 2) IL-4 to derive M2 macrophages, 3) $1\times10^9$ particles/mL plasma exosomes 4) $1\times10^9$ particles/mL 17IIA cMV, or 5) $1\times10^9$ particles/mL muscle MBV.

Gene expression: After 24 hr, RNA was collected with Trizol. 1000 ng RNA was converted in cDNA using the High Capacity cDNA Reverse Transcription Kit (ThermoFisher Scientific) following manufacturer's instructions. Real time qPCR was done using PowerUp™ SYBR® Green Master Mix. The relative gene expression was determined by $2^{-\Delta\Delta Ct}$ method compared with the no treatment (M0) control.

Statistical analysis: A two-way analysis of variance (ANOVA) and post-hoc analysis with Tukey correction determined significant comparisons between groups. All statistical analysis was completed with GraphPad Prism. *P<0.05, P<0.01, *P<0.001.

Example 17: MBV do not Express the Common Exosomal Markers CD63 or CD81

EXO-CHECK™ Exosome Antibody Array (System Biosciences) was used to compare the presence or absence of common exosomal markers on murine exosomes, murine bone marrow bone matrix vesicles (Bone MV), and murine matrix bound nanovesicles (MBV). The results are shown in the top panel of FIG. 24 and clearly show that MBV are virtually devoid of the canonical and well accepted markers of exosomes such as CD63 and CD81. In addition, the other signaling molecules identified in the top panel of FIG. 24 were absent in MBV, whereas they were present to either moderate or high degrees in bone microvesicles and exosomes. A densitometry plot of the expression values is shown in the bottom panel of FIG. 24.

The data show that while exosomes and Bone MV share a similar expression profile with moderate to high expression of these markers, MBV are significantly different in the expression of these EV markers. For example, MBV are also virtually devoid of, i.e., have "low" or "undetectable" levels of one or more of EpCAM, ANXA5, TSG101, FLOT1, ICAM1, and ALIX as indicated by blank wells as compared to the presence of dark rings or solid dark spots in the same positions on the exosome wells and by the relative expression levels of these markers as shown in the graph in the bottom panel. Bone MV also have higher levels of expression of all of these markers as compared to MBV as shown by the dark spots on the wells and by the relative expression levels of these markers as shown in the graph in the bottom panel.

In one embodiment, MBV have low or undetectable levels or one or more of CD63, CD81, EpCAM, ANXA5, TSG101, FLOT1, ICAM1, and ALIX as compared to a positive control of the EXO-CHECK™ Exosome Antibody Array. In one embodiment, MBV have low or undetectable levels of one or more of CD63, CD81, EpCAM, ANXA5, TSG101, FLOT1, ICAM1, and ALIX as compared to an exosome, for example, a plasma exosome. In one embodiment, MBV have low or undetectable levels or one or more of Cd63, CD81, EpCAM, ANXA5, TSG101, FLOT1, ICAM1, and ALIX as compared to a bone MV. In one embodiment, MBV are characterized by low or undetectable levels of ANXA5, TSG101, and ICAM1 as compared to exosomes or bone MV. In one embodiment, MBV are characterized by low or undetectable levels of CD81, CD63, ANXA5, TSG101, and ICAM1 as compared to bone MV or plasma exosome.

Example 18: MBV have Low or No Expression of Bone MV Markers

Figure 25:
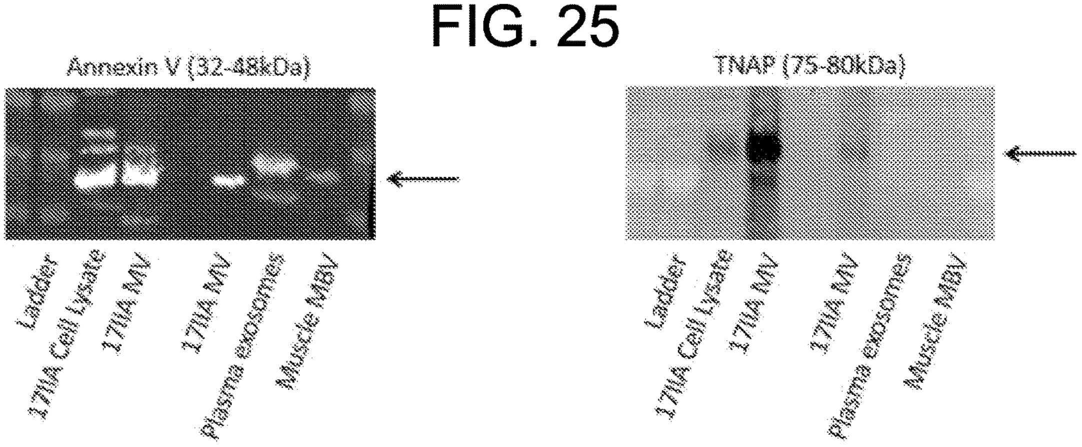
FIG. 25 shows the results of a Western blot analysis of plasma exosomes and muscle MBV to detect expression of the Bone MV markers Annexin V and Tissue Non-specific Alkaline Phosphatase (TNAP).

The expression of the Bone MV markers Annexin V, and Tissue Non-specific Alkaline Phosphatase (TNAP) were evaluated by Western blot analysis. The results are shown in FIG. 25. Lysate prepared from 1711A Cells was used as a positive control. The results of this experiment show that matrix bound nanovesicles (MBV) are devoid of any expression of both markers of bone microvesicles, TNAP and Annexin V. Plasma exosomes do express Annexin V, but do not express TNAP. These results clearly distinguish MBV from both exosomes and bone microvesicles

Figure 26:
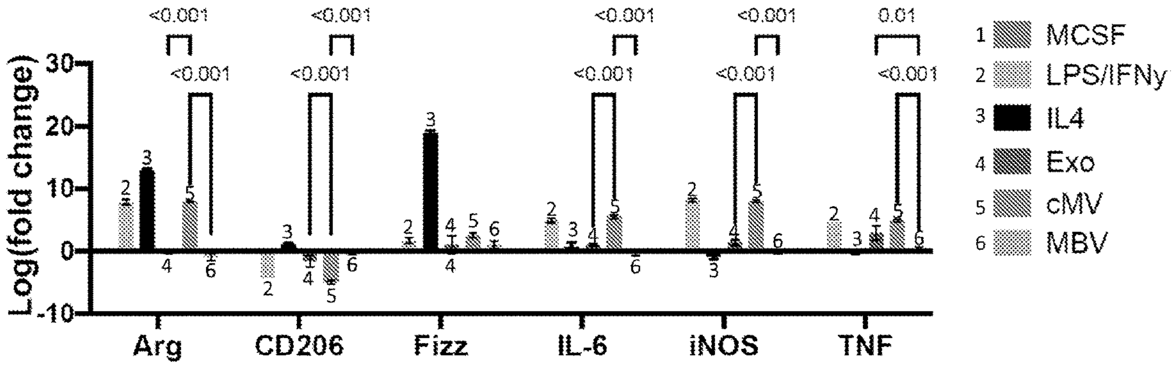
FIG. 26 is a bar graph showing the fold change of expression of various genes in various cell types—bone marrow derived macrophages that were untreated (MO) or treated IFNγ+LPS (M1) or IL-4 (M2) or exosomes derived from plasma, Bone MV derived from 17A cells, or MBV isolated from muscle.

Example 19:MBV have a Differential Immunomodulatory Effect Compared to Exosomes or Bone MV Bone Marrow-Derived Macrophages (BMDM) harvested from mice were untreated (M0) or treated with the following test articles for 24 hours: IFNγ+LPS to induce an M1 phenotype (M1), IL-4 to induce an M2-like phenotype (M2), Exosomes derived from plasma, Bone MV derived from 17A cell, or MBV isolated from muscle. After treatment, the fold change in the expression of the indicated genes was evaluated by qPCR. The results, shown in FIG. 26, show the downregulation of the pro-inflammatory markers IL-6 and TNF-α by MBV are clearly distinguished from the downregulation of the same two inflammatory mediators by exosomes and bone microvesicles. MBV had a potent anti-inflammatory effect; whereas exosomes and bone microvesicles did not.

INCORPORATION BY REFERENCE

Unless stated to the contrary, the entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method of treating acute respiratory distress syndrome (ARDS) in a subject that has ARDS comprising administering to the subject a pharmaceutical composition comprising a therapeutically effective amount of isolated matrix bound vesicles (MBV) derived from urinary bladder extracellular matrix, thereby treating the ARDS in the subject, wherein the MBV a) do not express CD63 or CD81, or b) are $CD63^{lo}CD81^{lo}$ and wherein the subject is infected with SARS-CoV-2 or influenza.

2. The method of claim 1, wherein the subject is infected with SARS-CoV-2.

3. The method of claim 1, wherein the subject is infected with influenza.

4. The method of claim 1, wherein the subject experiences hypercytokinemia, and wherein administration of the MBV reverses hypercytokinemia in the subject.

5. The method of claim 1, wherein the subject is a human subject.

6. The method of claim 1, wherein the pharmaceutical composition is administered by systemic intravenous (IV) injection.

7. The method of claim 1, wherein a) the pharmaceutical composition is administered to the subject's lungs as an aerosol via a nebulizer;

b) the pharmaceutical composition is administered by endotracheal instillation via an endotracheal tube placed in the subject; and/or c) the pharmaceutical composition is administered to the subject's lungs by a metered dose inhaler via intranasal administration.

8. The method of claim 1, wherein the MBV are derived from extracellular matrix from a mammalian vertebrate selected from a human, monkey, pig, cow, or sheep.

9. The method of claim 1, wherein a) the MBV are administered in an amount of $1\times10^6$ to $1\times10^{20}$ MBV per kg of body weight per administration;

b) the MBV are administered in an amount of $1\times10^6$ to $1\times10^{12}$ MBV per kg of body weight per administration; or c) the MBV are administered in an amount of $1\times10^9$ to $1\times10^{14}$ MBV per kg of body weight per administration.

10. The method of claim 1, wherein the subject has a reduced risk of secondary infection as a result of treatment with MBV as compared to a subject treated with an immunosuppressive agent.

11. The method of claim 10, wherein the secondary infection is a) a bacterial infection; or b) a viral infection.

12. The method of claim 1, wherein a) the subject experiences a decrease in the production of a pro-inflammatory cytokine after the administration of MBV; and/or b) the subject experiences an increase in the production of an anti-inflammatory cytokine after the administration of MBV.

13. The method of claim 1, wherein a) the MBV express low or undetectable levels of one or more of the following markers: EpCAM, ANXA5, TSG101, FLOT1, ICAM1, GM130, or ALIX;

b) the MBV express low or undetectable levels of one or more of the following markers: ANXA5, TSG101, or ICAM1; and/or c) the MBV express low or undetectable levels of ANXA5, TSG101, and ICAM1.

14. The method of claim 1, wherein the MBV comprise:

(a) a phospholipid content comprising at least 55% phosphatidylcholine (PC) and phosphatidyl inositol (PI) in combination;

(b) a phospholipid content comprising 10% or less sphingomyelin (SM);

(c) a phospholipid content comprising 20% or less phosphatidylethanolamine (PE); and/or (d) a phospholipid content comprising 15% or greater phosphatidylinositol (PI).

* * * * *

SEQUENCE LISTING

<160> NUMBER OF SEQ ID NOS: 3

<210> SEQ ID NO 1
<211> LENGTH: 88
<212> TYPE: RNA
<213> ORGANISM: Homo sapiens

<400> SEQUENCE: 1
caccuugucc ucacggucca guuuucccag gaaucccuua gaugcuaaga uggggauucc 60
uggaaauacu guucuugagg ucaugguu 88

<210> SEQ ID NO 2
<211> LENGTH: 110
<212> TYPE: RNA
<213> ORGANISM: Homo sapiens

<400> SEQUENCE: 2
agaagggcua ucaggccagc cuucagagga cuccaaggaa cauucaacgc ugucggugag 60

-continued

```
uuugggauuu gaaaaaacca cugaccguug acuguaccuu gggguccuua           110


<210> SEQ ID NO 3
<211> LENGTH: 106
<212> TYPE: DNA
<213> ORGANISM: Homo sapiens

<400> SEQUENCE: 3

gcgcagcgcc ctgtctccca gcctgaggtg cagtgctgca tctctggtca gttgggagtc     60

tgagatgaag cactgtagct caggaagaga gaagttgttc tgcagc                   106
```